US008048851B2

(12) United States Patent
Fogelman et al.

(10) Patent No.: US 8,048,851 B2
(45) Date of Patent: *Nov. 1, 2011

(54) PEPTIDES AND PEPTIDE MIMETICS TO TREAT PATHOLOGIES CHARACTERIZED BY AN INFLAMMATORY RESPONSE

(75) Inventors: Alan M. Fogelman, Beverly Hills, CA (US); Mohamad Navab, Los Angles, CA (US); Gattadahalli M. Anantharamaiah, Birmingham, AL (US)

(73) Assignees: The Regents of the University of California, Oakland, CA (US); The UAB Research Foundation, Birmingham, AL (US)

( * ) Notice: Subject to any disclaimer, the term of this patent is extended or adjusted under 35 U.S.C. 154(b) by 84 days.

This patent is subject to a terminal disclaimer.

(21) Appl. No.: 11/830,497

(22) Filed: Jul. 30, 2007

(65) Prior Publication Data
US 2008/0095821 A1   Apr. 24, 2008

Related U.S. Application Data

(63) Continuation of application No. 11/407,390, filed on Apr. 18, 2006, now Pat. No. 7,723,303, and a continuation-in-part of application No. 10/423,830, filed on Apr. 25, 2003, now Pat. No. 7,199,102, which is a continuation-in-part of application No. 10/273,386, filed on Oct. 16, 2002, now Pat. No. 7,166,578, which is a continuation-in-part of application No. 10/187,215, filed on Jun. 28, 2002, now Pat. No. 7,144,862, which is a continuation-in-part of application No. 09/896,841, filed on Jun. 29, 2001, now Pat. No. 6,933,279, which is a continuation-in-part of application No. 09/645,454, filed on Aug. 24, 2000, now Pat. No. 6,664,230.

(60) Provisional application No. 60/697,495, filed on Jul. 7, 2005, provisional application No. 60/676,431, filed on Apr. 29, 2005.

(51) Int. Cl.
A61F 2/82       (2006.01)
A61K 38/16      (2006.01)
C07K 14/00      (2006.01)

(52) U.S. Cl. ........ 514/1.9; 424/424; 514/21.3; 530/324; 530/345; 604/508; 623/1.42

(58) Field of Classification Search .................. None
See application file for complete search history.

(56) References Cited

U.S. PATENT DOCUMENTS

| | | |
|---|---|---|
| 3,767,040 A | 10/1973 | Tushaus |
| 4,155,913 A | 5/1979 | Hellerbach et al. |
| 4,428,938 A * | 1/1984 | Kisfaludy et al. |
| 4,643,988 A | 2/1987 | Segrest et al. |
| 4,684,520 A | 8/1987 | Bertelli |
| 5,298,490 A | 3/1994 | Heavner et al. |
| 5,304,470 A | 4/1994 | Fischer et al. |
| 5,344,822 A | 9/1994 | Levine et al. |
| 5,358,934 A | 10/1994 | Borovsky et al. |
| 5,480,869 A | 1/1996 | Wei et al. |
| 5,595,973 A | 1/1997 | Bogden |
| 5,721,138 A | 2/1998 | Lawn |
| 5,733,549 A | 3/1998 | Yamada et al. |
| 5,733,879 A | 3/1998 | Rosseneu et al. |
| 5,814,467 A | 9/1998 | Curtiss et al. |
| 5,854,238 A | 12/1998 | Kempen |
| 6,004,925 A | 12/1999 | Dasseux et al. |
| 6,011,002 A * | 1/2000 | Pastan et al. |
| 6,019,739 A * | 2/2000 | Rhee et al. |
| 6,037,323 A | 3/2000 | Dasseux et al. |
| 6,046,166 A | 4/2000 | Dasseux et al. |
| 6,086,918 A | 7/2000 | Stern et al. |
| 6,172,071 B1 | 1/2001 | Uckun et al. |
| 6,191,151 B1 * | 2/2001 | Zik |
| 6,228,989 B1 | 5/2001 | Traugh et al. |
| 6,265,377 B1 | 7/2001 | Dasseux et al. |
| 6,265,382 B1 | 7/2001 | Doherty et al. |
| 6,273,913 B1 | 8/2001 | Wright et al. |
| 6,287,590 B1 | 9/2001 | Dasseux et al. |
| 6,297,216 B1 | 10/2001 | Sarkadi et al. |
| 6,303,619 B1 | 10/2001 | Linden |
| 6,329,341 B1 | 12/2001 | Dasseux et al. |
| 6,376,464 B1 | 4/2002 | Dasseux et al. |
| 6,383,808 B1 | 5/2002 | Monia et al. |
| 6,444,230 B1 | 9/2002 | Godin et al. |
| 6,444,681 B1 | 9/2002 | Flavahan et al. |
| 6,455,088 B1 | 9/2002 | Dasseux et al. |
| 6,464,975 B2 | 10/2002 | Millis |

(Continued)

FOREIGN PATENT DOCUMENTS
AU    2001-286732    3/2002

(Continued)

OTHER PUBLICATIONS

U.S. Appl. No. 60/968,815, filed Aug. 29, 2007, Fogelman et al.
U.S. Appl. No. 10/269,755, filed Oct. 11, 2002, Fogelman et al.
U.S. Appl. No. 11/541,481, filed Sep. 26, 2006, Fogelman et al.
U.S. Appl. No. 11/541,482, filed Sep. 26, 2006, Fogelman et al.
U.S. Appl. No. 11/541,494, filed Sep. 26, 2006, Fogelman et al.
U.S. Appl. No. 11/835,338, filed Aug. 7, 2007, Fogelman et al.
U.S. Appl. No. 11/950,315, filed Dec. 4, 2007, Fogelman et al.
Australian Notice of Acceptance and Allowed Claims dated Sep. 21, 2005 issued in AU 2001286732.

(Continued)

Primary Examiner — Jeffrey E Russel
(74) Attorney, Agent, or Firm — Weaver Austin Villeneuve & Sampson LLP; Tom Hunter

(57) ABSTRACT

This invention provides novel active agents (e.g. peptides, small organic molecules, amino acid pairs, etc.) peptides that ameliorate one or more symptoms of atherosclerosis and/or other pathologies characterized by an inflammatory response. In certain embodiment, the peptides resemble a G* amphipathic helix of apolipoprotein J. The agents are highly stable and readily administered via an oral route.

14 Claims, 18 Drawing Sheets

U.S. PATENT DOCUMENTS

| | | |
|---|---|---|
| 6,498,038 B1 | 12/2002 | Ghosh et al. |
| 6,518,412 B1 | 2/2003 | Dasseux et al. |
| 6,525,083 B2 | 2/2003 | Acton et al. |
| 6,555,651 B2 | 4/2003 | Stern et al. |
| 6,573,239 B1 | 6/2003 | Dasseux et al. |
| 6,602,854 B1 | 8/2003 | Dasseux et al. |
| 6,630,450 B1 | 10/2003 | Dasseux et al. |
| 6,635,623 B1 | 10/2003 | Hoogeveen et al. |
| 6,642,239 B2 | 11/2003 | Missbach |
| 6,664,230 B1 | 12/2003 | Fogelman et al. |
| 6,696,545 B1 | 2/2004 | Buelow et al. |
| 6,716,816 B1 | 4/2004 | Dasseux et al. |
| 6,717,031 B2 | 4/2004 | Games et al. |
| 6,727,063 B1 | 4/2004 | Lander et al. |
| 6,734,169 B2 | 5/2004 | Dasseux et al. |
| 6,753,313 B1 | 6/2004 | Dasseux et al. |
| 6,815,426 B2 | 11/2004 | Scialdone et al. |
| 6,846,636 B1 | 1/2005 | Argraves et al. |
| 6,849,714 B1 | 2/2005 | Bridon et al. |
| 6,869,568 B2 | 3/2005 | Fogelman et al. |
| 6,887,470 B1 | 5/2005 | Bridon et al. |
| 6,933,279 B2 | 8/2005 | Fogelman et al. |
| 6,936,691 B2 | 8/2005 | Fiscella et al. |
| 6,982,348 B2 | 1/2006 | Kori et al. |
| 7,144,862 B2 | 12/2006 | Fogelman et al. |
| 7,148,197 B2 | 12/2006 | Fogelman et al. |
| 7,166,578 B2 | 1/2007 | Fogelman et al. |
| 7,166,625 B2 | 1/2007 | Egan et al. |
| 7,199,102 B2 | 4/2007 | Fogelman et al. |
| 7,291,590 B2 | 11/2007 | Kisilevsky et al. |
| 7,470,660 B2 * | 12/2008 | Schwartz et al. |
| 7,531,514 B2 * | 5/2009 | Fogelman et al. |
| 7,579,319 B2 * | 8/2009 | Fogelman |
| 7,723,303 B2 | 5/2010 | Fogelman et al. |
| 7,807,640 B2 | 10/2010 | Fogelman et al. |
| 7,820,784 B2 | 10/2010 | Fogelman et al. |
| 2001/0005714 A1 | 6/2001 | Boffelli et al. |
| 2002/0042441 A1 | 4/2002 | Acton et al. |
| 2002/0142369 A1 * | 10/2002 | Fersht |
| 2003/0027769 A1 | 2/2003 | Scialdone et al. |
| 2003/0040505 A1 | 2/2003 | Fogelman et al. |
| 2003/0045460 A1 * | 3/2003 | Fogelman et al. |
| 2003/0077641 A1 | 4/2003 | Laskowitz et al. |
| 2003/0087819 A1 * | 5/2003 | Bielicki |
| 2003/0096737 A1 | 5/2003 | Diu-Hercend et al. |
| 2003/0125260 A1 | 7/2003 | Haviv et al. |
| 2003/0171277 A1 | 9/2003 | Fogelman et al. |
| 2003/0191057 A1 | 10/2003 | Fogelman et al. |
| 2003/0203842 A1 * | 10/2003 | Dasseux et al. |
| 2003/0229015 A1 * | 12/2003 | Fogelman et al. ............. 514/12 |
| 2004/0059110 A1 | 3/2004 | Nakano et al. |
| 2004/0136989 A1 | 7/2004 | Banerjee et al. |
| 2004/0152623 A1 | 8/2004 | Varadhachary et al. |
| 2004/0254120 A1 | 12/2004 | Fogelman et al. |
| 2004/0266663 A1 | 12/2004 | Schwartz et al. |
| 2004/0266671 A1 * | 12/2004 | Fogelman et al. |
| 2005/0070996 A1 | 3/2005 | Dinh et al. |
| 2005/0154046 A1 | 7/2005 | Wang et al. |
| 2005/0164950 A1 | 7/2005 | Fogelman et al. |
| 2005/0197381 A1 | 9/2005 | Wang et al. |
| 2005/0239136 A1 | 10/2005 | Hazen et al. |
| 2005/0272634 A1 | 12/2005 | Bahlmann et al. |
| 2006/0069030 A1 | 3/2006 | Bachovchin |
| 2006/0205634 A1 | 9/2006 | Varadhachary et al. |
| 2006/0205669 A1 | 9/2006 | Fogelman et al. |
| 2006/0217298 A1 | 9/2006 | Srivastava |
| 2006/0217307 A1 | 9/2006 | Takashi et al. |
| 2006/0234908 A1 | 10/2006 | Fogelman et al. |
| 2007/0032430 A1 | 2/2007 | Fogelman et al. |
| 2007/0060527 A1 | 3/2007 | Fogelman et al. |
| 2007/0254839 A1 | 11/2007 | Fogelman et al. |
| 2008/0045459 A1 | 2/2008 | Fogelman et al. |
| 2008/0096814 A1 | 4/2008 | Fogelman et al. |
| 2008/0096815 A1 | 4/2008 | Fogelman et al. |
| 2008/0096816 A1 | 4/2008 | Fogelman et al. |
| 2008/0293639 A1 * | 11/2008 | Fogelman et al. |
| 2009/0028925 A1 | 1/2009 | Erion et al. |
| 2009/0286741 A1 * | 11/2009 | Fogelman et al. |
| 2010/0227825 A1 | 9/2010 | Fogelman et al. |

FOREIGN PATENT DOCUMENTS

| | | |
|---|---|---|
| AU | 2005-287004 | 3/2006 |
| CA | 2420222 | 2/2002 |
| CA | 2580501 | 3/2006 |
| CN | 1469754 | 10/2005 |
| CN | 1739787 A | 3/2006 |
| CN | 1943781 | 4/2007 |
| EA | 6488 | 12/2005 |
| EP | 1186299 | 3/2002 |
| EP | 1318828 | 6/2003 |
| EP | 1562624 | 8/2005 |
| EP | 1799242 | 6/2007 |
| IL | 154545 | 8/2001 |
| IN | 185761 | 5/1997 |
| JP | 61-126099 | 6/1986 |
| JP | 3-503178 | 7/1991 |
| JP | 7-507554 | 8/1995 |
| JP | 09-505559 | 6/1997 |
| JP | 11-500311 | 1/1999 |
| JP | 11-507376 | 6/1999 |
| JP | 2000-136202 | 5/2000 |
| JP | 2000-509020 | 7/2000 |
| JP | 3822167 | 9/2006 |
| JP | 2006-312650 | 11/2006 |
| MX | PA2010763 | 3/2003 |
| WO | WO 91/05043 | 4/1991 |
| WO | WO 96/41815 | 12/1996 |
| WO | WO 97/36927 | 10/1997 |
| WO | WO 98/09602 * | 3/1998 |
| WO | WO 99/06437 | 2/1999 |
| WO | WO 99/16408 | 4/1999 |
| WO | WO 99/16409 | 4/1999 |
| WO | WO 99/24460 | 5/1999 |
| WO | WO 99/47566 | 9/1999 |
| WO | WO 00/06599 | 2/2000 |
| WO | WO 00/34469 | 6/2000 |
| WO | WO 01/75168 | 10/2001 |
| WO | WO 01/75170 | 10/2001 |
| WO | WO 02/15923 | 2/2002 |
| WO | WO 02/22161 | 3/2002 |
| WO | WO 02/098446 * | 12/2002 |
| WO | WO 03/017924 | 3/2003 |
| WO | WO 03/038886 | 5/2003 |
| WO | WO 03/086326 | 10/2003 |
| WO | WO 2004/034977 | 4/2004 |
| WO | WO 2004/043396 * | 5/2004 |
| WO | WO 2005/000887 | 1/2005 |
| WO | WO 2005/016280 | 2/2005 |
| WO | WO 2006/020652 | 2/2006 |
| WO | WO 2006/034056 | 3/2006 |
| WO | WO 2006/063132 | 6/2006 |
| WO | WO 2006/118805 | 11/2006 |
| WO | WO 2008/021088 | 2/2008 |
| WO | PCT/US2008/074624 | 8/2008 |
| WO | WO 2009/073725 * | 6/2009 |

OTHER PUBLICATIONS

Australian Office Action dated Jan. 17, 2007 issued in AU 2006 2000035.
Australian Office Action dated Feb. 13, 2008 issued in AU 2007237157.
Canadian Office Action dated Feb. 25, 2005 issued in CA2420222.
Canadian Office Action dated Mar. 1, 2006 issued in CA2420222.
Canadian Office Action dated Jun. 1, 2007 issued in CA2420222.
Canadian Office Action dated Sep. 19, 2006 issued in CA2420222.
Chinese Office Action dated Apr. 19, 2007 issued in CN 200510103876.X.
Chinese Office Action dated Jan. 16, 2008 issued in CN 200480029870.6.
Chinese Office Action dated Nov. 23, 2007 issued in CN 200610100669.3.
Chinese Office Action dated Feb. 15, 2008 issued in CN200610100670.6.

Chinese Office Action dated May 8, 2008 issued in CN 200610100667.4.
Chinese Office Action dated Feb. 2, 2008 issued in CN200610100668.9.
Chinese Office Action dated Sep. 6, 2007 issued in CN 200380106367.1.
Chinese Office Action dated Jan. 6, 2006 issued in CN 2003812668.0.
Chinese Office Action dated Feb. 5, 2007 issued in CN 2003812668.0.
Chinese Office Action dated Aug. 3, 2007 issued in CN 2003812668.0.
Ecuadorian Opposition to Application dated Mar. 5, 2007 issued in EC-SP-066417.
Eurasian Office Action dated Mar. 30, 2003 issued in EA 2003 00289.
Eurasian Office Action dated Apr. 6, 2007 issued in EA 2005 01744.
European Examination Report dated Apr. 29, 2008 issued in EP07007775.5.
European Office Action dated Jan. 9, 2007 issued in EP 01966198.2 (EP1318828).
European Office Action dated Nov. 2, 2007 isssued in EP 01966198.2 (EP 1318828).
European Office Action dated Mar. 7, 2005 issued in EP 01966198.2 (EP 1318828).
European Search Report dated Nov. 7, 2007 isssued in EP 07007775 (EP1864675).
European Search Report dated Sep. 9, 2004 issued in EPO 1966198.2 (EP 1318828).
Indian Office Action dated Jun. 3, 2007 issued in IN 613/CHENP/2005.
International Search Report dated Jan. 3, 2002 from WO2002/015923.
International Search Report dated Oct. 25, 2002 from WO2002/015923.
International Written Opinion dated May 20, 2002 from WO2002/015923.
International Search Report and Written Opinion dated Sep. 8, 2004 from WO 2004/034977.
International Preliminary Examination Report dated Mar. 21, 2006 issued in WO 2005/016280.
International Search Report dated Nov. 18, 2005 issued in WO 2005/016280.
International Search Report and Written Opinion dated Apr. 19, 2006 from WO/2006/034056.
International Search Report and Written Opinion dated Jun. 21, 2006 from WO/2006/063132.
International Written Opinion issued Apr. 18, 2007 in WO/2006/118805.
Israeli Office Action dated Jan. 21, 2008 issued in IL 173626.
Israeli Office Action dated Nov. 20, 2007 issued in IL-154545.
Israeli Office Action dated Aug. 7, 2008 issued in IL-154545.
Japanese Office Action dated May 14, 2008 issued in JP2005-304531.
Japanese Office Action dated Oct. 31, 2006 issued in JP2006-220831.
Japanese Office Action dated Nov. 15, 2005 issued in JP2002-520844.
Japanese Office Action dated Feb. 14, 2006 issued in JP 2005-304531.
Japanese Office Action dated May 29, 2007 issued in JP2006-220831.
Japanese Office Action dated Jul. 19, 2005 issued in JP2002-520844.
Mexican Office Action dated Jan. 19, 2008 issued in MX/a/2007/013430.
New Zealand Examination Report dated Apr. 18, 2008 issued in NZ545240.
New Zealand Examination Report dated May 23, 2008 issued in NZ555826.
Russian Office Action dated Aug. 12, 2008 issued in RU2006-107605.
Singapore Office Action and Written Opinion dated Nov. 19, 2007 cited in SAG 2000600809-8.
Vietnamese Office Action date Oct. 2, 2007 from VN 1-2007-01344.
Vietnamese Office Action dated Feb. 21, 2008 issued in VN 1-2007-01344.
Vietnamese Office Action dated Feb. 28, 2008 issued in VN 9709/SHTT-SC3.
Vietnamese Office Action dated Sep. 28, 2006 issued in VN 1-2006-00370.
US Office Action dated Apr. 23, 2008 issued in U.S. Appl. No. 11/431,412.
US Final Office Action dated Apr. 11, 2005 issued in U.S. Appl. No. 10/187,215.
US Notice of Allowance dated May 1, 2006 issued in U.S. Appl. No. 10/187,215.
US Office Action dated Jan. 8, 2004 issued in U.S. Appl. No. 10/187,215.
US Office Action dated Oct. 28, 2005 issued in U.S. Appl. No. 10/187,215.
US Office Action dated Aug. 26, 2004 issued in U.S. Appl. No. 10/187,215.
US Notice of Allowance dated Jun. 25, 2003 issued in U.S. Appl. No. 09/645,454.
US Office Action dated Jan. 23, 2003 issued in U.S. Appl. No. 09/645,454.
US Office Action dated Sep. 12, 2002 issued in U.S. Appl. No. 09/645,454.
US Final Office Action dated May 7, 2004 issued in U.S. Appl. No. 09/896,841.
US Notice of Allowance dated Dec. 20, 2004 issued in U.S. Appl. No. 09/896,841.
US Office Action dated Oct. 21, 2003 issued in U.S. Appl. No. 09/896,841.
US Final Office Action dated Feb. 2, 2005 issued in U.S. Appl. No. 10/273,386.
US Final Office Action dated Mar. 31, 2006 issued in U.S. Appl. No. 10/273,386.
US Notice of Allowance dated Aug. 2, 2006 issued in U.S. Appl. No. 10/273,386.
US Office Action dated Jun. 21, 2004 issued in U.S. Appl. No. 10/273,386.
US Office Action dated Sep. 7, 2005 issued in U.S. Appl. No. 10/273,386.
US Final Office Action dated Nov. 15, 2005 issued in U.S. Appl. No. 10/423,830.
US Notice of Allowance dated Nov. 21, 2006 issued in U.S. Appl. No. 10/423,830.
US Office Action dated Apr. 18, 2005 issued in U.S. Appl. No. 10/423,830.
US Office Action dated Apr. 26, 2005 issued in U.S. Appl. No. 10/649,378.
US Office Action dated Nov. 4, 2005 issued in U.S. Appl. No. 10/649,378.
U.S. Notice of Allowance and Allowed Claims dated Mar. 9, 2006 issued in U.S. Appl. No. 10/649,378.
US Final Office Action dated Sep. 25, 2008 issued in U.S. Appl. No. 10/913,800.
US Office Action dated Jan. 17, 2008 issued in U.S. Appl. No. 10/913,800.
US Office Action dated Mar. 6, 2007 issued in U.S. Appl. No. 10/913,800.
US Final Office Action dated Apr. 30, 2008 issued in U.S. Appl. No. 11/229,042.
US Office Action dated Aug. 17, 2007 issued in U.S. Appl. No. 11/229042.
US Office Action dated Apr. 4, 2007 issued in U.S. Appl. No. 11/296,582.
US Office Action Final dated Feb. 5, 2008 issued in U.S. Appl. No. 11/296,582.
US Office Action Final dated Sep. 11, 2008 issued in U.S. Appl. No. 11/407,390.
US Office Action dated Jan. 17, 2008 issued in U.S. Appl. No. 11/407,390.
Anantharamaiah and Garber, (1996) "Chromatographic Methods for Quantitation of Apolipoprotein A-I", *Meth Enrymol* 263: 267-282.

Anantharamaiah et al., (1985) "Studies of Synthetic Peptide Analogs of the Amphipathic Helix", *The Journal of Biological Chemistry*, 260(18):10248-10255.

Anantharamaiah et al., (1990) "Use of Synthetic Peptide Analogues to Localize Lecithin: Cholsterol Acyltransferase Activating Domain in Apolipoprotein A-I", *Arteriosclerosis* 10:95-105.

Anantharamaiah et al., (1993) "An Atlas of the Amphipathic Helical Domains of Human Exchangeable Plasma Apolipoproteins", Chapter 6:109-142 in: The Amphipathic Helix (Epand, R. M., ed), CRC Press, Boca Raton, FL.

Anantharamaiah, (1986) "Synthetic Peptide Analogs of Appolipoproteins", *Methods in Enzymology*, 128:627-647.

Anderson et al., (1989) "Structure of Human Lactoferrin: Crystallographic Structure Analysis and Refinement at 2.8 Å Resolution", *J Mol Biol*, 209:711-734.

Aoyagi et al., (1988) "Synthesis of antibacterial peptides-gramicidin S analogs and designed amphiphilic oligopeptides", *Tetrahedron*; 44:877-886.

Aravinda et al., (2003) "Aromatic-Aromatic Interactions in Crystal Structures of Helical Peptide Scaffolds Containing Projecting Phenylalinine Residues", *J Am Chem Soc*, 125(18):5308-5315.

Armstrong et al., (1993) "D-Amino Acid Levels in Human Physiological Fluids", *Chirality*, 5: 375-378.

Ashby et al., (2001) "Lack of effect of serum amyloid A (SAA) on the ability of high-density lipoproteins to inhibit endothelial cell adhesion molecule expression", *Atherosclerosis*, 154:113-121.

Ashby et al., (1998) "Factors Influencing the Ability of HDL to Inhibit Expression of Vascular Cell Adhesion Molecule-1 in Endothelial Cells", *Arteriosclerosis, Thrombosis and Vascular Biology*, 18:1450-1455.

Asokan et al. (1989) "Separation and evaluation of changing pattern of glycosaminoglycans in 3-methyl cholanthrene induced fibrosarcoma", *Neoplasma* 36(3):273-9.

Asokan et al., (Apr. 21, 1993) "Purification and characterization of collagens from rat fibrosarcoma induced by 3-methylcholanthrene", *Mol Cell Biochem*, 121(2):99-107.

Badimon et al., (1990) "Regression of Atherosclerotic Lesions by High Density Lipoprotein Plasma Fraction in the Cholesterol-fed Rabbit", *J Clinical Investigation*, 85:1234-1241.

Baker et al., (1999) "Ability of reconstituted high density lipoproteins to inhibit cytokine-induced expression of vascular cell adhesion molecule-1 in human umbilical vein endothelial cells", *Journal of Lipid Research*, 40:345-353.

Baker et al., (2000) "Phospholipid composition of reconstituted high density lipoproteins influences their ability to inhibit endothelial cell adhesion molecule expression", *J Lipid Res*, 41:1261-1267.

Barter et al., (2002) "Effect of high-density lipoproteins on the expression of adhesion molecules in endothelial cells", *Current Opinion in Lipidology*, 13:285-288.

Barter et al., (1996) "High density lipoproteins and coronary heart disease", *Atherosclerosis*, 121:1-12.

Bauer et at., (1982) "SMS 201-995: A Very Potent and Selective Octapeptide Analogue of Somatostatin with Prolonged Action", *Life Sciences*, 31:1133-1140.

Baumbach et al., (2002) "Structure of Cerebral Arterioles in Cystathionine β-Synthase-Deficient Mice", *Circulation Res.*, 91:931-937.

Baumbach et al., (2003) "Cerebral Arteruikar Structure in Mice Overexpressing Human Renin and Angiotensinogen", *Hypertension*, 41: 50-55.

Bisoendial et al., (2003) Restoration of Endothelial Function by Increasing High-Density Lipoprotein in Subjects With Isolated Low High-Density Lipoprotein Circulation 107: 2944-2948.

Blankenberg et al. (2001) Circulating cell adhesion molecules and death in patients with coronary artery disease. Circulation 2001;104:1336-1342.

Boffelli et al., (1997) "Reconstitution and Further Characterization of the Cholesterol Transport Activity of the Small-Intestinal Brush Border Membrane", *Biochemistry*, 36:10784-10792.

Boffelli et al., (1997) "The uptake of cholesterol at the small-intestinal brush border membrane is inhibited by apolipoproteins", *FEBS Letters*, 411:7-11.

Borhani et al., (1997) "Crystal structure of truncated human apolipoprotein A-I suggests a lipid-bound conformation", Biochemistry, *PNAS* USA, 94:12291-12296.

Bourdillon et al., (2000) "ICAM-1 Deficiency Reduces Atherosclerotic Lesions in Double-Knockout Mice (ApoE$^{-/-}$ /ICAM-1$^{-/-}$) Fed a Fat or a Chow Diet", *Arterioscler Thromb Vasc Biol*, 20:2630-2635.

Bowry et al., (1992) "High density lipoprotein is the major carrier of lipid hydroperoxides in human blood plasma from fasting donors", *PNAS* USA, 89:10316-10320.

Brouillette and Anantharamaiah, (1995) "Structural models of human apolipoprotein A-I" *Biochim Biophys Acta*, 1256: 103-129.

Brouillette et al., (2001) Structural Models of Human Apolipoprotein A-I: A Critical Analysis and Review *Biochemica et Biophysica Acta* 55753:1-44.

Burger D, Dayer J-M, (2002) "High-density lipoprotein-associated apolipoprotein A-I: the missing link between infection and chronic inflammation?", *Autoimmunity Reviews*, 1:111-117.

Calabresi et al., (1997) "Inhibition of VCAM-1 Expression in Endothelial Cells by Reconstituted High Density Lipoproteins", *Biochem Biophys Res Commun*, 238:61-65.

Calabresi et al., (2002) "Elevated Soluble Cellular Adhesion Molecules in Subjects With Low HDL-Cholesterol", *Arterioscler Thromb Vasc Biol*, 22:656-661.

Campbell EJ, (1982) "Human leukocyte elastase, cathepesin G and lactoferrin: family of neutrophil granule glycoproteins that bind to an alveolar macrophage receptor", *PNAS USA*; 79:6941-6945.

Canadian Pharmacists Association, Starlix® General Monograph (2002) http://cpha.infinetcomm.com/content/hcp/tools/cps_cnp_updates/starlix.cfm.

Carlos et al., (1990) "Vascular cell adhesion molecule-1 mediates lymphocyte adherence to cytokine-activated cultured human endothelial cells", *Blood*, 76(5):965-970.

Carr et al., (2000) "Oxidation of LDL by myeloperoxidase and reactive nitrogen species", *Arterioscler Thromb Vasc Biol*, 20:1716-1723.

Casserly and Topol (2004) "Convergence of atherosclerosis and Alzheimer's disease: inflammation, cholestrol, and misfolded proteins", *Lancet* 363: 1139-1146.

Castelli et al., (1986) "Incidence of coronary heart disease and lipoprotein cholesterol levels. The Framingham Study", JAMA, 256(20):2835-2838.

Chiesa et al., (2002) "Recombinant Apolipoprotein A-I $_{Milano}$ Infusion Into Rabbit Carotid Artery Rapidly Removes Lipid from Fatty Streaks", *Circ Res*, 90:974-980.

Chillon and Baumbach (2004) "Effects of an Angiotensin-Converting Enzyme Inhibitor and a b-Blocker on Cerebral Arterioles in Rats", *Hypertension* 33: 856-861.

Christison et al., (1996) "Rapid reduction and removal of HDL—but not LDL-associated cholesteryl ester hydroperoxides by rat liver perfused in situ", *Biochem J*, 314:739-742.

Chung et at. (1985) "Studies of Synthetic Peptide Analogs of the Amphipathic Helix" *J Biol Chem*, 260(18):10256-10262.

Clay et al., (2001) "Time sequence of the inhibition of endothelial adhesion molecule expression by reconstituted high density lipoproteins", *Atherosclerosis*, 157:23-29.

Cockerill et al., (2001) "Elevation of Plasma High-Density Lipoprotein Concentration Reduces Interleukin-l-Induced Expression of E-Selectin in an in Vivo Model of Acute Inflammation", *Circulation*, 103:108-112.

Cockerill et al., (1995) "High-Density Lipoproteins Inhibit Cytokine-Induced Expression of Endothelial Cell Adhesion Molecules", *Arterioscler Thromb Vasc Biol*, 15:1987-1994.

Cockerill et al., (1999) "High-Density Lipoproteins Differentially Modulate Cytokine—Induced Expression of E-Selectin and Cyclooxygenase-2", *Arterioscler Thromb Vasc Biol*, 19:910-917.

Coyne et al. (2002) "Methods for isolation and characterization of intracerebral arterioles in the C57/BL6 wild-type mouse", *J. Neurosci. Meth.*, 120: 145-153.

Cybulsky et al., (2001) "A major role for VCAM-1, but not ICAM-1, in early atherosclerosis", *Journal of Clinical Investigation*, 107(10):1255-1262.

Cyrus et al., (2001) "Absence of 12/15-Lipoxygenase Expression Decreases Lipid Peroxidation and Atherogenesis in Apolipoprotein E-Deficient Mice", *Circulation*, 103:2277-2282.

Dansky et al., (2001) "Adhesion of Monocytes to Arterial Endothelium and Initiation of Atherosclerosis are Critically Dependent on Vascular Cell Adhesion Molecule-1 Gene Dosage", *Arterioscler Thromb Vasc Biol*, 21:1662-1667.

Dansky et al., (1999) "Apo A-I inhibits foam cell formation in Apo E-deficient mice after monocyte adherence to endothelium", *J Clin Invest*, 104:31-39.

Datta et al., (2001) "Effects of increasing hydrophobicity on the physical-chemical and biological properties of a class A amphipathic helical peptide", *J Lipid Research*, 42:1096-1104.

Davenport et al., (2003) "The Role of Interleukin-4 and Interleukin-12 in the Progression of Atherosclerosis in Apolipoprotein E-Deficient Mice", *Am J Pathol*, 163(3):1117-1125.

Davidson et at. (1994) "The Influence of Apolipoprotein Structure on the Efflux of Celluar Free Cholesterol to High Density Lipoprotein", *J Biol Chem*, 269(37):22975-22982.

Davies et al., (1993) "The expression of the adhesion molecules ICAM-1, VCAM-1, PECAM, and E-selectin in human atherosclerosis", *J Pathol*, 171(3):223-229.

De Caterina et al., (1998) "Structural requirements for inhibition of cytokine-induced endothelial activation by unsaturated fatty acids", *J Lipid Res*, 39:1062-1070.

de la Torre and Mussivand (1993) "Can disturbed brain microcirculation cause Alzheimer's disease?", *Neurol. Res.*,15(3): 146-153.

Diederich et al., (2001) "Apolipoprotein A1 and HDL3 Inhibit Spreading of Primary Human Monocytes through a Mechanism that Involves Cholesterol Depletion and Regulation C160 of CD42", *Atherosclerosis*, 159:313-324.

Dimayuga et al., (1999) "Reconstituted HDL Containing Human Apolipoprotein A-1 Reduces VCAM-1 Expression and Neointima Formation Following Periadventitial Cuff-Induced Carotid Injury in apoE Null Mice", *Biochem Biophys Res Commun*, 264(2):465-468.

Dooley et al., (1994) "An All D-Amino Acid Opioid Peptide with Central Analgesic Activity from a Combinatorial Library", *Science*, 266:2019-2022.

Drouet Let al., (1990) "The antithrombotic effect of KRDS, a lactotransferrin peptide, compared RGDS", *Nouv. Rev. fr. Hematol*, 32:59-62.

Dunlop and Neidle and Neidle, (1997) "The Origin and Turnover of D-Serine in Brain," *Biochemical and Biophysical Research Communication*, 235:26-30.

Ehara et al., (2001) "Elevated Levels of Oxidized Low Density Lipoprotein Show a Positive Relationship With the Severity of Acute Coronary Syndromes", *Circulation*, 103:1955-1960.

Epand et al., (1987) "Sudies of Synthetic Peptide Analogs of the Amphipathic Helix", *Journal of Biological Chemistry*, 262(19):9389-9396.

Epand RM, Stafford A, Leon B, Lock PE, Tytler EM, Segrest JP, Anantharamaiah GM, (1994) "HDL and apolipoprotein A-I protect erythrocytes against the generation of procoagulant activity", *Arterioscler Thromb*, 14(11):1775-1783.

Field et al., (2001) "Gene expression of sterol regulatory element-binding proteins in hamster small intestine", *Journal of Lipid Research*, 42:1-9.

Fielding and Fielding (1995) "Molecular physiology of reverse cholesterol transport", *Journal of Lipid Res*, 36: 211-228.

Fielding et al., (1972) "A Protein Cofactor of Lecithin: Cholesterol Acyltransferase", *Biochemical and Biophysical Research Comm*, 46(4):1493-1498.

Flaherty et al., (Feb. 1999) "Acute pancreatitis as a complication of polyarteritis Nodosa", *Intnl Jnl of Panc.*, 25(1):53-57.

Fleisher LN, Tall AR, Witte LD, Miller RW, Cannon PJ, (1982) "Stimulation of Arterial Endothelial Cell Prostacyclin Synthesis by High Density Lipoproteins", *Journal of Biol Chem*, 257:6653-6655.

Fogelman AM, (2004) "When good cholesterol goes bad", *Nat Med*, 10(9):902-903.

Fogelman AM, Shechter I, Seager J, Hokom M, Child JS, Edwards PA, (1980) "Malondialdehyde alteration of low density lipoproteins leads to cholesteryl ester accumulation in human monocyte-macrophages", *PNAS USA*, 77(4):2214-2218.

Forte TM, Subbanagounder G, Berliner JA, Blanche PJ, Clermont AO, Jia Z, Oda MN, Krauss RM, Bielicki JK, (2002) "Altered activities of anti-atherogenic enzymes LCAT, paraoxonase, and platelet-activating factor acetylhydrolase in atherosclerosis-susceptible mice", *J Lipid Res*, 43:477-485.

Fricker et al., (1995) "Enteral Absorption of Octreotide: Modulation of Intestinal Permeabiltyby Distinct Carbohydrates", *The Journal of Pharmacology andExperimental Therapeutics*, 274(2): 826-832.

Fuessl et al., (1987) "Oral absrorption of the somatostatin analogue SMS 201-995: theoretical and practial implications", *Clinical Science*, 72:255-257.

Fukuda, et al., (1990) "Bilayer forming ion-pair amphi-philes from single chain surfactants"; *J Am Chem Soc.*, 112:1635-1637.

Gabay C, Kushner I, (1999) "Acute-Phase Proteins and Other Systemic Responses to Inflammation", *N Engl J. Med*, 340(6):448-454.

Garber et al., (1992) "Turnover of Synthetic Class A Amphipathic Peptide Analogues of Exchangeable Apolipoproteins in Rats, Correlation with Physical Properties", *Arteriosclerosis and Thrombosis*, 12(8):886-894.

Garber et al., (1997) "Anti -Atherogenic Properties of a Model Amphipathic Helical Peptide: Studies in Transgenic Mice", *Circulation*, 96(8):1-490.

Garber et al., (1999) "Protection against Atherosclerosis in Mice by a Synthetic Class A Amphipathic Peptide Analog of Apolipoprotein A-I", *Circulation*, 100(18):2838.

Garber et al., (2001) "A new synthetic class A amphipathic peptide analogue protects mice from diet-induced atherosclerosis", *Journal of Lipid Research*, 42:545-552.

Garner et al., (1998) "Oxidation of High Density Lipoproteins. II. Evidence for Direct Reduction of Lipid Hydroperoxides by Methionine Residues of Apolipoproteins AI and AII", *J Biol Chem*, 273(11):6088-6095.

Garner et al., (1998) "Oxidation of high density lipoproteins. I. Formation of methionine sulfoxide in apolipoproteins at and an is an early event that accompanies lipid peroxidation and can be enhanced by α-tocopherol", *J Biol Chem*, 273(11):6080-6087.

Gaut et al., (2002) "Myeloperoxidase produces nitrating oxidants in vivo", *J Clin Invest* 109(10):1311-1319.

George et al., (2001) "12/15-Lipoxygenase Gene Disruption Attenuates Atherogenesis in LDL Receptor-Deficient Mice", *Circulation*, 104:1646-1650.

Ghersi-Egea et al., (1996) "Fate of Cerebrospinal Bluid-Borne Amyloid B-Peptide: Rapid Clearance into Blood and Appreciable Accumulation by Cerebral Arteries", *J. Neurochem*, 67: 880-883.

Glomset, (1968) "The Plasma lecithin: cholesterol acytransferase reaction", *J Lipid Res*9:155-167.

Gong et al., (1994) "Structural and functional properties of human and mouse apolipoprotein A-I", *Biochim Biophys Acta*, 1213:335-342.

Gordon et al., (1977) "High density lipoprotein as a protective factor against coronary heart disease. The Framingham Study", *Am J Med*, 62(5):707-714.

Gorski, A et al., (Feb.-Mar. 2001) "Cyclolinopeptide: a novel immunosuppressive agent with potential anti-lipemic activity", *Transplant Proceedings*, 33(1-2):553.

Gurfinkel et al., (2002) "Influenza Vaccine Pilot Study in Acute Coronary Syndromes and Planned Percutaneous Coronary Interventions. The Flu Vaccination Acute Coronary Syndromes (FLUVACS) Study", *Circulation*, 105:2143-2147.

Hamase et al. (2001) "Determination of Free D-Proline and D-Leucine in the Brains of Mutant Mice Lacking D-Amino Acid Oxidase Activity", Analytical Biochemistry298:253-258.

Harats et al., (2000) "Overexpression of 15-Lipoxygenase in Vascular Endothelium Accelerates Early Atherosclerosis in LDL Receptor-Deficient Mice", *Arterioscler Thromb Vasc Biol*, 20:2100-2105.

Hardy et al., (2001) "An Automated High-Performance Liquid Chromatography Procedure for the Quantitation of L- and D-Amino Acids by Means of Stepwise Precolumn Derivatization", *Analytical Biochemistry*, 291:297-299.

Harkin et al. (1997) The Effects of hyper-and hypocarbia on intraparenchymal arterioles in rat brian slices, *Neuroreport*, 8:1841-1844.

Hashimoto et al., (2000) "Improvement of intestinal absorption of peptides: absorption of B 1-Phe monoglucosylated insulin to rat intestinal brush-border membrane vesicles", *European Journal of Pharmaceutics & Biopharmaceutics*, 50:197-204.

Hauser et al., (1998) "Identification of a Receptor Mediating Absorption of Dietary Cholesterol in the Intestine", *Biochemistry*, 37(51):17843-17850.

Hayry et al., (1995) "Stabile D-peptide analog of insulin-like growth factor-1 inhibits smooth muscle cell proliferation after carotid ballooning injury in the rat", *FASEB J*, 9(13):1336-1344.

Hemachander et al., (Mar. 1, 2000) "Lipase from Ralstonia pickettii as an additive in laundry detergent formulations", *Process Biochem.* 35(8):809-814.

Henricksen et al., (1981) "Enhanced macrophage degradation of low density lipoprotein previously incubated with cultured endothelial cells: Recognition by receptor for acetylated low density lipoproteins", *PNAS* USA, 78(10):6499-6503.

Hessler et al., (1979) "LDL-induced cytotoxicity and its inhibition by HDL in human vascular smooth muscle and endothelial cells in culture", *Atherosclerosis*, 32(3):213-229.

Hoffman et al. (1997) "Isoprostanes: Free Radical-Generated Prostaglandins with constrictor Effects on cerebral Arterioles", *Stroke*, 28:844-849.

Hwang et al., (1997) "Circulating Adhesion Molecules VCAM-1, ICAM-1, and E-selectin in Carotid Atherosclerosis and Incident Coronary Heart Disease Cases. The Atherosclerosis Risk in Communities (ARIC) Study", *Circulation*, 96:4219-4225.

Hyka et al., (2001) "Apolipoprotein A-I Inhibits the Production of Interleukin-1β and Tumor Necrosis Factor-α by Blocking Contact-Mediated Activation of Monocytes by T Lymphocytes", *Blood*, 97(8):2381-2389.

Israelachvili et al. (1980) Physical principles of membrane organization. *Q Rev Biophys*, 13:121-200.

Jamaluddin, et al. (1987) "Aggregatory reactions of blood platelets in ustirred dilute suspensions and their monitoring by spectrophotometry", *Curr Sci*, 56:254-256.

Jamieson et al., (2001) "Detection of Lipoprotein(a) in Intraparenchymal Cerebral Vessels: Correlation with Vascular Pathology and Clinical History", *Exp. Mol. Pathol.*, 71: 99-105.

Jin et al., (2003) "Inhibition of endothelial lipase causes increased HDL cholesterol levels in vivo", *J Clin Invest*, 111(3):357-362.

Johnson et al., (1991) "Cholesterol transport between cells and high-density lipoproteins", *Biochem Biophys Acta*, 1085:273-298.

Jonas, (1991) "Lecithin-cholesterol acyltransferase in the metabolism of high-density lipoproteins", *Biochim Biophys Acta*, 1084:205-220.

Jonas, (2000) "Lecithin cholesterol acyltransferase", *Biochem Biophys Acta*, 1529:245-256.

Jones et al., (1992) "Computer Programs to Identify and Classify Amphipathic α Helical Domains", *Journal of Lipid Research*, 33:287-296.

Kaler et al., (1989) "Spontaneous vesicle formation in aqueous mixtures of single-tailed surfactants", *Science*, 245:1371-1374.

Karle et al., (2003) "Crystal structure of hydrophobic 19-residue peptide helix containing three centrally located D amino acids", *PNAS*, 100(24):13946-13951.

Karle et al., (2004) "A combined extended and helical backbone for Boc-(Ala-Leu-Ac7c-)2-OMe", *J Peptide Res*, 63:175-180.

Kigasawa et al., (1995) "Inhibition of corneal ulceration by tetrapeptidyl hydroxamic acid", *Japanese Journal Ophthamology*, 39(1):35-42.

Kluczyk A, Siemion IZ, Szewczuk Z, Wieczorek Z, (2002) "The immunosuppressive activity of peptide fragments of viccinia virus C1OL protein and a hypothesis on the role of this protein in the viral invasion", *Peptides*, 23:823-834.

Ko et al., (1993) "High-density lipoprotein reduces epidermal growth factor-induced DNA synthesis in vascular smooth muscle cells", *Atherosclerosis*, 99(2):253-259.

Kontos and Wei, (1998) "Cerebral arteriolar dilations by $K_{ATP}$ channel activators need L-lysine or L-arginine" *Am. J. Physiol.* 274 (*Heart Circ. Physiol.* 43): H974-H981.

Kreiger, (1999) "Charting the Fate of the "Good Cholesterol": Identifcation and Characterization of the High-Density Lipoprotein Receptor SR-BI", *Annu Rev Biochem*, 68:523-558.

Kullman et al., (1999) "Evaluation of the Enantiomeric Composition of Amino Acids in Tobacco", *Chirality* 11:669-673.

Kumar et al., (Jan. 2002) "A novel peptide derivative exhibits anti inflammatory and antioxidant activity in adjuvant induced arthritis in rats", *Mol Cell Biochem*, 229(1-2):9-17.

Kume et al., (1992) "Lysophosphatidylcholine, a Component of Atherogenic Lipoproteins, Induces Mononuclear Leukocyte Adhesion Molecules in Cultured Human and Rabbit Arterial Endothelial Cells", *Journal of Clinical Investigation*, 90:1138-1144.

Lancet, (Sep. 25, 1999) "New options developed for needle-free drug delivery", (Statistical Data Included) Author/s: Kathryn Senior.

Langer et al., (1992) "Somatic cell mapping of the bovine interferon-alpha receptor", *Mamm Genome*, 3(4):237-40.

Latimer et al., (1977) "Application of light scattering theory to the opticaleffects associated with the morphology of blood platelets", *Arch Biochem Biophys*, 180:151-159.

Lawrence et al., (1991) "Leukocytes roll on a selectin at physiologic flow rates: distinction from and prerequisite for adhesion through integrins", *Cell*, 65(5):859-873.

Lee et al., (2001) "Vitamin C-Induced Decomposition of Lipid Hydroperoxides to Endogenous Genotoxins", *Science*, 292:2083-2086.

Legrand et al., (1992) "Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin", *Biochemistry*, 31:9243-9251.

Levi et al., (2000) "A Retro-Inverso Minantibody with Anti-HIV Activity", *Aids Res & Human Retroviruses*, 16(1):59-65.

Levine et al., (1993) "In vivo protection against endotoxin by plasma high density lipoprotein", *PNAS* USA, 90:12040-12044.

Li et al., (1993) "An atherogenic diet rapidly induces VCAM-1, a cytokine-regulatable mononuclear leukocyte adhesion molecule, in rabbit aortic endothelium", *Arterioscler Thrombosis*, 13(2):197-204.

Libby et al., (2002) "Inflammation and Atherosclerosis", *Circulation*, 105:1135-1143.

Lumsden et al., (1997) "Anti-VLA-4 antibody reduces intimal hyperplasia in the endarterectomized carotid artery in nonhuman primates", *J Vasc Surg*, 26(1):87-93.

Lundin et al., (1986) "Absorption of Intragastrically Administered DDAVP in Conscious Dogs", *Life Sciences*, 38(8):703-709.

Mach et al., (1998) "Reduction of atherosclerosis in mice by inhibition of CD40 signalling", *Nature*, 394:200-203.

Man et al., (1987) "D-Aspartate in Human Brain", *J of Neurochem*, 48(2):510-515.

Manikandan et al. (2002) "Antioxidant potential of a novel tetrapeptide deri-vative in isoproterenol-induced myocardial", *Pharmacology*, 65:105-109.

Mathison et al., (2003) "Modulation of neutrophil function by the tripeptide feG", *BMC Immunology*, 4:1471-2172.

Mathison et al., (2003) "Identification of a binding site for the anti inflammatory tripeptide feG", *Peptides*, 24:1221-1230.

Mathison et al., (1998) "Attenuation of Intestinal and Cardiovascular Anaphylaxis by the Salivary Gland Tripeptide FEG and Its D-isometric Analog feG", *Peptides*, 19(6)1037-1042.

Mathison et al., (2001) "The tripeptide feG reduces endotoxin provoked perturbation of intestinal motility and inflammation", *Neurogastrointerol*, 13:599-603.

Mathison et al., (2001) "Regulation of leukocyte adhesion to heart by the tripeptides feG and feG(NH$_2$) Can", *J Physiol Pharm*, 79:785-792.

Mato et al., (Apr. 1996) "Involvement of specific macrophage-lineage cells surrounding arterioles in barrier and scavenger function in brain cortex", *PNAS* USA, 93:3269-3274.

Mazoyer et al., (1990) "KRDS, a new peptide derived from human lactotransferrin, inhibits platelet aggregation and release reaction", *Eur J Biochem* 194:43-49.

Meera et al. (Sep. 1999) "Inhibition of neutrophil derived lysosomal enzymes and reactive oxygen species by a novel tetrapeptide", *Inflamm Res*, 48(9):479-84.

Mehrabian et al., (2002) "Identification of 5-Lipoxygenase as a Major Gene Contributing to Atherosclerosis Susceptibility in Mice", *Circ Res*, 91:120-126.

Merrifield et al., (1995) "Retro and Retroenantio Analogs of Cecropin-Melittin Hybrids", *PNAS* USA, 92:3449-3453.

Metwally et al., (2002) "Probing for submandibular gland peptide-T receptors on leukocytes with biotinylated-Lys-[Gly]6-SGP-T", *Biochimica et Biophysica Acta*, 1593:37-44.

Metwally et al., (1999) "Tyrosine is detrimental to the biological activity of submandibular gland peptide-T (SGP-T)", *Proc West Pharmacol Soc*, 42: 65-66.

Metwally et al., (2003) "A Tree-Based Algorithm for Determining the Effects of Solvation on the Structure of Salivary Gland Tripeptide $NH_3+$-D-PHE-D-GLU-GLY-COO-", *Biophysical Journal*, 85(3):1503-1511.

Metwally et al., (2002) "Submandibular gland tripeptide FEG (Phe-Glu-Gly) and analogues: keys to structure determination", *Peptides*, 23:193-199.

Mishra et al., (1994) "Interaction of Synthetic Peptide Analogs of the Class A", *J Biol Chem*, 269(10):7185-7191.

Mishra et al., (1995) "Effect of the Arrangement of Tandem Repeating Units of Class A Amphipathic alpha-Helixes on Lipid Interaction", *J Biol Chem*, 270(4):1602-1611.

Mishra et al., (1998) "Studies of Synthetic Peptides of Human Apolipoprotein A-I Tandem Amphipathic alpha-Helixes", *Biochemistry*, 37:10313-10324.

Mor et al. (1992) "Enter a new post-translational modification: D-amino acids in gene-encoded peptides", *TIBS*, 17:481-485.

Morikawa et al., (2007) "Effects of Dipeptides Having a C-Terminal Lysine on the Cholesterol 7α-Hydroxylase mRNA Level in HepG2 Cells", *Biosci Biotechnol Biochem*, 71(3):821-825.

Moro and Rodriguez (1991) "Application of phase separation and mass action models to low aggregation number micelles", *Langmuir*, 7:2017-2020.

Mulder et al. (2004) Low-density lipoprotein receptor-knockout mice display impaired spatial memory associated with a decreased synaptic density in the hippocampus, *Neurobiology of Disease* 16: 212-219.

Murakami et al., (1985) "Aggregation Behavior of Amphiphiles Functionalized with Dipeptide Segments and Enantioselective Ester Hydrolysis in Their Bilayer Membranes", *Bulletin of the Chemical Society of Japan*, 58(1):172-180.

Murugesan G, Sa G, Fox PL, (1994) "High-density lipoprotein stimulates endothelial cell movement by a mechanism distinct from basic fibroblast growth factor", *Circ Res*, 74(6):1149-1156.

Nag (1996) "Immunohistochemical Localization of Extracellular Matrix Proteins in Cerebral Vessels in Chronic Hypertension", *J. Neuropath. Exp. Neurol.*, 55(3):381-388.

Nag et al. (1997) "Cerebrovascular Changes in Chronic Hypertension, Protective Effects of Enalapril in Rats", *Stroke*, 28:1028-1034.

Nagata et al. (1995) "Free D-Serine Concentration in Normal and Alzheimer Human Brain", *Brain Res. Bull.*, 38(2):181-183.

Nagata et al. (2002) "Hemodynamic Aspects of Alzheimer's Disease", *Ann. N.Y. Acad. Sci.*, 977: 391-402.

Nagata et al., (1994) "Distribution of free D-serine in vertebrate brains", *Brain Res*, 634: 291-295.

Nakamura et al., (1997) "Deposition of amyloid β protein (Aβ) subtypes [Aβ40 and Aβ42(43)] in canine senile plaques and cerebral amyoloid angiopathy", *Acta Neuropathol.* 94:323-328.

Nanjee et al., (2001) "Intravenous apoA-I/lecithin discs increase pre-β-HDL concentration in tissue fluid and stimulate reverse cholesterol transport in humans", *J Lipid Res*, 42:1586-1593.

Nanjee et al., (1999) "Acute Effects of Intravenous Infusion of ApoA1/Phosphatidylcholine Discs on Plasma Lipoproteins in Humans", *Arterioscler Thromb Vasc Biol*, 19:979-989.

Navab et al. (Aug. 22, 2005) "Oral Small Peptides Render HDL Antiinflammatory in Mice, and Monkeys and Reduce Atherosclerosis in ApoE Null Mice", *Circ. Res.*(http://circres.ahajournals.org) 97:524-532.

Navab et al., (2000) "Normal high-density lipoprotein inhibits three steps in the formation of midly oxidized low density lipoprotein: step 1", *J Lipid Res*, 41:1481-1494.

Navab et al., (2000) "Normal high-density lipoprotein inhibits three steps in the formation of mildly oxidized low density lipoprotein: steps 2 and 3", *J Lipid Res*, 41:1495-1508.

Navab et al., (2002) "Oral Administration of an Apo A-I Mimetic Peptide Synthesized from D-Amino Acids Dramatically Reduces Atherosclerosis in Mice Independent of Plasma Cholesterol", *Circulation*, 105:290-292.

Navab et al., (2006) "Potential clinical utility of high-density lipoprotein-mimetic peptides", *Current Opinion in Lipidology*, 17:440-444.

Navab et al. (Jul. 2005) "Apolipoprotein A-I Mimetic Peptides", *Arterioscler Thromb Vasc Bio*, 25:1325-1331.

Navab et al., (2004) "Oral D-4F Causes Formation of Pre-β High-Density Lipoprotein and Improves High-Density Lipoprotein-Mediated Cholesterol Efflux and Reverse Cholesterol Transport From Macrophages in Apolioprotein E-Null Mice", *Circulation*, 109:r120-r125.

Navab et al., (2004) "The oxidation hypothesis of therogenesis: the role of oxidized phospholipids and HDL", *Journal Lipid Res*, 45:993-1007.

Navab et al. (2001) "HDL and the Inflammatory Response Induced by LDL-Derived Oxidized Phospholipids", *Arterioscler Thromb Vasc Biol*, 21:481-488.

Navab et al., (2003) "Oral Synthetic Phospholipids (DMPC) Raises High-Density Lipoprotein Cholesterol Levels, Improves High-Density Lipoprotein Function, and Markedly Reduces Atherosclerosis in Apolipoprotein E-Null Mice", *Circulation*, 108:1735-1739.

Navab et al., (2001) "A cell-free assay for detecting HDL that is dysfunctional in preventing the formation of or inactivating oxidized phospholipids", *Journal Lipid Res*, 42:1308-1317.

Navab et al., (1997) "Mildly Oxidized LDL Induces an Increased Apolipoprotein J/Paraoxonase Ratio", *J Clin Invest*, 99(8):2005-2019.

Navab et al., (1991) "Monocyte Transmigration Induced by Modification of Low Density Lipoprotein in Cocultures of Human Aortic Wall Cells is due to Induction of Monocyte Chemotactic Protein 1 Synthesis and is Abolished by High Density Lipoprotein", *Journal of Clinical Investigation*, 88:2039-2046.

Nievelstein et al., (1991) "Lipid accumulation in rabbit aortic intima two hours after bolus infusion of low density lipoprotein: A deep-etch and immuno-localization study of ultra-rapidly frozen tissue", *Arteriosclerosis and Thrombosis*, 11(6):1795-1805.

Nirmala and Puvanakrishnan, (Jan. 12, 1996) "Effect of curcumin on certain lysosomal hydrolases in isoproterenol-induced myocardial infarction in rats", *Biochem Pharmacol.*, 51(1):47-51.

Nirmala and Puvanakrishnan (Jun. 21, 1996) "Protective role of curcumin against isoproterenol induced myocardial infarction in rats", *Mol Cell Biochem.*, 159(2):85-93.

Nirmala and Puvanakrishnan (Aug. 1998) Collagen profile in isoproterenol induced myocardial necrosis in rats. *Indian J Exp Biol.*, 36(8):763-767.

Nirmala et al. (Jul. 1999) "Curcumin treatment modulates collagen metabolism in isoproterenol induced myocardial necrosis in rats", *Mol Cell Bioche*, (1-2):31-37.

Nomoto et al., (1998) "Improvement of Intestinal Absorbtion of Peptide Drugs by Gyycosylation: Transport of Tetrapeptide by the Sodium Ion-Dependent D-Glucose Transporter", *J Pharmaceutics Science*, 87(3):326-332.

O'Brien et al., (1996) "Neovascular Expression of E-Selectin, Intercellular Adhesion Molecule-1, and Vascular Cell Adhesion Molecule-1 in Human Atherosclerosis and their Relation to Intimal Leukocyte Content", *Circulation*, 93:672-82.

O'Connell BJ, Genest J Jr., (2001) "High-Density Lipoproteins and Endothelial Function", *Circulation*, 104:1978-1983.

Oguchi et al., (2000) "Monoclonal Antibody Against Vascular Cell Adhesion Molecule-1 Inhibits Neointimal Formation After Periadventitial Carotid Artery Injury in Genetically Hypercholesterolemic Mice", *Arterioscler Thromb Vasc Biol*, 20:1729-1736.

Ohkuma et al. (1997) "Morphological Changes of Intraparenchymal Arterioles After Experimental Subaracvhnoid Hemorrhage in Dogs", *Neurosurgery*, 41(1): 230-236.

Ohtani et al., (1995) "Age-related changes in D-aspartic acid of rat teeth", *Growth Develop & Aging*, 59:55-61.

Opeskin (1996) "Cerebral Amyloid Angiopathy", *Am. J. Forensic Med. & Pathol.*, 17(3): 248-254.

Oram and Yokoyama, (1996) "Apolipoprotein-mediated removal of cellular cholesterol and phospholipids", *J Lipid Res*, 37: 2473-2491.

Ou et al. (2005) "Effects of D-4F on Vasodilation and Vessel Wall Thickness in Hyperholesterolemic LDL Receptor—Null and LDL Receptor/Apolipoprotein A-I Double-Knockout Mice on Western Diet", *Circ. Res.* 97:1190-1197.

Ou et al., (2003) "AP-4F, antennapedia peptide linked to an amphipathic α helical peptide, increases the efficiency of Lipofectamine-mediated gene transfection in endothelial cells", *Biochem Biophys Res Commun*, 305:605-610.

Ou J, Ou Z, Jones DW, et al., (2003) "L-4F, an Apolipoprotein A-I Mimetic, Dramatically Improves Vasodilation in Hypercholesterolemic and Sickle Cell Disease", *Circulation*, 107:2337-2341.

Ou et al., (2003) "L-4F, an Apolipoprotein A-I Mimetic, Restores Nitric Oxide and Superoxide Anion Balance in Low-Density Lipoprotein-Treated Endothelial Cells", *Circulation*, 107:1520-1524.

Owens et al., (1990) "Apolipoprotein A-I and its Amphipathic Helix Peptide Analogues Inhibit Human Immunodeficiency Virus-induced Syncytium Formation", *J Clin Invest*, 86:1142-1150.

Paigen et at., (1990) "Atherosclerosis Susceptibility Differences among Progenitors of Recombinant Inbred Strains of Mice", *Arteriosclerosis*, 10:316-323.

Palgunachari et al., (1996) "Only the Two End Helixes of Eight Tandem Amphipathic Helical Domains of Human Apo A-I Have Significant Lipid Affinity. Implications for HDL Assembly", *Arteriosclerosis, Thrombosis, & Vascular Biology*, 16:328-338.

Panizzutti et al., (2001) "A new strategy to decrease N-methyl-D-aspartate (NMDA) receptor coactivation: Inhibition of D-serine synthesis by converting serine racemase into an eliminase", *PNAS* 98(9):5294-5299.

Papo et al., (2002) "The Consequence of Sequence Alteration of an Amphipathic α-Helical Antimicrobial Peptide and its Diastereomers", *J Biol Chem*, 277(37): 33913-33921.

Pappenheimer et al., (1994) "Intestinal absorption and excretion of octapeptides composed of D amino acids", *PNAS USA* 91:1942-1945.

Pappenheimer et al., (1997) "Absorption and Excretion of Undegradable Peptides: Roles of Lipid Solubility and Net Charge", *J Pharmacology & Experimental Therapeutics*, 280(1):292-300.

Parthasarathy et al., (1994) "Mechanisms of oxidation antioxidants, and atherosclerosis", *Curr Opin Lipidol*, 5(5):371-375.

Pasceri et al., (2001) "Modulation of C-Reactive Protein-Mediated Monocyte Chemoattractant Protein-1 Induction in Human Endothelial cells by Anti-Atherosclerosis Drugs", *Circulation*, 103:2531-2534.

Pasceri V, Willerson JT, Yeh ET, (2000) "Direct Proinflammatory Effect of C-Reactive Protein on Human Endothelial Cells", *Circulation*, 102:2165-2168.

Paterno et al. (2004) "Reconstituted High-Density Lipoprotein Exhibits Neuroprotection in Two Rat Models of Stroke", *Cerebrovasc Dis*. 17(2-3):204-211, Epub Dec 29, 2003.

Patszty et al., (1994) "Apolipoprotein AI Transgene Corrects Apolipoprotein E Deficiency-induced Atherosclerosis in Mice", *J Clinical Investigation*, 94:899-903.

Peng et al., (2001) "Effects of L-glutamate, D-aspartate, and monensin on glycolytic and oxidative glucose metabolism in mouse astrocyte cultures: further evidence that glutamate uptake is metabolically driven by oxidative metabolism", *Neurochemistry International*, 38:437-443.

Pharmalicensing (Jan. 27, 2001) Esperion Builds a Novel Peptides Program (2 pages).

Pharmalicensing (Jan. 28, 2001) Multiple Peptide Systems Forms Joint Venture With Elan, 2 pages.

Pharmalicensing (Jan. 28, 2001) Unigene to Receive Patent for Delivery of Peptide Pharmaceuticals (2 pages).

Philips et al., (1993) "Plasma Lipoproteins and Progression of Coronary Artery Disease Evaluated by Angiography and Clinical Events", *Circulation*, 88: 2762-2770.

Pilone, (2000) "D-amino acid oxidase: new findings", *CMLS, Cell Mol Life Sci*, 57:1732 1747.

Plump et al., (1994) "Human apolipoprotein A-I gene expression increases high density lipoprotein and suppresses atherosclerosis in the apolipoprotein E-deficient mouse", *PNAS USA*, 91:9607-9611.

Purdue News (Oct. 2000) 'Microspheres' Offer Promise for Oral Drug Delivery (3 pages).

Purdue News (Sep. 12, 1997) New Oral Insulin Delivery System Shows Promise (3 pages).

Puvanakrishnan and Bose, (Oct. 1984) "Immobilization of pepsin on sand: preparation, characterization and application", *Indian J Biochem Biophys*, 21(5):323-6.

Puvanakrishnan and Langer (Jun. 1990) "Detection and analysis of interferon-alpha receptors on plasma membranes and in detergent extracts", *J Interferon Res.*, 10(3):299-307.

Qian et al. (1995) "Isolation and characterization of sheep lactoferrin, an inhibitor of platelet aggregation and comparison with human lactoferrin", *Biochim Biophys Acta*, 1243:25-32.

Raha et al., (1988) "KRDS a Tetrapeptide Derived From Lactotransferrin Inhibits Binding of Monoclonal Antibody Against Glycoprotein IIb-IIIa on ADP-Stimulated Platelets and Megakaryocytes", *Blood* 72:172-178.

Rajashree and Puvanakrishnan (Jan. 1996) "Alterations in certain lysosomal glycohydrolases and cathepsins in rats on dexamethasone administration", *Mol Cell Biochem*, 154(2):165-70.

Rajashree and Puvanakrishnan, (Apr. 1998) "Dexamethasone induced alterations in enzymatic and nonenzymatic antioxidant status in heart and kidney of rats", *Mol Cell Biochem*, 181(1-2):77-85.

Rajashree and Puvanakrishnan (Jul. 1999) "Dexamethasone induced alterations in the levels of proteases involved in blood pressure homeostasis and blood coagulation in rats", *Mol Cell Biochem*, 197(1-2):203-8.

Rajashree and Puvanakrishnan (Nov. 2000) "Alterations in collagen metabolism in heart and kidney on dexamethasone administration in rats", *Indian J Exp Biol*, 38(11):1117-23.

Ramesh et al. (Apr. 1995) "In vitro studies on a novel micelle-forming peptide with anticoagulant activity", *Int J Pept Protein Res.*,45(4):386-90.

Ramesh et al., (1998) "A novel surface-active peptide derivative exhibits in vitro inhibition of platelet aggregation", *Peptides*,19:1695-1702.

Ramesh et al. (Oct. 1998) "Effect of a novel tetrapeptide derivative in a model of isoproterenol induced myocardial necrosis", *Mol Cell Biochem*, 187(1-2):173-82.

Ranganathan et al., (2000) "Channel forming, self-assembling, bishelical amphiphilic peptides: design, synthesis and crystal structure of Py(Aib$_n$)$_2$, n=2, 3, 4", *J Peptide Res*, 56:416-426.

Ravichandran and Puvanakrishnan (Jun. 1991) "In vivo labeling studies on the biosynthesis and degradation of collagen in experimental myocardial infarction", *Biochem Int*, 24(3):405-14.

Ravichandran and Puvanakrishnan, (Oct. 1993) "Collagen levels in isoproterenol induced myocardial infarction in rats", *Indian J Exp Bio*, 31(10):825-30.

Ravichandran et al. (Oct. 1990) "Alterations in the heart lysosomal stability in isoproterenol induced myocardial infarction in rats", *Biochem Int*, 22(2):387-96.

Ravichandran et al. (Feb. 1991) "Influence of Isoproterenol-Induced Myocardial Infarction on Certain Glycohydrolases and Cathepsins in Rats", *Biochem Med Metab Biol*, 45(1):6-15.

Reape et al., (1999) "Chemokines and atherosclerosis", *Atherosclerosis*, 147:213-225.

Reddy et al., (2004) "Potential Role for Mitogen-Activated Protein Kinase Phosphatase-1 in the Development of Atherosclerotic Lesions in Mouse Models", *Arterioscler Thromb Vasc Biol*, 24:1676-1681.

Reddy et al., (2001) "Human Paraoxonase-3 is an HDL Associated Enzyme with Biological Activity Similar to Paraoxonase-1 Protein but is not Regulated by Oxidized Lipids", *Arterioscler Thromb Vasc Biol*, 21:542-547.

Reubsaet et al., (1999) "Qualitative and quantitative aspects of the degradation of several tripeptides derived from the antitumour peptide antagonist [Arg$^6$, D-Trp$^{7,9}$, MePhe$^8$] substance P{6-11}", *J Pharmaceut & Biomed Analysis*, 19(3-4):277-284.

Ridker PM, (2002) "On Evolutionary Biology, Inflammation, Infection, and the Causes of Atherosclerosis", *Circulation*, 105:2-4.

Roher et al., (1993) "18-Amyloid-(142) is a major component of cerebrovascular amyloid deposits: Implications for the pathology of Alzheimer disease", *PNAS*, USA, 90: 10836-10840.

Román et al., (2002) "Subcortical ischaemic vascular dementia", *Lancet Neurol.*, 1:426-436.

Rong et al., (2001) "Elevating High-Density Lipoprotein Cholesterol in Apolipoprotein E-Deficient Mice Remodels Advanced Atherosclerotic Lesions by Decreasing Macrophage and Increasing Smooth Muscle Cell Content", *Circulation*, 104:2447-2452.

Rubin et al., (1991) "Inhibition of early atherogenesis in transgenic mice by human apolipoprotein A1", *Nature*, 353:265-267.

Sabbatini et al., (2001) "Microanatomical changes of intracerebral arteries in spontaneously hypertensive rats: a model of cerebrovascular disease of the elderly", *Mech. Aging & Dev.*, 122: 1257-1268.

Sandana Mala JG et al., (Aug. 2001) "Strain improvement of *Aspergillus niger* for enhanced lipase production", *J Gen Appl Microbiol*, 47(4):181-186.

Sankaranarayanan et al., (Dec. 1987) "Affinity purification of hexosaminidases", *J Biochem Biophys Methods*, 15(3-4):207-14.

Sattler et al., (1993) "Greater selective uptake by Hep G2 cells of high-density lipoprotein cholesteryl ester hydroperoxides than of unoxidized cholesteryl esters", *Biochem J*, 294(Pt 3):771-778.

Schonbeck and Libby, (2004) "Inflamation, Immunity, and HMG-CoA Reductase Inhibitors, Statins as Antiinflammatory Agents?" *Circulation* 109(21 Suppl 1):II18-1126.

Segrest et al., (1974) "A Molecular Theory of Lipid-Protein Interaction in the Plasma Lipoproteins." *FEBS Lett*, 38(3):247-253.

Segrest et al., (1990) "Amphipathic Helix Motif: Classes and Properties", *PROTEINS: Structure, Function and Genetics*, 8:103-117.

Segrest et al., (1992) "The Amphipathic Helix in the Exchangeable Apolipoproteins: A Review of Secondary Structure and Function", *J Lipid Research* 33:141-166.

Segrest et al., (1994) "Amphipathic α Helix: A Multifunctional Structural Motif in Plasma Apolipoproteins", *Adv Prot Chem*, 45: 303-369.

Segrest et al., (2000) "Structure and function of apolipoprotein A-I and high-density lipoprotein", *Current Opin Lipidol*, 11:105-115.

Senior, (1999) "New options developed for needle-free drug delivery", *Lancet*, Sep. 25.

Shah et al., (1998) "Effects of Recombinant Apolipoprotein A-I$_{Milano}$ on Aortic Atherosclerosis in Apolipoprotein E-Deficient Mice", *Circulation*, 97(8):780-785.

Shah et al., (2001) "High-Dose Recombinant Apolipoprotein A-I Milano Mobilizes Tissue Cholesterol and Rapidly Reduces Plaque Lipid and Macrophage Content in Apolipoprotein E-Deficient Mice: Potential Implications for Acute Plaque Stabilization", *Circulation*, 103:3047-3050.

Shih et al., (2000) "Combined Serum Paraoxonase/Apolipoprotein E Knockout Mice Exhibit Increased Lipoprotein Oxidation and Atherosclerosis", *J Biol Chem*, 275(23):17527-17535.

Shih et al., (1999) "Minimally modified low-density lipoprotein induces monocyte adhesion to endothelial connecting segment-1 by activating β1 integrin", *J Clin Invest*, 103(5):613-625.

Shishehbor et al., (2003) "Association of Nitrotyrosine Levels with Cardiovascular Disease and Modulation by Statin Therapy", *JAMA*, 289(13):1675-1680.

Siemion et al., (1999) "Cyclolinopeptides and their analogs—a new family of peptide immunosuppressants affecting the calcineurin system", *Arch Immunol Ther Exp*, 47(3):143-153.

Siemion et al., (2003) "Analogs of RGDVY and GRGD peptides inhibit Mycobacterium kansaii phagocytosis", *Peptides*, 24:1109-1115.

Siemion I, and Wieczorek Z, (2003) "Antiadhesive peptides as the inhibitors of Mycobacterium kansasii phagocytosis", *Peptides*, 24: 623-628.

Silkensen et al., (1999) "Identification of clusterin sequences mediating renal tubular cell interactions", *J. Peptide Res.*, 54:449-547.

Singh et al., (2000) "Innate Defences Against Viraemia", *Rev Med Virol*, 10:395-403.

Sonntag et al. (1997) "Decreases in Cerebral Microvasculature with Age Are Associated with the Decline in Growth Hormone and Insulin-Like Growth Factor 1*", *Endocrinol* 138(8):3515-3520.

Sorescu et al., (2001) "NAD(P)H oxidases and their relevance to atherosclerosis", *Trends Cardiovas Med*, 11(3-4):124-131.

Spieker et al., (2002) "High-Density Lipoprotein Restores Endothelial Function in Hypercholesterolemic Men", *Circulation*, 105:1399-1402.

Sprecher et al., (1993) "The Low HDL Cholesterol/ High Triglyceride Trait", *Arterioscler Thromb*, 13:495-504.

Springer TA, (1990) "Adhesion receptors of the immune system", *Nature*, 346:425-434.

Srinivas et al., (1990) "Antivrial Effects of Apolipoprotein A-I and Its Synthetic Amphipathic Peptide Analogs", *Virology*, 176:48-57.

Stannard et al., (2001) "Inability of plasma high-density lipoproteins to inhibit cell adhesion molecule expression in human coronary artery endothelial cells", *Atherosclerosis*, 154:31-38.

Starlix MC-Amino Acid Fact Sheet. (2002) http://starlix.com/media_center/content/pages/amino.htm.

Su and Amidon, (1995) "Investigation into the intestinal metabolism of [D-Ala$^1$] peptide T amide: implication for oral drug delivery", *Biochim et Biophys*, 1245: 62-68.

Sugatani et al., (1996) "High-density lipoprotein inhibits the synthesis of platelet-activating factor in human vascular endothelial cells", *J Lipid Mediators Cell Signal*, 13:73-88.

Sumitra et al. (Aug. 2001) "Experimental myocardial necrosis in rats: role of arjunolic acid on platelet aggregation, coagulation and antioxidant status", *Mol Cell Biochem*, 224(1-2).

Sundal, E., (1993) "Thymopentin prophylactic treatment in patients with recurrent respirator infections", *Br J Clin Pract*, 47(4):198-204.

Suresh (Oct. 1992) "Alterations in human gingival glycosaminoglycan pattern in inflammation and in phenytoin induced overgrowth", *Mol Cell Biochem*, 115(2):149-54.

Szewczuk, Z., (2001) "Immunosuppressory activity of the cyclodimetric peptide with RGD-sequences", *Acta Biochimica Polonica*, 48(1):121-130.

Tan et al., (2000) "The carboxamine feG(NH2) inhibits endotoxin perturbation of intestinal motility", *Eurp Jol of Pharm*, 409:203-205.

Tan et al., (1997) "A novel, highly efficient peptide-HLA class I binding assay using unfolded heavy chain molecules; identification of HIV-1 derived peptides that bind to HLA-A* 0201 and HLA-A* 0301", *J Immunol Meth*, 205:201-209.

The Wall Street Journal (Jan. 13, 2000) "Emisphere technologies develops oral Heparin".

Thomas, Eric C. (1999) "Brain macrophages: on the role of pericytes and perivascular cells", *Brain Res Rev*, 31:42-57.

Tian et al. (2002) "Structure-affinity relationships in the gp41 ELDKWA epitope for the HIV-1 neutralizing monoclonal antibody 2F$_5$: effects of side-chain and backbone modifications and conformational constraints", *J. Peptide Res.* 59:264-276.

Toyoda et al. (1997) "Effect of Aging on Regulation of Brain Stem Circulation During Hypotension", *J. Cerebral Blood Flow & Metab.*, 17(6): 680-685.

Tsai et al., (1998) "D-Serine Added to Antipsychotics for the Treatment of Schizophrenia", *Biol. Psychiatry*, 44:1081-1089.

Tsao et al., (2001) "Hibernation-induction peptide and cell death: [D-Ala$^2$, D-Leu$^5$]enkephalin blocks Bax-related apoptotic processes", *European Journal of Pharmacology* 428:149-151.

Tsimikas et al., (2001) "Measuring Circulating Oxidized Low-Density Lipoprotein to Evaluate Coronary Risk", *Circulation* 103:1930-1932.

Turesin, F. et al., (2002) "The tripeptide feG ameliorates systemic inflammatory responses to rat intestinal anaphylaxis", *BMC Physiology*, 2(13):1472-6793.

Tward et al., (2002) "Decreased Atherosclerotic Lesion Formation in Human Serum Paraoxonase Transgenic Mice", *Circulation* 106:484-490.

Van Lenten et al., (1995) "Anti-inflammatory HDL Becomes Proinflammatory during the Acute Phase Response. Loss of Protective Effect of HDL against LDL Oxidation in Aortic Wall Cell Cocultures", *J Clin Invest*, 96:2758-2767.

Van Lenten et al., (2002) "Influenza Infection Promotes Macrophage Traffic into Arteries of Mice that is Prevented by D-4F, an Apolipoprotein A-I Mimetic Peptide", *Circulation*, 106:1127-1132.

Van Lenten et al., (2001) "High-Density Lipoprotein Loses its Anti-Inflammatory Properties During Acute Influenza A Infection", *Circulation* 103:2283-2288.

Van Lenten et al., (Sep. 2001) "Acute Influenza a Infection Promotes Increased Macrophage Infiltration into the Artery Wall that is Prevented by Apolipoprotein A-I", *Supplement to Circulation*, 104(12):11-97, 470, Abstract.

Venkatachalapathi et al., (1993) "Effect of End Group Blockage on the Properties of a Class A Amphipathic Helical Peptide", *Proteins: Structure, Function, and Genetics*, 15:349-359.

Venkatesan et al. (Dec. 31, 1993) "Angiotensin I converting enzyme activity in adriamycin induced nephrosis in rats", *Toxicology*, 85(2-3):137-48.

Venugopal et al., (2002) "Demonstration That C-Reactive Protein Decreases eNOS Expression and Bioactivity in Human Aortic Endothelial Cells", *Circulation*,106:1439-1441.

Vinters et al. (1996) "Brain Parenchymal and Microvascular Amyloid in Alzheimer's Disease", *Brain Pathol*, 6(2):179-195.

Vinters et al. (1998) "Secondary microvascular degeneration in amyloid angiopathy of patients with hereditary cerebral hemorrhage with amyloidosis, Dutch type (HCHWA-D)", *Acta Neuropathol*, 95:235-244.

Vishwanath et al. (Oct. 1997) "Fate of Mycobacterium tuberculosis inside rat peritoneal macrophages in vitro", *Mol Cell Biochem*, 175(1-2):169-75.

Vovenko, Eugene (1999) "Distribution of oxygen tension on the surface of arterioles, capillaries and venules of brain cortex and in tissue in normoxia; an experimental study on rats", *Eur J Physiol*, 437:617-623.

Walpola PL, Gotlieb AI, Cybulsky MI, Langille BL, (1995) "Expression of ICAM-1 and VCAM-1 and Monocyte Adherence in Arteries Exposed to Altered Shear Stress", *Arterioscler Thromb Vasc Biol*, 15:2-10.

Watson et al., (1995) "Protective Effect of High Density Lipoprotein Associated Paraoxonase. Inhibition of the Biological Activity of Minimally Oxidized Low Density Lipoprotein", *J Clin Invest*, 96:2882-2891.

Watson et al., (1995) "Effect of Platelet Activating Factor—Acetylhydrolase on the Formation and Action of Minimally Oxidized Low Density Lipoprotein", *J Clin Invest*, 95:774-782.

Wei et al. (1998) "Antioxidants Inhibit ATP-Sensitive Potassium Channels in Cerebral Arterioles", *Stroke*, 29:817-823.

Wilson et al., (1988) "High Density Lipoprotein Cholesterol and Mortality: The Framingham Heart Study", *Arteriosclerosis*, 8:737-741.

Wu et al. (1992) "Inhibition Effects of KRDS, a Peptide Derived from Lactotransferrin, on Platelet Function and Arterial Thrombus Formation in Dogs", *Haemostasis*, 22:1-6.

Xia et al., (1999) "High Density Lipoproteins (HDL) Interrupt the Sphingosine Kinase Signaling Pathway. A Possible Mechanism for Protection Against Atherosclerosis by HDL", *J Biol Chem*, 274:33143-33147.

Yakubu et al. (1997) "Role of lysophosphatidic acid in endothlin-1- and heatoma-induced alteration of cerebral microcirculation", *Am. J. Physiol.*, 273(2 pt 2): R703-9.

Yamashita S, Maruyama T, Hirano K, et al., (2000) " Molecular mechanisms, lipoprotein abnormalities and atherogenicity of hyperalphalipoproteinemia", *Atherosclerosis*, 152:271-285.

Yan et al., (2004) "PLTP deficiency improves the anti-inflammatory properties of HDL and reduces the ability of LDL to induce monocyte chemotactic activity", *J Lipid Res*, 45:1852-1858.

Yancey et al., (1995) "Efflux of Cellular Cholesterol and Phospholipid to Lipid-Free Apolipoproteins and Class A Amphipathic Peptides", *Biochemistry*, 34:7955-7965.

Yui et al., (1998) "Serum Prostacyclin Stabilizing Factor Is Identical to Apolipoprotein A-I (Apo A-I). A novel function of Apo A-I", *J. Clin. Invest*, 82:803-807.

Zeiher et al., (1994) "Atherosclerosis/Coronary Heart Disease: Coronary Atherosclerotic Wall Thickening and Vascular Reactivity in Humans Elevated High-Density Lipoprotein Levels Ameliorate Abnormal Vasoconstriction in Early Atherosclerosis", *Circulation*, 89(6):2525-2532.

Zhang and Olsson (1997) "The angiopathy of subcortical arteriosclerotic encephalopathy (Binswanger's disease): immunohistochemical studies using markers for components of extracelluar matrix, smooth muscle actin and endothelial cells", *Acta Neuropathol*, 93:219-224.

Zhang et al., (2002) "Myeloperoxidase Functions as a Major Enzymatic Catalyst for Initiation of Lipid Peroxidation at Sites of Inflammation", *J Biol Chem*, 277(48):46116-46122.

Zhang et al., (2002) "Lack of inhibitory effect of HDL on TNFα-induced adhesion molecule expression in human aortic endothelial cells", *Atherosclerosis*, 165:241-249.

Zhao et al., (2002) "Selective Interleukin-12 Synthesis Defect in 12/15- Lipoxygenase-deficient Macrophages Associated with Reduced Atherosclerosis in a Mouse Model of Familial Hypercholesterolemia", *J Biol Chem*, 277(38):35350-35356.

Canadian Office Action dated Feb. 12, 2009 issued in CA 2,639,651.*

Chinese Office Action dated Jul. 9, 2004 issued in CN 01817280.6.*

Chinese Office Action dated Jun. 19, 2009 issued in CN 200510103876.X.*

Chinese Office Action dated Aug. 28, 2009 issued in CN200610100668.9.*

Chinese Office Action dated Nov. 17, 2008 issued in CN 200610100667.4.*

European Office Action dated Jul. 15, 2009 issued in EP 07 007 775.5.

Japanese Office Action dated Jan. 8, 2009 issued in JP2006-220831.

Australian Examination Report dated Sep. 11, 2008 issued in AU 2003284129.

Chinese Office Action dated Feb. 18, 2009 issued in CN 200380106367.1.

European Supplementary Search Report dated Jun. 29, 2009 issued in EP 03 77 6360.4-2403 / 1562624.

European Examination Report dated Oct. 7, 2009 issued in EP 03 776 360.4-2403.

Japanese Office Action dated Jul. 28, 2009 issued in JP 2005-501402.

Chinese First Office Action dated Sep. 25, 2009 issued in CN 200580039224.2.

European Extended Search Report; Supplemental EP Search Report and EP Search Opinion dated Sep. 14, 2009 issued in EP 05803724.3-2405.

New Zealand Examination Report dated Jul. 3, 2009 issued in NZ555826.

Singapore Search Report and Written Opinion dated Sep. 22, 2008 issued in SG 200703988-6.

Singapore Second Written Opinion dated May 12, 2009 issued in SG 200703988-6.

International Search Report dated Apr. 18, 2007 issued in WO 2006/118805.

European Extended Search Report; Supplementary European Search Report and the European Search Opinion dated Sep. 30, 2009 issued in EP06750791.3-2403.

Israeli Office Action (description) dated Mar. 2, 2009 issued in IL 186959.

New Zealand Examination Report dated Jan. 20, 2009 issued in NZ 563187.

New Zealand Examination Report dated Nov. 20, 2009 issued in NZ 563187.

Singapore Search Report and Written Opinion dated Mar. 12, 2009 issued in SG 200717107-7.

Declaration of Non-Establishment of International Search Report and Written Opinion dated Apr. 24, 2009 issued in WO 2009/073725 (PCT/US2008/085409).

US Notice of Allowance dated Dec. 11, 2008 issued in U.S. Appl. No. 11/431,412.

US Office Action dated Nov. 26, 2008, issued in U.S. Appl. No. 11/689,037.

US Office Action Final dated Jun. 23, 2009 issued in U.S. Appl. No. 11/689,037.

US Office Action (and Interview Summary) dated Sep. 28, 2009 issued in U.S. Appl. No. 11/689,037.

US Office Action dated May 1, 2009 issued in U.S. Appl. No. 11/830,664.

US Office Action (Examiner's Interview Summary) dated Apr. 27, 2009 issued in U.S. Appl. No. 11/830,675.

US Office Action dated Jun. 5, 2009 issued in U.S. Appl. No. 11/830,675.
US Office Action dated Sep. 9, 2009 issued in U.S. Appl. No. 11/830,687.
US Office Action dated Jan. 26, 2009 issued in U.S. Appl. No. 11/229,042.
US Office Action Final dated Oct. 5, 2009 issued in U.S. Appl. No. 11/229,042.
US Notice of Allowance dated Mar. 9, 2009 issued in U.S. Appl. No. 11/296,582.
US Office Action (*Ex Parte Quayle*) dated Aug. 14, 2009 issued in U.S. Appl. No. 11/407,390.
US Office Action (Examiner Interview Summary) dated Sep. 23, 2009 issued in U.S. Appl. No. 11/407,390.
US Notice of Allowance dated Dec. 2, 2009 issued in U.S. Appl. No. 11/407,390.
Anatharamaiah et al., (2007) "Structural requirements for antioxidative and anti-inflammatory properties of apolipoprotein A-1 Mimetic peptides", *Journal of Lipid Research*, 48:1915-1923.
Bergt et al. (Feb. 27, 2004) "Lysine Residues Direct the Chlorination of Tyrosines in Y*XX*K Motifs of Apolipoprotein A-I When Hypochlorous Acid Oxidizes High Density Lipoprotein", *The Journal of Biological Chemistry*, 279(9):7856-7866.
Datta et al, (2004) "Aromatic Residue Position on the Nonpolar Face of Class A Amphipathic Helical Peptides Determines Biological Activity", *Journal of Biological Chemistry*, 279(24):26509-26517.
Fogelman (retrieved from http://www.ekatius.com/i/presentations/details/050406/05A on Jan. 13, 2009 corresponding transcription (pp. 2-7 of the document) and powerpoint presentation (pp. 8-68) total of 68 pages).
Futterman, et al., (May 2004) "Statin Plciotropy: Fact or Fiction?", *Am J Crit Care*, 13(3):244-249.
Getz et al., (2009) "Apoprotein A-1 mimetic peptides and their potential anti-atherogenic mechanisms of action", *Current Opinion in Lipidology*, 20:1-5.
Graf et al., (Oct. 1996) "Random circular permutation of genes and expressed polypeptide chains: Application of the method to the catalytic chains of aspartate transcarbamoylase", *Proc. Natl. Acad. Sci. USA, Biochemistry*, 93:11591-11596.
Hein et al., (2001) "Integrin-binding peptides containing RGD produce coronary arteriolar dilation via cyclooxygenase activation", *Am J Physiol Heart Circ Physiol*, 281:H2378-H2384.
Nomoto et al., (1998) "Improvement of Intestinal Absorption of Peptide Drugs by Glycosylation: Transport of Tetrapeptide by the Sodium Ion-Dependent D-Glucose Transporter", *J Pharmaceutical Science*, 87(3):326-332.
Pasqui et al., (2005) "Structural and functional abnormality of systemic microvessels in cardiac syndrome X", *Nutrition, Metabolism and Cardiovascular Diseases*, 15:56-64.
Toledo et al. (2004) "Functional independence of a peptide with the sequence of human apolipoprotein A-I central region", *Archives of Biochemistry and Biophysics*, 428(2):188-197.
Wool et al. (2008) "Apolipoprotein A-1 mimetic peptide helix number and helix linker influence potentially anti-atherogenic properties", *Journal of Lipid Research*, 49:1268-1283.
Wool et al. (2009) "An apoA-I mimetic peptide containing a proline residue has greater in vivo HDL binding and anti-inflammatory ability than the 4F peptide", *Journal of Lipid Research*, vol. 1 [downloaded from www.jlr.org at UCLA Biomedical Lib/Serials on May 12, 2009] 43 pages.
Yip K-P et al., (1997) "An Arg-Gly-Asp peptide stimulates constriction in rat afferent arteriole", *Am J Physiol Renal Physiol*, 273:768-776.
Australian Examiner's First Report dated Jun. 6, 2005 issued in AU 2001286732.
Canadian Office Action dated Apr. 1, 2008 issued in CA2420222.
Chinese Third Office Action dated Apr. 9, 2010 issued in CN200610100668.9.
Chinese Second Office Action dated Apr. 15, 2010 issued in CN200610100670.6.
Chinese Second Office Action dated May 28, 2010 issued in CN 200610100669.3.
European Partial Search Report dated May 7, 2010 issued in EP 10 00 2402-2401.
Israeli Office Action dated Nov. 10, 2009 issued in IL-154545.
Japanese First Office Action dated May 10, 2010 issued in JP2007-118451.
U.S. Appl. No. 12/721,366, filed Mar. 10, 2010, Fogelman et al.
Canadian First Office Action dated May 28, 2010 issued in CA 2,501,943.
European Communication and Search Opinion dated Jan. 20, 2010 issued in EP 05803724-2405.
Chinese Office Action dated Jan. 8, 2010 issued in CN 200580047756.0.
Israeli Office Action (description) dated Oct. 26, 2009 issued in IL 183689.
Malaysian Examination and Search Report dated Jun. 30, 2010 issued in PI 20070907.
New Zealand Examination Report dated Nov. 2, 2009 issued in NZ580650.
Russian First Office Action dated Apr. 26, 2010 issued in RU 2007125589.
Chinese First Office Action dated May 20, 2010 issued in CN200680023011.5.
Eurasian Search Report dated May 26, 2010 issued in EA 200900786.
European Examination Report dated Jun. 7, 2010 issued in EP 06 750 791.3-2403.
Israeli First Substantive Examination Report (translation) dated Mar. 15, 2010 issued in IL 186959 (138784).
New Zealand Examination Report dated Nov. 10, 2009 issued in NZ 580954.
Singapore Second Written Opinion dated Oct. 29, 2009 issued in SG 200717107-7.
Vietnamese First Office Action dated May 26, 2010 issued in Appln. No. 1-2007-02543.
US Office Action (Examiner Interview Summary) dated Nov. 17, 2009 issued in U.S. Appl. No. 11/689,037.
US Office Action (Advisory Action Before the Filing of an Appeal Brief) dated Dec. 9, 2009 issued in U.S. Appl. No. 11/689,037.
US Notice of Allowance dated Apr. 8, 2010 issued in U.S. Appl. No. 11/689,037.
US Office Action Final dated Nov. 10, 2009 issued in U.S. Appl. No. 11/830,664.
US Office Action Final dated Dec. 18, 2009 issued in U.S. Appl. No. 11/830,675.
US Notice of Allowance dated Jun. 18, 2010 issued in U.S. Appl. No. 11/830,675.
US Office Action Final dated Feb. 26, 2010 issued in U.S. Appl. No. 11/830,687.
US Office Action dated Jul. 1, 2010 issued in U.S. Appl. No. 11/830,687.
US Office Action dated Nov. 24, 2009 issued in U.S. Appl. No. 11/950,315.
US Office Action Final dated Jun. 16, 2010 issued in U.S. Appl. No. 11/950,315.
Charles-Schoeman et al., (2008) "Treatment with an apolipoprotein A-1 mimetic peptide in combination with pravastatin inhibits collagen-induced arthritis", *Clinical Immunology*,127:234-244.
Kruger et al. (2005) "D-4F Induces Heme Oxygenase-1 and Extracellular Superoxide Dismutase, Decreases Endothelial Cell Sloughing, and Improves Vascular Reactivity in Rat Model of Diabetes", *Circulation*, 111(23):3126-3134.
Mala, John Geraldine Sandana et al. (Aug. 2001) "Strain improvement of *Aspergillus niger* for enhanced lipase production", *J Gen Appl Microbiol*, 47(4):181-186.
Meyrier et al.(1998) "Ischemic renal diseases: New insights into old entities", *Kidney International*, 54:2-13.
Peterson et al. (2009) "The L-4F mimetic peptide prevents insulin resistance through increased levels of HO-1, pAMPK, and pAKT in obese mice", *J. Lipid Res.*, 50:1293-1304.
European Extended Search Report dated Nov. 2, 2010 issued in EP 10 00 2402.5-2401/2198877.

European Reminder Concerning Payment of Designation Fee and Examination Fee dated Dec. 6, 2010 issued in EP 10 00 2402.5-2401/ 2198877.
Israeli Office Action dated Nov. 2, 2010 issued in IL-154545.
Japanese Office Action dated Jul. 7, 2010 issued in JP2007-250264.
Chinese First Office Action dated Jan. 25, 2011 issued in CN 201010156423.4.
Australian Examiner's First Report dated Nov. 10, 2010 issued in AU 2005287004.
Chinese Second Office Action dated Dec. 1, 2010 issued in CN 200580039224.2.
Russian First Office Action dated Dec. 7, 2010 issued in RU 2007114144.
Indonesian Office Action dated Oct. 26, 2010 issued in Indonesian Patent Application No. W-00200701762.
European Examination Report dated Dec. 17, 2010 issued in EP 06 750 791.3-2403.

European Extended Search Report and Written Opinion dated Nov. 24, 2010 issued in EP 10177858.7-2403.
US Office Action (Notice of Abandonment) dated Jun. 18, 2010 issued in U.S. Appl. No. 11/830,664.
US Office Action Final dated Jan. 11, 2011 issued in U.S. Appl. No. 11/830,687.
US Office Action dated Jan. 13, 2011 issued in U.S. Appl. No. 12/478,593.
Moody et al., (Sep. 1997) "Cerebral Microvascular Alterations in Aging, Leukoaraiosis, and Alzheimer's Disease", *Annals of the New York Academy of Sciences*, 826:103-116.
Schröder et al., (1969) "Synthesis, Occurrence, and Action of Biologically Active Polypeptides", *The Peptides*, vol. II, p. 26 (and relevant passage translated to English).

* cited by examiner

Asp • Phe • Trp • Lys • Ala • Phe • Tyr • Asp • Lys • Val • Ala • Glu • Lys • Phe
Lys • Glu • Ala • Phe

Hydrophobic moment/residue = 2.812078

Hydrophobicity/residue of the nonpolar face = 2.050000

SEQUENCE LISTING

```
<160> NUMBER OF SEQ ID NOS: 1139

<210> SEQ ID NO 1
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 1

Asp Trp Leu Lys Ala Phe Tyr Asp Lys Val Ala Glu Lys Leu Lys Glu
1               5                   10                  15

Ala Phe

<210> SEQ ID NO 2
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 3

Asp Trp Phe Lys Ala Phe Tyr Asp Lys Val Ala Glu Lys Leu Lys Glu
```

```
1               5                   10                  15
Ala Phe

<210> SEQ ID NO 4
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 4

Asp Trp Leu Lys Ala Phe Tyr Asp Lys Val Ala Glu Lys Phe Lys Glu
1               5                   10                  15
Ala Phe

<210> SEQ ID NO 5
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 5

Asp Trp Phe Lys Ala Phe Tyr Asp Lys Val Ala Glu Lys Phe Lys Glu
1               5                   10                  15
Ala Phe

<210> SEQ ID NO 6
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 6

Asp Trp Leu Lys Ala Phe Tyr Asp Lys Val Phe Glu Lys Phe Lys Glu
1               5                   10                  15
Phe Phe

<210> SEQ ID NO 7
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 7

Asp Trp Leu Lys Ala Phe Tyr Asp Lys Phe Phe Glu Lys Phe Lys Glu
1               5                   10                  15
Phe Phe

<210> SEQ ID NO 8
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 8

Asp Trp Phe Lys Ala Phe Tyr Asp Lys Phe Phe Glu Lys Phe Lys Glu
```

```
1               5                   10                  15
Phe Phe

<210> SEQ ID NO 9
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 9

Asp Trp Leu Lys Ala Phe Tyr Asp Lys Val Ala Glu Lys Leu Lys Glu
1               5                   10                  15

Phe Phe

<210> SEQ ID NO 10
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 11

Asp Trp Leu Lys Ala Phe Tyr Asp Lys Val Phe Glu Lys Leu Lys Glu
1               5                   10                  15

Phe Phe

<210> SEQ ID NO 12
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 12

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 13

Asp Trp Leu Lys Ala Phe Tyr Asp Lys Val Phe Glu Lys Phe Lys Glu
```

```
1               5                  10                 15
Phe Phe

<210> SEQ ID NO 14
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 14

Glu Trp Leu Lys Leu Phe Tyr Glu Lys Val Leu Glu Lys Phe Lys Glu
1               5                  10                 15
Ala Phe

<210> SEQ ID NO 15
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 15

Glu Trp Leu Lys Ala Phe Tyr Asp Lys Val Ala Glu Lys Phe Lys Glu
1               5                  10                 15
Ala Phe

<210> SEQ ID NO 16
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 16

Glu Trp Leu Lys Ala Phe Tyr Asp Lys Val Ala Glu Lys Leu Lys Glu
1               5                  10                 15
Phe Phe

<210> SEQ ID NO 17
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 17

Glu Trp Leu Lys Ala Phe Tyr Asp Lys Val Phe Glu Lys Phe Lys Glu
1               5                  10                 15
Ala Phe

<210> SEQ ID NO 18
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 18

Glu Trp Leu Lys Ala Phe Tyr Asp Lys Val Phe Glu Lys Leu Lys Glu
```

```
1               5                   10                  15

Phe Phe

<210> SEQ ID NO 19
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 19

Glu Trp Leu Lys Ala Phe Tyr Asp Lys Val Ala Glu Lys Phe Lys Glu
1               5                   10                  15

Phe Phe

<210> SEQ ID NO 20
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 20

Glu Trp Leu Lys Ala Phe Tyr Asp Lys Val Phe Glu Lys Phe Lys Glu
1               5                   10                  15

Phe Phe

<210> SEQ ID NO 21
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 21

Ala Phe Tyr Asp Lys Val Ala Glu Lys Leu Lys Glu Ala Phe
1               5                   10

<210> SEQ ID NO 22
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 22

Ala Phe Tyr Asp Lys Val Ala Glu Lys Phe Lys Glu Ala Phe
1               5                   10

<210> SEQ ID NO 23
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 23

Ala Phe Tyr Asp Lys Val Ala Glu Lys Phe Lys Glu Ala Phe
1               5                   10

<210> SEQ ID NO 24
```

```
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 24

Ala Phe Tyr Asp Lys Phe Phe Glu Lys Phe Lys Glu Phe Phe
1               5                   10

<210> SEQ ID NO 25
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 25

Ala Phe Tyr Asp Lys Phe Phe Glu Lys Phe Lys Glu Phe Phe
1               5                   10

<210> SEQ ID NO 26
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 27

Ala Phe Tyr Asp Lys Val Ala Glu Lys Leu Lys Glu Phe Phe
1               5                   10

<210> SEQ ID NO 28
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 29

Ala Phe Tyr Asp Lys Val Phe Glu Lys Leu Lys Glu Phe Phe
```

<210> SEQ ID NO 30
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 30

Ala Phe Tyr Asp Lys Val Ala Glu Lys Phe Lys Glu Phe Phe
1               5                   10

<210> SEQ ID NO 31
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 31

Lys Ala Phe Tyr Asp Lys Val Phe Glu Lys Phe Lys Glu Phe
1               5                   10

<210> SEQ ID NO 32
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 32

Leu Phe Tyr Glu Lys Val Leu Glu Lys Phe Lys Glu Ala Phe
1               5                   10

<210> SEQ ID NO 33
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial
<220> FEATURE:
<223> OTHER INFORMATION: Synthetic peptide optionally bearing
      protecting groups.

```
<400> SEQUENCE: 35

Ala Phe Tyr Asp Lys Val Phe Glu Lys Phe Lys Glu Ala Phe
1               5                   10

<210> SEQ ID NO 36
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 36

Ala Phe Tyr Asp Lys Val Phe Glu Lys Leu Lys Glu Phe Phe
1               5                   10

<210> SEQ ID NO 37
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 39

Asp Trp Leu Lys Ala Leu Tyr Asp Lys Val Ala Glu Lys Leu Lys Glu
1               5                   10                  15

Ala Leu

<210> SEQ ID NO 40
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 40

Asp Trp Phe Lys Ala Phe Tyr Glu Lys Val Ala Glu Lys Leu Lys Glu
1               5                   10                  15

Phe Phe
```

```
<210> SEQ ID NO 41
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 41

Asp Trp Phe Lys Ala Phe Tyr Glu Lys Phe Phe Glu Lys Phe Lys Glu
1               5                   10                  15

Phe Phe

<210> SEQ ID NO 42
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 42

Glu Trp Leu Lys Ala Leu Tyr Glu Lys Val Ala Glu Lys Leu Lys Glu
1               5                   10                  15

Ala Leu

<210> SEQ ID NO 43
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 43

Glu Trp Leu Lys Ala Phe Tyr Glu Lys Val Ala Glu Lys Leu Lys Glu
1               5                   10                  15

Ala Phe

<210> SEQ ID NO 44
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 44

Glu Trp Phe Lys Ala Phe Tyr Glu Lys Val Ala Glu Lys Leu Lys Glu
1               5                   10                  15

Phe Phe

<210> SEQ ID NO 45
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 45

Glu Trp Leu Lys Ala Phe Tyr Glu Lys Val Phe Glu Lys Phe Lys Glu
1               5                   10                  15

Phe Phe
```

```
<210> SEQ ID NO 46
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 46

Glu Trp Leu Lys Ala Phe Tyr Glu Lys Phe Phe Glu Lys Phe Lys Glu
1               5                   10                  15

Phe Phe

<210> SEQ ID NO 47
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 47

Glu Trp Phe Lys Ala Phe Tyr Glu Lys Phe Phe Glu Lys Phe Lys Glu
1               5                   10                  15

Phe Phe

<210> SEQ ID NO 48
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 48

Asp Phe Leu Lys Ala Trp Tyr Asp Lys Val Ala Glu Lys Leu Lys Glu
1               5                   10                  15

Ala Trp

<210> SEQ ID NO 49
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 49

Glu Phe Leu Lys Ala Trp Tyr Glu Lys Val Ala Glu Lys Leu Lys Glu
1               5                   10                  15

Ala Trp

<210> SEQ ID NO 50
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 50

Asp Phe Trp Lys Ala Trp Tyr Asp Lys Val Ala Glu Lys Leu Lys Glu
1               5                   10                  15

Trp Trp
```

```
<210> SEQ ID NO 51
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 51

Glu Phe Trp Lys Ala Trp Tyr Glu Lys Val Ala Glu Lys Leu Lys Glu
1               5                   10                  15

Trp Trp

<210> SEQ ID NO 52
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 52

Asp Lys Leu Lys Ala Phe Tyr Asp Lys Val Phe Glu Trp Ala Lys Glu
1               5                   10                  15

Ala Phe

<210> SEQ ID NO 53
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 53

Asp Lys Trp Lys Ala Val Tyr Asp Lys Phe Ala Glu Ala Phe Lys Glu
1               5                   10                  15

Phe Leu

<210> SEQ ID NO 54
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 54

Glu Lys Leu Lys Ala Phe Tyr Glu Lys Val Phe Glu Trp Ala Lys Glu
1               5                   10                  15

Ala Phe

<210> SEQ ID NO 55
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 55

Glu Lys Trp Lys Ala Val Tyr Glu Lys Phe Ala Glu Ala Phe Lys Glu
1               5                   10                  15

Phe Leu
```

```
<210> SEQ ID NO 56
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 56

Asp Trp Leu Lys Ala Phe Val Asp Lys Phe Ala Glu Lys Phe Lys Glu
1               5                   10                  15

Ala Tyr

<210> SEQ ID NO 57
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 57

Glu Lys Trp Lys Ala Val Tyr Glu Lys Phe Ala Glu Ala Phe Lys Glu
1               5                   10                  15

Phe Leu

<210> SEQ ID NO 58
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 58

Asp Trp Leu Lys Ala Phe Val Tyr Asp Lys Val Phe Lys Leu Lys Glu
1               5                   10                  15

Phe Phe

<210> SEQ ID NO 59
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 59

Glu Trp Leu Lys Ala Phe Val Tyr Glu Lys Val Phe Lys Leu Lys Glu
1               5                   10                  15

Phe Phe

<210> SEQ ID NO 60
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 60

Asp Trp Leu Arg Ala Phe Tyr Asp Lys Val Ala Glu Lys Leu Lys Glu
1               5                   10                  15

Ala Phe
```

-continued

```
<210> SEQ ID NO 61
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 61

Glu Trp Leu Arg Ala Phe Tyr Glu Lys Val Ala Glu Lys Leu Lys Glu
1               5                   10                  15

Ala Phe

<210> SEQ ID NO 62
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 62

Asp Trp Leu Lys Ala Phe Tyr Asp Arg Val Ala Glu Lys Leu Lys Glu
1               5                   10                  15

Ala Phe

<210> SEQ ID NO 63
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 63

Glu Trp Leu Lys Ala Phe Tyr Glu Arg Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 64

Asp Trp Leu Lys Ala Phe Tyr Asp Lys Val Ala Glu Arg Leu Lys Glu
1               5                   10                  15

Ala Phe

<210> SEQ ID NO 65
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 65

Glu Trp Leu Lys Ala Phe Tyr Glu Lys Val Ala Glu Arg Leu Lys Glu
1               5                   10                  15

Ala Phe
```

```
<210> SEQ ID NO 66
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 66

Asp Trp Leu Lys Ala Phe Tyr Asp Lys Val Ala Glu Lys Leu Arg Glu
1               5                   10                  15

Ala Phe

<210> SEQ ID NO 67
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 67

Glu Trp Leu Lys Ala Phe Tyr Glu Lys Val Ala Glu Lys Leu Arg Glu
1               5                   10                  15

Ala Phe

<210> SEQ ID NO 68
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 68

Asp Trp Leu Lys Ala Phe Tyr Asp Arg Val Ala Glu Arg Leu Lys Glu
1               5                   10                  15

Ala Phe

<210> SEQ ID NO 69
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 69

Glu Trp Leu Lys Ala Phe Tyr Glu Arg Val Ala Glu Arg Leu Lys Glu
1               5                   10                  15

Ala Phe

<210> SEQ ID NO 70
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 70

Asp Trp Leu Arg Ala Phe Tyr Asp Lys Val Ala Glu Lys Leu Arg Glu
1               5                   10                  15

Ala Phe
```

```
<210> SEQ ID NO 71
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 71

Glu Trp Leu Arg Ala Phe Tyr Glu Lys Val Ala Glu Lys Leu Arg Glu
1               5                   10                  15

Ala Phe

<210> SEQ ID NO 72
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 72

Asp Trp Leu Arg Ala Phe Tyr Asp Arg Val Ala Glu Lys Leu Lys Glu
1               5                   10                  15

Ala Phe

<210> SEQ ID NO 73
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 73

Glu Trp Leu Arg Ala Phe Tyr Glu Arg Val Ala Glu Lys Leu Lys Glu
1               5                   10                  15

Ala Phe

<210> SEQ ID NO 74
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 74

Asp Trp Leu Lys Ala Phe Tyr Asp Lys Val Ala Glu Arg Leu Arg Glu
1               5                   10                  15

Ala Phe

<210> SEQ ID NO 75
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 75

Glu Trp Leu Lys Ala Phe Tyr Glu Lys Val Ala Glu Arg Leu Arg Glu
1               5                   10                  15

Ala Phe
```

```
<210> SEQ ID NO 76
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 76

Asp Trp Leu Arg Ala Phe Tyr Asp Lys Val Ala Glu Arg Leu Lys Glu
1               5                   10                  15

Ala Phe

<210> SEQ ID NO 77
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 77

Glu Trp Leu Arg Ala Phe Tyr Glu Lys Val Ala Glu Arg Leu Lys Glu
1               5                   10                  15

Ala Phe

<210> SEQ ID NO 78
<211> LENGTH: 37
<212> TYPE: PRT
<213> ORGANISM: Artificial
<220> FEATURE:
<223> OTHER INFORMATION: Synthetic peptide optionally bearing
      protecting groups.

<400> SEQUENCE: 78

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
        35

<210> SEQ ID NO 79
<211> LENGTH: 37
<212> TYPE: PRT
<213> ORGANISM: Artificial
<220> FEATURE:
<223> OTHER INFORMATION: Synthetic peptide optionally bearing
      protecting groups.

<400> SEQUENCE: 79

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
        35

<210> SEQ ID NO 80
<211> LENGTH: 37
<212> TYPE: PRT
<213> ORGANISM: Artificial
<220> FEATURE:
<223> OTHER INFORMATION: Synthetic peptide optionally bearing
      protecting groups.
```

```
<400> SEQUENCE: 80

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
            20                  25                  30

Leu Lys Glu Ala Phe
            35

<210> SEQ ID NO 81
<211> LENGTH: 37
<212> TYPE: PRT
<213> ORGANISM: Artificial
<220> FEATURE:
<223> OTHER INFORMATION: Synthetic peptide optionally bearing
      protecting groups.

<400> SEQUENCE: 81

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
            20                  25                  30

Leu Lys Glu Ala Phe
            35

<210> SEQ ID NO 82
<211> LENGTH: 37
<212> TYPE: PRT
<213> ORGANISM: Artificial
<220> FEATURE:
<223> OTHER INFORMATION: Synthetic peptide optionally bearing
      protecting groups.

<400> SEQUENCE: 82

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
            35

<210> SEQ ID NO 83
<211> LENGTH: 37
<212> TYPE: PRT
<213> ORGANISM: Artificial
<220> FEATURE:
<223> OTHER INFORMATION: Synthetic peptide optionally bearing
      protecting groups.

<400> SEQUENCE: 83

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
            35

<210> SEQ ID NO 84
<211> LENGTH: 37
<212> TYPE: PRT
<213> ORGANISM: Artificial
<220> FEATURE:
<223> OTHER INFORMATION: Synthetic peptide optionally bearing
      protecting groups.
```

```
<400> SEQUENCE: 84

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
            20                  25                  30

Leu Lys Glu Phe Phe
        35

<210> SEQ ID NO 85
<211> LENGTH: 37
<212> TYPE: PRT
<213> ORGANISM: Artificial
<220> FEATURE:
<223> OTHER INFORMATION: Synthetic peptide optionally bearing
      protecting groups.

<400> SEQUENCE: 85

Asp Trp Leu Lys Ala Phe Tyr Asp Lys Phe Ala Glu Lys Phe Lys Glu
1               5                   10                  15

Phe Phe Pro Asp Trp Leu Lys Ala Phe Tyr Asp Lys Phe Ala Glu Lys
            20                  25                  30

Phe Lys Glu Phe Phe
        35

<210> SEQ ID NO 86
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 86

Glu Trp Phe Lys Ala Phe Tyr Glu Lys Val Ala Glu Lys Phe Lys Glu
1               5                   10                  15

Ala Phe

<210> SEQ ID NO 87
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 87

Asp Trp Phe Lys Ala Phe Tyr Asp Lys Val Ala Glu Lys Phe
1               5                   10

<210> SEQ ID NO 88
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 88

Phe Lys Ala Phe Tyr Asp Lys Val Ala Glu Lys Phe Lys Glu
1               5                   10

<210> SEQ ID NO 89
<211> LENGTH: 14
<212> TYPE: PRT
```

```
<213> ORGANISM: Artificial
<220> FEATURE:
<223> OTHER INFORMATION: Synthetic peptide optionally bearing
      protecting groups.

<400> SEQUENCE: 89

Phe Lys Ala Phe Tyr Glu Lys Val Ala Glu Lys Phe Lys Glu
1               5                   10

<210> SEQ ID NO 90
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 90

Asn Met Ala Phe Lys Ala Phe Tyr Asp Lys Val Ala Glu Lys Phe Lys
1               5                   10                  15

Glu

<210> SEQ ID NO 91
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 91

Asn Met Ala Phe Lys Ala Phe Tyr Glu Lys Val Ala Glu Lys Phe Lys
1               5                   10                  15

Glu

<210> SEQ ID NO 92
<211> LENGTH: 21
<212> TYPE: PRT
<213> ORGANISM: Artificial
<220> FEATURE:
<223> OTHER INFORMATION: Synthetic peptide optionally bearing
      protecting groups.

<400> SEQUENCE: 92

Asn Met Ala Asp Trp Phe Lys Ala Phe Tyr Asp Lys Val Ala Glu Lys
1               5                   10                  15

Phe Lys Glu Ala Phe
            20

<210> SEQ ID NO 93
<211> LENGTH: 21
<212> TYPE: PRT
<213> ORGANISM: Artificial
<220> FEATURE:
<223> OTHER INFORMATION: Synthetic peptide optionally bearing
      protecting groups.

<400> SEQUENCE: 93

Asn Met Ala Glu Trp Phe Lys Ala Phe Tyr Glu Lys Val Ala Glu Lys
1               5                   10                  15

Phe Lys Glu Ala Phe
            20

<210> SEQ ID NO 94
<211> LENGTH: 17
<212> TYPE: PRT
```

<213> ORGANISM: Artificial
<220> FEATURE:
<223> OTHER INFORMATION: Synthetic peptide optionally bearing
      protecting groups.

<400> SEQUENCE: 94

Asn Met Ala Ala Phe Tyr Asp Lys Val Ala Glu Lys Phe Lys Glu Ala
1               5                   10                  15
Phe

<210> SEQ ID NO 95
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 95

Asn Met Ala Asp Trp Phe Lys Ala Phe Tyr Asp Lys Val Ala Glu Lys
1               5                   10                  15
Phe

<210> SEQ ID NO 96
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 96

Asp Trp Leu Lys Ala Phe Tyr Asp Lys Val Phe Glu Lys Phe Lys Glu
1               5                   10                  15
Phe Phe

<210> SEQ ID NO 97
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 97

Glu Trp Leu Lys Ala Phe Tyr Glu Lys Val Phe Glu Lys Phe Lys Glu
1               5                   10                  15
Phe Phe

<210> SEQ ID NO 98
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 98

Ala Phe Tyr Asp Lys Val Phe Glu Lys Phe Lys Glu Phe Phe
1               5                   10

<210> SEQ ID NO 99
<211> LENGTH: 14
<212> TYPE: PRT
<213> ORGANISM: Artificial
<220> FEATURE:

```
<223> OTHER INFORMATION: Synthetic peptide optionally bearing
      protecting groups.

<400> SEQUENCE: 99

Ala Phe Tyr Glu Lys Val Phe Glu Lys Phe Lys Glu Phe Phe
1               5                   10

<210> SEQ ID NO 100
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 100

Asp Trp Leu Lys Ala Phe Tyr Asp Lys Val Phe Glu Lys Phe
1               5                   10

<210> SEQ ID NO 101
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 101

Glu Trp Leu Lys Ala Phe Tyr Glu Lys Val Phe Glu Lys Phe
1               5                   10

<210> SEQ ID NO 102
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 102

Leu Lys Ala Phe Tyr Asp Lys Val Phe Glu Lys Phe Lys Glu
1               5                   10

<210> SEQ ID NO 103
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 103

Leu Lys Ala Phe Tyr Glu Lys Val Phe Glu Lys Phe Lys Glu
1               5                   10

<210> SEQ ID NO 104
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 104

Phe Ala Glu Lys Phe Lys Glu Ala Val Lys Asp Tyr Phe Ala Lys Phe
1               5                   10                  15

Trp Asp
```

```
<210> SEQ ID NO 105
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 105

Asp Lys Trp Lys Ala Val Tyr Asp Lys Phe Ala Glu Ala Phe Lys Glu
1               5                   10                  15

Phe Leu

<210> SEQ ID NO 106
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 106

Asp Lys Leu Lys Ala Phe Tyr Asp Lys Val Phe Glu Trp Ala Lys Glu
1               5                   10                  15

Ala Phe

<210> SEQ ID NO 107
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 107

Glu Trp Phe Lys Ala Phe Tyr Glu Lys Val Ala Asp Lys Phe Lys Asp
1               5                   10                  15

Ala Phe

<210> SEQ ID NO 108
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 108

Glu Trp Phe Lys Ala Phe Tyr Asp Lys Val Ala Asp Lys Phe Lys Glu
1               5                   10                  15

Ala Phe

<210> SEQ ID NO 109
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 109

Asp Trp Phe Lys Ala Phe Tyr Glu Lys Val Ala Asp Lys Phe Lys Glu
1               5                   10                  15

Ala Phe
```

```
<210> SEQ ID NO 110
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 110

Asp Trp Phe Lys Ala Phe Tyr Glu Lys Val Ala Glu Lys Phe Lys Asp
1               5                   10                  15

Ala Phe

<210> SEQ ID NO 111
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 111

Asp Phe Trp Lys Ala Phe Tyr Asp Lys Val Ala Glu Lys Phe Lys Glu
1               5                   10                  15

Ala Phe

<210> SEQ ID NO 112
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 112

Glu Phe Trp Lys Ala Phe Tyr Glu Lys Val Ala Asp Lys Phe Lys Asp
1               5                   10                  15

Ala Phe

<210> SEQ ID NO 113
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 113

Glu Phe Trp Lys Ala Phe Tyr Asp Lys Val Ala Asp Lys Phe Lys Glu
1               5                   10                  15

Ala Phe

<210> SEQ ID NO 114
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 114

Asp Phe Trp Lys Ala Phe Tyr Glu Lys Val Ala Asp Lys Phe Lys Glu
1               5                   10                  15

Ala Phe
```

```
<210> SEQ ID NO 115
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 115

Asp Phe Trp Lys Ala Phe Tyr Glu Lys Val Ala Glu Lys Phe Lys Asp
1               5                   10                  15

Ala Phe

<210> SEQ ID NO 116
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 116

Asp Trp Phe Lys Ala Tyr Phe Asp Lys Val Ala Glu Lys Phe Lys Glu
1               5                   10                  15

Ala Phe

<210> SEQ ID NO 117
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 117

Glu Trp Phe Lys Ala Tyr Phe Glu Lys Val Ala Asp Lys Phe Lys Asp
1               5                   10                  15

Ala Phe

<210> SEQ ID NO 118
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 118

Glu Trp Phe Lys Ala Tyr Phe Asp Lys Val Ala Asp Lys Phe Lys Glu
1               5                   10                  15

Ala Phe

<210> SEQ ID NO 119
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 119

Asp Trp Phe Lys Ala Tyr Phe Glu Lys Val Ala Asp Lys Phe Lys Glu
1               5                   10                  15

Ala Phe
```

```
<210> SEQ ID NO 120
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 120

Asp Trp Phe Lys Ala Tyr Phe Glu Lys Val Ala Glu Lys Phe Lys Asp
1               5                   10                  15

Ala Phe

<210> SEQ ID NO 121
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 121

Asp Trp Phe Lys Ala Phe Val Asp Lys Tyr Ala Glu Lys Phe Lys Glu
1               5                   10                  15

Ala Phe

<210> SEQ ID NO 122
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 122

Glu Trp Phe Lys Ala Phe Val Glu Lys Tyr Ala Asp Lys Phe Lys Asp
1               5                   10                  15

Ala Phe

<210> SEQ ID NO 123
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 123

Glu Trp Phe Lys Ala Phe Val Asp Lys Tyr Ala Asp Lys Phe Lys Glu
1               5                   10                  15

Ala Phe

<210> SEQ ID NO 124
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 124

Asp Trp Phe Lys Ala Phe Val Glu Lys Tyr Ala Asp Lys Phe Lys Glu
1               5                   10                  15

Ala Phe
```

```
<210> SEQ ID NO 125
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 125

Asp Trp Phe Lys Ala Phe Val Glu Lys Tyr Ala Glu Lys Phe Lys Asp
1               5                   10                  15

Ala Phe

<210> SEQ ID NO 126
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 126

Asp Trp Phe Lys Ala Phe Tyr Asp Lys Ala Val Glu Lys Phe Lys Glu
1               5                   10                  15

Ala Phe

<210> SEQ ID NO 127
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 127

Glu Trp Phe Lys Ala Phe Tyr Glu Lys Ala Val Asp Lys Phe Lys Asp
1               5                   10                  15

Ala Phe

<210> SEQ ID NO 128
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 128

Glu Trp Phe Lys Ala Phe Tyr Asp Lys Ala Val Asp Lys Phe Lys Glu
1               5                   10                  15

Ala Phe

<210> SEQ ID NO 129
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 129

Asp Trp Phe Lys Ala Phe Tyr Glu Lys Ala Val Asp Lys Phe Lys Glu
1               5                   10                  15

Ala Phe
```

<210> SEQ ID NO 130
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 130

Asp Trp Phe Lys Ala Phe Tyr Glu Lys Ala Val Glu Lys Phe Lys Asp
1               5                   10                  15

Ala Phe

<210> SEQ ID NO 131
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 131

Asp Trp Phe Lys Ala Phe Tyr Asp Lys Val Phe Glu Lys Ala Lys Glu
1               5                   10                  15

Ala Phe

<210> SEQ ID NO 132
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 132

Glu Trp Phe Lys Ala Phe Tyr Glu Lys Val Phe Asp Lys Ala Lys Asp
1               5                   10                  15

Ala Phe

<210> SEQ ID NO 133
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 133

Glu Trp Phe Lys Ala Phe Tyr Asp Lys Val Phe Asp Lys Ala Lys Glu
1               5                   10                  15

Ala Phe

<210> SEQ ID NO 134
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 134

Asp Trp Phe Lys Ala Phe Tyr Glu Lys Val Phe Asp Lys Ala Lys Glu
1               5                   10                  15

Ala Phe

```
<210> SEQ ID NO 135
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 135

Asp Trp Phe Lys Ala Phe Tyr Glu Lys Val Phe Glu Lys Ala Lys Asp
1               5                   10                  15

Ala Phe

<210> SEQ ID NO 136
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 136

Asp Trp Phe Lys Ala Phe Tyr Asp Lys Val Ala Glu Lys Ala Lys Glu
1               5                   10                  15

Phe Phe

<210> SEQ ID NO 137
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 137

Glu Trp Phe Lys Ala Phe Tyr Glu Lys Val Ala Asp Lys Ala Lys Asp
1               5                   10                  15

Phe Phe

<210> SEQ ID NO 138
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 138

Glu Trp Phe Lys Ala Phe Tyr Asp Lys Val Ala Asp Lys Ala Lys Glu
1               5                   10                  15

Phe Phe

<210> SEQ ID NO 139
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 139

Asp Trp Phe Lys Ala Phe Tyr Glu Lys Val Ala Asp Lys Ala Lys Glu
1               5                   10                  15

Phe Phe
```

<210> SEQ ID NO 140
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 140

Asp Trp Phe Lys Ala Phe Tyr Glu Lys Val Ala Glu Lys Ala Lys Asp
1               5                   10                  15

Phe Phe

<210> SEQ ID NO 141
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 141

Asp Trp Phe Lys Ala Phe Tyr Asp Lys Val Ala Glu Lys Phe Lys Glu
1               5                   10                  15

Phe Ala

<210> SEQ ID NO 142
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 142

Glu Trp Phe Lys Ala Phe Tyr Glu Lys Val Ala Asp Lys Phe Lys Asp
1               5                   10                  15

Phe Ala

<210> SEQ ID NO 143
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 143

Glu Trp Phe Lys Ala Phe Tyr Asp Lys Val Ala Asp Lys Phe Lys Glu
1               5                   10                  15

Phe Ala

<210> SEQ ID NO 144
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 144

Asp Trp Phe Lys Ala Phe Tyr Glu Lys Val Ala Asp Lys Phe Lys Glu
1               5                   10                  15

Phe Ala

```
<210> SEQ ID NO 145
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 145

Asp Trp Phe Lys Ala Phe Tyr Glu Lys Val Ala Glu Lys Phe Lys Asp
1               5                   10                  15

Phe Ala

<210> SEQ ID NO 146
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 146

Asp Ala Phe Lys Ala Phe Tyr Asp Lys Val Ala Glu Lys Phe Lys Glu
1               5                   10                  15

Trp Phe

<210> SEQ ID NO 147
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 147

Glu Ala Phe Lys Ala Phe Tyr Glu Lys Val Ala Asp Lys Phe Lys Asp
1               5                   10                  15

Trp Phe

<210> SEQ ID NO 148
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 148

Glu Ala Phe Lys Ala Phe Tyr Asp Lys Val Ala Asp Lys Phe Lys Glu
1               5                   10                  15

Trp Phe

<210> SEQ ID NO 149
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 149

Asp Ala Phe Lys Ala Phe Tyr Glu Lys Val Ala Asp Lys Phe Lys Glu
1               5                   10                  15

Trp Phe
```

```
<210> SEQ ID NO 150
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 150

Asp Ala Phe Lys Ala Phe Tyr Glu Lys Val Ala Glu Lys Phe Lys Asp
1               5                   10                  15

Trp Phe

<210> SEQ ID NO 151
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 151

Asp Ala Phe Lys Ala Phe Tyr Asp Lys Val Trp Glu Lys Phe Lys Glu
1               5                   10                  15

Ala Phe

<210> SEQ ID NO 152
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 152

Glu Ala Phe Lys Ala Phe Tyr Glu Lys Val Trp Asp Lys Phe Lys Asp
1               5                   10                  15

Ala Phe

<210> SEQ ID NO 153
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 153

Glu Ala Phe Lys Ala Phe Tyr Asp Lys Val Trp Asp Lys Phe Lys Glu
1               5                   10                  15

Ala Phe

<210> SEQ ID NO 154
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 154

Asp Ala Phe Lys Ala Phe Tyr Glu Lys Val Trp Asp Lys Phe Lys Glu
1               5                   10                  15

Ala Phe
```

-continued

<210> SEQ ID NO 155
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 155

Asp Ala Phe Lys Ala Phe Tyr Glu Lys Val Trp Glu Lys Phe Lys Asp
1               5                   10                  15

Ala Phe

<210> SEQ ID NO 156
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 156

Asp Tyr Phe Lys Ala Phe Trp Asp Lys Val Ala Glu Lys Phe Lys Glu
1               5                   10                  15

Ala Phe

<210> SEQ ID NO 157
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 157

Glu Tyr Phe Lys Ala Phe Trp Glu Lys Val Ala Asp Lys Phe Lys Asp
1               5                   10                  15

Ala Phe

<210> SEQ ID NO 158
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 158

Glu Tyr Phe Lys Ala Phe Trp Asp Lys Val Ala Asp Lys Phe Lys Glu
1               5                   10                  15

Ala Phe

<210> SEQ ID NO 159
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 159

Asp Tyr Phe Lys Ala Phe Trp Glu Lys Val Ala Asp Lys Phe Lys Glu
1               5                   10                  15

Ala Phe

```
<210> SEQ ID NO 160
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 160

Asp Tyr Phe Lys Ala Phe Trp Glu Lys Val Ala Glu Lys Phe Lys Asp
1               5                   10                  15

Ala Phe

<210> SEQ ID NO 161
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 161

Asp Trp Ala Lys Ala Phe Tyr Asp Lys Val Ala Glu Lys Phe Lys Glu
1               5                   10                  15

Phe Phe

<210> SEQ ID NO 162
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 162

Glu Trp Ala Lys Ala Phe Tyr Glu Lys Val Ala Asp Lys Phe Lys Asp
1               5                   10                  15

Phe Phe

<210> SEQ ID NO 163
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 163

Glu Trp Ala Lys Ala Phe Tyr Asp Lys Val Ala Asp Lys Phe Lys Glu
1               5                   10                  15

Phe Phe

<210> SEQ ID NO 164
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 164

Asp Trp Ala Lys Ala Phe Tyr Glu Lys Val Ala Asp Lys Phe Lys Glu
1               5                   10                  15

Phe Phe
```

```
<210> SEQ ID NO 165
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 165

Asp Trp Ala Lys Ala Phe Tyr Glu Lys Val Ala Glu Lys Phe Lys Asp
1               5                   10                  15

Phe Phe

<210> SEQ ID NO 166
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 166

Asp Trp Phe Lys Ala Ala Tyr Asp Lys Val Ala Glu Lys Phe Lys Glu
1               5                   10                  15

Phe Phe

<210> SEQ ID NO 167
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 167

Glu Trp Phe Lys Ala Ala Tyr Glu Lys Val Ala Asp Lys Phe Lys Asp
1               5                   10                  15

Phe Phe

<210> SEQ ID NO 168
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 168

Glu Trp Phe Lys Ala Ala Tyr Asp Lys Val Ala Asp Lys Phe Lys Glu
1               5                   10                  15

Phe Phe

<210> SEQ ID NO 169
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 169

Asp Trp Phe Lys Ala Ala Tyr Glu Lys Val Ala Asp Lys Phe Lys Glu
1               5                   10                  15

Phe Phe
```

```
<210> SEQ ID NO 170
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 170

Asp Trp Phe Lys Ala Ala Tyr Glu Lys Val Ala Glu Lys Phe Lys Asp
1               5                   10                  15

Phe Phe

<210> SEQ ID NO 171
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 171

Asp Trp Phe Lys Ala Phe Ala Asp Lys Val Ala Glu Lys Phe Lys Glu
1               5                   10                  15

Tyr Phe

<210> SEQ ID NO 172
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 172

Glu Trp Phe Lys Ala Phe Ala Glu Lys Val Ala Asp Lys Phe Lys Asp
1               5                   10                  15

Tyr Phe

<210> SEQ ID NO 173
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 173

Glu Trp Phe Lys Ala Phe Ala Asp Lys Val Ala Asp Lys Phe Lys Glu
1               5                   10                  15

Tyr Phe

<210> SEQ ID NO 174
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 174

Asp Trp Phe Lys Ala Phe Ala Glu Lys Val Ala Asp Lys Phe Lys Glu
1               5                   10                  15

Tyr Phe
```

```
<210> SEQ ID NO 175
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 175

Asp Trp Phe Lys Ala Phe Ala Glu Lys Val Ala Glu Lys Phe Lys Asp
1               5                   10                  15

Tyr Phe

<210> SEQ ID NO 176
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 176

Asp Trp Phe Lys Ala Phe Tyr Asp Lys Ala Ala Glu Lys Phe Lys Glu
1               5                   10                  15

Val Phe

<210> SEQ ID NO 177
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 177

Glu Trp Phe Lys Ala Phe Tyr Glu Lys Ala Ala Asp Lys Phe Lys Asp
1               5                   10                  15

Val Phe

<210> SEQ ID NO 178
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 178

Glu Trp Phe Lys Ala Phe Tyr Asp Lys Ala Ala Asp Lys Phe Lys Glu
1               5                   10                  15

Val Phe

<210> SEQ ID NO 179
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 179

Asp Trp Phe Lys Ala Phe Tyr Glu Lys Ala Ala Asp Lys Phe Lys Glu
1               5                   10                  15

Val Phe
```

```
<210> SEQ ID NO 180
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 180

Asp Trp Phe Lys Ala Phe Tyr Glu Lys Ala Ala Glu Lys Phe Lys Asp
1               5                   10                  15

Val Phe

<210> SEQ ID NO 181
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 181

Asp Trp Tyr Lys Ala Phe Phe Asp Lys Val Ala Glu Lys Phe Lys Glu
1               5                   10                  15

Ala Phe

<210> SEQ ID NO 182
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 182

Glu Trp Tyr Lys Ala Phe Phe Glu Lys Val Ala Asp Lys Phe Lys Asp
1               5                   10                  15

Ala Phe

<210> SEQ ID NO 183
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 183

Glu Trp Tyr Lys Ala Phe Phe Asp Lys Val Ala Asp Lys Phe Lys Glu
1               5                   10                  15

Ala Phe

<210> SEQ ID NO 184
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 184

Asp Trp Tyr Lys Ala Phe Phe Glu Lys Val Ala Asp Lys Phe Lys Glu
1               5                   10                  15

Ala Phe
```

```
<210> SEQ ID NO 185
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 185

Asp Trp Tyr Lys Ala Phe Phe Glu Lys Val Ala Glu Lys Phe Lys Asp
1               5                   10                  15

Ala Phe

<210> SEQ ID NO 186
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 186

Asp Trp Val Lys Ala Phe Tyr Asp Lys Phe Ala Glu Lys Phe Lys Glu
1               5                   10                  15

Ala Phe

<210> SEQ ID NO 187
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 187

Glu Trp Val Lys Ala Phe Tyr Glu Lys Phe Ala Asp Lys Phe Lys Asp
1               5                   10                  15

Ala Phe

<210> SEQ ID NO 188
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 188

Glu Trp Val Lys Ala Phe Tyr Asp Lys Phe Ala Asp Lys Phe Lys Glu
1               5                   10                  15

Ala Phe

<210> SEQ ID NO 189
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 189

Asp Trp Val Lys Ala Phe Tyr Glu Lys Phe Ala Asp Lys Phe Lys Glu
1               5                   10                  15

Ala Phe
```

```
<210> SEQ ID NO 190
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 190

Asp Trp Val Lys Ala Phe Tyr Glu Lys Phe Ala Glu Lys Phe Lys Asp
1               5                   10                  15

Ala Phe

<210> SEQ ID NO 191
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 191

Asp Trp Phe Lys Ala Phe Phe Asp Lys Val Ala Glu Lys Tyr Lys Glu
1               5                   10                  15

Ala Phe

<210> SEQ ID NO 192
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 192

Glu Trp Phe Lys Ala Phe Phe Glu Lys Val Ala Asp Lys Tyr Lys Asp
1               5                   10                  15

Ala Phe

<210> SEQ ID NO 193
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 193

Glu Trp Phe Lys Ala Phe Phe Asp Lys Val Ala Asp Lys Tyr Lys Glu
1               5                   10                  15

Ala Phe

<210> SEQ ID NO 194
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 194

Asp Trp Phe Lys Ala Phe Phe Glu Lys Val Ala Asp Lys Tyr Lys Glu
1               5                   10                  15

Ala Phe
```

```
<210> SEQ ID NO 195
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 195

Asp Trp Phe Lys Ala Phe Phe Glu Lys Val Ala Asp Lys Tyr Lys Glu
1               5                   10                  15

Ala Phe

<210> SEQ ID NO 196
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 196

Asp Trp Phe Lys Ala Phe Phe Asp Lys Val Ala Glu Lys Phe Lys Glu
1               5                   10                  15

Ala Tyr

<210> SEQ ID NO 197
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 197

Glu Trp Phe Lys Ala Phe Phe Glu Lys Val Ala Asp Lys Phe Lys Asp
1               5                   10                  15

Ala Tyr

<210> SEQ ID NO 198
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 198

Glu Trp Phe Lys Ala Phe Phe Asp Lys Val Ala Asp Lys Phe Lys Glu
1               5                   10                  15

Ala Tyr

<210> SEQ ID NO 199
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 199

Asp Trp Phe Lys Ala Phe Phe Glu Lys Val Ala Asp Lys Phe Lys Glu
1               5                   10                  15

Ala Tyr
```

```
<210> SEQ ID NO 200
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 200

Asp Trp Phe Lys Ala Phe Phe Glu Lys Val Ala Glu Lys Phe Lys Asp
1               5                   10                  15

Ala Tyr

<210> SEQ ID NO 201
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 201

Asp Trp Phe Lys Ala Phe Tyr Asp Lys Phe Ala Glu Lys Phe Lys Glu
1               5                   10                  15

Ala Val

<210> SEQ ID NO 202
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 202

Glu Trp Phe Lys Ala Phe Tyr Glu Lys Phe Ala Asp Lys Phe Lys Asp
1               5                   10                  15

Ala Val

<210> SEQ ID NO 203
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 203

Glu Trp Phe Lys Ala Phe Tyr Asp Lys Phe Ala Asp Lys Phe Lys Glu
1               5                   10                  15

Ala Val

<210> SEQ ID NO 204
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 204

Asp Trp Phe Lys Ala Phe Tyr Glu Lys Phe Ala Asp Lys Phe Lys Glu
1               5                   10                  15

Ala Val
```

```
<210> SEQ ID NO 205
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 205

Asp Trp Phe Lys Ala Phe Tyr Glu Lys Phe Ala Glu Lys Phe Lys Asp
1               5                   10                  15

Ala Val

<210> SEQ ID NO 206
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 206

Asp Lys Phe Lys Ala Phe Tyr Asp Lys Val Ala Glu Lys Phe Trp Glu
1               5                   10                  15

Ala Phe

<210> SEQ ID NO 207
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 207

Glu Lys Phe Lys Ala Phe Tyr Glu Lys Val Ala Asp Lys Phe Trp Asp
1               5                   10                  15

Ala Phe

<210> SEQ ID NO 208
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 208

Glu Lys Phe Lys Ala Phe Tyr Asp Lys Val Ala Asp Lys Phe Trp Glu
1               5                   10                  15

Ala Phe

<210> SEQ ID NO 209
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 209

Asp Lys Phe Lys Ala Phe Tyr Glu Lys Val Ala Asp Lys Phe Trp Glu
1               5                   10                  15

Ala Phe
```

```
<210> SEQ ID NO 210
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 210

Asp Lys Phe Lys Ala Phe Tyr Glu Lys Val Ala Glu Lys Phe Trp Asp
1               5                   10                  15

Ala Phe

<210> SEQ ID NO 211
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 211

Asp Lys Trp Lys Ala Phe Tyr Asp Lys Val Ala Glu Lys Phe Phe Glu
1               5                   10                  15

Ala Phe

<210> SEQ ID NO 212
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 212

Glu Lys Trp Lys Ala Phe Tyr Glu Lys Val Ala Asp Lys Phe Phe Asp
1               5                   10                  15

Ala Phe

<210> SEQ ID NO 213
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 213

Glu Lys Trp Lys Ala Phe Tyr Asp Lys Val Ala Asp Lys Phe Phe Glu
1               5                   10                  15

Ala Phe

<210> SEQ ID NO 214
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 214

Asp Lys Trp Lys Ala Phe Tyr Glu Lys Val Ala Asp Lys Phe Phe Glu
1               5                   10                  15

Ala Phe
```

<210> SEQ ID NO 215
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 215

Asp Lys Trp Lys Ala Phe Tyr Glu Lys Val Ala Glu Lys Phe Phe Asp
1               5                   10                  15

Ala Phe

<210> SEQ ID NO 216
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 216

Asp Lys Phe Lys Ala Phe Tyr Asp Lys Trp Ala Glu Val Phe Lys Glu
1               5                   10                  15

Ala Phe

<210> SEQ ID NO 217
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 217

Glu Lys Phe Lys Ala Phe Tyr Glu Lys Trp Ala Asp Val Phe Lys Asp
1               5                   10                  15

Ala Phe

<210> SEQ ID NO 218
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 218

Glu Lys Phe Lys Ala Phe Tyr Asp Lys Trp Ala Asp Val Phe Lys Glu
1               5                   10                  15

Ala Phe

<210> SEQ ID NO 219
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 219

Asp Lys Phe Lys Ala Phe Tyr Glu Lys Trp Ala Asp Val Phe Lys Glu
1               5                   10                  15

Ala Phe

<210> SEQ ID NO 220
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 220

Asp Lys Phe Lys Ala Phe Tyr Glu Lys Trp Ala Glu Val Phe Lys Asp
1               5                   10                  15

Ala Phe

<210> SEQ ID NO 221
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 221

Asp Lys Phe Lys Ala Phe Tyr Asp Lys Val Ala Glu Phe Trp Lys Glu
1               5                   10                  15

Ala Phe

<210> SEQ ID NO 222
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 222

Glu Lys Phe Lys Ala Phe Tyr Glu Lys Val Ala Asp Phe Trp Lys Asp
1               5                   10                  15

Ala Phe

<210> SEQ ID NO 223
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 223

Glu Lys Phe Lys Ala Phe Tyr Asp Lys Val Ala Asp Phe Trp Lys Glu
1               5                   10                  15

Ala Phe

<210> SEQ ID NO 224
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 224

Asp Lys Phe Lys Ala Phe Tyr Glu Lys Val Ala Asp Phe Trp Lys Glu
1               5                   10                  15

Ala Phe

```
<210> SEQ ID NO 225
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 225

Asp Lys Phe Lys Ala Phe Tyr Glu Lys Val Ala Glu Phe Trp Lys Asp
1               5                   10                  15

Ala Phe

<210> SEQ ID NO 226
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 226

Phe Ala Glu Lys Phe Lys Glu Ala Val Lys Asp Tyr Phe Ala Lys Phe
1               5                   10                  15

Trp Asp

<210> SEQ ID NO 227
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 227

Phe Ala Asp Lys Phe Lys Asp Ala Val Lys Glu Tyr Phe Ala Lys Phe
1               5                   10                  15

Trp Glu

<210> SEQ ID NO 228
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 228

Phe Ala Asp Lys Phe Lys Glu Ala Val Lys Asp Tyr Phe Ala Lys Phe
1               5                   10                  15

Trp Glu

<210> SEQ ID NO 229
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 229

Phe Ala Glu Lys Phe Lys Asp Ala Val Lys Glu Tyr Phe Ala Lys Phe
1               5                   10                  15

Trp Asp
```

-continued

<210> SEQ ID NO 230
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 230

Phe Ala Glu Lys Phe Lys Asp Ala Val Lys Asp Tyr Phe Ala Lys Phe
1               5                   10                  15

Trp Glu

<210> SEQ ID NO 231
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 231

Phe Trp Glu Lys Phe Lys Glu Ala Val Lys Asp Tyr Phe Ala Lys Phe
1               5                   10                  15

Ala Asp

<210> SEQ ID NO 232
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 232

Phe Trp Asp Lys Phe Lys Asp Ala Val Lys Glu Tyr Phe Ala Lys Phe
1               5                   10                  15

Ala Glu

<210> SEQ ID NO 233
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 233

Phe Ala Asp Lys Phe Lys Glu Ala Val Lys Asp Tyr Phe Ala Lys Phe
1               5                   10                  15

Trp Glu

<210> SEQ ID NO 234
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 234

Phe Ala Glu Lys Phe Lys Asp Ala Val Lys Glu Tyr Phe Ala Lys Phe
1               5                   10                  15

Trp Asp

```
<210> SEQ ID NO 235
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 235

Phe Ala Glu Lys Phe Lys Asp Ala Val Lys Asp Tyr Phe Ala Lys Phe
1               5                   10                  15

Trp Glu

<210> SEQ ID NO 236
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 236

Phe Phe Glu Lys Phe Lys Glu Ala Val Lys Asp Tyr Phe Ala Lys Ala
1               5                   10                  15

Trp Asp

<210> SEQ ID NO 237
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 237

Phe Phe Asp Lys Phe Lys Asp Ala Val Lys Glu Tyr Phe Ala Lys Ala
1               5                   10                  15

Trp Glu

<210> SEQ ID NO 238
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 238

Phe Phe Asp Lys Phe Lys Glu Ala Val Lys Asp Tyr Phe Ala Lys Ala
1               5                   10                  15

Trp Glu

<210> SEQ ID NO 239
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 239

Phe Phe Glu Lys Phe Lys Asp Ala Val Lys Glu Tyr Phe Ala Lys Ala
1               5                   10                  15

Trp Asp
```

-continued

```
<210> SEQ ID NO 240
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 240

Phe Phe Glu Lys Phe Lys Asp Ala Val Lys Asp Tyr Phe Ala Lys Ala
1               5                   10                  15

Trp Glu

<210> SEQ ID NO 241
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 241

Phe Ala Glu Lys Ala Lys Glu Phe Val Lys Asp Tyr Phe Ala Lys Phe
1               5                   10                  15

Trp Asp

<210> SEQ ID NO 242
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 242

Phe Ala Asp Lys Ala Lys Asp Phe Val Lys Glu Tyr Phe Ala Lys Phe
1               5                   10                  15

Trp Glu

<210> SEQ ID NO 243
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 243

Phe Ala Asp Lys Ala Lys Glu Phe Val Lys Asp Tyr Phe Ala Lys Phe
1               5                   10                  15

Trp Glu

<210> SEQ ID NO 244
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 244

Phe Ala Glu Lys Ala Lys Asp Phe Val Lys Glu Tyr Phe Ala Lys Phe
1               5                   10                  15

Trp Asp
```

```
<210> SEQ ID NO 245
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 245

Phe Ala Glu Lys Ala Lys Asp Phe Val Lys Asp Tyr Phe Ala Lys Phe
1               5                   10                  15

Trp Glu

<210> SEQ ID NO 246
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 246

Phe Ala Glu Lys Phe Lys Glu Val Ala Lys Asp Tyr Phe Ala Lys Phe
1               5                   10                  15

Trp Asp

<210> SEQ ID NO 247
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 247

Phe Ala Asp Lys Phe Lys Asp Val Ala Lys Glu Tyr Phe Ala Lys Phe
1               5                   10                  15

Trp Glu

<210> SEQ ID NO 248
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 248

Phe Ala Asp Lys Phe Lys Glu Val Ala Lys Asp Tyr Phe Ala Lys Phe
1               5                   10                  15

Trp Glu

<210> SEQ ID NO 249
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 249

Phe Ala Glu Lys Phe Lys Asp Val Ala Lys Glu Tyr Phe Ala Lys Phe
1               5                   10                  15

Trp Asp
```

```
<210> SEQ ID NO 250
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 250

Phe Ala Glu Lys Phe Lys Asp Val Ala Lys Asp Tyr Phe Ala Lys Phe
1               5                   10                  15

Trp Glu

<210> SEQ ID NO 251
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 251

Phe Ala Glu Lys Phe Lys Glu Ala Tyr Lys Asp Val Phe Ala Lys Phe
1               5                   10                  15

Trp Asp

<210> SEQ ID NO 252
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 252

Phe Ala Asp Lys Phe Lys Asp Ala Tyr Lys Glu Val Phe Ala Lys Phe
1               5                   10                  15

Trp Glu

<210> SEQ ID NO 253
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 253

Phe Ala Asp Lys Phe Lys Glu Ala Tyr Lys Asp Val Phe Ala Lys Phe
1               5                   10                  15

Trp Glu

<210> SEQ ID NO 254
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 254

Phe Ala Glu Lys Phe Lys Asp Ala Tyr Lys Glu Val Phe Ala Lys Phe
1               5                   10                  15

Trp Asp
```

```
<210> SEQ ID NO 255
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 255

Phe Ala Glu Lys Phe Lys Asp Ala Tyr Lys Asp Val Phe Ala Lys Phe
1               5                   10                  15

Trp Glu

<210> SEQ ID NO 256
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 256

Phe Ala Glu Lys Phe Lys Glu Ala Val Lys Asp Phe Tyr Ala Lys Phe
1               5                   10                  15

Trp Asp

<210> SEQ ID NO 257
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 257

Phe Ala Asp Lys Phe Lys Asp Ala Val Lys Glu Phe Tyr Ala Lys Phe
1               5                   10                  15

Trp Glu

<210> SEQ ID NO 258
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 258

Phe Ala Asp Lys Phe Lys Glu Ala Val Lys Asp Phe Tyr Ala Lys Phe
1               5                   10                  15

Trp Glu

<210> SEQ ID NO 259
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 259

Phe Ala Glu Lys Phe Lys Asp Ala Val Lys Glu Phe Tyr Ala Lys Phe
1               5                   10                  15

Trp Asp
```

```
<210> SEQ ID NO 260
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 260

Phe Ala Glu Lys Phe Lys Asp Ala Val Lys Asp Phe Tyr Ala Lys Phe
1               5                   10                  15

Trp Glu

<210> SEQ ID NO 261
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 261

Phe Ala Glu Lys Phe Trp Glu Ala Val Lys Asp Tyr Phe Ala Lys Phe
1               5                   10                  15

Lys Asp

<210> SEQ ID NO 262
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 262

Phe Ala Asp Lys Phe Trp Asp Ala Val Lys Glu Tyr Phe Ala Lys Phe
1               5                   10                  15

Lys Glu

<210> SEQ ID NO 263
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 263

Phe Ala Asp Lys Phe Trp Glu Ala Val Lys Asp Tyr Phe Ala Lys Phe
1               5                   10                  15

Lys Glu

<210> SEQ ID NO 264
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 264

Phe Ala Glu Lys Phe Trp Asp Ala Val Lys Glu Tyr Phe Ala Lys Phe
1               5                   10                  15

Lys Asp
```

```
<210> SEQ ID NO 265
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 265

Phe Ala Glu Lys Phe Trp Asp Ala Val Lys Asp Tyr Phe Ala Lys Phe
1               5                   10                  15

Lys Glu

<210> SEQ ID NO 266
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 266

Ala Phe Glu Lys Phe Lys Glu Ala Val Lys Asp Tyr Phe Ala Lys Phe
1               5                   10                  15

Trp Asp

<210> SEQ ID NO 267
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 267

Ala Phe Asp Lys Phe Lys Asp Ala Val Lys Glu Tyr Phe Ala Lys Phe
1               5                   10                  15

Trp Glu

<210> SEQ ID NO 268
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 268

Ala Phe Asp Lys Phe Lys Glu Ala Val Lys Asp Tyr Phe Ala Lys Phe
1               5                   10                  15

Trp Glu

<210> SEQ ID NO 269
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 269

Ala Phe Glu Lys Phe Lys Asp Ala Val Lys Glu Tyr Phe Ala Lys Phe
1               5                   10                  15

Trp Asp
```

```
<210> SEQ ID NO 270
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 270

Ala Phe Glu Lys Phe Lys Asp Ala Val Lys Asp Tyr Phe Ala Lys Phe
1               5                  10                  15

Trp Glu

<210> SEQ ID NO 271
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 271

Val Ala Glu Lys Phe Lys Glu Ala Phe Lys Asp Tyr Phe Ala Lys Phe
1               5                  10                  15

Trp Asp

<210> SEQ ID NO 272
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 272

Val Ala Asp Lys Phe Lys Asp Ala Phe Lys Glu Tyr Phe Ala Lys Phe
1               5                  10                  15

Trp Glu

<210> SEQ ID NO 273
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 273

Val Ala Asp Lys Phe Lys Glu Ala Phe Lys Asp Tyr Phe Ala Lys Phe
1               5                  10                  15

Trp Glu

<210> SEQ ID NO 274
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 274

Val Ala Glu Lys Phe Lys Asp Ala Phe Lys Glu Tyr Phe Ala Lys Phe
1               5                  10                  15

Trp Asp
```

-continued

<210> SEQ ID NO 275
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 275

Val Ala Glu Lys Phe Lys Asp Ala Phe Lys Asp Tyr Phe Ala Lys Phe
1               5                   10                  15

Trp Glu

<210> SEQ ID NO 276
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 276

Tyr Ala Glu Lys Phe Lys Glu Ala Val Lys Asp Phe Phe Ala Lys Phe
1               5                   10                  15

Trp Asp

<210> SEQ ID NO 277
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 277

Tyr Ala Asp Lys Phe Lys Asp Ala Val Lys Glu Phe Phe Ala Lys Phe
1               5                   10                  15

Trp Glu

<210> SEQ ID NO 278
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 278

Tyr Ala Asp Lys Phe Lys Glu Ala Val Lys Asp Phe Phe Ala Lys Phe
1               5                   10                  15

Trp Glu

<210> SEQ ID NO 279
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 279

Tyr Ala Glu Lys Phe Lys Asp Ala Val Lys Glu Phe Phe Ala Lys Phe
1               5                   10                  15

Trp Asp

<210> SEQ ID NO 280
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 280

Tyr Ala Glu Lys Phe Lys Asp Ala Val Lys Asp Phe Phe Ala Lys Phe
1               5                   10                  15

Trp Glu

<210> SEQ ID NO 281
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 281

Ala Ala Glu Lys Phe Lys Glu Phe Val Lys Asp Tyr Phe Ala Lys Phe
1               5                   10                  15

Trp Asp

<210> SEQ ID NO 282
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 282

Ala Ala Asp Lys Phe Lys Asp Phe Val Lys Glu Tyr Phe Ala Lys Phe
1               5                   10                  15

Trp Glu

<210> SEQ ID NO 283
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 283

Ala Ala Asp Lys Phe Lys Glu Phe Val Lys Asp Tyr Phe Ala Lys Phe
1               5                   10                  15

Trp Glu

<210> SEQ ID NO 284
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 284

Ala Ala Glu Lys Phe Lys Asp Phe Val Lys Glu Tyr Phe Ala Lys Phe
1               5                   10                  15

Trp Asp

```
<210> SEQ ID NO 285
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 285

Ala Ala Glu Lys Phe Lys Asp Phe Val Lys Asp Tyr Phe Ala Lys Phe
1               5                   10                  15

Trp Glu

<210> SEQ ID NO 286
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 286

Phe Phe Glu Lys Ala Lys Glu Ala Val Lys Asp Tyr Phe Ala Lys Phe
1               5                   10                  15

Trp Asp

<210> SEQ ID NO 287
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 287

Phe Phe Asp Lys Ala Lys Asp Ala Val Lys Glu Tyr Phe Ala Lys Phe
1               5                   10                  15

Trp Glu

<210> SEQ ID NO 288
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 288

Phe Phe Asp Lys Ala Lys Glu Ala Val Lys Asp Tyr Phe Ala Lys Phe
1               5                   10                  15

Trp Glu

<210> SEQ ID NO 289
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 289

Phe Phe Glu Lys Ala Lys Asp Ala Val Lys Glu Tyr Phe Ala Lys Phe
1               5                   10                  15

Trp Asp
```

-continued

```
<210> SEQ ID NO 290
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 290

Phe Phe Glu Lys Ala Lys Asp Ala Val Lys Asp Tyr Phe Ala Lys Phe
1               5                   10                  15

Trp Glu

<210> SEQ ID NO 291
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 291

Phe Tyr Glu Lys Phe Lys Glu Ala Val Lys Asp Ala Phe Ala Lys Phe
1               5                   10                  15

Trp Asp

<210> SEQ ID NO 292
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 292

Phe Tyr Asp Lys Phe Lys Asp Ala Val Lys Glu Ala Phe Ala Lys Phe
1               5                   10                  15

Trp Glu

<210> SEQ ID NO 293
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 293

Phe Tyr Asp Lys Phe Lys Glu Ala Val Lys Asp Ala Phe Ala Lys Phe
1               5                   10                  15

Trp Glu

<210> SEQ ID NO 294
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 294

Phe Tyr Glu Lys Phe Lys Asp Ala Val Lys Glu Ala Phe Ala Lys Phe
1               5                   10                  15

Trp Asp
```

-continued

<210> SEQ ID NO 295
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 295

Phe Tyr Glu Lys Phe Lys Asp Ala Val Lys Asp Ala Phe Ala Lys Phe
1               5                   10                  15

Trp Glu

<210> SEQ ID NO 296
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 296

Phe Val Glu Lys Phe Lys Glu Ala Ala Lys Asp Tyr Phe Ala Lys Phe
1               5                   10                  15

Trp Asp

<210> SEQ ID NO 297
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 297

Phe Val Asp Lys Phe Lys Asp Ala Ala Lys Glu Tyr Phe Ala Lys Phe
1               5                   10                  15

Trp Glu

<210> SEQ ID NO 298
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 298

Phe Val Asp Lys Phe Lys Glu Ala Ala Lys Asp Tyr Phe Ala Lys Phe
1               5                   10                  15

Trp Glu

<210> SEQ ID NO 299
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 299

Phe Val Glu Lys Phe Lys Asp Ala Ala Lys Glu Tyr Phe Ala Lys Phe
1               5                   10                  15

Trp Asp

```
<210> SEQ ID NO 300
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 300

Phe Val Glu Lys Phe Lys Asp Ala Ala Lys Asp Tyr Phe Ala Lys Phe
1               5                   10                  15

Trp Glu

<210> SEQ ID NO 301
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 301

Phe Ala Glu Lys Tyr Lys Glu Ala Val Lys Asp Phe Phe Ala Lys Phe
1               5                   10                  15

Trp Asp

<210> SEQ ID NO 302
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 302

Phe Ala Asp Lys Tyr Lys Asp Ala Val Lys Glu Phe Phe Ala Lys Phe
1               5                   10                  15

Trp Glu

<210> SEQ ID NO 303
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 303

Phe Ala Asp Lys Tyr Lys Glu Ala Val Lys Asp Phe Phe Ala Lys Phe
1               5                   10                  15

Trp Glu

<210> SEQ ID NO 304
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 304

Phe Ala Glu Lys Tyr Lys Asp Ala Val Lys Glu Phe Phe Ala Lys Phe
1               5                   10                  15

Trp Asp
```

```
<210> SEQ ID NO 305
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 305

Phe Ala Glu Lys Tyr Lys Asp Ala Val Lys Asp Phe Phe Ala Lys Phe
1               5                   10                  15

Trp Glu

<210> SEQ ID NO 306
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 306

Phe Ala Glu Lys Val Lys Glu Ala Phe Lys Asp Tyr Phe Ala Lys Phe
1               5                   10                  15

Trp Asp

<210> SEQ ID NO 307
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 307

Phe Ala Asp Lys Val Lys Asp Ala Phe Lys Glu Tyr Phe Ala Lys Phe
1               5                   10                  15

Trp Glu

<210> SEQ ID NO 308
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 308

Phe Ala Asp Lys Val Lys Glu Ala Phe Lys Asp Tyr Phe Ala Lys Phe
1               5                   10                  15

Trp Glu

<210> SEQ ID NO 309
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 309

Phe Ala Glu Lys Val Lys Asp Ala Phe Lys Glu Tyr Phe Ala Lys Phe
1               5                   10                  15

Trp Asp
```

```
<210> SEQ ID NO 310
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 310

Phe Ala Glu Lys Val Lys Asp Ala Phe Lys Asp Tyr Phe Ala Lys Phe
1               5                   10                  15

Trp Glu

<210> SEQ ID NO 311
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 311

Phe Ala Glu Lys Phe Lys Glu Tyr Val Lys Asp Ala Phe Ala Lys Phe
1               5                   10                  15

Trp Asp

<210> SEQ ID NO 312
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 312

Phe Ala Asp Lys Phe Lys Asp Tyr Val Lys Glu Ala Phe Ala Lys Phe
1               5                   10                  15

Trp Glu

<210> SEQ ID NO 313
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 313

Phe Ala Asp Lys Phe Lys Glu Tyr Val Lys Asp Ala Phe Ala Lys Phe
1               5                   10                  15

Trp Glu

<210> SEQ ID NO 314
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 314

Phe Ala Glu Lys Phe Lys Asp Tyr Val Lys Glu Ala Phe Ala Lys Phe
1               5                   10                  15

Trp Asp
```

<210> SEQ ID NO 315
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 315

Phe Ala Glu Lys Phe Lys Asp Tyr Val Lys Asp Ala Phe Ala Lys Phe
1               5                   10                  15

Trp Glu

<210> SEQ ID NO 316
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 316

Phe Ala Glu Lys Phe Lys Glu Ala Phe Lys Asp Tyr Val Ala Lys Phe
1               5                   10                  15

Trp Asp

<210> SEQ ID NO 317
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 317

Phe Ala Asp Lys Phe Lys Asp Ala Phe Lys Glu Tyr Val Ala Lys Phe
1               5                   10                  15

Trp Glu

<210> SEQ ID NO 318
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 318

Phe Ala Asp Lys Phe Lys Glu Ala Phe Lys Asp Tyr Val Ala Lys Phe
1               5                   10                  15

Trp Glu

<210> SEQ ID NO 319
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 319

Phe Ala Glu Lys Phe Lys Asp Ala Phe Lys Glu Tyr Val Ala Lys Phe
1               5                   10                  15

Trp Asp

```
<210> SEQ ID NO 320
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 320

Phe Ala Glu Lys Phe Lys Asp Ala Phe Lys Asp Tyr Val Ala Lys Phe
1               5                   10                  15

Trp Glu

<210> SEQ ID NO 321
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 321

Phe Ala Glu Lys Phe Lys Glu Ala Phe Lys Asp Tyr Phe Ala Lys Val
1               5                   10                  15

Trp Asp

<210> SEQ ID NO 322
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 322

Phe Ala Asp Lys Phe Lys Asp Ala Phe Lys Glu Tyr Phe Ala Lys Val
1               5                   10                  15

Trp Glu

<210> SEQ ID NO 323
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 323

Phe Ala Asp Lys Phe Lys Glu Ala Phe Lys Asp Tyr Phe Ala Lys Val
1               5                   10                  15

Trp Glu

<210> SEQ ID NO 324
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 324

Phe Ala Glu Lys Phe Lys Asp Ala Phe Lys Glu Tyr Phe Ala Lys Val
1               5                   10                  15

Trp Asp
```

-continued

```
<210> SEQ ID NO 325
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 325

Phe Ala Glu Lys Phe Lys Asp Ala Phe Lys Asp Tyr Phe Ala Lys Val
1               5                   10                  15

Trp Glu

<210> SEQ ID NO 326
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 326

Phe Ala Glu Lys Phe Lys Glu Ala Val Lys Asp Phe Phe Ala Lys Tyr
1               5                   10                  15

Trp Asp

<210> SEQ ID NO 327
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 327

Phe Ala Asp Lys Phe Lys Asp Ala Val Lys Glu Phe Phe Ala Lys Tyr
1               5                   10                  15

Trp Glu

<210> SEQ ID NO 328
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 328

Phe Ala Asp Lys Phe Lys Glu Ala Val Lys Asp Phe Phe Ala Lys Tyr
1               5                   10                  15

Trp Glu

<210> SEQ ID NO 329
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 329

Phe Ala Glu Lys Phe Lys Asp Ala Val Lys Glu Phe Phe Ala Lys Tyr
1               5                   10                  15

Trp Asp
```

<210> SEQ ID NO 330
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 330

Phe Ala Glu Lys Phe Lys Asp Ala Val Lys Asp Phe Phe Ala Lys Tyr
1               5                   10                  15

Trp Glu

<210> SEQ ID NO 331
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 331

Trp Ala Glu Lys Phe Phe Glu Ala Val Lys Asp Tyr Phe Ala Lys Phe
1               5                   10                  15

Lys Asp

<210> SEQ ID NO 332
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 332

Trp Ala Asp Lys Phe Phe Asp Ala Val Lys Glu Tyr Phe Ala Lys Phe
1               5                   10                  15

Lys Glu

<210> SEQ ID NO 333
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 333

Trp Ala Asp Lys Phe Phe Glu Ala Val Lys Asp Tyr Phe Ala Lys Phe
1               5                   10                  15

Lys Glu

<210> SEQ ID NO 334
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 334

Trp Ala Glu Lys Phe Phe Asp Ala Val Lys Glu Tyr Phe Ala Lys Phe
1               5                   10                  15

Lys Asp

<210> SEQ ID NO 335
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 335

Trp Ala Glu Lys Phe Phe Asp Ala Val Lys Asp Tyr Phe Ala Lys Phe
1               5                   10                  15

Lys Glu

<210> SEQ ID NO 336
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 336

Phe Ala Glu Lys Trp Phe Glu Ala Val Lys Asp Tyr Phe Ala Lys Phe
1               5                   10                  15

Lys Asp

<210> SEQ ID NO 337
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 337

Phe Ala Asp Lys Trp Phe Asp Ala Val Lys Glu Tyr Phe Ala Lys Phe
1               5                   10                  15

Lys Glu

<210> SEQ ID NO 338
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 338

Phe Ala Asp Lys Trp Phe Glu Ala Val Lys Asp Tyr Phe Ala Lys Phe
1               5                   10                  15

Lys Glu

<210> SEQ ID NO 339
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 339

Phe Ala Glu Lys Trp Phe Asp Ala Val Lys Glu Tyr Phe Ala Lys Phe
1               5                   10                  15

Lys Asp

```
<210> SEQ ID NO 340
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 340

Phe Ala Glu Lys Trp Phe Asp Ala Val Lys Asp Tyr Phe Ala Lys Phe
1               5                   10                  15

Lys Glu

<210> SEQ ID NO 341
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 341

Phe Ala Glu Lys Phe Val Glu Ala Trp Lys Asp Tyr Phe Ala Lys Phe
1               5                   10                  15

Lys Asp

<210> SEQ ID NO 342
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 342

Phe Ala Asp Lys Phe Val Asp Ala Trp Lys Glu Tyr Phe Ala Lys Phe
1               5                   10                  15

Lys Glu

<210> SEQ ID NO 343
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 343

Phe Ala Asp Lys Phe Val Glu Ala Trp Lys Asp Tyr Phe Ala Lys Phe
1               5                   10                  15

Lys Glu

<210> SEQ ID NO 344
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 344

Phe Ala Glu Lys Phe Val Asp Ala Trp Lys Glu Tyr Phe Ala Lys Phe
1               5                   10                  15

Lys Asp
```

<210> SEQ ID NO 345
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 345

Phe Ala Glu Lys Phe Val Asp Ala Trp Lys Asp Tyr Phe Ala Lys Phe
1               5                   10                  15

Lys Glu

<210> SEQ ID NO 346
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 346

Phe Tyr Glu Lys Phe Ala Glu Ala Val Lys Asp Trp Phe Ala Lys Phe
1               5                   10                  15

Lys Asp

<210> SEQ ID NO 347
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 347

Phe Tyr Asp Lys Phe Ala Asp Ala Val Lys Glu Trp Phe Ala Lys Phe
1               5                   10                  15

Lys Glu

<210> SEQ ID NO 348
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 348

Phe Tyr Asp Lys Phe Ala Glu Ala Val Lys Asp Trp Phe Ala Lys Phe
1               5                   10                  15

Lys Glu

<210> SEQ ID NO 349
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 349

Phe Tyr Glu Lys Phe Ala Asp Ala Val Lys Glu Trp Phe Ala Lys Phe
1               5                   10                  15

Lys Asp

-continued

<210> SEQ ID NO 350
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 350

Phe Tyr Glu Lys Phe Ala Asp Ala Val Lys Asp Trp Phe Ala Lys Phe
1               5                   10                  15

Lys Glu

<210> SEQ ID NO 351
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is Lys or Arg
<220> FEATURE:
<221> NAME/KEY: misc_feature
<222> LOCATION: (2)..(3)
<223> OTHER INFORMATION: Xaa is Leu, norLeu, Val, Ile, Trp, Phe, Tyr,
      beta-Nal, or alpha-Nal
<220> FEATURE:
<221> NAME/KEY: misc_feature
<222> LOCATION: (4)..(4)
<223> OTHER INFORMATION: Xaa is Lys or Arg
<220> FEATURE:
<221> NAME/KEY: misc_feature
<222> LOCATION: (5)..(5)
<223> OTHER INFORMATION: Xaa is Ala, His, Ser, Gln, Asn, or Thr
<220> FEATURE:
<221> NAME/KEY: misc_feature
<222> LOCATION: (6)..(7)
<223> OTHER INFORMATION: Xaa is Leu, norLeu, Val, Ile, Trp, Phe, Tyr,
      beta-Nal, or alpha-Nal
<220> FEATURE:
<221> NAME/KEY: misc_feature
<222> LOCATION: (8)..(8)
<223> OTHER INFORMATION: Xaa is Lys or Arg
<220> FEATURE:
<221> NAME/KEY: misc_feature
<222> LOCATION: (9)..(9)
<223> OTHER INFORMATION: Xaa is Lys or Arg
<220> FEATURE:
<221> NAME/KEY: misc_feature
<222> LOCATION: (10)..(10)
<223> OTHER INFORMATION: Xaa is Leu, norLeu, Val, Ile, Trp, Phe, Tyr,
      beta-Nal, or alpha-Nal
<220> FEATURE:
<221> NAME/KEY: misc_feature
<222> LOCATION: (11)..(11)
<223> OTHER INFORMATION: Xaa is Ala, His, Ser, Gln, Asn, or Thr
<220> FEATURE:
<221> NAME/KEY: misc_feature
<222> LOCATION: (12)..(12)
<223> OTHER INFORMATION: Xaa is Lys or Arg
<220> FEATURE:
<221> NAME/KEY: misc_feature
<222> LOCATION: (13)..(13)
<223> OTHER INFORMATION: Xaa is Lys or Arg
<220> FEATURE:
<221> NAME/KEY: misc_feature
<222> LOCATION: (14)..(14)
<223> OTHER INFORMATION: Xaa is Leu, norLeu, Val, Ile, Trp, Phe, Tyr,
      beta-Nal, or alpha-Nal
<220> FEATURE:
<221> NAME/KEY: misc_feature
<222> LOCATION: (15)..(15)
<223> OTHER INFORMATION: Xaa is Lys or Arg

```
<220> FEATURE:
<221> NAME/KEY: misc_feature
<222> LOCATION: (16)..(16)
<223> OTHER INFORMATION: Xaa is Lys or Arg
<220> FEATURE:
<221> NAME/KEY: misc_feature
<222> LOCATION: (17)..(17)
<223> OTHER INFORMATION: Xaa is Ala, His, Ser, Gln, Asn, or Thr
<220> FEATURE:
<221> NAME/KEY: misc_feature
<222> LOCATION: (18)..(18)
<223> OTHER INFORMATION: Xaa is Leu, norLeu, Val, Ile, Trp, Phe, Tyr,
      beta-Nal, or alpha-Nal

<400> SEQUENCE: 351

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 352
<211> LENGTH: 18
<212> TYPE: PRT
<213> ORGANISM: Artificial
<220> FEATURE:
<223> OTHER INFORMATION: Synthetic peptide optionally bearing protecting
      groups.

<400> SEQUENCE: 352

Asp Trp Phe Lys His Phe Tyr Asp Lys Val Ala Glu Lys Phe Lys Glu
1               5                   10                  15

Ala Phe

<210> SEQ ID NO 353
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 353

Glu Trp Phe Lys His Phe Tyr Glu Lys Val Ala Asp Lys Phe Lys Asp
1               5                   10                  15

Ala Phe

<210> SEQ ID NO 354
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 354

Glu Trp Phe Lys His Phe Tyr Asp Lys Val Ala Glu Lys Phe Lys Glu
1               5                   10                  15

Ala Phe

<210> SEQ ID NO 355
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 355
```

Asp Trp Phe Lys His Phe Tyr Glu Lys Val Ala Glu Lys Phe Lys Glu
1               5                   10                  15

Ala Phe

<210> SEQ ID NO 356
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 356

Asp Trp Phe Lys His Phe Tyr Asp Lys Val Ala Asp Lys Phe Lys Glu
1               5                   10                  15

Ala Phe

<210> SEQ ID NO 357
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 357

Asp Trp Phe Lys His Phe Tyr Asp Lys Val Ala Glu Lys Phe Lys Asp
1               5                   10                  15

Ala Phe

<210> SEQ ID NO 358
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 358

Asp Trp His Lys Phe Phe Tyr Asp Lys Val Ala Glu Lys Phe Lys Glu
1               5                   10                  15

Ala Phe

<210> SEQ ID NO 359
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 359

Glu Trp His Lys Phe Phe Tyr Glu Lys Val Ala Asp Lys Phe Lys Asp
1               5                   10                  15

Ala Phe

<210> SEQ ID NO 360
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 360

Glu Trp His Lys Phe Phe Tyr Asp Lys Val Ala Glu Lys Phe Lys Glu
1               5                   10                  15

Ala Phe

<210> SEQ ID NO 361
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 361

Asp Trp His Lys Phe Phe Tyr Glu Lys Val Ala Glu Lys Phe Lys Glu
1               5                   10                  15

Ala Phe

<210> SEQ ID NO 362
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 362

Asp Trp His Lys Phe Phe Tyr Asp Lys Val Ala Asp Lys Phe Lys Glu
1               5                   10                  15

Ala Phe

<210> SEQ ID NO 363
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 363

Asp Trp His Lys Phe Phe Tyr Asp Lys Val Ala Glu Lys Phe Lys Asp
1               5                   10                  15

Ala Phe

<210> SEQ ID NO 364
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 364

Asp Trp Phe Lys Phe His Tyr Asp Lys Val Ala Glu Lys Phe Lys Glu
1               5                   10                  15

Ala Phe

<210> SEQ ID NO 365
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 365

```
Glu Trp Phe Lys Phe His Tyr Glu Lys Val Ala Asp Lys Phe Lys Asp
1               5                   10                  15

Ala Phe
```

<210> SEQ ID NO 366
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 366

```
Glu Trp Phe Lys Phe His Tyr Asp Lys Val Ala Glu Lys Phe Lys Glu
1               5                   10                  15

Ala Phe
```

<210> SEQ ID NO 367
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 367

```
Asp Trp Phe Lys Phe His Tyr Glu Lys Val Ala Glu Lys Phe Lys Glu
1               5                   10                  15

Ala Phe
```

<210> SEQ ID NO 368
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 368

```
Asp Trp Phe Lys Phe His Tyr Asp Lys Val Ala Asp Lys Phe Lys Glu
1               5                   10                  15

Ala Phe
```

<210> SEQ ID NO 369
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 369

```
Asp Trp Phe Lys Phe His Tyr Asp Lys Val Ala Glu Lys Phe Lys Asp
1               5                   10                  15

Ala Phe
```

<210> SEQ ID NO 370
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 370

Asp Trp Phe Lys Val Phe Tyr Asp Lys His Ala Glu Lys Phe Lys Glu
1               5                   10                  15

Ala Phe

<210> SEQ ID NO 371
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 371

Glu Trp Phe Lys Val Phe Tyr Glu Lys His Ala Asp Lys Phe Lys Asp
1               5                   10                  15

Ala Phe

<210> SEQ ID NO 372
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 372

Glu Trp Phe Lys Val Phe Tyr Asp Lys His Ala Glu Lys Phe Lys Glu
1               5                   10                  15

Ala Phe

<210> SEQ ID NO 373
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 373

Asp Trp Phe Lys Val Phe Tyr Glu Lys His Ala Glu Lys Phe Lys Glu
1               5                   10                  15

Ala Phe

<210> SEQ ID NO 374
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 374

Asp Trp Phe Lys Val Phe Tyr Asp Lys His Ala Asp Lys Phe Lys Glu
1               5                   10                  15

Ala Phe

<210> SEQ ID NO 375
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 375

Asp Trp Phe Lys Val Phe Tyr Asp Lys His Ala Glu Lys Phe Lys Asp
1               5                   10                  15

Ala Phe

<210> SEQ ID NO 376
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 376

Asp Trp Phe Lys Ala Phe Tyr Asp Lys Val Ala Glu Lys Phe Lys Glu
1               5                   10                  15

His Phe

<210> SEQ ID NO 377
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 377

Glu Trp Phe Lys Ala Phe Tyr Glu Lys Val Ala Asp Lys Phe Lys Asp
1               5                   10                  15

His Phe

<210> SEQ ID NO 378
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 378

Glu Trp Phe Lys Ala Phe Tyr Asp Lys Val Ala Glu Lys Phe Lys Glu
1               5                   10                  15

His Phe

<210> SEQ ID NO 379
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 379

Asp Trp Phe Lys Ala Phe Tyr Glu Lys Val Ala Glu Lys Phe Lys Glu
1               5                   10                  15

His Phe

<210> SEQ ID NO 380
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 380

Asp Trp Phe Lys Ala Phe Tyr Asp Lys Val Ala Asp Lys Phe Lys Glu
1               5                   10                  15

His Phe

<210> SEQ ID NO 381
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 381

Asp Trp Phe Lys Ala Phe Tyr Asp Lys Val Ala Glu Lys Phe Lys Asp
1               5                   10                  15

His Phe

<210> SEQ ID NO 382
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 382

Asp Trp Phe Lys Ala Phe Tyr Asp Lys Val Ala Glu Lys Phe Lys Glu
1               5                   10                  15

Phe His

<210> SEQ ID NO 383
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 383

Glu Trp Phe Lys Ala Phe Tyr Glu Lys Val Ala Asp Lys Phe Lys Asp
1               5                   10                  15

Phe His

<210> SEQ ID NO 384
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 384

Glu Trp Phe Lys Ala Phe Tyr Asp Lys Val Ala Glu Lys Phe Lys Glu
1               5                   10                  15

Phe His

<210> SEQ ID NO 385
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 385

```
Asp Trp Phe Lys Ala Phe Tyr Asp Lys Val Ala Glu Lys Phe Lys Glu
1               5                   10                  15

Phe His

<210> SEQ ID NO 386
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 386

Asp Trp Phe Lys Ala Phe Tyr Glu Lys Val Ala Glu Lys Phe Lys Glu
1               5                   10                  15

Phe His

<210> SEQ ID NO 387
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 387

Asp Trp Phe Lys Ala Phe Tyr Asp Lys Val Ala Glu Lys Phe Lys Glu
1               5                   10                  15

Phe His

<210> SEQ ID NO 388
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 388

Asp Trp Phe Lys Ala Phe Tyr Asp Lys Val Ala Glu Lys Phe Lys Asp
1               5                   10                  15

Phe His

<210> SEQ ID NO 389
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 389

Phe Ala Glu Lys Phe Lys Glu Ala Val Lys Asp Tyr Phe Ala Lys Phe
1               5                   10                  15

Trp Asp

<210> SEQ ID NO 390
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 390
```

-continued

Phe His Glu Lys Phe Lys Glu Ala Val Lys Asp Tyr Phe Ala Lys Phe
1               5                   10                  15

Trp Asp

<210> SEQ ID NO 391
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 391

Phe His Glu Lys Phe Lys Glu Ala Val Lys Glu Tyr Phe Ala Lys Phe
1               5                   10                  15

Trp Glu

<210> SEQ ID NO 392
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 392

Phe His Asp Lys Phe Lys Asp Ala Val Lys Asp Tyr Phe Ala Lys Phe
1               5                   10                  15

Trp Asp

<210> SEQ ID NO 393
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 393

Phe His Asp Lys Phe Lys Asp Ala Val Lys Glu Tyr Phe Ala Lys Phe
1               5                   10                  15

Trp Glu

<210> SEQ ID NO 394
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 394

Phe His Asp Lys Phe Lys Glu Ala Val Lys Asp Tyr Phe Ala Lys Phe
1               5                   10                  15

Trp Asp

<210> SEQ ID NO 395
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 395

Phe His Glu Lys Phe Lys Asp Ala Val Lys Asp Tyr Phe Ala Lys Phe
1               5                   10                  15

Trp Asp

<210> SEQ ID NO 396
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 396

Phe His Glu Lys Phe Lys Glu Ala Val Lys Glu Tyr Phe Ala Lys Phe
1               5                   10                  15

Trp Asp

<210> SEQ ID NO 397
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 397

Phe His Glu Lys Phe Lys Glu Ala Val Lys Asp Tyr Phe Ala Lys Phe
1               5                   10                  15

Trp Glu

<210> SEQ ID NO 398
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 398

His Phe Glu Lys Phe Lys Glu Ala Val Lys Asp Tyr Phe Ala Lys Phe
1               5                   10                  15

Trp Asp

<210> SEQ ID NO 399
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 399

His Phe Asp Lys Phe Lys Asp Ala Val Lys Glu Tyr Phe Ala Lys Phe
1               5                   10                  15

Trp Glu

<210> SEQ ID NO 400
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 400

His Phe Glu Lys Phe Lys Glu Ala Val Lys Glu Tyr Phe Ala Lys Phe
1               5                   10                  15

Trp Glu

<210> SEQ ID NO 401
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 401

His Phe Asp Lys Phe Lys Glu Ala Val Lys Asp Tyr Phe Ala Lys Phe
1               5                   10                  15

Trp Asp

<210> SEQ ID NO 402
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 402

His Phe Glu Lys Phe Lys Asp Ala Val Lys Asp Tyr Phe Ala Lys Phe
1               5                   10                  15

Trp Asp

<210> SEQ ID NO 403
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 403

His Phe Glu Lys Phe Lys Glu Ala Val Lys Glu Tyr Phe Ala Lys Phe
1               5                   10                  15

Trp Asp

<210> SEQ ID NO 404
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 404

His Phe Glu Lys Phe Lys Glu Ala Val Lys Asp Tyr Phe Ala Lys Phe
1               5                   10                  15

Trp Glu

<210> SEQ ID NO 405
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 405

-continued

Phe Phe Glu Lys His Lys Glu Ala Val Lys Asp Tyr Phe Ala Lys Phe
1               5                   10                  15

Trp Asp

<210> SEQ ID NO 406
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 406

Phe Phe Asp Lys His Lys Asp Ala Val Lys Glu Tyr Phe Ala Lys Phe
1               5                   10                  15

Trp Glu

<210> SEQ ID NO 407
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 407

Phe Phe Glu Lys His Lys Glu Ala Val Lys Glu Tyr Phe Ala Lys Phe
1               5                   10                  15

Trp Glu

<210> SEQ ID NO 408
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 408

Phe Phe Asp Lys His Lys Asp Ala Val Lys Asp Tyr Phe Ala Lys Phe
1               5                   10                  15

Trp Asp

<210> SEQ ID NO 409
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 409

Phe Phe Asp Lys His Lys Glu Ala Val Lys Asp Tyr Phe Ala Lys Phe
1               5                   10                  15

Trp Asp

<210> SEQ ID NO 410
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 410

Phe Phe Glu Lys His Lys Glu Ala Val Lys Glu Tyr Phe Ala Lys Phe
1               5                   10                  15

Trp Asp

<210> SEQ ID NO 411
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 411

Phe Phe Glu Lys His Lys Glu Ala Val Lys Asp Tyr Phe Ala Lys Phe
1               5                   10                  15

Trp Glu

<210> SEQ ID NO 412
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 412

Phe Val Glu Lys Phe Lys Glu Ala His Lys Asp Tyr Phe Ala Lys Phe
1               5                   10                  15

Trp Asp

<210> SEQ ID NO 413
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 413

Phe Val Asp Lys Phe Lys Asp Ala His Lys Glu Tyr Phe Ala Lys Phe
1               5                   10                  15

Trp Glu

<210> SEQ ID NO 414
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 414

Phe Val Glu Lys Phe Lys Glu Ala His Lys Glu Tyr Phe Ala Lys Phe
1               5                   10                  15

Trp Glu

<210> SEQ ID NO 415
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 415

```
Phe Val Asp Lys Phe Lys Asp Ala His Lys Asp Tyr Phe Ala Lys Phe
1               5                   10                  15

Trp Asp

<210> SEQ ID NO 416
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 416

Phe Val Asp Lys Phe Lys Glu Ala His Lys Asp Tyr Phe Ala Lys Phe
1               5                   10                  15

Trp Asp

<210> SEQ ID NO 417
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 417

Phe Val Glu Lys Phe Lys Asp Ala His Lys Asp Tyr Phe Ala Lys Phe
1               5                   10                  15

Trp Asp

<210> SEQ ID NO 418
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 418

Phe Val Glu Lys Phe Lys Glu Ala His Lys Glu Tyr Phe Ala Lys Phe
1               5                   10                  15

Trp Asp

<210> SEQ ID NO 419
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 419

Phe Val Glu Lys Phe Lys Glu Ala His Lys Asp Tyr Phe Ala Lys Phe
1               5                   10                  15

Trp Glu

<210> SEQ ID NO 420
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 420
```

Phe Ala Glu Lys Phe Lys Glu His Val Lys Asp Tyr Phe Ala Lys Phe
1               5                   10                  15

Trp Asp

<210> SEQ ID NO 421
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 421

Phe Ala Asp Lys Phe Lys Asp His Val Lys Glu Tyr Phe Ala Lys Phe
1               5                   10                  15

Trp Glu

<210> SEQ ID NO 422
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 422

Phe Ala Glu Lys Phe Lys Glu His Val Lys Glu Tyr Phe Ala Lys Phe
1               5                   10                  15

Trp Glu

<210> SEQ ID NO 423
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 423

Phe Ala Asp Lys Phe Lys Asp His Val Lys Asp Tyr Phe Ala Lys Phe
1               5                   10                  15

Trp Asp

<210> SEQ ID NO 424
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 424

Phe Ala Asp Lys Phe Lys Glu His Val Lys Asp Tyr Phe Ala Lys Phe
1               5                   10                  15

Trp Asp

<210> SEQ ID NO 425
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 425

```
Phe Ala Glu Lys Phe Lys Asp His Val Lys Asp Tyr Phe Ala Lys Phe
1               5                   10                  15

Trp Asp

<210> SEQ ID NO 426
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 426

Phe Ala Glu Lys Phe Lys Glu His Val Lys Glu Tyr Phe Ala Lys Phe
1               5                   10                  15

Trp Asp

<210> SEQ ID NO 427
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 427

Phe Ala Glu Lys Phe Lys Glu His Val Lys Asp Tyr Phe Ala Lys Phe
1               5                   10                  15

Trp Glu

<210> SEQ ID NO 428
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 428

Phe Ala Glu Lys Phe Lys Glu Phe Val Lys Asp Tyr His Ala Lys Phe
1               5                   10                  15

Trp Asp

<210> SEQ ID NO 429
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 429

Phe Ala Asp Lys Phe Lys Asp Phe Val Lys Glu Tyr His Ala Lys Phe
1               5                   10                  15

Trp Glu

<210> SEQ ID NO 430
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 430
```

```
Phe Ala Asp Lys Phe Lys Glu Phe Val Lys Asp Tyr His Ala Lys Phe
1               5                   10                  15

Trp Asp

<210> SEQ ID NO 431
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 431

Phe Ala Glu Lys Phe Lys Asp Phe Val Lys Asp Tyr His Ala Lys Phe
1               5                   10                  15

Trp Asp

<210> SEQ ID NO 432
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 432

Phe Ala Asp Lys Phe Lys Asp Phe Val Lys Asp Tyr His Ala Lys Phe
1               5                   10                  15

Trp Asp

<210> SEQ ID NO 433
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 433

Phe Ala Glu Lys Phe Lys Glu Phe Val Lys Glu Tyr His Ala Lys Phe
1               5                   10                  15

Trp Glu

<210> SEQ ID NO 434
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 434

Phe Ala Glu Lys Phe Lys Glu Phe Val Lys Glu Tyr His Ala Lys Phe
1               5                   10                  15

Trp Asp

<210> SEQ ID NO 435
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 435
```

Phe Ala Glu Lys Phe Lys Glu Phe Val Lys Asp Tyr His Ala Lys Phe
1               5                   10                  15

Trp Glu

<210> SEQ ID NO 436
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 436

Phe Ala Glu Lys Phe Lys Glu Phe Val Lys Asp Tyr Phe Ala Lys His
1               5                   10                  15

Trp Asp

<210> SEQ ID NO 437
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 437

Phe Ala Asp Lys Phe Lys Asp Phe Val Lys Glu Tyr Phe Ala Lys His
1               5                   10                  15

Trp Glu

<210> SEQ ID NO 438
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 438

Phe Ala Glu Lys Phe Lys Glu Phe Val Lys Glu Tyr Phe Ala Lys His
1               5                   10                  15

Trp Glu

<210> SEQ ID NO 439
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 439

Phe Ala Asp Lys Phe Lys Asp Phe Val Lys Asp Tyr Phe Ala Lys His
1               5                   10                  15

Trp Asp

<210> SEQ ID NO 440
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 440

```
Phe Ala Asp Lys Phe Lys Glu Phe Val Lys Asp Tyr Phe Ala Lys His
1               5                   10                  15

Trp Asp

<210> SEQ ID NO 441
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 441

Phe Ala Glu Lys Phe Lys Asp Phe Val Lys Asp Tyr Phe Ala Lys His
1               5                   10                  15

Trp Asp

<210> SEQ ID NO 442
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 442

Phe Ala Glu Lys Phe Lys Glu Phe Val Lys Glu Tyr Phe Ala Lys His
1               5                   10                  15

Trp Asp

<210> SEQ ID NO 443
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 443

Phe Ala Glu Lys Phe Lys Glu Phe Val Lys Asp Tyr Phe Ala Lys His
1               5                   10                  15

Trp Glu

<210> SEQ ID NO 444
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 444
```

```
Asp Trp Xaa Lys Ala Xaa Tyr Asp Lys Val Ala Glu Lys Xaa Lys Glu
1               5                   10                  15

Ala Xaa

<210> SEQ ID NO 445
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 445

Glu Trp Xaa Lys Ala Xaa Tyr Glu Lys Val Ala Asp Lys Xaa Lys Asp
1               5                   10                  15

Ala Xaa

<210> SEQ ID NO 446
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 446

Glu Trp Xaa Lys Ala Xaa Tyr Glu Lys Val Ala Glu Lys Xaa Lys Glu
1               5                   10                  15

Ala Xaa

<210> SEQ ID NO 447
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
```

```
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 447

Asp Trp Xaa Lys Ala Xaa Tyr Asp Lys Val Ala Asp Lys Xaa Lys Asp
1               5                   10                  15

Ala Xaa

<210> SEQ ID NO 448
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 448

Glu Trp Xaa Lys Ala Xaa Tyr Asp Lys Val Ala Glu Lys Xaa Lys Glu
1               5                   10                  15

Ala Xaa

<210> SEQ ID NO 449
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 449
```

```
Asp Trp Xaa Lys Ala Xaa Tyr Glu Lys Val Ala Glu Lys Xaa Lys Glu
1               5                   10                  15

Ala Xaa

<210> SEQ ID NO 450
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 450

Asp Trp Xaa Lys Ala Xaa Tyr Asp Lys Val Ala Asp Lys Xaa Lys Glu
1               5                   10                  15

Ala Xaa

<210> SEQ ID NO 451
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph
<220> FEATURE:
<221> NAME/KEY: misc_feature
<222> LOCATION: (6)..(6)
<223> OTHER INFORMATION: Xaa is Nph
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 451

Asp Trp Xaa Lys Ala Xaa Tyr Asp Lys Val Ala Glu Lys Xaa Lys Asp
1               5                   10                  15

Ala Xaa

<210> SEQ ID NO 452
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
```

-continued

<223> OTHER INFORMATION: Xaa is Nph
<220> FEATURE:
<221> NAME/KEY: misc_feature
<222> LOCATION: (6)..(6)
<223> OTHER INFORMATION: Xaa is Nph

<400> SEQUENCE: 452

Asp Trp Xaa Lys Ala Xaa Tyr Asp Lys Val Ala Glu Lys Phe Lys Glu
1               5                   10                  15

Ala Phe

<210> SEQ ID NO 453
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (14)..(14)
<223> OTHER INFORMATION: Xaa is Nph
<220> FEATURE:
<221> NAME/KEY: misc_feature
<222> LOCATION: (18)..(18)
<223> OTHER INFORMATION: Xaa is Nph

<400> SEQUENCE: 453

Asp Trp Phe Lys Ala Phe Tyr Asp Lys Val Ala Glu Lys Xaa Lys Glu
1               5                   10                  15

Ala Xaa

<210> SEQ ID NO 454
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is Nph

<400> SEQUENCE: 454

Asp Trp Xaa Lys Ala Phe Tyr Asp Lys Val Ala Glu Lys Phe Lys Glu
1               5                   10                  15

Ala Phe

<210> SEQ ID NO 455
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (6)..(6)
<223> OTHER INFORMATION: Xaa is Nph

<400> SEQUENCE: 455

Asp Trp Phe Lys Ala Xaa Tyr Asp Lys Val Ala Glu Lys Phe Lys Glu
1               5                   10                  15

Ala Phe

<210> SEQ ID NO 456
<211> LENGTH: 18

```
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (14)..(14)
<223> OTHER INFORMATION: Xaa is Nph

<400> SEQUENCE: 456

Asp Trp Phe Lys Ala Phe Tyr Asp Lys Val Ala Glu Lys Xaa Lys Glu
1               5                   10                  15

Ala Phe

<210> SEQ ID NO 457
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (18)..(18)
<223> OTHER INFORMATION: Xaa is Nph

<400> SEQUENCE: 457

Asp Trp Phe Lys Ala Phe Tyr Asp Lys Val Ala Glu Lys Phe Lys Glu
1               5                   10                  15

Ala Xaa

<210> SEQ ID NO 458
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is Nph
<220> FEATURE:
<221> NAME/KEY: misc_feature
<222> LOCATION: (5)..(5)
<223> OTHER INFORMATION: Xaa is Nph
<220> FEATURE:
<221> NAME/KEY: misc_feature
<222> LOCATION: (13)..(13)
<223> OTHER INFORMATION: Xaa is Nph
<220> FEATURE:
<221> NAME/KEY: misc_feature
<222> LOCATION: (16)..(16)
<223> OTHER INFORMATION: Xaa is Nph

<400> SEQUENCE: 458

Xaa Ala Glu Lys Xaa Lys Glu Ala Val Lys Asp Tyr Xaa Ala Lys Xaa
1               5                   10                  15

Trp Asp

<210> SEQ ID NO 459
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
```

```
<223> OTHER INFORMATION: Xaa is Nph
<220> FEATURE:
<221> NAME/KEY: misc_feature
<222> LOCATION: (5)..(5)
<223> OTHER INFORMATION: Xaa is Nph

<400> SEQUENCE: 459

Xaa Ala Glu Lys Xaa Lys Glu Ala Val Lys Asp Tyr Phe Ala Lys Phe
1               5                   10                  15

Trp Asp

<210> SEQ ID NO 460
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (13)..(13)
<223> OTHER INFORMATION: Xaa is Nph
<220> FEATURE:
<221> NAME/KEY: misc_feature
<222> LOCATION: (16)..(16)
<223> OTHER INFORMATION: Xaa is Nph

<400> SEQUENCE: 460

Phe Ala Glu Lys Phe Lys Glu Ala Val Lys Asp Tyr Xaa Ala Lys Xaa
1               5                   10                  15

Trp Asp

<210> SEQ ID NO 461
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is Nph

<400> SEQUENCE: 461

Xaa Ala Glu Lys Phe Lys Glu Ala Val Lys Asp Tyr Phe Ala Lys Phe
1               5                   10                  15

Trp Asp

<210> SEQ ID NO 462
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (5)..(5)
<223> OTHER INFORMATION: Xaa is Nph

<400> SEQUENCE: 462

Phe Ala Glu Lys Xaa Lys Glu Ala Val Lys Asp Tyr Phe Ala Lys Phe
1               5                   10                  15

Trp Asp

<210> SEQ ID NO 463
<211> LENGTH: 18
```

```
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (13)..(13)
<223> OTHER INFORMATION: Xaa is Nph

<400> SEQUENCE: 463

Phe Ala Glu Lys Phe Lys Glu Ala Val Lys Asp Tyr Xaa Ala Lys Phe
1               5                   10                  15

Trp Asp

<210> SEQ ID NO 464
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (16)..(16)
<223> OTHER INFORMATION: Xaa is Nph

<400> SEQUENCE: 464

Phe Ala Glu Lys Phe Lys Glu Ala Val Lys Asp Tyr Phe Ala Lys Xaa
1               5                   10                  15

Trp Asp

<210> SEQ ID NO 465
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 465

Phe Ala Glu Lys Phe Lys Glu Ala Val Lys Glu Tyr Phe Ala Lys Phe
1               5                   10                  15

Trp Glu

<210> SEQ ID NO 466
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 466

Phe Ala Asp Lys Phe Lys Asp Ala Val Lys Asp Tyr Phe Ala Lys Phe
1               5                   10                  15

Trp Asp

<210> SEQ ID NO 467
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 467
```

```
Phe Ala Glu Arg Phe Arg Glu Ala Val Lys Asp Tyr Phe Ala Lys Phe
1               5                   10                  15

Trp Asp

<210> SEQ ID NO 468
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 468

Phe Ala Glu Lys Phe Arg Glu Ala Val Lys Asp Tyr Phe Ala Lys Phe
1               5                   10                  15

Trp Asp

<210> SEQ ID NO 469
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 469

Phe Ala Glu Lys Phe Lys Glu Ala Val Arg Asp Tyr Phe Ala Lys Phe
1               5                   10                  15

Trp Asp

<210> SEQ ID NO 470
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 470

Phe Ala Glu Lys Phe Lys Glu Ala Val Lys Asp Tyr Phe Ala Arg Phe
1               5                   10                  15

Trp Asp

<210> SEQ ID NO 471
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 471

Phe Ala Glu Lys Phe Lys Glu Ala Val Lys Glu Tyr Phe Ala Lys Phe
1               5                   10                  15

Trp Glu

<210> SEQ ID NO 472
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 472
```

-continued

Phe Ala Asp Lys Phe Lys Asp Ala Val Lys Asp Tyr Phe Ala Lys Phe
1               5                   10                  15

Trp Asp

<210> SEQ ID NO 473
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 473

Phe Ala Glu Arg Phe Arg Glu Ala Val Lys Asp Tyr Phe Ala Lys Phe
1               5                   10                  15

Trp Asp

<210> SEQ ID NO 474
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 474

Phe Ala Glu Lys Phe Arg Glu Ala Val Lys Asp Tyr Phe Ala Lys Phe
1               5                   10                  15

Trp Asp

<210> SEQ ID NO 475
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 475

Phe Ala Glu Lys Phe Lys Glu Ala Val Arg Asp Tyr Phe Ala Lys Phe
1               5                   10                  15

Trp Asp

<210> SEQ ID NO 476
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 476

Phe Ala Glu Lys Phe Lys Glu Ala Val Lys Asp Tyr Phe Ala Arg Phe
1               5                   10                  15

Trp Asp

<210> SEQ ID NO 477
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 477

Phe Ala Glu Lys Phe Lys Glu Ala Val Lys Glu Tyr Phe Ala Lys Phe
1               5                   10                  15

Trp Glu

<210> SEQ ID NO 478
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 478

Phe Ala Asp Lys Phe Lys Asp Ala Val Lys Asp Tyr Phe Ala Lys Phe
1               5                   10                  15

Trp Asp

<210> SEQ ID NO 479
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 479

Phe Ala Glu Arg Phe Arg Glu Ala Val Lys Asp Tyr Phe Ala Lys Phe
1               5                   10                  15

Trp Asp

<210> SEQ ID NO 480
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 480

Phe Ala Glu Lys Phe Arg Glu Ala Val Lys Asp Tyr Phe Ala Lys Phe
1               5                   10                  15

Trp Asp

<210> SEQ ID NO 481
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 481

Phe Ala Glu Lys Phe Lys Glu Ala Val Arg Asp Tyr Phe Ala Lys Phe
1               5                   10                  15

Trp Asp

<210> SEQ ID NO 482
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 482

-continued

Phe Ala Glu Lys Phe Lys Glu Ala Val Lys Asp Tyr Phe Ala Arg Phe
1               5                   10                  15

Trp Asp

<210> SEQ ID NO 483
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 483

Phe Ala Glu Arg Phe Arg Glu Ala Val Lys Asp Tyr Phe Ala Lys Phe
1               5                   10                  15

Trp Asp

<210> SEQ ID NO 484
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 484

Phe Ala Glu Lys Phe Arg Glu Ala Val Lys Asp Tyr Phe Ala Lys Phe
1               5                   10                  15

Trp Asp

<210> SEQ ID NO 485
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 485

Phe Ala Glu Lys Phe Lys Glu Ala Val Arg Asp Tyr Phe Ala Lys Phe
1               5                   10                  15

Trp Asp

<210> SEQ ID NO 486
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 486

Phe Ala Glu Lys Phe Lys Glu Ala Val Lys Asp Tyr Phe Ala Arg Phe
1               5                   10                  15

Trp Asp

<210> SEQ ID NO 487
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 487

```
Phe Ala Glu Lys Phe Lys Glu Ala Val Lys Glu Tyr Phe Ala Lys Phe
1               5                   10                  15

Trp Glu

<210> SEQ ID NO 488
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 488

Phe Ala Asp Lys Phe Lys Asp Ala Val Lys Asp Tyr Phe Ala Lys Phe
1               5                   10                  15

Trp Asp

<210> SEQ ID NO 489
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 489

Phe Ala Glu Arg Phe Arg Glu Ala Val Lys Asp Tyr Phe Ala Lys Phe
1               5                   10                  15

Trp Asp

<210> SEQ ID NO 490
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 490

Phe Ala Glu Lys Phe Arg Glu Ala Val Lys Asp Tyr Phe Ala Lys Phe
1               5                   10                  15

Trp Asp

<210> SEQ ID NO 491
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 491

Phe Ala Glu Lys Phe Lys Glu Ala Val Arg Asp Tyr Phe Ala Lys Phe
1               5                   10                  15

Trp Asp

<210> SEQ ID NO 492
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 492
```

Phe Ala Glu Lys Phe Lys Glu Ala Val Lys Asp Tyr Phe Ala Arg Phe
1               5                   10                  15

Trp Asp

<210> SEQ ID NO 493
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 493

Leu Phe Glu Lys Phe Ala Glu Ala Phe Lys Asp Tyr Val Ala Lys Trp
1               5                   10                  15

Lys Asp

<210> SEQ ID NO 494
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 494

Leu Phe Glu Arg Phe Ala Glu Ala Phe Lys Asp Tyr Val Ala Lys Trp
1               5                   10                  15

Lys Asp

<210> SEQ ID NO 495
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 495

Leu Phe Glu Lys Phe Ala Glu Ala Phe Arg Asp Tyr Val Ala Lys Trp
1               5                   10                  15

Lys Asp

<210> SEQ ID NO 496
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 496

Leu Phe Glu Lys Phe Ala Glu Ala Phe Lys Asp Tyr Val Ala Arg Trp
1               5                   10                  15

Lys Asp

<210> SEQ ID NO 497
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 497

-continued

Leu Phe Glu Lys Phe Ala Glu Ala Phe Lys Asp Tyr Val Ala Lys Trp
1               5                   10                  15

Arg Asp

<210> SEQ ID NO 498
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 498

Leu Phe Glu Lys Phe Ala Glu Ala Phe Lys Glu Tyr Val Ala Lys Trp
1               5                   10                  15

Lys Glu

<210> SEQ ID NO 499
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 499

Leu Phe Asp Lys Phe Ala Asp Ala Phe Lys Asp Tyr Val Ala Lys Trp
1               5                   10                  15

Lys Asp

<210> SEQ ID NO 500
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 500

Leu Phe Asp Lys Phe Ala Glu Ala Phe Lys Asp Tyr Val Ala Lys Trp
1               5                   10                  15

Lys Asp

<210> SEQ ID NO 501
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 501

Leu Phe Glu Lys Phe Ala Asp Ala Phe Lys Asp Tyr Val Ala Lys Trp
1               5                   10                  15

Lys Asp

<210> SEQ ID NO 502
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 502

```
Leu Phe Glu Lys Phe Ala Glu Ala Phe Lys Glu Tyr Val Ala Lys Trp
1               5                   10                  15

Lys Asp

<210> SEQ ID NO 503
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 503

Leu Phe Glu Lys Phe Ala Glu Ala Phe Lys Asp Tyr Val Ala Lys Trp
1               5                   10                  15

Lys Glu

<210> SEQ ID NO 504
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 504

Phe Ala Glu Lys Ala Trp Glu Phe Val Lys Asp Tyr Phe Ala Lys Leu
1               5                   10                  15

Lys Asp

<210> SEQ ID NO 505
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 505

Phe Ala Glu Arg Ala Trp Glu Phe Val Lys Asp Tyr Phe Ala Lys Leu
1               5                   10                  15

Lys Asp

<210> SEQ ID NO 506
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 506

Phe Ala Glu Lys Ala Trp Glu Phe Val Lys Asp Tyr Phe Ala Lys Leu
1               5                   10                  15

Lys Asp

<210> SEQ ID NO 507
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 507
```

```
Phe Ala Glu Lys Ala Trp Glu Phe Val Lys Asp Tyr Phe Ala Lys Leu
1               5                   10                  15

Lys Asp

<210> SEQ ID NO 508
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 508

Phe Ala Glu Lys Ala Trp Glu Phe Val Lys Asp Tyr Phe Ala Lys Leu
1               5                   10                  15

Arg Asp

<210> SEQ ID NO 509
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 509

Phe Ala Glu Lys Ala Trp Glu Phe Val Lys Glu Tyr Phe Ala Lys Leu
1               5                   10                  15

Lys Glu

<210> SEQ ID NO 510
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 510

Phe Ala Asp Lys Ala Trp Asp Phe Val Lys Asp Tyr Phe Ala Lys Leu
1               5                   10                  15

Lys Asp

<210> SEQ ID NO 511
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 511

Phe Ala Asp Lys Ala Trp Glu Phe Val Lys Asp Tyr Phe Ala Lys Leu
1               5                   10                  15

Lys Asp

<210> SEQ ID NO 512
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 512
```

Phe Ala Glu Lys Ala Trp Asp Phe Val Lys Asp Tyr Phe Ala Lys Leu
1               5                   10                  15

Lys Asp

<210> SEQ ID NO 513
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 513

Phe Ala Glu Lys Ala Trp Glu Phe Val Lys Glu Tyr Phe Ala Lys Leu
1               5                   10                  15

Lys Asp

<210> SEQ ID NO 514
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 514

Phe Ala Glu Lys Ala Trp Glu Phe Val Lys Asp Tyr Phe Ala Lys Leu
1               5                   10                  15

Lys Glu

<210> SEQ ID NO 515
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 515

Phe Phe Glu Lys Phe Lys Glu Phe Val Lys Asp Tyr Phe Ala Lys Leu
1               5                   10                  15

Trp Asp

<210> SEQ ID NO 516
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 516

Phe Phe Glu Lys Phe Lys Glu Phe Val Lys Glu Tyr Phe Ala Lys Leu
1               5                   10                  15

Trp Glu

<210> SEQ ID NO 517
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 517

Phe Phe Asp Lys Phe Lys Asp Phe Val Lys Asp Tyr Phe Ala Lys Leu
1               5                   10                  15

Trp Asp

<210> SEQ ID NO 518
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 518

Phe Phe Glu Arg Phe Lys Glu Phe Val Lys Asp Tyr Phe Ala Lys Leu
1               5                   10                  15

Trp Asp

<210> SEQ ID NO 519
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 519

Phe Phe Glu Lys Phe Arg Glu Phe Val Lys Asp Tyr Phe Ala Lys Leu
1               5                   10                  15

Trp Asp

<210> SEQ ID NO 520
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 520

Phe Phe Glu Lys Phe Lys Glu Phe Val Arg Asp Tyr Phe Ala Lys Leu
1               5                   10                  15

Trp Asp

<210> SEQ ID NO 521
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 521

Phe Phe Glu Lys Phe Lys Glu Phe Val Lys Asp Tyr Phe Ala Arg Leu
1               5                   10                  15

Trp Asp

<210> SEQ ID NO 522
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 522

Phe Phe Asp Lys Phe Lys Glu Phe Val Lys Asp Tyr Phe Ala Lys Leu
1               5                   10                  15

Trp Asp

<210> SEQ ID NO 523
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 523

Phe Phe Glu Lys Phe Lys Asp Phe Val Lys Asp Tyr Phe Ala Lys Leu
1               5                   10                  15

Trp Asp

<210> SEQ ID NO 524
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 524

Phe Phe Glu Lys Phe Lys Glu Phe Val Lys Glu Tyr Phe Ala Lys Leu
1               5                   10                  15

Trp Asp

<210> SEQ ID NO 525
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 525

Phe Phe Glu Lys Phe Lys Glu Phe Val Lys Asp Tyr Phe Ala Lys Leu
1               5                   10                  15

Trp Glu

<210> SEQ ID NO 526
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 526

Phe Leu Glu Lys Phe Lys Glu Phe Val Lys Asp Tyr Phe Ala Lys Phe
1               5                   10                  15

Trp Asp

<210> SEQ ID NO 527
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 527

Phe Leu Glu Lys Phe Lys Glu Phe Val Lys Glu Tyr Phe Ala Lys Phe
1               5                   10                  15

Trp Glu

<210> SEQ ID NO 528
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 528

Phe Leu Asp Lys Phe Lys Glu Phe Val Lys Asp Tyr Phe Ala Lys Phe
1               5                   10                  15

Trp Asp

<210> SEQ ID NO 529
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 529

Phe Leu Asp Lys Phe Lys Glu Phe Val Lys Asp Tyr Phe Ala Lys Phe
1               5                   10                  15

Trp Asp

<210> SEQ ID NO 530
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 530

Phe Leu Glu Lys Phe Lys Asp Phe Val Lys Asp Tyr Phe Ala Lys Phe
1               5                   10                  15

Trp Asp

<210> SEQ ID NO 531
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 531

Phe Leu Glu Lys Phe Lys Glu Phe Val Lys Glu Tyr Phe Ala Lys Phe
1               5                   10                  15

Trp Asp

<210> SEQ ID NO 532
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 532

-continued

Phe Leu Glu Lys Phe Lys Glu Phe Val Lys Asp Tyr Phe Ala Lys Phe
1               5                   10                  15

Trp Glu

<210> SEQ ID NO 533
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 533

Phe Leu Glu Arg Phe Lys Glu Phe Val Lys Asp Tyr Phe Ala Lys Phe
1               5                   10                  15

Trp Asp

<210> SEQ ID NO 534
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 534

Phe Leu Glu Lys Phe Arg Glu Phe Val Lys Asp Tyr Phe Ala Lys Phe
1               5                   10                  15

Trp Asp

<210> SEQ ID NO 535
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 535

Phe Leu Glu Lys Phe Lys Glu Phe Val Arg Asp Tyr Phe Ala Lys Phe
1               5                   10                  15

Trp Asp

<210> SEQ ID NO 536
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 536

Phe Leu Glu Lys Phe Lys Glu Phe Val Lys Asp Tyr Phe Ala Arg Phe
1               5                   10                  15

Trp Asp

<210> SEQ ID NO 537
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 537

```
Phe Phe Glu Lys Phe Lys Glu Phe Phe Lys Asp Tyr Phe Ala Lys Leu
1               5                   10                  15

Trp Asp
```

<210> SEQ ID NO 538
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 538

```
Phe Phe Glu Lys Phe Lys Glu Phe Phe Lys Glu Tyr Phe Ala Lys Leu
1               5                   10                  15

Trp Glu
```

<210> SEQ ID NO 539
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 539

```
Phe Phe Asp Lys Phe Lys Asp Phe Phe Lys Asp Tyr Phe Ala Lys Leu
1               5                   10                  15

Trp Asp
```

<210> SEQ ID NO 540
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 540

```
Phe Phe Glu Arg Phe Lys Glu Phe Phe Lys Asp Tyr Phe Ala Lys Leu
1               5                   10                  15

Trp Asp
```

<210> SEQ ID NO 541
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 541

```
Phe Phe Glu Lys Phe Arg Glu Phe Phe Lys Asp Tyr Phe Ala Lys Leu
1               5                   10                  15

Trp Asp
```

<210> SEQ ID NO 542
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 542

Phe Phe Glu Lys Phe Lys Glu Phe Arg Asp Tyr Phe Ala Lys Leu
1               5                   10                  15

Trp Asp

<210> SEQ ID NO 543
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 543

Phe Phe Glu Arg Phe Lys Glu Phe Phe Lys Asp Tyr Phe Ala Arg Leu
1               5                   10                  15

Trp Asp

<210> SEQ ID NO 544
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 544

Phe Phe Asp Lys Phe Lys Glu Phe Phe Lys Asp Tyr Phe Ala Lys Leu
1               5                   10                  15

Trp Asp

<210> SEQ ID NO 545
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 545

Phe Phe Glu Lys Phe Lys Asp Phe Phe Lys Asp Tyr Phe Ala Lys Leu
1               5                   10                  15

Trp Asp

<210> SEQ ID NO 546
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 546

Phe Phe Glu Lys Phe Lys Glu Phe Phe Lys Glu Tyr Phe Ala Lys Leu
1               5                   10                  15

Trp Asp

<210> SEQ ID NO 547
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 547

```
Phe Phe Glu Lys Phe Lys Glu Phe Phe Lys Asp Tyr Phe Ala Lys Leu
1               5                   10                  15

Trp Glu

<210> SEQ ID NO 548
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 548

Phe Ala Glu Lys Phe Lys Glu Ala Val Lys Asp Tyr Phe Ala Lys Phe
1               5                   10                  15

Trp Asp

<210> SEQ ID NO 549
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 549

Phe Ala Glu Lys Phe Lys Glu Ala Val Lys Glu Tyr Phe Ala Lys Phe
1               5                   10                  15

Trp Glu

<210> SEQ ID NO 550
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 550

Phe Ala Asp Lys Phe Lys Asp Ala Val Lys Asp Tyr Phe Ala Lys Phe
1               5                   10                  15

Trp Asp

<210> SEQ ID NO 551
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 551

Phe Ala Glu Arg Phe Arg Glu Ala Val Lys Asp Tyr Phe Ala Lys Phe
1               5                   10                  15

Trp Asp

<210> SEQ ID NO 552
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 552
```

```
Phe Ala Glu Lys Phe Arg Glu Ala Val Lys Asp Tyr Phe Ala Lys Phe
1               5                   10                  15

Trp Asp

<210> SEQ ID NO 553
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 553

Phe Ala Glu Lys Phe Lys Glu Ala Val Arg Asp Tyr Phe Ala Lys Phe
1               5                   10                  15

Trp Asp

<210> SEQ ID NO 554
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 554

Phe Ala Glu Lys Phe Lys Glu Ala Val Lys Asp Tyr Phe Ala Arg Phe
1               5                   10                  15

Trp Asp

<210> SEQ ID NO 555
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 555

Asp Lys Trp Lys Ala Val Tyr Asp Lys Phe Ala Glu Ala Phe Lys Glu
1               5                   10                  15

Phe Phe

<210> SEQ ID NO 556
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 556

Glu Lys Trp Lys Ala Val Tyr Glu Lys Phe Ala Glu Ala Phe Lys Glu
1               5                   10                  15

Phe Phe

<210> SEQ ID NO 557
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 557
```

```
Asp Lys Trp Lys Ala Val Tyr Asp Lys Phe Ala Asp Ala Phe Lys Asp
1               5                   10                  15

Phe Phe

<210> SEQ ID NO 558
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 558

Asp Arg Trp Lys Ala Val Tyr Asp Lys Phe Ala Glu Ala Phe Lys Glu
1               5                   10                  15

Phe Phe

<210> SEQ ID NO 559
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 559

Asp Lys Trp Arg Ala Val Tyr Asp Lys Phe Ala Glu Ala Phe Lys Glu
1               5                   10                  15

Phe Phe

<210> SEQ ID NO 560
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 560

Asp Lys Trp Lys Ala Val Tyr Asp Arg Phe Ala Glu Ala Phe Lys Glu
1               5                   10                  15

Phe Phe

<210> SEQ ID NO 561
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 561

Asp Lys Trp Lys Ala Val Tyr Asp Lys Phe Ala Glu Ala Phe Arg Glu
1               5                   10                  15

Phe Phe

<210> SEQ ID NO 562
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 562
```

Phe Phe Glu Lys Phe Ala Glu Ala Phe Lys Asp Tyr Val Ala Lys Trp
1               5                   10                  15

Lys Asp

<210> SEQ ID NO 563
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 563

Phe Phe Glu Lys Phe Ala Glu Ala Phe Lys Glu Tyr Val Ala Lys Trp
1               5                   10                  15

Lys Glu

<210> SEQ ID NO 564
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 564

Phe Phe Asp Lys Phe Ala Asp Ala Phe Lys Asp Tyr Val Ala Lys Trp
1               5                   10                  15

Lys Asp

<210> SEQ ID NO 565
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 565

Phe Phe Glu Arg Phe Ala Glu Ala Phe Lys Asp Tyr Val Ala Lys Trp
1               5                   10                  15

Lys Asp

<210> SEQ ID NO 566
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 566

Phe Phe Glu Arg Phe Ala Glu Ala Phe Arg Asp Tyr Val Ala Lys Trp
1               5                   10                  15

Lys Asp

<210> SEQ ID NO 567
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 567

```
Phe Phe Glu Lys Phe Ala Glu Ala Phe Lys Asp Tyr Val Ala Arg Trp
1               5                   10                  15

Lys Asp

<210> SEQ ID NO 568
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 568

Phe Phe Glu Arg Phe Ala Glu Ala Phe Lys Asp Tyr Val Ala Lys Trp
1               5                   10                  15

Arg Asp

<210> SEQ ID NO 569
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 569

Phe Phe Asp Lys Phe Ala Glu Ala Phe Lys Asp Tyr Val Ala Lys Trp
1               5                   10                  15

Lys Asp

<210> SEQ ID NO 570
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 570

Phe Phe Glu Lys Phe Ala Asp Ala Phe Lys Asp Tyr Val Ala Lys Trp
1               5                   10                  15

Lys Asp

<210> SEQ ID NO 571
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 571

Phe Phe Glu Arg Phe Ala Glu Ala Phe Lys Glu Tyr Val Ala Lys Trp
1               5                   10                  15

Lys Asp

<210> SEQ ID NO 572
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 572
```

```
Phe Phe Glu Arg Phe Ala Glu Ala Phe Lys Asp Tyr Val Ala Lys Trp
1               5                   10                  15

Lys Glu

<210> SEQ ID NO 573
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 573

Phe Phe Glu Lys Phe Lys Glu Phe Phe Lys Asp Tyr Phe Ala Lys Phe
1               5                   10                  15

Trp Asp

<210> SEQ ID NO 574
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 574

Phe Phe Asp Lys Phe Lys Asp Phe Phe Lys Asp Tyr Phe Ala Lys Phe
1               5                   10                  15

Trp Asp

<210> SEQ ID NO 575
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 575

Phe Phe Glu Lys Phe Lys Glu Phe Phe Lys Glu Tyr Phe Ala Lys Phe
1               5                   10                  15

Trp Glu

<210> SEQ ID NO 576
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 576

Phe Phe Glu Arg Phe Lys Glu Phe Phe Lys Asp Tyr Phe Ala Lys Phe
1               5                   10                  15

Trp Asp

<210> SEQ ID NO 577
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 577
```

Phe Phe Glu Lys Phe Arg Glu Phe Phe Lys Asp Tyr Phe Ala Lys Phe
1               5                   10                  15

Trp Asp

<210> SEQ ID NO 578
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 578

Phe Phe Glu Lys Phe Lys Glu Phe Phe Arg Asp Tyr Phe Ala Lys Phe
1               5                   10                  15

Trp Asp

<210> SEQ ID NO 579
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 579

Phe Phe Glu Lys Phe Lys Glu Phe Phe Lys Asp Tyr Phe Ala Arg Phe
1               5                   10                  15

Trp Asp

<210> SEQ ID NO 580
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 580

Phe Phe Asp Lys Phe Lys Glu Phe Phe Lys Asp Tyr Phe Ala Lys Phe
1               5                   10                  15

Trp Asp

<210> SEQ ID NO 581
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 581

Phe Phe Glu Lys Phe Lys Asp Phe Phe Lys Asp Tyr Phe Ala Lys Phe
1               5                   10                  15

Trp Asp

<210> SEQ ID NO 582
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 582

```
Phe Phe Glu Lys Phe Lys Glu Phe Phe Lys Glu Tyr Phe Ala Lys Phe
1               5                   10                  15

Trp Asp

<210> SEQ ID NO 583
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 583

Phe Phe Glu Lys Phe Lys Glu Phe Phe Lys Asp Tyr Phe Ala Lys Phe
1               5                   10                  15

Trp Glu

<210> SEQ ID NO 584
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 584

Asp Trp Phe Lys Ala Phe Tyr Asp Lys Val Ala Glu Lys Phe Lys Glu
1               5                   10                  15

Ala Phe

<210> SEQ ID NO 585
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 585

Asp Trp Phe Lys Ala Phe Tyr Asp Lys Val Ala Glu Lys Phe Lys Glu
1               5                   10                  15

Ala Phe

<210> SEQ ID NO 586
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 586

Asp Trp Phe Lys Ala Phe Tyr Asp Lys Val Ala Glu Lys Phe Lys Glu
1               5                   10                  15

Ala Phe

<210> SEQ ID NO 587
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 587
```

Asp Trp Phe Lys Ala Phe Tyr Asp Lys Val Ala Glu Lys Phe Lys Glu
1               5                   10                  15

Ala Phe

<210> SEQ ID NO 588
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 588

Asp Trp Phe Lys Ala Phe Tyr Asp Lys Val Ala Glu Lys Phe Lys Glu
1               5                   10                  15

Ala Phe

<210> SEQ ID NO 589
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 589

Asp Trp Phe Lys Ala Phe Tyr Asp Lys Val Ala Glu Lys Phe Lys Glu
1               5                   10                  15

Ala Phe

<210> SEQ ID NO 590
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 590

Asp Trp Phe Lys Ala Phe Tyr Asp Lys Val Ala Glu Lys Phe Lys Glu
1               5                   10                  15

Ala Phe

<210> SEQ ID NO 591
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 591

Asp Trp Phe Lys Ala Phe Tyr Asp Lys Val Ala Glu Lys Phe Lys Glu
1               5                   10                  15

Ala Phe

<210> SEQ ID NO 592
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 592

Asp Trp Phe Lys Ala Phe Tyr Asp Lys Val Ala Glu Lys Phe Lys Glu
1               5                   10                  15

Ala Phe

<210> SEQ ID NO 593
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 593

Asp Trp Phe Lys Ala Phe Tyr Asp Lys Val Ala Glu Lys Phe Lys Glu
1               5                   10                  15

Ala Phe

<210> SEQ ID NO 594
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 594

Asp Trp Phe Lys Ala Phe Tyr Asp Lys Val Ala Glu Lys Phe Lys Glu
1               5                   10                  15

Ala Phe

<210> SEQ ID NO 595
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 595

Asp Trp Phe Lys Ala Phe Tyr Asp Lys Val Ala Glu Lys Phe Lys Glu
1               5                   10                  15

Ala Phe

<210> SEQ ID NO 596
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 596

Asp Trp Phe Lys Ala Phe Tyr Asp Lys Val Ala Glu Lys Phe Lys Glu
1               5                   10                  15

Ala Phe

<210> SEQ ID NO 597
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 597

Asp Trp Phe Lys Ala Phe Tyr Asp Lys Val Ala Glu Lys Phe Lys Glu
1               5                   10                  15

Ala Phe

<210> SEQ ID NO 598
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 598

Asp Trp Phe Lys Ala Phe Tyr Asp Lys Val Ala Glu Lys Phe Lys Glu
1               5                   10                  15

Ala Phe

<210> SEQ ID NO 599
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 599

Asp Trp Phe Lys Ala Phe Tyr Asp Lys Val Ala Glu Lys Phe Lys Glu
1               5                   10                  15

Ala Phe

<210> SEQ ID NO 600
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 600

Asp Trp Phe Lys Ala Phe Tyr Asp Lys Val Ala Glu Lys Phe Lys Glu
1               5                   10                  15

Ala Phe

<210> SEQ ID NO 601
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 601

Asp Trp Phe Lys Ala Phe Tyr Asp Lys Val Ala Glu Lys Phe Lys Glu
1               5                   10                  15

Ala Phe

<210> SEQ ID NO 602
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 602

-continued

Asp Trp Phe Lys Ala Phe Tyr Asp Lys Val Ala Glu Lys Phe Lys Glu
1               5                   10                  15

Ala Phe

<210> SEQ ID NO 603
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 603

Asp Trp Phe Lys Ala Phe Tyr Asp Lys Val Ala Glu Lys Phe Lys Glu
1               5                   10                  15

Ala Phe

<210> SEQ ID NO 604
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 604

Asp Trp Phe Lys Ala Phe Tyr Asp Lys Val Ala Glu Lys Phe Lys Glu
1               5                   10                  15

Ala Phe

<210> SEQ ID NO 605
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 605

Asp Trp Phe Lys Ala Phe Tyr Asp Lys Val Ala Glu Lys Phe Lys Glu
1               5                   10                  15

Ala Phe

<210> SEQ ID NO 606
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 606

Asp Trp Phe Lys Ala Phe Tyr Asp Lys Val Ala Glu Lys Phe Lys Glu
1               5                   10                  15

Ala Phe

<210> SEQ ID NO 607
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 607

```
Asp Trp Phe Lys Ala Phe Tyr Asp Lys Val Ala Glu Lys Phe Lys Glu
1               5                   10                  15

Ala Phe

<210> SEQ ID NO 608
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 608

Asp Trp Phe Lys Ala Phe Tyr Asp Lys Val Ala Glu Lys Phe Lys Glu
1               5                   10                  15

Ala Phe

<210> SEQ ID NO 609
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 609

Asp Trp Phe Xaa Ala Phe Tyr Asp Xaa Val Ala Glu Xaa Phe Xaa Glu
1               5                   10                  15

Ala Phe

<210> SEQ ID NO 610
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 610
```

-continued

```
Asp Trp Phe Xaa Ala Phe Tyr Asp Xaa Val Ala Glu Xaa Phe Xaa Glu
1               5                   10                  15

Ala Phe

<210> SEQ ID NO 611
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 611

Asp Trp Phe Xaa Ala Phe Tyr Asp Xaa Val Ala Glu Xaa Phe Xaa Glu
1               5                   10                  15

Ala Phe

<210> SEQ ID NO 612
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 612

Asp Trp Phe Xaa Ala Phe Tyr Asp Xaa Val Ala Glu Xaa Phe Xaa Glu
1               5                   10                  15

Ala Phe

<210> SEQ ID NO 613
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
```

```
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 613

Asp Trp Phe Xaa Ala Phe Tyr Asp Xaa Val Ala Glu Xaa Phe Xaa Glu
1               5                   10                  15

Ala Phe

<210> SEQ ID NO 614
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 614

Asp Trp Phe Xaa Ala Phe Tyr Asp Xaa Val Ala Glu Xaa Phe Xaa Glu
1               5                   10                  15

Ala Phe

<210> SEQ ID NO 615
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 615
```

```
Asp Trp Phe Xaa Ala Phe Tyr Asp Xaa Val Ala Glu Xaa Phe Xaa Glu
1               5                   10                  15

Ala Phe

<210> SEQ ID NO 616
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 616

Asp Trp Phe Xaa Ala Phe Tyr Asp Xaa Val Ala Glu Xaa Phe Xaa Glu
1               5                   10                  15

Ala Phe

<210> SEQ ID NO 617
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 617

Asp Trp Phe Xaa Ala Phe Tyr Asp Xaa Val Ala Glu Xaa Phe Xaa Glu
1               5                   10                  15

Ala Phe

<210> SEQ ID NO 618
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
```

```
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(115)
<223> OTHER INFORMATION: Xaa is Ornithine (Orn).

<400> SEQUENCE: 618

Asp Trp Phe Xaa Ala Phe Tyr Asp Xaa Val Ala Glu Xaa Phe Xaa Glu
1               5                   10                  15

Ala Phe

<210> SEQ ID NO 619
<211> LENGTH: 18
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is Ornithine (Orn).
<220> FEATURE:
<221> NAME/KEY: misc_feature
<222> LOCATION: (9)..(9)
<223> OTHER INFORMATION: Xaa is Ornithine (Orn).
<220> FEATURE:
<221> NAME/KEY: misc_feature
<222> LOCATION: (13)..(13)
<223> OTHER INFORMATION: Xaa is Ornithine (Orn).
<220> FEATURE:
<221> NAME/KEY: misc_feature
<222> LOCATION: (15)..(15)
<223> OTHER INFORMATION: Xaa is Ornithine (Orn).

<400> SEQUENCE: 619

Asp Trp Phe Xaa Ala Phe Tyr Asp Xaa Val Ala Glu Xaa Phe Xaa Glu
1               5                   10                  15

Ala Phe

<210> SEQ ID NO 620
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is hydrophobic.
<220> FEATURE:
<221> NAME/KEY: misc_feature
<222> LOCATION: (2)..(3)
<223> OTHER INFORMATION: Xaa is acidic or basic
<220> FEATURE:
<221> NAME/KEY: misc_feature
<222> LOCATION: (4)..(4)
<223> OTHER INFORMATION: Xaa is hydrophobic.

<400> SEQUENCE: 620

Xaa Xaa Xaa Xaa
1
```

```
<210> SEQ ID NO 621
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is hydrophobic
<220> FEATURE:
<221> NAME/KEY: misc_feature
<222> LOCATION: (2)..(2)
<223> OTHER INFORMATION: Xaa is acidic or basic
<220> FEATURE:
<221> NAME/KEY: misc_feature
<222> LOCATION: (3)..(3)
<223> OTHER INFORMATION: Xaa is hydrophobic

<400> SEQUENCE: 621

Xaa Xaa Xaa
1

<210> SEQ ID NO 622
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 622

Lys Arg Ser
1

<210> SEQ ID NO 623
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 623

Lys Arg Thr
1

<210> SEQ ID NO 624
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 624

Trp Arg Ile
1

<210> SEQ ID NO 625
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 625

Trp Arg Leu
1
```

<210> SEQ ID NO 626
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 626

Phe Arg Ile
1

<210> SEQ ID NO 627
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 627

Phe Arg Leu
1

<210> SEQ ID NO 628
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 628

Lys Glu Ser
1

<210> SEQ ID NO 629
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 629

Lys Glu Thr
1

<210> SEQ ID NO 630
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 630

Lys Asp Ser
1

<210> SEQ ID NO 631
<211> LENGTH: 3
<212> TYPE: PRT
<213> ORGANISM: Artificial
<220> FEATURE:
<223> OTHER INFORMATION: Synthetic peptide optionally bearing
      protecting groups.

```
<400> SEQUENCE: 631

Lys Asp Thr
1

<210> SEQ ID NO 632
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 632

Lys Arg Ser
1

<210> SEQ ID NO 633
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 633

Lys Arg Thr
1

<210> SEQ ID NO 634
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 634

Leu Glu Ser
1

<210> SEQ ID NO 635
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 635

Leu Glu Thr
1

<210> SEQ ID NO 636
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 636

Trp Arg Ser
1

<210> SEQ ID NO 637
<211> LENGTH: 3
<212> TYPE: PRT
<213> ORGANISM: Artificial
```

-continued

```
<220> FEATURE:
<223> OTHER INFORMATION: Synthetic peptide optionally bearing
      protecting groups.

<400> SEQUENCE: 637

Trp Asp Ser
1

<210> SEQ ID NO 638
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 638

Trp Glu Ser
1

<210> SEQ ID NO 639
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 639

Trp Arg Ser
1

<210> SEQ ID NO 640
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 640

Lys Glu Leu
1

<210> SEQ ID NO 641
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 641

Leu Arg Ser
1

<210> SEQ ID NO 642
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 642

Leu Asp Ser
1
```

```
<210> SEQ ID NO 643
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 643

Leu Glu Ser
1

<210> SEQ ID NO 644
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 644

Leu Arg Ser
1

<210> SEQ ID NO 645
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 645

Leu Arg Thr
1

<210> SEQ ID NO 646
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 646

Glu Asp Tyr
1

<210> SEQ ID NO 647
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 647

Lys Arg Ser
1

<210> SEQ ID NO 648
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 648
```

Trp Arg Ile
1

<210> SEQ ID NO 649
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 649

Trp Arg Leu
1

<210> SEQ ID NO 650
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 650

Phe Arg Ile
1

<210> SEQ ID NO 651
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 651

Phe Arg Leu
1

<210> SEQ ID NO 652
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 652

Trp Arg Phe
1

<210> SEQ ID NO 653
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 653

Trp Arg Tyr
1

<210> SEQ ID NO 654
<211> LENGTH: 3
<212> TYPE: PRT
<213> ORGANISM: Artificial
<220> FEATURE:
<223> OTHER INFORMATION: Synthetic peptide optionally bearing

```
            protecting groups.

<400> SEQUENCE: 654

Trp Arg Phe
1

<210> SEQ ID NO 655
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 655

Trp Arg Tyr
1

<210> SEQ ID NO 656
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn).

<400> SEQUENCE: 656

Xaa Arg Ser
1

<210> SEQ ID NO 657
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 657

Lys Arg Ser
1

<210> SEQ ID NO 658
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 658

Lys Arg Thr
1

<210> SEQ ID NO 659
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 659

Leu Asp Thr
1
```

```
<210> SEQ ID NO 660
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 660

Leu Glu Thr
1

<210> SEQ ID NO 661
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 661

Leu Arg Thr
1

<210> SEQ ID NO 662
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 662

Xaa Arg Ser
1

<210> SEQ ID NO 663
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 663

Xaa Asp Ser
1

<210> SEQ ID NO 664
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 664
```

Xaa Glu Ser
1

<210> SEQ ID NO 665
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 665

Lys Arg Ser
1

<210> SEQ ID NO 666
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 666

Lys Arg Thr
1

<210> SEQ ID NO 667
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 667

Lys Glu Ser
1

<210> SEQ ID NO 668
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 668

Lys Glu Thr
1

<210> SEQ ID NO 669
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 669

Lys Asp Ser
1

<210> SEQ ID NO 670
<211> LENGTH: 3
<212> TYPE: PRT
<213> ORGANISM: Artificial
<220> FEATURE:
<223> OTHER INFORMATION: Synthetic peptide optionally bearing protecting groups.

<400> SEQUENCE: 670

Lys Asp Thr
1

<210> SEQ ID NO 671
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 671

Lys Glu Leu
1

<210> SEQ ID NO 672
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 672

Lys Arg Leu
1

<210> SEQ ID NO 673
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 673

Lys Arg Thr
1

<210> SEQ ID NO 674
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 674

Lys Glu Ser
1

<210> SEQ ID NO 675
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 675

Lys Glu Thr
1

<210> SEQ ID NO 676
<211> LENGTH: 3

```
<212> TYPE: PRT
<213> ORGANISM: Artificial
<220> FEATURE:
<223> OTHER INFORMATION: Synthetic peptide optionally bearing
      protecting groups.

<400> SEQUENCE: 676

Lys Asp Ser
1

<210> SEQ ID NO 677
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 677

Lys Asp Thr
1

<210> SEQ ID NO 678
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 678

Lys Arg Ser
1

<210> SEQ ID NO 679
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 679

Lys Glu Leu
1

<210> SEQ ID NO 680
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 680

Lys Asp Ser
1

<210> SEQ ID NO 681
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 681

Lys Asp Thr
1
```

```
<210> SEQ ID NO 682
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 682

Lys Arg Thr
1

<210> SEQ ID NO 683
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 683

Lys Glu Leu
1

<210> SEQ ID NO 684
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 684

Xaa Glu Ser
1

<210> SEQ ID NO 685
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 685

Xaa Asp Ser
1

<210> SEQ ID NO 686
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 686
```

```
Xaa Asp Thr
1

<210> SEQ ID NO 687
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 687

Xaa Arg Thr
1

<210> SEQ ID NO 688
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (norLeu)

<400> SEQUENCE: 688

Xaa Glu Thr
1

<210> SEQ ID NO 689
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 689

Trp Asp Ile
1

<210> SEQ ID NO 690
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 690

Trp Arg Ile
1

<210> SEQ ID NO 691
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 691

Trp Glu Ile
1
```

-continued

```
<210> SEQ ID NO 692
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 692

Trp Asp Leu
1

<210> SEQ ID NO 693
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 693

Trp Glu Leu
1

<210> SEQ ID NO 694
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 694

Phe Asp Ile
1

<210> SEQ ID NO 695
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 695

Phe Asp Leu
1

<210> SEQ ID NO 696
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 696

Phe Glu Leu
1

<210> SEQ ID NO 697
<211> LENGTH: 3
<212> TYPE: PRT
<213> ORGANISM: Artificial
<220> FEATURE:
<223> OTHER INFORMATION: Synthetic peptide optionally bearing
      protecting groups.
```

```
<400> SEQUENCE: 697

Trp Arg Phe
1

<210> SEQ ID NO 698
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 698

Trp Glu Phe
1

<210> SEQ ID NO 699
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 699

Trp Asp Phe
1

<210> SEQ ID NO 700
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 700

Trp Asp Tyr
1

<210> SEQ ID NO 701
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 701

Trp Arg Tyr
1

<210> SEQ ID NO 702
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 702

Trp Glu Tyr
1

<210> SEQ ID NO 703
<211> LENGTH: 3
<212> TYPE: PRT
<213> ORGANISM: Artificial
```

```
<220> FEATURE:
<223> OTHER INFORMATION: Synthetic peptide optionally bearing
      protecting groups.

<400> SEQUENCE: 703

Trp Arg Thr
1

<210> SEQ ID NO 704
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 704

Trp Asp Thr
1

<210> SEQ ID NO 705
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 705

Trp Glu Thr
1

<210> SEQ ID NO 706
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is norleucine (Nle)

<400> SEQUENCE: 706

Phe Arg Xaa
1

<210> SEQ ID NO 707
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is norleucine (Nle)

<400> SEQUENCE: 707

Phe Glu Xaa
1

<210> SEQ ID NO 708
<211> LENGTH: 3
<212> TYPE: PRT
<213> ORGANISM: Artificial
<220> FEATURE:
<223> OTHER INFORMATION: Synthetic peptide optionally bearing
``` protecting groups.
<220> FEATURE:
<221> NAME/KEY: misc_feature
<222> LOCATION: (3)..(3)
<223> OTHER INFORMATION: Xaa is norleucine (Nle)

<400> SEQUENCE: 708

Phe Asp Xaa
1

<210> SEQ ID NO 709
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 709

Glu His Tyr
1

<210> SEQ ID NO 710
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 710

Leu His Ser
1

<210> SEQ ID NO 711
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 711

Leu His Thr
1

<210> SEQ ID NO 712
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 712

Lys His Ser
1

<210> SEQ ID NO 713
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 713

Lys His Thr
1

```
<210> SEQ ID NO 714
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 714

Lys His Leu
1

<210> SEQ ID NO 715
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 715

Lys His Ser
1

<210> SEQ ID NO 716
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 716

Lys His Thr
1

<210> SEQ ID NO 717
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 717

Lys His Leu
1

<210> SEQ ID NO 718
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 718

Xaa His Ser
1

<210> SEQ ID NO 719
<211> LENGTH: 3
<212> TYPE: PRT
<213> ORGANISM: Artificial
```

```
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 719

Xaa His Thr
1

<210> SEQ ID NO 720
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 720

Phe His Ile
1

<210> SEQ ID NO 721
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 721

Phe His Leu
1

<210> SEQ ID NO 722
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is norleucine (Nle)

<400> SEQUENCE: 722

Phe His Xaa
1

<210> SEQ ID NO 723
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 723

Phe Lys Leu
1

<210> SEQ ID NO 724
<211> LENGTH: 3
<212> TYPE: PRT
<213> ORGANISM: Artificial
<220> FEATURE:
<223> OTHER INFORMATION: Synthetic peptide optionally bearing
``` protecting groups.

<400> SEQUENCE: 724

Trp His Ile
1

<210> SEQ ID NO 725
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 725

Trp His Leu
1

<210> SEQ ID NO 726
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 726

Trp His Phe
1

<210> SEQ ID NO 727
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 727

Trp His Tyr
1

<210> SEQ ID NO 728
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 728

Phe Lys Leu
1

<210> SEQ ID NO 729
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 729

Lys His Ser
1

<210> SEQ ID NO 730
<211> LENGTH: 3

```
<212> TYPE: PRT
<213> ORGANISM: Artificial
<220> FEATURE:
<223> OTHER INFORMATION: Synthetic peptide optionally bearing
      protecting groups.

<400> SEQUENCE: 730

Lys His Thr
1

<210> SEQ ID NO 731
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 731

Lys His Leu
1

<210> SEQ ID NO 732
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 732

Leu His Ser
1

<210> SEQ ID NO 733
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 733

Leu His Thr
1

<210> SEQ ID NO 734
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 734

Lys His Ser
1

<210> SEQ ID NO 735
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 735

Lys His Thr
1
```

<210> SEQ ID NO 736
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 736

Lys His Leu
1

<210> SEQ ID NO 737
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 737

Lys His Ser
1

<210> SEQ ID NO 738
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 738

Lys His Thr
1

<210> SEQ ID NO 739
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (Nle)

<400> SEQUENCE: 739

Xaa His Ser
1

<210> SEQ ID NO 740
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 740

Phe His Ile
1

<210> SEQ ID NO 741
<211> LENGTH: 3
<212> TYPE: PRT
<213> ORGANISM: Artificial

```
<220> FEATURE:
<223> OTHER INFORMATION: Synthetic peptide optionally bearing
      protecting groups.

<400> SEQUENCE: 741

Phe His Leu
1

<210> SEQ ID NO 742
<211> LENGTH: 3
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (3)..(3)
<223> OTHER INFORMATION: Xaa is norleucine (Nle)

<400> SEQUENCE: 742

Phe His Xaa
1

<210> SEQ ID NO 743
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 743

Trp His Ser
1

<210> SEQ ID NO 744
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 744

Trp His Ile
1

<210> SEQ ID NO 745
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 745

Trp His Leu
1

<210> SEQ ID NO 746
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 746
```

-continued

Trp His Phe
1

<210> SEQ ID NO 747
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 747

Trp His Tyr
1

<210> SEQ ID NO 748
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 748

Trp His Thr
1

<210> SEQ ID NO 749
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 749

Lys His Ser
1

<210> SEQ ID NO 750
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 750

Lys His Thr
1

<210> SEQ ID NO 751
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 751

Lys Arg Asp Ser
1

<210> SEQ ID NO 752
<211> LENGTH: 4
<212> TYPE: PRT
<213> ORGANISM: Artificial
<220> FEATURE:
<223> OTHER INFORMATION: Synthetic peptide optionally bearing protecting groups.

<400> SEQUENCE: 752

Lys Arg Asp Thr
1

<210> SEQ ID NO 753
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 753

Trp Arg Asp Ile
1

<210> SEQ ID NO 754
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 754

Trp Arg Asp Leu
1

<210> SEQ ID NO 755
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 755

Phe Arg Asp Leu
1

<210> SEQ ID NO 756
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 756

Phe Arg Asp Ile
1

<210> SEQ ID NO 757
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 757

Phe Arg Asp Xaa
1

<210> SEQ ID NO 758
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 758

Phe Arg Glu Xaa
1

<210> SEQ ID NO 759
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 759

Phe Arg Glu Ile
1

<210> SEQ ID NO 760
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 760

Phe Asp Arg Ile
1

<210> SEQ ID NO 761
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 761

Phe Glu Arg Ile
1

<210> SEQ ID NO 762
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 762

Phe Asp Arg Leu
1

<210> SEQ ID NO 763
<211> LENGTH: 4
<212> TYPE: PRT
<213> ORGANISM: Artificial

```
<220> FEATURE:
<223> OTHER INFORMATION: Synthetic peptide optionally bearing
      protecting groups.

<400> SEQUENCE: 763

Phe Arg Glu Leu
1

<210> SEQ ID NO 764
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 764

Phe Glu Arg Leu
1

<210> SEQ ID NO 765
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 765

Phe Asp Arg Xaa
1

<210> SEQ ID NO 766
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 766

Phe Glu Arg Xaa
1

<210> SEQ ID NO 767
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 767

Lys Glu Arg Ser
1

<210> SEQ ID NO 768
<211> LENGTH: 4
<212> TYPE: PRT
<213> ORGANISM: Artificial
<220> FEATURE:
<223> OTHER INFORMATION: Synthetic peptide optionally bearing
```

```
                              protecting groups.

<400> SEQUENCE: 768

Lys Glu Arg Thr
1

<210> SEQ ID NO 769
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 769

Lys Asp Arg Ser
1

<210> SEQ ID NO 770
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 770

Lys Asp Arg Thr
1

<210> SEQ ID NO 771
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 771

Lys Arg Glu Ser
1

<210> SEQ ID NO 772
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 772

Lys Arg Glu Thr
1

<210> SEQ ID NO 773
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 773

Leu Glu Arg Ser
1

<210> SEQ ID NO 774
<211> LENGTH: 4
```

```
<212> TYPE: PRT
<213> ORGANISM: Artificial
<220> FEATURE:
<223> OTHER INFORMATION: Synthetic peptide optionally bearing
      protecting groups.

<400> SEQUENCE: 774

Leu Glu Arg Thr
1

<210> SEQ ID NO 775
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 775

Trp Arg Asp Ser
1

<210> SEQ ID NO 776
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 776

Trp Asp Arg Ser
1

<210> SEQ ID NO 777
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 777

Trp Glu Arg Ser
1

<210> SEQ ID NO 778
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 778

Trp Arg Glu Ser
1

<210> SEQ ID NO 779
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 779

Lys Glu Arg Leu
1
```

<210> SEQ ID NO 780
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 780

Leu Arg Asp Ser
1

<210> SEQ ID NO 781
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 781

Leu Asp Arg Ser
1

<210> SEQ ID NO 782
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 782

Leu Glu Arg Ser
1

<210> SEQ ID NO 783
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 783

Leu Arg Glu Ser
1

<210> SEQ ID NO 784
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 784

Leu Arg Asp Thr
1

<210> SEQ ID NO 785
<211> LENGTH: 4
<212> TYPE: PRT
<213> ORGANISM: Artificial
<220> FEATURE:
<223> OTHER INFORMATION: Synthetic peptide optionally bearing
      protecting groups.

```
<400> SEQUENCE: 785

Glu Asp Arg Tyr
1

<210> SEQ ID NO 786
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 786

Lys Arg Asp Ser
1

<210> SEQ ID NO 787
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 787

Trp Arg Asp Ile
1

<210> SEQ ID NO 788
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 788

Trp Arg Asp Leu
1

<210> SEQ ID NO 789
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 789

Phe Arg Asp Ile
1

<210> SEQ ID NO 790
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 790

Phe Arg Asp Leu
1

<210> SEQ ID NO 791
<211> LENGTH: 4
<212> TYPE: PRT
<213> ORGANISM: Artificial
```

```
<220> FEATURE:
<223> OTHER INFORMATION: Synthetic peptide optionally bearing
      protecting groups.

<400> SEQUENCE: 791

Trp Arg Asp Phe
1

<210> SEQ ID NO 792
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 792

Trp Arg Asp Tyr
1

<210> SEQ ID NO 793
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 793

Trp Arg Asp Phe
1

<210> SEQ ID NO 794
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 794

Trp Arg Asp Tyr
1

<210> SEQ ID NO 795
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 795

Xaa Arg Glu Ser
1

<210> SEQ ID NO 796
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 796
```

Lys Arg Asp Ser
1

<210> SEQ ID NO 797
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 797

Lys Arg Asp Thr
1

<210> SEQ ID NO 798
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 798

Leu Asp Arg Thr
1

<210> SEQ ID NO 799
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 799

Leu Glu Arg Thr
1

<210> SEQ ID NO 800
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 800

Leu Arg Glu Thr
1

<210> SEQ ID NO 801
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (Nle)

<400> SEQUENCE: 801

Xaa Arg Asp Ser
1

<210> SEQ ID NO 802
<211> LENGTH: 4

```
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (Nle)

<400> SEQUENCE: 802

Xaa Asp Arg Ser
1

<210> SEQ ID NO 803
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (Nle)

<400> SEQUENCE: 803

Xaa Glu Arg Ser
1

<210> SEQ ID NO 804
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is norleucine (Nle)

<400> SEQUENCE: 804

Xaa Arg Glu Ser
1

<210> SEQ ID NO 805
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 805

Lys Arg Asp Ser
1

<210> SEQ ID NO 806
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 806

Lys Arg Asp Thr
1
```

```
<210> SEQ ID NO 807
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 807

Lys Glu Arg Ser
1

<210> SEQ ID NO 808
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 808

Lys Glu Arg Thr
1

<210> SEQ ID NO 809
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 809

Lys Asp Arg Ser
1

<210> SEQ ID NO 810
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 810

Lys Asp Arg Thr
1

<210> SEQ ID NO 811
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 811

Lys Arg Glu Ser
1

<210> SEQ ID NO 812
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 812
```

-continued

Lys Arg Glu Thr
1

<210> SEQ ID NO 813
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 813

Lys Glu Arg Leu
1

<210> SEQ ID NO 814
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 814

Lys Arg Glu Leu
1

<210> SEQ ID NO 815
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 815

Lys Arg Asp Thr
1

<210> SEQ ID NO 816
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 816

Lys Glu Arg Ser
1

<210> SEQ ID NO 817
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 817

Lys Glu Arg Thr
1

<210> SEQ ID NO 818
<211> LENGTH: 4
<212> TYPE: PRT
<213> ORGANISM: Artificial
<220> FEATURE:
<223> OTHER INFORMATION: Synthetic peptide optionally bearing -continued

```
        protecting groups.

<400> SEQUENCE: 818

Lys Asp Arg Ser
1

<210> SEQ ID NO 819
<211> LENGTH: 4
<212> TYPE: PRT
<213> ORGANISM: Artificial
<220> FEATURE:
<223> OTHER INFORMATION: Synthetic peptide optionally bearing
        protecting groups.

<400> SEQUENCE: 819

Lys Asp Arg Thr
1

<210> SEQ ID NO 820
<211> LENGTH: 4
<212> TYPE: PRT
<213> ORGANISM: Artificial
<220> FEATURE:
<223> OTHER INFORMATION: Synthetic peptide optionally bearing
        protecting groups.

<400> SEQUENCE: 820

Lys Arg Glu Ser
1

<210> SEQ ID NO 821
<211> LENGTH: 4
<212> TYPE: PRT
<213> ORGANISM: Artificial
<220> FEATURE:
<223> OTHER INFORMATION: Synthetic peptide optionally bearing
        protecting groups.

<400> SEQUENCE: 821

Lys Arg Glu Thr
1

<210> SEQ ID NO 822
<211> LENGTH: 4
<212> TYPE: PRT
<213> ORGANISM: Artificial
<220> FEATURE:
<223> OTHER INFORMATION: Synthetic peptide optionally bearing
        protecting groups.

<400> SEQUENCE: 822

Lys Glu Arg Leu
1

<210> SEQ ID NO 823
<211> LENGTH: 4
<212> TYPE: PRT
<213> ORGANISM: Artificial
<220> FEATURE:
<223> OTHER INFORMATION: Synthetic peptide optionally bearing
        protecting groups.

<400> SEQUENCE: 823

Lys Arg Asp Ser
1

<210> SEQ ID NO 824
<211> LENGTH: 4
```

```
<212> TYPE: PRT
<213> ORGANISM: Artificial
<220> FEATURE:
<223> OTHER INFORMATION: Synthetic peptide optionally bearing
      protecting groups.

<400> SEQUENCE: 824

Lys Arg Asp Thr
1

<210> SEQ ID NO 825
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 825

Lys Glu Arg Ser
1

<210> SEQ ID NO 826
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 826

Lys Glu Arg Thr
1

<210> SEQ ID NO 827
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 827

Lys Asp Arg Ser
1

<210> SEQ ID NO 828
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 828

Lys Asp Arg Thr
1

<210> SEQ ID NO 829
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 829

Lys Arg Glu Ser
1
```

<210> SEQ ID NO 830
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 830

Lys Arg Glu Thr
1

<210> SEQ ID NO 831
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 831

Lys Glu Arg Leu
1

<210> SEQ ID NO 832
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 832

Xaa Arg Glu Ser
1

<210> SEQ ID NO 833
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 833

Xaa Glu Arg Ser
1

<210> SEQ ID NO 834
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 834

```
Xaa Arg Asp Ser
1

<210> SEQ ID NO 835
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 835

Xaa Asp Arg Ser
1

<210> SEQ ID NO 836
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 836

Xaa Asp Arg Thr
1

<210> SEQ ID NO 837
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 837

Xaa Arg Asp Thr
1

<210> SEQ ID NO 838
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 838

Xaa Glu Arg Thr
1

<210> SEQ ID NO 839
<211> LENGTH: 4
<212> TYPE: PRT
<213> ORGANISM: Artificial
```

```
<220> FEATURE:
<223> OTHER INFORMATION: Synthetic peptide optionally bearing
      protecting groups.
<220> FEATURE:
<221> NAME/KEY: misc_feature
<222> LOCATION: (1)..(1)
<223> OTHER INFORMATION: Xaa is ornithine (Orn)

<400> SEQUENCE: 839

Xaa Arg Glu Thr
1

<210> SEQ ID NO 840
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 840

Trp Asp Arg Ile
1

<210> SEQ ID NO 841
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 841

Trp Arg Glu Ile
1

<210> SEQ ID NO 842
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 842

Trp Glu Arg Ile
1

<210> SEQ ID NO 843
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 843

Trp Asp Arg Leu
1

<210> SEQ ID NO 844
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 844
```

Trp Arg Glu Leu
1

<210> SEQ ID NO 845
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 845

Trp Glu Arg Leu
1

<210> SEQ ID NO 846
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 846

Phe Asp Arg Ile
1

<210> SEQ ID NO 847
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 847

Phe Arg Glu Ile
1

<210> SEQ ID NO 848
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 848

Phe Glu Arg Ile
1

<210> SEQ ID NO 849
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 849

Phe Asp Arg Leu
1

<210> SEQ ID NO 850
<211> LENGTH: 4
<212> TYPE: PRT
<213> ORGANISM: Artificial
<220> FEATURE:
<223> OTHER INFORMATION: Synthetic peptide optionally bearing

```
        protecting groups.

<400> SEQUENCE: 850

Phe Arg Glu Leu
1

<210> SEQ ID NO 851
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 851

Phe Glu Arg Leu
1

<210> SEQ ID NO 852
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 852

Trp Arg Asp Phe
1

<210> SEQ ID NO 853
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 853

Trp Arg Glu Phe
1

<210> SEQ ID NO 854
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 854

Trp Glu Arg Phe
1

<210> SEQ ID NO 855
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 855

Trp Asp Arg Tyr
1

<210> SEQ ID NO 856
<211> LENGTH: 4
```

```
<212> TYPE: PRT
<213> ORGANISM: Artificial
<220> FEATURE:
<223> OTHER INFORMATION: Synthetic peptide optionally bearing
      protecting groups.

<400> SEQUENCE: 856

Trp Arg Glu Tyr
1

<210> SEQ ID NO 857
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 857

Trp Glu Arg Tyr
1

<210> SEQ ID NO 858
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 858

Trp Arg Asp Thr
1

<210> SEQ ID NO 859
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 859

Trp Asp Arg Thr
1

<210> SEQ ID NO 860
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 860

Trp Arg Glu Thr
1

<210> SEQ ID NO 861
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 861

Trp Glu Arg Thr
1
```

```
<210> SEQ ID NO 862
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 862

Phe Arg Asp Xaa
1

<210> SEQ ID NO 863
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 863

Phe Arg Glu Xaa
1

<210> SEQ ID NO 864
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 864

Phe Lys Asp Leu
1

<210> SEQ ID NO 865
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 865

Phe Asp Lys Leu
1

<210> SEQ ID NO 866
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 866

Phe Lys Glu Leu
1
```

```
<210> SEQ ID NO 867
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 867

Phe Glu Lys Leu
1

<210> SEQ ID NO 868
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 868

Phe Lys Asp Ile
1

<210> SEQ ID NO 869
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 869

Phe Asp Lys Ile
1

<210> SEQ ID NO 870
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 870

Phe Lys Glu Ile
1

<210> SEQ ID NO 871
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 871

Phe Glu Lys Ile
1

<210> SEQ ID NO 872
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
```

```
<223> OTHER INFORMATION: Xaa is norleucine (Nle)

<400> SEQUENCE: 872

Phe Lys Asp Xaa
1

<210> SEQ ID NO 873
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 873

Phe Asp Lys Xaa
1

<210> SEQ ID NO 874
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 874

Phe Lys Glu Xaa
1

<210> SEQ ID NO 875
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 875

Phe Glu Lys Xaa
1

<210> SEQ ID NO 876
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 876

Phe His Asp Leu
1

<210> SEQ ID NO 877
<211> LENGTH: 4
<212> TYPE: PRT
<213> ORGANISM: Artificial
```

```
<220> FEATURE:
<223> OTHER INFORMATION: Synthetic peptide optionally bearing
      protecting groups.

<400> SEQUENCE: 877

Phe Asp His Leu
1

<210> SEQ ID NO 878
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 878

Phe His Glu Leu
1

<210> SEQ ID NO 879
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 879

Phe Glu His Leu
1

<210> SEQ ID NO 880
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 880

Phe His Asp Ile
1

<210> SEQ ID NO 881
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 881

Phe Asp His Ile
1

<210> SEQ ID NO 882
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 882

Phe His Glu Ile
1
```

```
<210> SEQ ID NO 883
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 883

Phe Glu His Ile
1

<210> SEQ ID NO 884
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 884

Phe His Asp Xaa
1

<210> SEQ ID NO 885
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 885

Phe Asp His Xaa
1

<210> SEQ ID NO 886
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)

<400> SEQUENCE: 886

Phe His Glu Xaa
1

<210> SEQ ID NO 887
<211> LENGTH: 4
<212> TYPE: PRT
<213> ORGANISM: Artificial
<220> FEATURE:
<223> OTHER INFORMATION: Synthetic peptide optionally bearing
      protecting groups.
<220> FEATURE:
<221> NAME/KEY: misc_feature
<222> LOCATION: (4)..(4)
<223> OTHER INFORMATION: Xaa is norleucine (Nle)
```

```
<400> SEQUENCE: 887

Phe Glu His Xaa
1

<210> SEQ ID NO 888
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 888

Lys Lys Asp Ser
1

<210> SEQ ID NO 889
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 889

Lys Asp Lys Ser
1

<210> SEQ ID NO 890
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 890

Lys Lys Glu Ser
1

<210> SEQ ID NO 891
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 891

Lys Glu Lys Ser
1

<210> SEQ ID NO 892
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 892

Lys His Asp Ser
1

<210> SEQ ID NO 893
<211> LENGTH: 4
<212> TYPE: PRT
<213> ORGANISM: Artificial
```

```
<220> FEATURE:
<223> OTHER INFORMATION: Synthetic peptide optionally bearing
      protecting groups.

<400> SEQUENCE: 893

Lys Asp His Ser
1

<210> SEQ ID NO 894
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 894

Lys His Glu Ser
1

<210> SEQ ID NO 895
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 895

Lys Glu His Ser
1

<210> SEQ ID NO 896
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 896

Lys Leu Arg Ser
1

<210> SEQ ID NO 897
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 897

Lys Arg Leu Ser
1

<210> SEQ ID NO 898
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 898

Lys Leu Arg Thr
1
```

```
<210> SEQ ID NO 899
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 899

Lys Arg Leu Thr
1

<210> SEQ ID NO 900
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 900

Lys Glu Leu Ser
1

<210> SEQ ID NO 901
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 901

Lys Leu Glu Ser
1

<210> SEQ ID NO 902
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 902

Lys Glu Leu Thr
1

<210> SEQ ID NO 903
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 903

Lys Leu Glu Thr
1

<210> SEQ ID NO 904
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 904
```

Lys Leu Arg Ser
1

<210> SEQ ID NO 905
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 905

Lys Leu Arg Thr
1

<210> SEQ ID NO 906
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 906

Lys Glu Leu Ser
1

<210> SEQ ID NO 907
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 907

Lys Glu Leu Thr
1

<210> SEQ ID NO 908
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 908

Lys Glu Ile Thr
1

<210> SEQ ID NO 909
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 909

Lys Leu Arg Ser
1

<210> SEQ ID NO 910
<211> LENGTH: 4
<212> TYPE: PRT
<213> ORGANISM: Artificial
<220> FEATURE:
<223> OTHER INFORMATION: Synthetic peptide optionally bearing protecting groups.

<400> SEQUENCE: 910

Lys Leu Arg Thr
1

<210> SEQ ID NO 911
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 911

Lys Glu Leu Ser
1

<210> SEQ ID NO 912
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 912

Lys Glu Leu Thr
1

<210> SEQ ID NO 913
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 913

Lys Leu Arg Ser
1

<210> SEQ ID NO 914
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 914

Lys Arg Phe Thr
1

<210> SEQ ID NO 915
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 915

Lys Leu Arg Thr
1

<210> SEQ ID NO 916
<211> LENGTH: 4

```
<212> TYPE: PRT
<213> ORGANISM: Artificial
<220> FEATURE:
<223> OTHER INFORMATION: Synthetic peptide optionally bearing
      protecting groups.

<400> SEQUENCE: 916

Lys Glu Ile Thr
1

<210> SEQ ID NO 917
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 917

Lys Glu Val Thr
1

<210> SEQ ID NO 918
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 918

Lys Glu Ala Thr
1

<210> SEQ ID NO 919
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 919

Lys Glu Gly Thr
1

<210> SEQ ID NO 920
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 920

Lys Glu Leu Ser
1

<210> SEQ ID NO 921
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 921

Lys Glu Leu Thr
1
```

```
<210> SEQ ID NO 922
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 922

Lys Arg Trp Tyr
1

<210> SEQ ID NO 923
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 923

Lys Trp Arg Tyr
1

<210> SEQ ID NO 924
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 924

Lys Arg Tyr Trp
1

<210> SEQ ID NO 925
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 925

Lys Tyr Arg Trp
1

<210> SEQ ID NO 926
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 926

Lys Arg Tyr Trp Thr
1               5

<210> SEQ ID NO 927
<211> LENGTH: 4
<212> TYPE: PRT
<213> ORGANISM: Artificial
<220> FEATURE:
<223> OTHER INFORMATION: Synthetic peptide optionally bearing
      protecting groups.
```

```
<400> SEQUENCE: 927

Lys Arg Tyr Thr
1

<210> SEQ ID NO 928
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 928

Lys Arg Trp Thr
1

<210> SEQ ID NO 929
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 929

Lys Arg Trp Tyr
1

<210> SEQ ID NO 930
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 930

Lys Arg Tyr Trp
1

<210> SEQ ID NO 931
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 931

Lys Arg Tyr Trp Thr
1               5

<210> SEQ ID NO 932
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 932

Lys Arg Tyr Thr
1

<210> SEQ ID NO 933
<211> LENGTH: 4
<212> TYPE: PRT
<213> ORGANISM: Artificial
```

```
<220> FEATURE:
<223> OTHER INFORMATION: Synthetic peptide optionally bearing
      protecting groups.

<400> SEQUENCE: 933

Lys Arg Trp Thr
1

<210> SEQ ID NO 934
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 934

Lys Arg Trp Tyr
1

<210> SEQ ID NO 935
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 935

Lys Arg Tyr Trp
1

<210> SEQ ID NO 936
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 936

Lys Arg Tyr Trp Thr
1               5

<210> SEQ ID NO 937
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 937

Lys Arg Tyr Thr
1

<210> SEQ ID NO 938
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 938

Lys Arg Trp Thr
1
```

```
<210> SEQ ID NO 939
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 939

Glu Lys Arg Tyr
1

<210> SEQ ID NO 940
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 940

Lys Arg Trp Tyr
1

<210> SEQ ID NO 941
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 941

Lys Arg Tyr Trp
1

<210> SEQ ID NO 942
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 942

Lys Arg Tyr Trp Thr
1               5

<210> SEQ ID NO 943
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 943

Lys Arg Tyr Thr
1

<210> SEQ ID NO 944
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 944
```

Lys Arg Phe Thr
1

<210> SEQ ID NO 945
<211> LENGTH: 4
<212> TYPE: PRT
<213> ORGANISM: Artificial
<220> FEATURE:
<223> OTHER INFORMATION: Synthetic peptide optionally bearing
      protecting groups.

<400> SEQUENCE: 945

Lys Arg Trp Thr
1

<210> SEQ ID NO 946
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 946

Lys Phe Trp Phe Ser
1               5

<210> SEQ ID NO 947
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 947

Lys Phe Trp Phe Thr
1               5

<210> SEQ ID NO 948
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 948

Lys Phe Tyr Phe Ser
1               5

<210> SEQ ID NO 949
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 949

Lys Phe Tyr Phe Thr
1               5

<210> SEQ ID NO 950
<211> LENGTH: 5
<212> TYPE: PRT
<213> ORGANISM: Artificial
<220> FEATURE:
<223> OTHER INFORMATION: Synthetic peptide optionally bearing protecting groups.

<400> SEQUENCE: 950

Lys Phe His Phe Ser
1               5

<210> SEQ ID NO 951
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 951

Lys Phe His Phe Thr
1               5

<210> SEQ ID NO 952
<211> LENGTH: 6
<212> TYPE: PRT
<213> ORGANISM: Artificial
<220> FEATURE:
<223> OTHER INFORMATION: Synthetic peptide optionally bearing
      protecting groups.

<400> SEQUENCE: 952

Lys Val Phe Phe Tyr Ser
1               5

<210> SEQ ID NO 953
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 953

Lys Phe Trp Phe Ser
1               5

<210> SEQ ID NO 954
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 954

Lys Phe Trp Phe Thr
1               5

<210> SEQ ID NO 955
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 955

Lys Phe Tyr Phe Ser
1               5

<210> SEQ ID NO 956
<211> LENGTH: 5

```
<212> TYPE: PRT
<213> ORGANISM: Artificial
<220> FEATURE:
<223> OTHER INFORMATION: Synthetic peptide optionally bearing
      protecting groups.

<400> SEQUENCE: 956

Lys Phe Tyr Phe Thr
1               5

<210> SEQ ID NO 957
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 957

Lys Phe His Phe Ser
1               5

<210> SEQ ID NO 958
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 958

Lys Phe His Phe Thr
1               5

<210> SEQ ID NO 959
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 959

Leu Phe Trp Phe Thr
1               5

<210> SEQ ID NO 960
<211> LENGTH: 5
<212> TYPE: PRT
<213> ORGANISM: Artificial
<220> FEATURE:
<223> OTHER INFORMATION: Synthetic peptide optionally bearing
      protecting groups.

<400> SEQUENCE: 960

Leu Phe Trp Phe Ser
1               5

<210> SEQ ID NO 961
<211> LENGTH: 22
<212> TYPE: PRT
<213> ORGANISM: Artificial
<220> FEATURE:
<223> OTHER INFORMATION: Synthetic peptide optionally bearing
      protecting groups.

<400> SEQUENCE: 961

Leu Leu Glu Gln Leu Asn Glu Gln Phe Asn Trp Val Ser Arg Leu Ala
1               5                   10                  15
```

```
Asn Leu Thr Gln Gly Glu
            20

<210> SEQ ID NO 962
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 962

Leu Leu Glu Gln Leu Asn Glu Gln Phe Asn Trp Val Ser Arg Leu Ala
1               5                   10                  15

Asn Leu

<210> SEQ ID NO 963
<211> LENGTH: 25
<212> TYPE: PRT
<213> ORGANISM: Artificial
<220> FEATURE:
<223> OTHER INFORMATION: Synthetic peptide optionally bearing
      protecting groups.

<400> SEQUENCE: 963

Asn Glu Leu Gln Glu Met Ser Asn Gln Gly Ser Lys Tyr Val Asn Lys
1               5                   10                  15

Glu Ile Gln Asn Ala Val Asn Gly Val
            20                  25

<210> SEQ ID NO 964
<211> LENGTH: 21
<212> TYPE: PRT
<213> ORGANISM: Artificial
<220> FEATURE:
<223> OTHER INFORMATION: Synthetic peptide optionally bearing
      protecting groups.

<400> SEQUENCE: 964

Ile Gln Asn Ala Val Asn Gly Val Lys Gln Ile Lys Thr Leu Ile Glu
1               5                   10                  15

Lys Thr Asn Glu Glu
            20

<210> SEQ ID NO 965
<211> LENGTH: 32
<212> TYPE: PRT
<213> ORGANISM: Artificial
<220> FEATURE:
<223> OTHER INFORMATION: Synthetic peptide optionally bearing
      protecting groups.

<400> SEQUENCE: 965

Arg Lys Thr Leu Leu Ser Asn Leu Glu Glu Ala Lys Lys Lys Lys Glu
1               5                   10                  15

Asp Ala Leu Asn Glu Thr Arg Glu Ser Glu Thr Lys Leu Lys Glu Leu
            20                  25                  30

<210> SEQ ID NO 966
<211> LENGTH: 16
<212> TYPE: PRT
<213> ORGANISM: Artificial
<220> FEATURE:
<223> OTHER INFORMATION: Synthetic peptide optionally bearing
      protecting groups.
```

-continued

```
<400> SEQUENCE: 966

Pro Gly Val Cys Asn Glu Thr Met Met Ala Leu Trp Glu Glu Cys Lys
1               5                   10                  15

<210> SEQ ID NO 967
<211> LENGTH: 16
<212> TYPE: PRT
<213> ORGANISM: Artificial
<220> FEATURE:
<223> OTHER INFORMATION: Synthetic peptide optionally bearing
      protecting groups.

<400> SEQUENCE: 967

Pro Cys Leu Lys Gln Thr Cys Met Lys Phe Tyr Ala Arg Val Cys Arg
1               5                   10                  15

<210> SEQ ID NO 968
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 968

Glu Cys Lys Pro Cys Leu Lys Gln Thr Cys Met Lys Phe Tyr Ala Arg
1               5                   10                  15

Val Cys Arg

<210> SEQ ID NO 969
<211> LENGTH: 10
<212> TYPE: PRT
<213> ORGANISM: Artificial
<220> FEATURE:
<223> OTHER INFORMATION: Synthetic peptide optionally bearing
      protecting groups.

<400> SEQUENCE: 969

Leu Val Gly Arg Gln Leu Glu Glu Phe Leu
1               5                   10

<210> SEQ ID NO 970
<211> LENGTH: 12
<212> TYPE: PRT
<213> ORGANISM: Artificial
<220> FEATURE:
<223> OTHER INFORMATION: Synthetic peptide optionally bearing
      protecting groups.

<400> SEQUENCE: 970

Met Asn Gly Asp Arg Ile Asp Ser Leu Leu Glu Asn
1               5                   10

<210> SEQ ID NO 971
<211> LENGTH: 11
<212> TYPE: PRT
<213> ORGANISM: Artificial
<220> FEATURE:
<223> OTHER INFORMATION: Synthetic peptide optionally bearing
      protecting groups.

<400> SEQUENCE: 971

Gln Gln Thr His Met Leu Asp Val Met Gln Asp
1               5                   10

<210> SEQ ID NO 972
<211> LENGTH: 14
```

```
<212> TYPE: PRT
<213> ORGANISM: Artificial
<220> FEATURE:
<223> OTHER INFORMATION: Synthetic peptide optionally bearing
      protecting groups.

<400> SEQUENCE: 972

Phe Ser Arg Ala Ser Ser Ile Ile Asp Glu Leu Phe Gln Asp
1               5                   10

<210> SEQ ID NO 973
<211> LENGTH: 15
<212> TYPE: PRT
<213> ORGANISM: Artificial
<220> FEATURE:
<223> OTHER INFORMATION: Synthetic peptide optionally bearing
      protecting groups.

<400> SEQUENCE: 973

Pro Phe Leu Glu Met Ile His Glu Ala Gln Gln Ala Met Asp Ile
1               5                   10                  15

<210> SEQ ID NO 974
<211> LENGTH: 11
<212> TYPE: PRT
<213> ORGANISM: Artificial
<220> FEATURE:
<223> OTHER INFORMATION: Synthetic peptide optionally bearing
      protecting groups.

<400> SEQUENCE: 974

Pro Thr Glu Phe Ile Arg Glu Gly Asp Asp Asp
1               5                   10

<210> SEQ ID NO 975
<211> LENGTH: 15
<212> TYPE: PRT
<213> ORGANISM: Artificial
<220> FEATURE:
<223> OTHER INFORMATION: Synthetic peptide optionally bearing
      protecting groups.

<400> SEQUENCE: 975

Arg Met Lys Asp Gln Cys Asp Lys Cys Arg Glu Ile Leu Ser Val
1               5                   10                  15

<210> SEQ ID NO 976
<211> LENGTH: 32
<212> TYPE: PRT
<213> ORGANISM: Artificial
<220> FEATURE:
<223> OTHER INFORMATION: Synthetic peptide optionally bearing
      protecting groups.

<400> SEQUENCE: 976

Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
            20                  25                  30

<210> SEQ ID NO 977
<211> LENGTH: 22
<212> TYPE: PRT
<213> ORGANISM: Artificial
<220> FEATURE:
<223> OTHER INFORMATION: Synthetic peptide optionally bearing
      protecting groups.

<400> SEQUENCE: 977
```

```
Leu Leu Glu Gln Leu Asn Glu Gln Phe Asn Trp Val Ser Arg Leu Ala
1               5                   10                  15

Asn Leu Thr Glu Gly Glu
            20

<210> SEQ ID NO 978
<211> LENGTH: 11
<212> TYPE: PRT
<213> ORGANISM: Artificial
<220> FEATURE:
<223> OTHER INFORMATION: Synthetic peptide optionally bearing
      protecting groups.

<400> SEQUENCE: 978

Asp Gln Tyr Tyr Leu Arg Val Thr Thr Val Ala
1               5                   10

<210> SEQ ID NO 979
<211> LENGTH: 14
<212> TYPE: PRT
<213> ORGANISM: Artificial
<220> FEATURE:
<223> OTHER INFORMATION: Synthetic peptide optionally bearing
      protecting groups.

<400> SEQUENCE: 979

Pro Ser Gly Val Thr Glu Val Val Val Lys Leu Phe Asp Ser
1               5                   10

<210> SEQ ID NO 980
<211> LENGTH: 21
<212> TYPE: PRT
<213> ORGANISM: Artificial
<220> FEATURE:
<223> OTHER INFORMATION: Synthetic peptide optionally bearing
      protecting groups.

<400> SEQUENCE: 980

Pro Lys Phe Met Glu Thr Val Ala Glu Lys Ala Leu Gln Glu Tyr Arg
1               5                   10                  15

Lys Lys His Arg Glu
            20

<210> SEQ ID NO 981
<211> LENGTH: 26
<212> TYPE: PRT
<213> ORGANISM: Artificial
<220> FEATURE:
<223> OTHER INFORMATION: Synthetic peptide optionally bearing
      protecting groups.

<400> SEQUENCE: 981

Trp Asp Arg Val Lys Asp Leu Ala Thr Val Tyr Val Asp Val Leu Lys
1               5                   10                  15

Asp Ser Gly Arg Asp Tyr Val Ser Gln Phe
            20                  25

<210> SEQ ID NO 982
<211> LENGTH: 25
<212> TYPE: PRT
<213> ORGANISM: Artificial
<220> FEATURE:
<223> OTHER INFORMATION: Synthetic peptide optionally bearing
      protecting groups.

<400> SEQUENCE: 982
```

Val Ala Thr Val Met Trp Asp Tyr Phe Ser Gln Leu Ser Asn Asn Ala
1               5                   10                  15

Lys Glu Ala Val Glu His Leu Gln Lys
            20                  25

<210> SEQ ID NO 983
<211> LENGTH: 27
<212> TYPE: PRT
<213> ORGANISM: Artificial
<220> FEATURE:
<223> OTHER INFORMATION: Synthetic peptide optionally bearing
      protecting groups.

<400> SEQUENCE: 983

Arg Trp Glu Leu Ala Leu Gly Arg Phe Trp Asp Tyr Leu Arg Trp Val
1               5                   10                  15

Gln Thr Leu Ser Glu Gln Val Gln Glu Glu Leu
            20                  25

<210> SEQ ID NO 984
<211> LENGTH: 35
<212> TYPE: PRT
<213> ORGANISM: Artificial
<220> FEATURE:
<223> OTHER INFORMATION: Synthetic peptide optionally bearing
      protecting groups.

<400> SEQUENCE: 984

Leu Ser Ser Gln Val Thr Gln Glu Leu Arg Ala Leu Met Asp Glu Thr
1               5                   10                  15

Met Lys Glu Leu Lys Glu Leu Lys Ala Tyr Lys Ser Glu Leu Glu Glu
            20                  25                  30

Gln Leu Thr
        35

<210> SEQ ID NO 985
<211> LENGTH: 26
<212> TYPE: PRT
<213> ORGANISM: Artificial
<220> FEATURE:
<223> OTHER INFORMATION: Synthetic peptide optionally bearing
      protecting groups.

<400> SEQUENCE: 985

Ala Arg Leu Ser Lys Glu Leu Gln Ala Ala Gln Ala Arg Leu Gly Ala
1               5                   10                  15

Asp Met Glu Asp Val Cys Gly Arg Leu Val
            20                  25

<210> SEQ ID NO 986
<211> LENGTH: 26
<212> TYPE: PRT
<213> ORGANISM: Artificial
<220> FEATURE:
<223> OTHER INFORMATION: Synthetic peptide optionally bearing
      protecting groups.

<400> SEQUENCE: 986

Val Arg Leu Ala Ser His Leu Arg Lys Leu Arg Lys Arg Leu Leu Arg
1               5                   10                  15

Asp Ala Asp Asp Leu Gln Lys Arg Leu Ala
            20                  25

<210> SEQ ID NO 987
<211> LENGTH: 19

```
<212> TYPE: PRT
<213> ORGANISM: Artificial
<220> FEATURE:
<223> OTHER INFORMATION: Synthetic peptide optionally bearing
      protecting groups.

<400> SEQUENCE: 987

Pro Leu Val Glu Asp Met Gln Arg Gln Trp Ala Gly Leu Val Glu Lys
1               5                   10                  15
Val Gln Ala

<210> SEQ ID NO 988
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 988

Met Ser Thr Tyr Thr Gly Ile Phe Thr Asp Gln Val Leu Ser Val Leu
1               5                   10                  15
Lys

<210> SEQ ID NO 989
<211> LENGTH: 22
<212> TYPE: PRT
<213> ORGANISM: Artificial
<220> FEATURE:
<223> OTHER INFORMATION: Synthetic peptide optionally bearing
      protecting groups.

<400> SEQUENCE: 989

Leu Leu Ser Phe Met Gln Gly Tyr Met Lys His Ala Thr Lys Thr Ala
1               5                   10                  15
Lys Asp Ala Leu Ser Ser
            20

<210> SEQ ID NO 990
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 990

Lys Trp Ile Tyr His Leu Thr Glu Gly Ser Thr Asp Leu Arg Thr Glu
1               5                   10                  15
Gly

<210> SEQ ID NO 991
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 991

Lys Trp Phe Tyr His Leu Thr Glu Gly Ser Thr Asp Leu Arg Thr Glu
1               5                   10                  15
Gly

<210> SEQ ID NO 992
```

```
<210> SEQ ID NO 992
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 992

Lys Trp Leu Tyr His Leu Thr Glu Gly Ser Thr Asp Leu Arg Thr Glu
1               5                   10                  15

Gly

<210> SEQ ID NO 993
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 993

Lys Trp Val Tyr His Leu Thr Glu Gly Ser Thr Asp Leu Arg Thr Glu
1               5                   10                  15

Gly

<210> SEQ ID NO 994
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 994

Lys Tyr Ile Trp His Leu Thr Glu Gly Ser Thr Asp Leu Arg Thr Glu
1               5                   10                  15

Gly

<210> SEQ ID NO 995
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 995

Lys Trp Ile Tyr His Phe Thr Glu Gly Ser Thr Asp Leu Arg Thr Glu
1               5                   10                  15

Gly

<210> SEQ ID NO 996
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 996

Lys Trp Phe Tyr His Ile Thr Glu Gly Ser Thr Asp Leu Arg Thr Glu
1               5                   10                  15

Gly

<210> SEQ ID NO 997
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 997

Lys Trp Leu Tyr His Val Thr Glu Gly Ser Thr Asp Leu Arg Thr Glu
1               5                   10                  15

Gly

<210> SEQ ID NO 998
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 998

Lys Trp Val Tyr His Tyr Thr Glu Gly Ser Thr Asp Leu Arg Thr Glu
1               5                   10                  15

Gly

<210> SEQ ID NO 999
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 999

Lys Tyr Ile Trp His Phe Thr Glu Gly Ser Thr Asp Leu Arg Thr Glu
1               5                   10                  15

Gly

<210> SEQ ID NO 1000
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1000

Lys Tyr Ile Trp His Ile Thr Glu Gly Ser Thr Asp Leu Arg Thr Glu
1               5                   10                  15

Gly

<210> SEQ ID NO 1001
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1001

Lys Tyr Ile Trp His Val Thr Glu Gly Ser Thr Asp Leu Arg Thr Glu
1               5                   10                  15

Gly

<210> SEQ ID NO 1002
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1002

Lys Tyr Ile Trp His Tyr Thr Glu Gly Ser Thr Asp Leu Arg Thr Glu
1               5                   10                  15

Gly

<210> SEQ ID NO 1003
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1003

Lys Phe Ile Trp His Leu Thr Glu Gly Ser Thr Asp Leu Arg Thr Glu
1               5                   10                  15

Gly

<210> SEQ ID NO 1004
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1004

Lys Leu Ile Trp His Leu Thr Glu Gly Ser Thr Asp Leu Arg Thr Glu
1               5                   10                  15

Gly

<210> SEQ ID NO 1005
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1005

Lys Ile Ile Trp His Leu Thr Glu Gly Ser Thr Asp Leu Arg Thr Glu
1               5                   10                  15

Gly

<210> SEQ ID NO 1006
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1006

Lys Tyr Ile Trp Phe Leu Thr Glu Gly Ser Thr Asp Leu Arg Thr Glu
1               5                   10                  15

Gly

<210> SEQ ID NO 1007
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1007

Lys Trp Ile Tyr Phe Leu Thr Glu Gly Ser Thr Asp Leu Arg Thr Glu
1               5                   10                  15

Gly

<210> SEQ ID NO 1008
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1008

Lys Trp Ile Tyr Leu Leu Thr Glu Gly Ser Thr Asp Leu Arg Thr Glu
1               5                   10                  15

Gly

<210> SEQ ID NO 1009
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1009

Lys Trp Ile Tyr His Phe Thr Glu Gly Ser Thr Asp Leu Arg Thr Glu
1               5                   10                  15

Gly

<210> SEQ ID NO 1010
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1010

Lys Trp Ile Tyr His Tyr Thr Glu Gly Ser Thr Asp Leu Arg Thr Glu
1               5                   10                  15

Gly

<210> SEQ ID NO 1011
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1011

Lys Trp Ile Tyr His Ile Thr Glu Gly Ser Thr Asp Leu Arg Thr Glu
1               5                   10                  15

Gly

<210> SEQ ID NO 1012
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1012

Lys Trp Ile Tyr His Leu Ser Glu Gly Ser Thr Asp Leu Arg Thr Glu
1               5                   10                  15

Gly

<210> SEQ ID NO 1013
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1013

Lys Trp Ile Tyr His Leu Thr Asp Gly Ser Thr Asp Leu Arg Thr Glu
1               5                   10                  15

Gly

<210> SEQ ID NO 1014
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1014

Lys Trp Ile Tyr His Leu Thr Glu Gly Thr Ser Asp Leu Arg Thr Glu
1               5                   10                  15

Gly

<210> SEQ ID NO 1015
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1015

Lys Trp Ile Tyr His Leu Thr Glu Gly Ser Thr Glu Leu Arg Thr Glu
1               5                   10                  15

Gly

<210> SEQ ID NO 1016
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1016

Lys Trp Ile Tyr His Leu Thr Glu Gly Ser Thr Asp Phe Arg Thr Glu
1               5                   10                  15

Gly

<210> SEQ ID NO 1017
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1017

Lys Trp Ile Tyr His Leu Thr Glu Gly Ser Thr Asp Tyr Arg Thr Glu
1               5                   10                  15

Gly

<210> SEQ ID NO 1018
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1018

Lys Trp Ile Tyr His Leu Thr Glu Gly Ser Thr Asp Ile Arg Thr Glu
1               5                   10                  15

Gly

<210> SEQ ID NO 1019
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1019

Lys Trp Ile Tyr His Leu Thr Glu Gly Ser Thr Asp Val Arg Thr Glu
1               5                   10                  15

Gly

<210> SEQ ID NO 1020
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1020

Lys Trp Ile Tyr His Leu Thr Glu Gly Ser Thr Asp Leu Lys Thr Glu
1               5                   10                  15

Gly

<210> SEQ ID NO 1021
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1021

Lys Trp Ile Tyr His Leu Thr Glu Gly Ser Thr Asp Leu Arg Ser Glu
1               5                   10                  15

Gly

<210> SEQ ID NO 1022
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1022

Lys Trp Ile Tyr His Leu Thr Glu Gly Ser Thr Asp Leu Arg Thr Asp
1               5                   10                  15

Gly

<210> SEQ ID NO 1023
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1023

Lys Trp Ile Tyr His Leu Thr Glu Gly Ser Thr Asp Ile Lys Thr Glu
1               5                   10                  15

Gly

<210> SEQ ID NO 1024
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1024

Lys Trp Ile Tyr His Leu Thr Glu Gly Ser Thr Asp Ile Arg Ser Glu
1               5                   10                  15

Gly

<210> SEQ ID NO 1025
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1025

Lys Trp Ile Tyr His Leu Thr Glu Gly Ser Thr Asp Ile Lys Ser Glu
1               5                   10                  15

Gly

<210> SEQ ID NO 1026
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1026

Lys Trp Ile Tyr His Leu Thr Glu Gly Ser Thr Asp Ile Lys Ser Asp
1               5                   10                  15

Gly

<210> SEQ ID NO 1027
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1027

Arg Trp Ile Tyr His Leu Thr Glu Gly Ser Thr Asp Leu Arg Thr Glu
1               5                   10                  15

Gly

<210> SEQ ID NO 1028
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1028

Arg Tyr Ile Trp His Leu Thr Glu Gly Ser Thr Asp Ile Arg Thr Glu
1               5                   10                  15

Gly

<210> SEQ ID NO 1029
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1029

Arg Trp Ile Tyr His Leu Thr Glu Gly Ser Thr Asp Ile Arg Thr Asp
1               5                   10                  15

Gly

<210> SEQ ID NO 1030
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1030

Arg Trp Ile Phe His Leu Thr Glu Gly Ser Thr Asp Ile Arg Thr Glu
1               5                   10                  15

Gly

<210> SEQ ID NO 1031
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1031

Arg Trp Ile Tyr His Leu Thr Glu Gly Ser Thr Asp Leu Lys Thr Glu
1               5                   10                  15

Gly

<210> SEQ ID NO 1032
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1032

Arg Trp Ile Tyr His Leu Thr Asp Gly Ser Thr Asp Ile Arg Thr Glu
1               5                   10                  15

Gly

<210> SEQ ID NO 1033
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1033

Arg Trp Ile Tyr His Leu Thr Asp Gly Ser Thr Asp Leu Arg Thr Glu
1               5                   10                  15

Gly

<210> SEQ ID NO 1034
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1034

Arg Trp Ile Tyr Phe Leu Thr Glu Gly Ser Thr Asp Ile Arg Thr Glu
1               5                   10                  15

Gly

<210> SEQ ID NO 1035
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1035

Arg Trp Ile Tyr Phe Leu Thr Glu Gly Ser Thr Asp Leu Arg Thr Glu
1               5                   10                  15

Gly

<210> SEQ ID NO 1036
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1036

Lys Trp Phe Tyr His Leu Thr Glu Gly Ser Thr Asp Phe Arg Thr Glu
1               5                   10                  15

Gly

<210> SEQ ID NO 1037
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1037

Arg Trp Phe Tyr His Leu Thr Glu Gly Ser Thr Asp Leu Arg Thr Glu
1               5                   10                  15

Gly

<210> SEQ ID NO 1038
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1038

Lys Trp Ile Phe His Leu Thr Glu Gly Ser Thr Asp Ile Arg Thr Asp
1               5                   10                  15

Gly

<210> SEQ ID NO 1039
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1039

Arg Trp Ile Tyr His Leu Thr Glu Gly Ser Thr Asp Ile Arg Thr Asp
1               5                   10                  15

Gly

<210> SEQ ID NO 1040
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1040

Arg Trp Ile Tyr His Leu Thr Glu Gly Ser Thr Asp Leu Arg Thr Asp
1               5                   10                  15

Gly

<210> SEQ ID NO 1041
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1041

Lys Trp Ile Tyr His Leu Thr Glu Gly Ser Thr Asp Ile Lys Thr Glu
1               5                   10                  15

Gly

<210> SEQ ID NO 1042
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1042

Lys Trp Ile Tyr His Leu Thr Glu Gly Ser Thr Asp Ile Lys Thr Asp
1               5                   10                  15

Gly

<210> SEQ ID NO 1043
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1043

Lys Trp Ile Tyr His Leu Thr Glu Gly Ser Thr Asp Phe Lys Thr Glu
1               5                   10                  15

Gly

<210> SEQ ID NO 1044
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1044

Lys Trp Ile Tyr His Leu Thr Glu Gly Ser Thr Asp Tyr Lys Thr Glu
1               5                   10                  15

Gly

<210> SEQ ID NO 1045
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1045

Lys Trp Ile Tyr His Leu Thr Glu Gly Ser Thr Asp Ile Arg Thr Glu
1               5                   10                  15

Gly

<210> SEQ ID NO 1046
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1046

Lys Trp Phe Tyr His Phe Thr Glu Gly Ser Thr Asp Leu Arg Thr Glu
1               5                   10                  15

Gly

<210> SEQ ID NO 1047
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1047

Arg Trp Phe Tyr His Phe Thr Glu Gly Ser Thr Asp Leu Arg Thr Glu
1               5                   10                  15

Gly

<210> SEQ ID NO 1048
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1048

Lys Trp Phe Tyr His Phe Thr Glu Gly Ser Thr Asp Phe Arg Thr Glu
1               5                   10                  15

Gly

<210> SEQ ID NO 1049
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1049

Lys Trp Phe Tyr His Phe Thr Asp Gly Ser Thr Asp Ile Arg Thr Glu
1               5                   10                  15

Gly

<210> SEQ ID NO 1050
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1050

Arg Trp Phe Tyr His Phe Thr Glu Gly Ser Thr Asp Leu Arg Thr Glu
1               5                   10                  15

Gly

<210> SEQ ID NO 1051
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1051

Arg Trp Phe Tyr His Phe Thr Glu Gly Ser Thr Asp Phe Arg Thr Glu
1               5                   10                  15

Gly

<210> SEQ ID NO 1052
```

```
<211> LENGTH: 17
<212> TYPE: PRT
<213> ORGANISM: Artificial
<220> FEATURE:
<223> OTHER INFORMATION: Synthetic peptide optionally bearing
      protecting groups.

<400> SEQUENCE: 1052

Arg Trp Phe Tyr His Phe Thr Glu Gly Ser Thr Asp Phe Arg Thr Asp
1               5                   10                  15

Gly

<210> SEQ ID NO 1053
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1053

Glu Lys Cys Val Glu Glu Phe Lys Ser Leu Thr Ser Cys Leu Asp Ser
1               5                   10                  15

Lys Ala Phe

<210> SEQ ID NO 1054
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1054

Asp Lys Cys Val Glu Glu Phe Lys Ser Leu Thr Ser Cys Leu Asp Ser
1               5                   10                  15

Lys Ala Phe

<210> SEQ ID NO 1055
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1055

Glu Lys Cys Val Asp Glu Phe Lys Ser Leu Thr Ser Cys Leu Asp Ser
1               5                   10                  15

Lys Ala Phe

<210> SEQ ID NO 1056
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1056

Glu Lys Cys Val Glu Asp Phe Lys Ser Leu Thr Ser Cys Leu Asp Ser
1               5                   10                  15

Lys Ala Phe

<210> SEQ ID NO 1057
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1057

Glu Arg Cys Val Glu Glu Phe Lys Ser Leu Thr Ser Cys Leu Asp Ser
1               5                   10                  15

Lys Ala Phe

<210> SEQ ID NO 1058
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1058

Asp Lys Cys Val Asp Asp Phe Lys Ser Leu Thr Ser Cys Leu Asp Ser
1               5                   10                  15

Lys Ala Phe

<210> SEQ ID NO 1059
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1059

Asp Arg Cys Val Glu Glu Phe Lys Ser Leu Thr Ser Cys Leu Asp Ser
1               5                   10                  15

Lys Ala Phe

<210> SEQ ID NO 1060
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1060

Glu Arg Cys Val Asp Asp Phe Lys Ser Leu Thr Ser Cys Leu Asp Ser
1               5                   10                  15

Lys Ala Phe

<210> SEQ ID NO 1061
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1061

Glu Lys Cys Val Glu Glu Phe Lys Ser Phe Thr Ser Cys Leu Asp Ser
1               5                   10                  15

Lys Ala Phe

<210> SEQ ID NO 1062
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1062

Glu Lys Cys Val Glu Glu Phe Lys Ser Ile Thr Ser Cys Leu Asp Ser
1               5                   10                  15

Lys Ala Phe

<210> SEQ ID NO 1063
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1063

Glu Lys Cys Val Glu Glu Phe Lys Ser Val Thr Ser Cys Leu Asp Ser
1               5                   10                  15

Lys Ala Phe

<210> SEQ ID NO 1064
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1064

Glu Arg Cys Val Glu Glu Phe Lys Ser Tyr Thr Ser Cys Leu Asp Ser
1               5                   10                  15

Lys Ala Phe

<210> SEQ ID NO 1065
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1065

Glu Arg Cys Val Glu Glu Phe Lys Ser Phe Thr Ser Cys Leu Asp Ser
1               5                   10                  15

Lys Ala Phe

<210> SEQ ID NO 1066
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1066

Glu Arg Cys Val Glu Glu Phe Lys Ser Ile Thr Ser Cys Leu Asp Ser
1               5                   10                  15

Lys Ala Phe

<210> SEQ ID NO 1067
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1067

Glu Arg Cys Val Glu Glu Phe Lys Ser Val Thr Ser Cys Leu Asp Ser
1               5                   10                  15

Lys Ala Phe

<210> SEQ ID NO 1068
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1068

Glu Arg Cys Val Glu Glu Phe Lys Ser Tyr Thr Ser Cys Leu Asp Ser
1               5                   10                  15

Lys Ala Phe

<210> SEQ ID NO 1069
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1069

Glu Lys Cys Val Glu Glu Phe Lys Ser Phe Thr Thr Cys Leu Asp Ser
1               5                   10                  15

Lys Ala Phe

<210> SEQ ID NO 1070
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1070

Glu Lys Cys Val Glu Glu Phe Lys Ser Ile Ser Ser Cys Leu Asp Ser
1               5                   10                  15

Lys Ala Phe

<210> SEQ ID NO 1071
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1071

Glu Lys Cys Val Glu Glu Phe Lys Ser Val Ser Thr Cys Leu Asp Ser
1               5                   10                  15

Lys Ala Phe

<210> SEQ ID NO 1072
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1072

Glu Lys Cys Val Glu Glu Phe Lys Ser Tyr Thr Ser Cys Leu Asp Ser
1               5                   10                  15

Lys Ala Phe

<210> SEQ ID NO 1073
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1073

Glu Lys Cys Val Glu Glu Phe Lys Ser Phe Thr Thr Cys Leu Asp Ser
1               5                   10                  15

Lys Ala Phe

<210> SEQ ID NO 1074
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1074

Glu Lys Cys Val Glu Glu Phe Lys Ser Phe Ser Ser Cys Leu Asp Ser
1               5                   10                  15

Lys Ala Phe

<210> SEQ ID NO 1075
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1075

Glu Lys Cys Val Glu Glu Phe Lys Ser Phe Thr Ser Cys Leu Asp Ser
1               5                   10                  15

Lys Ala Phe

<210> SEQ ID NO 1076
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1076

Glu Lys Cys Val Glu Glu Phe Lys Ser Phe Thr Ser Cys Leu Asp Ser
1               5                   10                  15

Lys Ala Phe

<210> SEQ ID NO 1077
```

<211> LENGTH: 19
<212> TYPE: PRT
<213> ORGANISM: Artificial
<220> FEATURE:
<223> OTHER INFORMATION: Synthetic peptide optionally bearing
    protecting groups.

<400> SEQUENCE: 1077

Glu Lys Cys Val Glu Glu Phe Lys Ser Phe Thr Ser Cys Leu Asp Ser
1               5                   10                  15

Lys Ala Phe

<210> SEQ ID NO 1078
<211> LENGTH: 19
<212> TYPE: PRT
<213> ORGANISM: Artificial
<220> FEATURE:
<223> OTHER INFORMATION: Synthetic peptide optionally bearing
    protecting groups.

<400> SEQUENCE: 1078

Glu Lys Cys Val Glu Glu Phe Lys Ser Phe Thr Ser Cys Phe Asp Ser
1               5                   10                  15

Lys Ala Phe

<210> SEQ ID NO 1079
<211> LENGTH: 19
<212> TYPE: PRT
<213> ORGANISM: Artificial
<220> FEATURE:
<223> OTHER INFORMATION: Synthetic peptide optionally bearing
    protecting groups.

<400> SEQUENCE: 1079

Glu Lys Cys Val Glu Glu Phe Lys Ser Phe Thr Ser Cys Phe Glu Ser
1               5                   10                  15

Lys Ala Phe

<210> SEQ ID NO 1080
<211> LENGTH: 19
<212> TYPE: PRT
<213> ORGANISM: Artificial
<220> FEATURE:
<223> OTHER INFORMATION: Synthetic peptide optionally bearing
    protecting groups.

<400> SEQUENCE: 1080

Glu Lys Cys Val Glu Glu Phe Lys Ser Phe Thr Ser Cys Leu Glu Ser
1               5                   10                  15

Lys Ala Phe

<210> SEQ ID NO 1081
<211> LENGTH: 19
<212> TYPE: PRT
<213> ORGANISM: Artificial
<220> FEATURE:
<223> OTHER INFORMATION: Synthetic peptide optionally bearing
    protecting groups.

<400> SEQUENCE: 1081

Glu Lys Cys Val Glu Glu Phe Lys Ser Phe Thr Ser Cys Ile Asp Ser
1               5                   10                  15

Lys Ala Phe

<210> SEQ ID NO 1082

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1082

Glu Lys Cys Val Glu Glu Leu Lys Ser Phe Thr Ser Cys Phe Asp Ser
1               5                   10                  15

Lys Ala Phe

<210> SEQ ID NO 1083
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1083

Asp Lys Cys Val Glu Glu Phe Lys Ser Phe Thr Ser Cys Phe Asp Ser
1               5                   10                  15

Lys Ala Phe

<210> SEQ ID NO 1084
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1084

Asp Lys Cys Val Glu Glu Phe Lys Ser Phe Thr Ser Cys Phe Glu Ser
1               5                   10                  15

Lys Ala Phe

<210> SEQ ID NO 1085
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1085

Glu Arg Cys Val Glu Glu Phe Lys Ser Phe Thr Ser Cys Phe Asp Ser
1               5                   10                  15

Lys Ala Phe

<210> SEQ ID NO 1086
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1086

Glu Lys Cys Phe Glu Glu Phe Lys Ser Phe Thr Ser Cys Phe Asp Ser
1               5                   10                  15

Lys Ala Phe

<210> SEQ ID NO 1087
```

-continued

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1087

Glu Lys Cys Phe Glu Glu Phe Lys Ser Phe Thr Ser Cys Phe Glu Ser
1               5                   10                  15

Lys Ala Phe

<210> SEQ ID NO 1088
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1088

Glu Lys Cys Val Glu Glu Phe Lys Ser Phe Ser Ser Cys Phe Glu Ser
1               5                   10                  15

Lys Ala Phe

<210> SEQ ID NO 1089
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1089

Glu Lys Cys Val Glu Glu Phe Lys Ser Phe Gln Ser Cys Phe Asp Ser
1               5                   10                  15

Lys Ala Phe

<210> SEQ ID NO 1090
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1090

Glu Lys Cys Phe Glu Glu Phe Lys Ser Phe Gln Ser Cys Phe Asp Ser
1               5                   10                  15

Lys Ala Phe

<210> SEQ ID NO 1091
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1091

Glu Lys Cys Val Glu Glu Phe Lys Gln Phe Thr Ser Cys Phe Asp Ser
1               5                   10                  15

Lys Ala Phe

<210> SEQ ID NO 1092
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1092

Glu Lys Cys Val Glu Glu Phe Lys Gln Leu Thr Ser Cys Leu Asp Ser
1               5                  10                  15

Lys Ala Phe

<210> SEQ ID NO 1093
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1093

Glu Lys Cys Phe Glu Glu Phe Lys Ser Phe Gln Ser Cys Leu Asp Ser
1               5                  10                  15

Lys Ala Phe

<210> SEQ ID NO 1094
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1094

Glu Lys Cys Val Glu Glu Phe Lys Gln Phe Thr Ser Cys Phe Asp Ser
1               5                  10                  15

Lys Ala Phe

<210> SEQ ID NO 1095
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1095

Glu Lys Cys Val Glu Glu Phe Lys Ser Phe Thr Ser Cys Phe Glu Ser
1               5                  10                  15

Lys Ala Phe

<210> SEQ ID NO 1096
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1096

Glu Arg Cys Phe Glu Glu Phe Lys Ser Phe Thr Ser Cys Phe Asp Ser
1               5                  10                  15

Lys Ala Phe

<210> SEQ ID NO 1097
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1097

Asp Lys Cys Phe Glu Glu Phe Lys Ser Phe Thr Ser Cys Phe Asp Ser
1               5                   10                  15

Lys Ala Phe

<210> SEQ ID NO 1098
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1098

Glu Arg Cys Val Glu Glu Phe Lys Ser Leu Thr Ser Cys Leu Glu Ser
1               5                   10                  15

Lys Ala Phe

<210> SEQ ID NO 1099
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1099

Glu Lys Cys Val Glu Glu Phe Lys Ser Leu Thr Ser Cys Leu Asp Ser
1               5                   10                  15

Lys Phe Phe

<210> SEQ ID NO 1100
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1100

Glu Lys Cys Phe Glu Glu Phe Lys Ser Phe Thr Ser Cys Phe Asp Ser
1               5                   10                  15

Lys Phe Phe

<210> SEQ ID NO 1101
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1101

Asp Lys Cys Phe Glu Glu Phe Lys Ser Phe Thr Ser Cys Leu Asp Ser
1               5                   10                  15

Lys Phe Phe

<210> SEQ ID NO 1102
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1102

Asp Lys Cys Phe Glu Glu Phe Lys Ser Phe Thr Ser Cys Leu Glu Ser
1               5                   10                  15

Lys Phe Phe

<210> SEQ ID NO 1103
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1103

Asp Lys Cys Phe Glu Glu Leu Lys Ser Phe Thr Ser Cys Leu Asp Ser
1               5                   10                  15

Lys Phe Phe

<210> SEQ ID NO 1104
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1104

Glu Arg Cys Phe Glu Glu Phe Lys Ser Phe Thr Ser Cys Leu Asp Ser
1               5                   10                  15

Lys Phe Phe

<210> SEQ ID NO 1105
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1105

Glu Lys Ala Val Glu Glu Phe Lys Ser Phe Thr Ser Cys Leu Asp Ser
1               5                   10                  15

Lys Ala Phe

<210> SEQ ID NO 1106
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1106

Asp Lys Ala Val Glu Glu Phe Lys Ser Phe Thr Ser Cys Leu Asp Ser
1               5                   10                  15

Lys Phe Phe

<210> SEQ ID NO 1107
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1107

Glu Lys Ala Val Glu Glu Phe Lys Ser Phe Thr Ser Ala Leu Asp Ser
1               5                   10                  15

Lys Ala Phe

<210> SEQ ID NO 1108
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1108

Asp Lys Ala Val Glu Glu Phe Lys Ser Phe Thr Ser Ala Leu Asp Ser
1               5                   10                  15

Lys Ala Phe

<210> SEQ ID NO 1109
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1109

Asp Arg Ala Phe Glu Glu Phe Lys Ser Phe Thr Ser Cys Leu Asp Ser
1               5                   10                  15

Lys Phe Phe

<210> SEQ ID NO 1110
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1110

Asp Arg Ala Phe Glu Glu Phe Lys Ser Phe Thr Ser Ala Leu Asp Ser
1               5                   10                  15

Lys Phe Phe

<210> SEQ ID NO 1111
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1111

Asp Lys Cys Phe Glu Glu Phe Lys Ser Phe Thr Ser Cys Phe Glu Ser
1               5                   10                  15

Lys Phe Phe

<210> SEQ ID NO 1112
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1112

Glu Lys Cys Tyr Glu Glu Phe Lys Ser Phe Thr Ser Cys Leu Asp Ser
1               5                   10                  15

Lys Phe Phe

<210> SEQ ID NO 1113
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1113

Asp Lys Cys Trp Glu Glu Phe Lys Ser Phe Thr Ser Cys Leu Asp Ser
1               5                   10                  15

Lys Phe Phe

<210> SEQ ID NO 1114
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1114

Glu Lys Cys Phe Glu Glu Phe Lys Ser Tyr Thr Ser Cys Leu Asp Ser
1               5                   10                  15

Lys Phe Phe

<210> SEQ ID NO 1115
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1115

Glu Lys Cys Phe Glu Glu Phe Lys Ser Trp Thr Ser Cys Leu Asp Ser
1               5                   10                  15

Lys Phe Phe

<210> SEQ ID NO 1116
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1116

Glu Lys Cys Val Glu Glu Phe Lys Ser Trp Thr Ser Cys Leu Asp Ser
1               5                   10                  15

Lys Ala Phe

<210> SEQ ID NO 1117
```

```
<211> LENGTH: 19
<212> TYPE: PRT
<213> ORGANISM: Artificial
<220> FEATURE:
<223> OTHER INFORMATION: Synthetic peptide optionally bearing
      protecting groups.

<400> SEQUENCE: 1117

Asp Lys Cys Phe Glu Glu Phe Lys Ser Trp Thr Ser Cys Leu Asp Ser
1               5                   10                  15

Lys Ala Phe

<210> SEQ ID NO 1118
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 1118

Asp Val Trp Lys Ala Ala Tyr Asp Lys Phe Ala Glu Lys Phe Lys Glu
1               5                   10                  15

Phe Phe

<210> SEQ ID NO 1119
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 1119

Asp Val Trp Lys Ala Phe Tyr Asp Lys Phe Ala Glu Lys Phe Lys Glu
1               5                   10                  15

Ala Phe

<210> SEQ ID NO 1120
<211> LENGTH: 18
<212> TYPE: PRT
<213> ORGANISM: Artificial
<220> FEATURE:
<223> OTHER INFORMATION: Synthetic peptide optionally bearing
      protecting groups.

<400> SEQUENCE: 1120

Asp Phe Trp Lys Ala Phe Tyr Asp Lys Val Ala Glu Lys Phe Lys Glu
1               5                   10                  15

Ala Phe

<210> SEQ ID NO 1121
<211> LENGTH: 3
<212> TYPE: PRT
<213> ORGANISM: Artificial
<220> FEATURE:
<223> OTHER INFORMATION: Synthetic peptide optionally bearing
      protecting groups.

<400> SEQUENCE: 1121

Arg Phe Lys
1

<210> SEQ ID NO 1122
<211> LENGTH: 7
<212> TYPE: PRT
```

<213> ORGANISM: Artificial
<220> FEATURE:
<223> OTHER INFORMATION: Synthetic peptide optionally bearing
      protecting groups.

<400> SEQUENCE: 1122

Leu Ala Glu Tyr His Ala Lys
1               5

<210> SEQ ID NO 1123
<211> LENGTH: 7
<212> TYPE: PRT
<213> ORGANISM: Artificial
<220> FEATURE:
<223> OTHER INFORMATION: Peptide linker

<400> SEQUENCE: 1123

Gly Gly Gly Gly Ser Ser Ser
1               5

<210> SEQ ID NO 1124
<211> LENGTH: 45
<212> TYPE: PRT
<213> ORGANISM: Artificial
<220> FEATURE:
<223> OTHER INFORMATION: Synthetic peptide optionally bearing
      protecting groups.

<400> SEQUENCE: 1124

Leu Leu Glu Gln Leu Asn Glu Gln Phe Asn Trp Val Ser Arg Leu Ala
1               5                   10                  15

Asn Leu Thr Gln Gly Glu Pro Leu Leu Glu Gln Leu Asn Glu Gln Phe
            20                  25                  30

Asn Trp Val Ser Arg Leu Ala Asn Leu Thr Gln Gly Glu
        35                  40                  45

<210> SEQ ID NO 1125
<211> LENGTH: 41
<212> TYPE: PRT
<213> ORGANISM: Artificial
<220> FEATURE:
<223> OTHER INFORMATION: Synthetic peptide optionally bearing
      protecting groups.

<400> SEQUENCE: 1125

Leu Leu Glu Gln Leu Asn Glu Gln Phe Asn Trp Val Ser Arg Leu Ala
1               5                   10                  15

Asn Leu Thr Gln Gly Glu Pro Asp Trp Phe Lys Ala Phe Tyr Asp Lys
            20                  25                  30

Val Ala Glu Lys Phe Lys Glu Ala Phe
        35                  40

<210> SEQ ID NO 1126
<211> LENGTH: 22
<212> TYPE: PRT
<213> ORGANISM: Artificial
<220> FEATURE:
<223> OTHER INFORMATION: Synthetic peptide optionally bearing
      protecting groups.

<400> SEQUENCE: 1126

Leu Leu Glu Gln Leu Asn Glu Gln Phe Asn Trp Val Ser Arg Leu Ala
1               5                   10                  15

Asn Leu Thr Gln Gly Glu
            20

<210> SEQ ID NO 1127
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1127

Lys Phe Lys Glu Ala Phe
1               5

<210> SEQ ID NO 1128
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1128

Tyr Asp Lys Val Ala Glu
1               5

<210> SEQ ID NO 1129
<211> LENGTH: 6
<212> TYPE: PRT
<213> ORGANISM: Artificial
<220> FEATURE:
<223> OTHER INFORMATION: Fragment of synthetic D-4F pepitde

<400> SEQUENCE: 1129

Asp Trp Phe Lys Ala Phe
1               5

<210> SEQ ID NO 1130
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1130

Lys Phe Lys Glu Ala Phe
1               5

<210> SEQ ID NO 1131
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1131

Lys Phe Lys Glu Ala Phe
1               5

<210> SEQ ID NO 1132
<211> LENGTH: 11
<212> TYPE: PRT
<213> ORGANISM: Artificial
<220> FEATURE:
<223> OTHER INFORMATION: Fragment of synthetic D-4F peptide

<400> SEQUENCE: 1132

Tyr Asp Lys Val Ala Glu Lys Phe Lys Glu Phe
1               5                   10

<210> SEQ ID NO 1133

```
<211> LENGTH: 18
<212> TYPE: PRT
<213> ORGANISM: Artificial
<220> FEATURE:
<223> OTHER INFORMATION: Synthetic peptide bearing protecting groups.

<400> SEQUENCE: 1133

Asp Trp Phe Lys Ala Phe Tyr Asp Lys Val Ala Glu Lys Phe Lys Glu
1               5                   10                  15

Ala Phe

<210> SEQ ID NO 1134
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1134

Asp Trp Phe Lys Ala Phe
1               5

<210> SEQ ID NO 1135
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1135

Tyr Asp Lys Val Ala Glu
1               5

<210> SEQ ID NO 1136
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1136

Lys Phe Lys Glu Ala Phe
1               5

<210> SEQ ID NO 1137
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1137

Asp Trp Phe Lys Ala Phe
1               5

<210> SEQ ID NO 1138
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1138

Tyr Asp Lys Val Ala Glu
1               5

<210> SEQ ID NO 1139
```

```
<211> LENGTH: 6
<212> TYPE: PRT
<213> ORGANISM: Artificial
<220> FEATURE:
<223> OTHER INFORMATION: Fragment of synthetic D-4F peptide

<400> SEQUENCE: 1139

Lys Phe Lys Glu Ala Phe
1               5
```

US 8,048,851 B2

PEPTIDES AND PEPTIDE MIMETICS TO TREAT PATHOLOGIES CHARACTERIZED BY AN INFLAMMATORY RESPONSE

This application is a Continuation of U.S. Ser. No. 11/407,390, filed on Apr. 18, 2006, which claims priority to and benefit of U.S. Ser. No. 60/697,495, filed Jul. 7, 2005 and to U.S. Ser. No. 60/676,431 filed on Apr. 29, 2005, both of which are incorporated herein by reference in their entirety for all purposes. U.S. Ser. No. 11/407,390, now issued U.S. Pat. No. 7,723,303, is also a Continuation-in-Part of U.S. Ser. No. 10/423,830, filed on Apr. 25, 2003, which is a Continuation-in-Part of U.S. Ser. No. 10/273,386, filed on Oct. 16, 2002, which is a Continuation-in-Part of U.S. Ser. No. 10/187,215, filed on Jun. 28, 2002, which is a Continuation-in-Part of U.S. Ser. No. 09/896,841, filed on Jun. 29, 2001, now issued U.S. Pat. No. 6,933,279, which is a Continuation-in-Part of U.S. Ser. No. 09/645,454, filed on Aug. 24, 2000, now issued U.S. Pat. No. 6,664,230, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made, in part, by government support under Grant No: HL30568 awarded by the National Institutes of Health. The government has certain rights in this invention.

FIELD OF THE INVENTION

This invention relates to the field of atherosclerosis and other conditions characterized by inflammation and/or the formation of various oxidized species. In particular, this invention pertains to the identification of classes of active agents that are orally administrable and that ameliorate one or more symptoms of conditions characterized by an inflammatory response and/or the formation of various oxidized species.

BACKGROUND OF THE INVENTION

The introduction of statins (e.g., Mevacor®, Lipitor®, etc.) has reduced mortality from heart attack and stroke by about one-third. However, heart attack and stroke remain the major cause of death and disability, particularly in the United States and in Western European countries. Heart attack and stroke are the result of a chronic inflammatory condition, which is called atherosclerosis.

Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of ratelimiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include the amount and type of fat (saturated and polyunsaturated fatty acids), the amount of cholesterol, amount and type of fiber, and perhaps the amounts of vitamins such as vitamin C and D and minerals such as calcium.

Low density lipoprotein (LDL) oxidation has been strongly implicated in the pathogenesis of atherosclerosis. High density lipoprotein (HDL) has been found to be capable of protecting against LDL oxidation, but in some instances has been found to accelerate LDL oxidation. Important initiating factors in atherosclerosis include the production of LDL-derived oxidized phospholipids.

Normal HDL has the capacity to prevent the formation of these oxidized phospholipids and also to inactivate these oxidized phospholipids once they have formed. However, under some circumstances HDL can be converted from an anti-inflammatory molecule to a pro-inflammatory molecule that actually promotes the formation of these oxidized phospholipids.

It has been suggested that HDL and LDL function as part of the innate immune system (Navab et al. (2001) *Arterioscler. Thromb. Vasc. Biol.*, 21: 481-488). The generation of anti-inflammatory HDL has been achieved using class A amphipathic helical peptides that mimic the major protein of HDL, apolipoprotein A-I (apo A-I) (see, e.g., WO 02/15923).

SUMMARY OF THE INVENTION

This invention provides novel compositions and methods to ameliorate one or more symptoms of a vascular condition and/or a condition characterized by an inflammatory response and/or a condition characterized by the formation of oxidized reactive species in a mammal.

Thus, in certain embodiments, this invention provides a peptide that ameliorates a symptom of atherosclerosis, where the peptide comprises the amino acid sequence or the retro amino acid sequence of a peptide listed in Table 6. In another embodiment this invention provides a peptide that ameliorates a symptom of atherosclerosis, where the peptide: consists of 18 amino acids, the 18 amino acids consisting of 3 alanines (A), 2 aspartates (D), 2 glutamates (E), 4 phenylalanines (F), 4 lysines (K), 1 valine (V), 1 tryptophan (W), and 1 tyrosine (Y); where the peptide forms a class A amphipathic helix; comprises at least one "D" amino acid residue; and protects a phospholipid against oxidation by an oxidizing agent. In certain embodiments these peptides include but are not limited to a peptide having the amino acid sequence or the retro amino acid sequence of a peptide listed in Table 4. In still another embodiment, this invention provides a peptide that ameliorates a symptom of atherosclerosis, where the peptide: ranges in length from about 18 to 37 amino acids and comprises at least 3 alanines (A), 2 aspartates (D), 2 glutamates (E), 4 phenylalanines (F), 4 lysines (K), 1 valine (V), 1 tryptophan (W), 1 tyrosine (Y); where the peptide forms a class A amphipathic helix; comprises at least one "D" amino acid residue; and protects a phospholipid against oxidation by an oxidizing agent. In certain embodiments these peptides comprise an amino acid sequence selected from the group consisting of D-W-F-K-A-F-Y-D-K-V-A-E-K-F-K-E-A-F (SEQ ID NO:5), D-W-L-K-A-F-Y-D-K-V-A-E-K-L-K-E-A-F-P-D-W-L-K-A-F-Y-D-K-V-A-E-K-L-K-E-A-F (SEQ ID NO:78), D-W-L-K-A-F-Y-D-K-V-A-E-K-L-K-E-F-F-P-D-W-L-K-A-F-Y-D-K-V-A-E-K-L-K-E-F-F (SEQ ID NO:79), D-W-F-K-A-F-Y-D-K-V-A-E-K-L-K-E-A-F-P-D-W-F-K-A-F-Y-D-K-V-A-E-K-L-K-E-A-F (SEQ ID NO:80), D-K-L-K-A-F-Y-D-K-V-F-E-W-A-K-E-A-F-P-D-K-L-K-A-F-Y-D-K-V-F-E-W-L-K-E-A-F (SEQ ID NO:81), D-K-W-K-A-V-Y-D-K-F-A-E-A-F-K-E-F-L-P-D-K-W-K-A-V-Y-D-K-F-A-E-A-F-K-E-F-L (SEQ ID NO:82), D-W-F-K-A-F-Y-D-K-V-A-E-K-F-K-E-A-F-P-D-W-F-K-A-F-Y-D-K-V-A-E-K-F-K-E-A-F (SEQ ID NO:83), or the reverse of any of these sequences. In still yet another embodiment this invention provides a peptide that forms a class A amphipathic helix or a class Y amphipathic helix and is described by the formula: $D^1$-$X^1$-$X^2$-$K^1$-$Y^1$-$X^3$-$X^4$-$D^2$-$K^2$-$X^5$-$Y$-$D^3$-$K^3$-$X^6$-$K^4$-$D^4$-$Y^2$-$X^7$(SEQ ID NO:351), where $X^1$, $X^2$, $X^3$, $X^4$, $X^5$, and $X^6$ are independently selected from the group consisting of Leu, norLeu, Val, Ile, Trp, Phe, Tyr, β-Nal, and α-Nal, and all X residues are on the non-polar face of the peptide, except for one that can be on the polar face between two K residues; $K^1$, $K^2$, $K^3$, and $K^4$ are independently Lys or Arg, and no more than two K's are adjacent to each other in a helical wheel diagram of the peptide; $Y^1$ and $Y^2$ are independently selected from the group consisting of Ala, His, Ser, Gln, Asn, and Thr, when present on the non-polar face of the molecule; when one of $Y^1$ or $Y^2$ are present on the polar face of the molecule, the $Y^1$ or $Y^2$ on the polar face of the molecule is selected from the group consisting of Ala, His, Ser, Gln, Asn, and Thr; $D^1$, $D^2$, $D^3$, and $D^4$ are independently Asp or Glu, and no more than 3 Ds are contiguous in a helical wheel diagram of the peptide, and the remaining D is separated from the other D's by a Y. In certain embodiments these peptides comprise the amino acid sequence or the retro amino acid sequence of a peptide listed in Table 5.

In certain embodiments any one or more of these peptides further comprise a protecting group coupled to the amino or carboxyl terminus. In certain embodiments the peptides comprise a first protecting group coupled to the amino terminus and a second protecting group coupled to the carboxyl terminus. In certain embodiments the protecting groups can be independently selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl -2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

In certain embodiments the peptide comprises a protecting group coupled to the amino terminal and the amino terminal protecting group is a protecting group selected from the group consisting of acetyl, propeonyl, and a 3 to 20 carbon alkyl. In certain embodiments the peptide comprises a protecting group coupled to the carboxyl terminal and the carboxyl terminal protecting group is an amide. In certain embodiments the peptide comprises: a first protecting group coupled to the amino terminus where the protecting group is a protecting group selected from the group consisting of acetyl, propeonyl, and a 3 to 20 carbon alkyl; and a second protecting group coupled to the carboxyl terminal and the carboxyl terminal protecting group is an amide.

In various embodiments one or more amino acids comprising the peptide are "D" amino acids. In various embodiments all amino acids comprising the peptide "D" amino acids. The peptide(s) can, optionally, be mixed/combined with a pharmacologically acceptable excipient. In certain embodiments the excipient is an excipient suitable for oral administration to a mammal.

In certain embodiments this invention provides methods of treating a vascular condition and/or a condition characterized by an inflammatory response and/or a condition characterized by the formation of oxidized reactive species in a mammal. The methods typically involve administering to a mammal in need thereof one or more of the active agents described in Tables 2-18, and/or a small organic molecule as described herein in an amount sufficient to ameliorate one or more symptoms of the condition. In certain embodiments the active agent is a polypeptide comprising the amino acid sequence of 4F (SEQ ID NO:5). In certain embodiments the administration is by a route selected from the group consisting of oral administration, nasal administration, rectal administration, intraperitoneal injection, and intravascular injection, subcutaneous injection, transcutaneous administration, and intramuscular injection. In certain embodiments the active agent is administered in conjunction with a drug selected from the group consisting of CETP inhibitors, FTY720, Certican, DPP4 inhibitors, Calcium channel blockers, ApoA1 derivative or mimetic or agonist, PPAR agonists, Steroids, Gleevec, Cholesterol Absorption blockers (Zetia), Vytorin, Any Renin Angiotensin pathway blockers, Angiotensin II receptor antagonist (Diovan etc), ACE inhibitors, Renin inhibitors, MR antagonist and Aldosterone synthase inhibitor, Beta-blockers, Alpha-adrenergic antagonists, LXR agonist, FXR agonist, Scavenger Receptor B1 agonist, ABCA1 agonist, Adiponectic receptor agonist or adiponectin inducers, Stearoyl-CoA Desaturase I (SCD1) inhibitor, Cholesterol synthesis inhibitors (non-statins), Diacylglycerol Acyltransferase I (DGAT1) inhibitor, Acetyl CoA Carboxylase 2 inhibitor, PAI-1 inhibitor, LP-PLA2 inhibitor, GLP-1, Glucokinase activator, CB-1 agonist, AGE inhibitoribreaker, PKC inhibitors, Anti-thrombotic/coagulants: Aspirin, ADP receptor blockers e.g. Clopidigrel, Factor Xa inhibitor, GPIIb/IIIa inhibitor, Factor VIIa inhibitor, Warfarin, Low molecular weight heparin, Tissue factor inhibitor, Anti-inflammatory drugs: Probucol and derivative e.g. AGI-1067 etc, CCR2 antagonist, CX3CR1 antagonist, IL-1 antagonist, Nitrates and NO donors, and Phosphodiesterase inhibitors.

In various embodiments this invention provides for the use of an active agent described in Tables 2-18, and/or a small organic molecule as described herein in a treatment of a condition selected from the group consisting of atherosclerotic plaque formation, atherosclerotic lesion formation, myocardial infarction, stroke, congestive heart failure, arteriole function, arteriolar disease, arteriolar disease associated with aging, arteriolar disease associated with Alzheimer's disease, arteriolar disease associated with chronic kidney disease, arteriolar disease associated with hypertension, arteriolar disease associated with multi-infarct dementia, arteriolar disease associated with subarachnoid hemorrhage, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, rheumatoid arthritis, polyarteritis nodosa, polymyalgia rheumatica, lupus erythematosus, multiple sclerosis, Wegener's granulomatosis, central nervous system vasculitis (CNSV), Sjögren's syndrome, scleroderma, polymyositis, AIDS inflammatory response, bacterial infection, fungal infection, viral infection, parasitic infection, influenza, avian flu, viral pneumonia, endotoxic shock syndrome, sepsis, sepsis syndrome, trauma/wound, organ transplant, transplant atherosclerosis, transplant rejection, corneal ulcer, chronic/non-healing wound, ulcerative colitis, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer osteoarthritis, inflammatory bowel disease, allergic rhinitis, cachexia, diabetes, Alzheimer's disease, implanted prosthesis, biofilm formation, Crohns' disease, dermatitis, acute and chronic, eczema, psoriasis, contact dermatitis, scleroderma, Type I Diabetes, Type II Diabetes, juvenile onset diabetes, prevention of the onset of diabetes, diabetic nephropathy, diabetic neuropathy, diabetic retinopathy, erectile dysfunction, macular degeneration, multiple sclerosis, nephropathy, neuropathy, Parkinson's Disease, peripheral vascular disease, and meningitis.

This invention additionally provides for the use of active agent described in Tables 2-18, and/or a small organic molecule as described herein for the manufacture of a medicament for the treatment of a condition selected from the group consisting of atherosclerotic plaque formation, atherosclerotic lesion formation, myocardial infarction, stroke, congestive heart failure, arteriole function, arteriolar disease, arteriolar disease associated with aging, arteriolar disease associated with Alzheimer's disease, arteriolar disease associated with chronic kidney disease, arteriolar disease associated with hypertension, arteriolar disease associated with multi-infarct dementia, arteriolar disease associated with subarachnoid hemorrhage, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, rheumatoid arthritis, polyarteritis nodosa, polymyalgia rheumatica, lupus erythematosus, multiple sclerosis, Wegener's granulomatosis, central nervous system vasculitis (CNSV), Sjögren's syndrome, scleroderma, polymyositis, AIDS inflammatory response, bacterial infection, fungal infection, viral infection, parasitic infection, influenza, avian flu, viral pneumonia, endotoxic shock syndrome, sepsis, sepsis syndrome, trauma/wound, organ transplant, transplant atherosclerosis, transplant rejection, corneal ulcer, chronic/non-healing wound, ulcerative colitis, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer, osteoarthritis, inflammatory bowel disease, allergic rhinitis, cachexia, diabetes, Alzheimer's disease, implanted prosthesis, biofilm formation, Crohns' disease, dermatitis, acute and chronic, eczema, psoriasis, contact dermatitis, scleroderma, Type I Diabetes, Type II Diabetes, juvenile onset diabetes, prevention of the onset of diabetes, diabetic nephropathy, diabetic retinopathy, erectile dysfunction, macular degeneration, multiple sclerosis, nephropathy, Parkinson's Disease, peripheral vascular disease, and meningitis.

In certain embodiments this invention provides a stent for delivering drugs to a vessel in a body. The stent typically comprises a stent framework including a plurality of reservoirs formed therein, and a peptide comprising the amino acid sequence or the retro amino acid sequence of a peptide listed in Tables 2-18 (e.g., Table 4, Table 5, or Table 6) and/or the inverse thereof. In certain embodiments the stent comprises a peptide comprising the amino acid sequence of 4F (SEQ ID NO:5) or the inverse thereof. In certain embodiments the active agent is contained within a polymer. In certain embodiments the stent framework comprises one of a metallic base or a polymeric base. In certain embodiments the stent framework base comprises a material selected from the group consisting of stainless steel, nitinol, tantalum, MP35N alloy, platinum, titanium, a suitable biocompatible alloy, a suitable biocompatible polymer, and a combination thereof. The reservoir(s) comprising said stent can, in some embodiments, comprise micropores (e.g. having a diameter of about 20 microns or less). In certain embodiments the micropores have a diameter in the range of about 20 microns to about 50 microns. In various embodiments the micropores have a depth in the range of about 10 to about 50 microns. The micropores, in certain embodiments, extend through the stent framework having an opening on an interior surface of the stent and an opening on an exterior surface of the stent. In various embodiments the stent can further comprise a cap layer disposed on the interior surface of the stent framework, the cap layer covering at least a portion of the through-holes and providing a barrier characteristic to control an elution rate of a drug in the drug polymer from the interior surface of the stent framework. In various embodiments the reservoirs comprise channels along an exterior surface of the stent framework. In various embodiments the polymer comprises a first layer of a first drug polymer having a first pharmaceutical characteristic and the polymer layer comprises a second drug polymer having a second pharmaceutical characteristic. In certain embodiments the stent further comprises a barrier layer positioned between the polymer comprising the active agent. In various embodiments a catheter can be coupled to the stent framework. In certain embodiments the catheter can include a balloon used to expand the stent. In certain embodiments the catheter includes a sheath that retracts to allow expansion of the stent.

Also provided is a method of manufacturing a drug-polymer stent. The method typically involves providing a stent framework; cutting a plurality of reservoirs in the stent framework; applying a composition comprising one or more peptides comprising the amino acid sequence or the retro amino acid sequence of a peptide listed in any of Tables 2-18 to at least one reservoir; and drying the composition. The method can further involve applying a polymer layer to the dried composition; and drying the polymer layer.

This invention also provides a method of treating a vascular condition. The method involves positioning a stent as described above, within a vessel of a body; expanding the stent; and eluting at least one active agent (e.g., an active agent from any of Tables 2-18) from at least a surface of the stent.

In certain embodiments, this invention expressly excludes one or more of the peptides described in U.S. Pat. Nos. 6,037,323; 4,643,988; 6,933,279; 6,930,085; 6,664,230; 3,767,040; 6,037,323; U.S. Patent Publications 2005/0164950; 2004/0266671; 2004/0254120; 2004/0057871; 2003/0229015; 2003/0191057; 2003/0171277; 2003/0045460; 2003/0040505; PCT Publications WO 2002/15923; WO 1999/16408; WO 1997/36927; and/or in Garber et al. (1992) *Arte-* riosclerosis and Thrombosis, 12: 886-894, which are incorporated herein by reference.

DEFINITIONS

The term "treat" when used with reference to treating, e.g. a pathology or disease refers to the mitigation and/or elimination of one or more symptoms of that pathology or disease, and/or a reduction in the rate of onset or severity of one or more symptoms of that pathology or disease, and/or the prevention of that pathology or disease.

The terms "isolated", "purified", or "biologically pure" when referring to an isolated polypeptide refer to material that is substantially or essentially free from components that normally accompany it as found in its native state. With respect to nucleic acids and/or polypeptides the term can refer to nucleic acids or polypeptides that are no longer flanked by the sequences typically flanking them in nature. Chemically synthesized polypeptides are "isolated" because they are not found in a native state (e.g. in blood, serum, etc.). In certain embodiments, the term "isolated" indicates that the polypeptide is not found in nature.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "an amphipathic helical peptide" refers to a peptide comprising at least one amphipathic helix (amphipathic helical domain). Certain amphipathic helical peptides of this invention can comprise two or more (e.g., 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) *Proteins: Structure, Function, and Genetics* 8: 103-117).

"Apolipoprotein J" (apo J) is known by a variety of names including clusterin, TRPM2, GP80, and SP 40 (see, e.g., Fritz (1995) Pp 112 In: *Clusterin: Role in Vertebrate Development, Function, and Adaptation* (Harmony JAK Ed.), R. G. Landes, Georgetown, Tex.,). It was first described as a heterodimeric glycoprotein and a component of the secreted proteins of cultured rat Sertoli cells (see, e.g., Kissinger et al. (1982) *Biol. Reprod.;* 27: 233240). The translated product is a single-chain precursor protein that undergoes intracellular cleavage into a disulfide-linked 34 kDa α subunit and a 47 kDa β subunit (see, e.g., Collard and Griswold (1987) *Biochem.,* 26: 3297-3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) *Biochem.,* 40: 11828-11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, e.g., Segrest et al. (1990) *Proteins: Structure, Function, and Genetics.* 8: 103-117; Erratum (1991) *Proteins: Structure, Function and Genetics,* 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see, e.g., Segrest et al. (1992) *J. Lipid Res.,* 33: 141-166; Anantharamaiah et al. (1993) Pp. 109-142 In: *The Amphipathic Helix*, Epand, R. M. Ed CRC Press, Boca Raton, Fla.). Computer programs to identify and classify amphipathic helical domains have been described by Jones et al. (1992) *J. Lipid Res.* 33: 287-296) and include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art. Amino acids are designated herein using standard 1-letter or three-letter codes, e.g. as designated in Standard ST.25 in the Handbook On Industrial Property Information and Documentation.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propeonyl, formyl and others. Preferred carboxyl terminal protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)—HPODE, 15-(S)—HPETE, HPODE, HPETE, HODE, HETE, etc.).

The terms "low density lipoprotein" or "LDL" is defined in accordance with common usage of those of skill in the art.

Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations may be used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phosphocholine; ChC18:2: cholesteryl linoleate; ChC18:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; BL/6: C57BL/6J; C3H:C3H/HeJ.

The term "conservative substitution" is used in reference to proteins or peptides to reflect amino acid substitutions that do not substantially alter the activity (specificity (e.g. for lipoproteins)) or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "in conjunction with" when used in reference to the use of one or more drugs in conjunction with one or more active agents described herein indicates that the drug(s) and the active agent(s) are administered so that there is at least some chronological overlap in their physiological activity on the organism. Thus the drug(s) and active agent(s) can be administered simultaneously and/or sequentially. In sequential administration there may even be some substantial delay (e.g., minutes or even hours or days) before administration of the second moiety as long as the first administered drug/agent has exerted some physiological alteration on the organism when the second administered agent is administered or becomes active in the organism.

The phrases "adjacent to each other in a helical wheel diagram of a peptide" or "contiguous in a helical wheel diagram of a peptide" when referring to residues in a helical peptide indicates that in the helical wheel representation the residues appear adjacent or contiguous even though they may not be adjacent or contiguous in the linear peptide. Thus, for example, the residues "A, E, K, W, K, and F" are contiguous in the helical wheel diagrams shown in FIG. 15 even though these residues are not contiguous in the linear peptide.

BRIEF DESCRIPTION OF THE DRAWINGS

FIG. 10A: $V^2W^3A^5F^{10,17}$-D-4F; FIG. 10B: $W^3$-D-4F; FIG. 10C: $V^2W^3F^{10}$-D-4F:

DETAILED DESCRIPTION

I. Methods of Treatment.

The active agents (e.g. peptides, small organic molecules, amino acid pairs, etc.) described herein are effective for mitigating one or more symptoms and/or reducing the rate of onset and/or severity of one or more indications described herein. In particular, the active agents (e.g. peptides, small organic molecules, amino acid pairs, etc.) described herein are effective for mitigating one or more symptoms of atherosclerosis. Without being bound to a particular theory, it is believed that the peptides bind the "seeding molecules" required for the formation of pro-inflammatory oxidized phospholipids such as Ox-PAPC, POVPC, PGPC, and PEIPC.

In addition, since many inflammatory conditions and/or other pathologies are mediated at least in part by oxidized lipids, we believe that the peptides of this invention are effective in ameliorating conditions that are characterized by the formation of biologically active oxidized lipids. In addition, there are a number of other conditions for which the active agents described herein appear to be efficacious.

A number of pathologies for which the active agents described herein appear to be a palliative and/or a preventative are described below.

A) Atherosclerosis and Associated Pathologies.

We discovered that normal HDL inhibits three steps in the formation of mildly oxidized LDL. In particular, we demonstrated that treating human LDL in vitro with apo A-I or an apo A-I mimetic peptide (37pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures.

Figure 1:
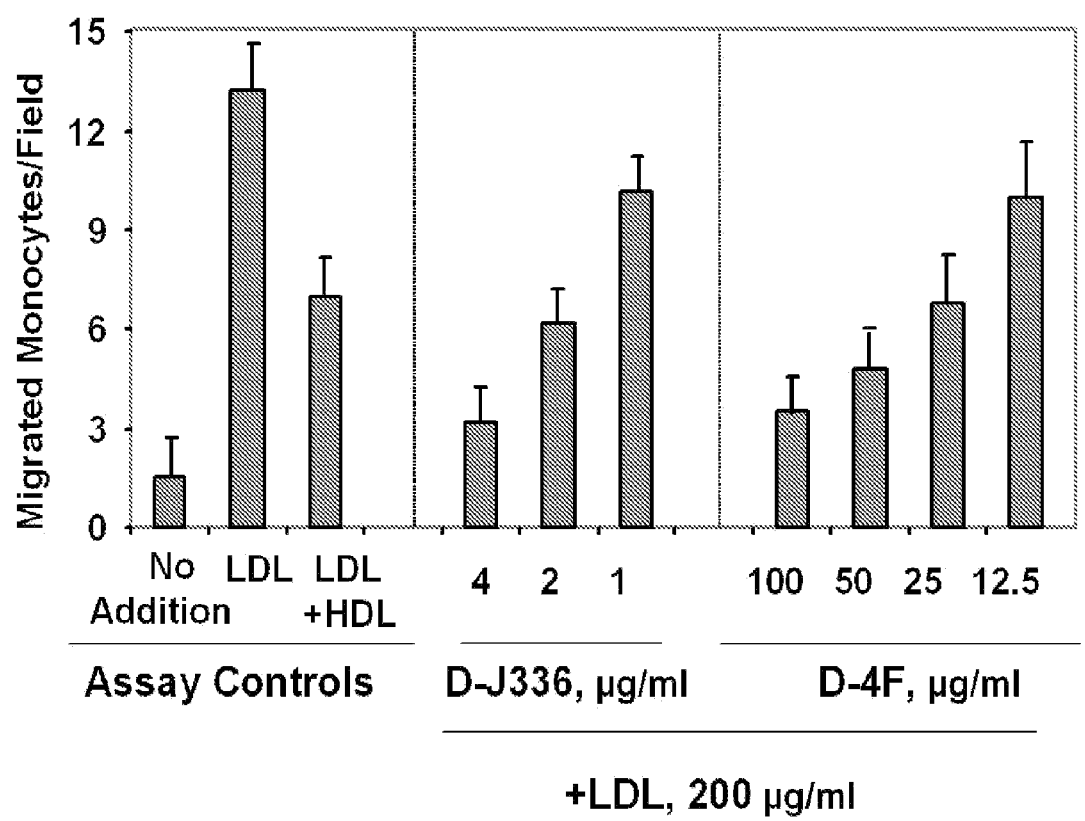
FIG. 1 shows a comparison of the effect of D4F (Navab, et al. (2002)*Circulation*, 105: 290-292) and apo-J peptide 336 made from D amino acids (D-J336*) on the prevention of LDL-induced monocyte chemotactic activity in vitro in a co-incubation experiment. The data are mean ±SD of the number of migrated monocytes in nine high power fields in quadruple cultures. (D-J336 =Ac-LLEQLNEQFNWVSR-LANLTQGE-NH$_2$, SEQ ID NO:961).
Figure 2:
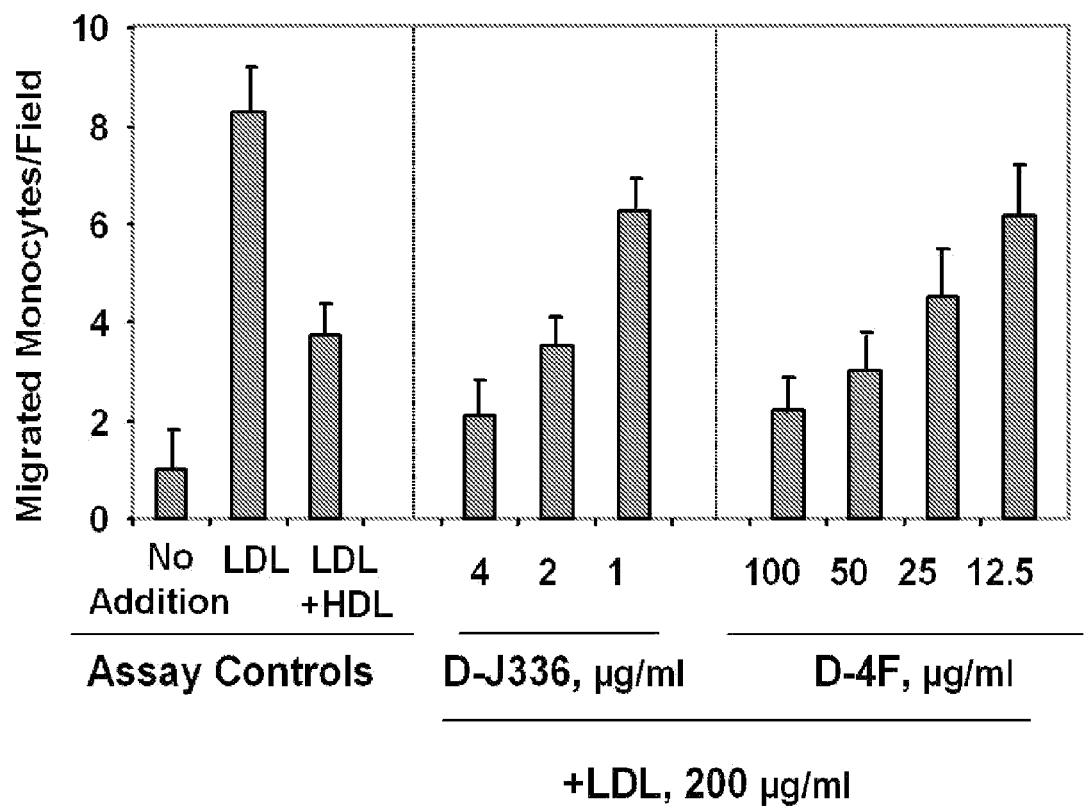
FIG. 2 illustrates the prevention of LDL-induced monocyte chemotactic activity by pre-treatment of artery wall cells with D-J336 as compared to D-4F. The data are mean ±SD of the number of migrated monocytes in nine high power fields in quadruple cultures.
Figure 3:
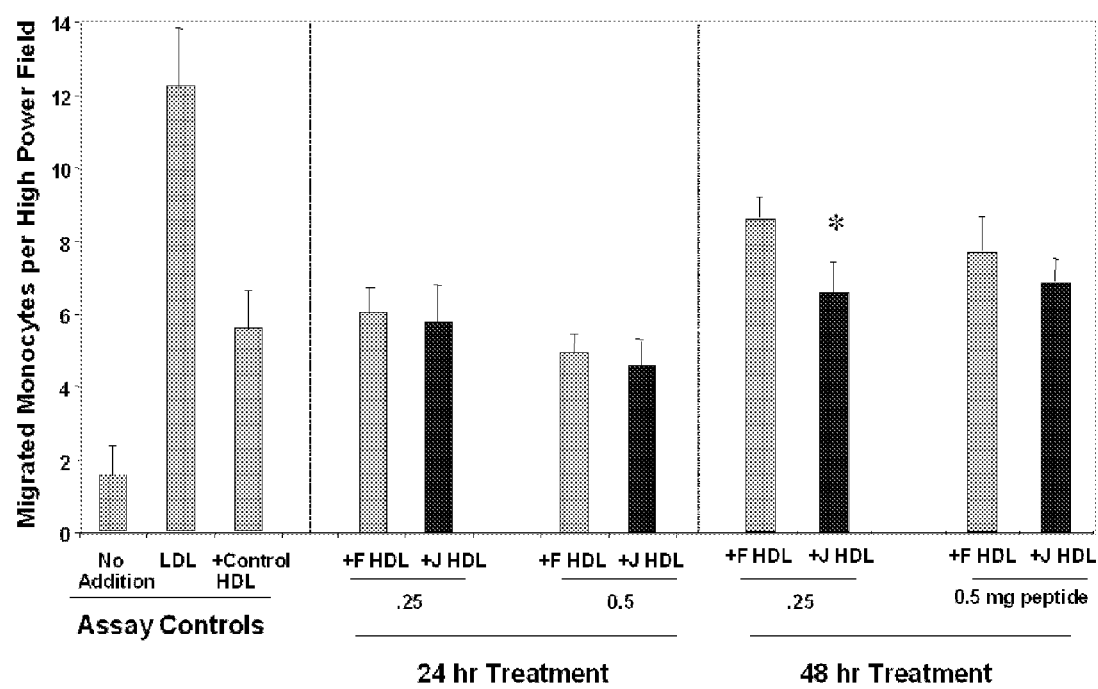
FIG. 3 illustrates he effect of apo J peptide mimetics on HDL protective capacity in LDL receptor null mice. The values are the mean ±SD of the number of migrated monocytes in 9 high power fields from each of quadruple assay wells.
Figure 4:
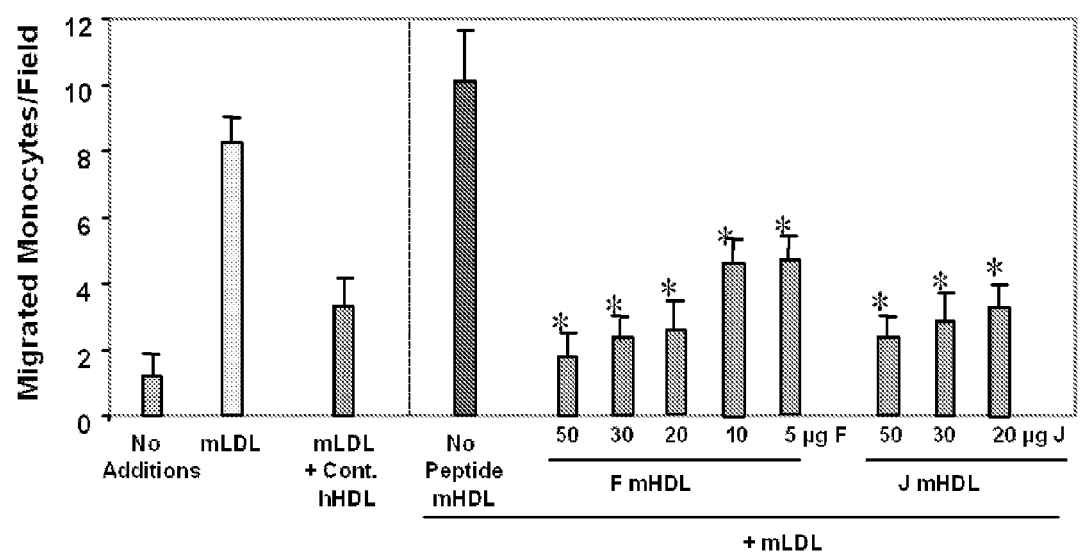
FIG. 4 illustrates protection against LDL-induced monocyte chemotactic activity by HDL from apo E null mice given oral peptides. The values are the mean ±SD of the number of migrated monocytes in 9 high power fields from each of quadruple assay wells. Asterisks indicate significant difference (p<0.05) as compared to No Peptide mHDL.

The protective function of various active agents of this invention is illustrated in the parent applications (Ser. No. 09/645,454, filed Aug. 24, 2000, Ser. No. 09/896,841, filed Jun. 29, 2001, and WO 02/15923 (PCT/US01/26497), filed Jun. 29, 2001, see, e.g., FIGS. 1-5 in WO 02/15923. FIG. 1, panels A, B, C, and D in WO 02/15923 show the association of $^{14}$C-D-5F with blood components in an ApoE null mouse. It is also demonstrated that HDL from mice that were fed an atherogenic diet and injected with PBS failed to inhibit the oxidation of human LDL and failed to inhibit LDL-induced monocyte chemotactic activity in human artery wall cocultures. In contrast, HDL from mice fed an atherogenic diet and injected daily with peptides described herein was as effective in inhibiting human LDL oxidation and preventing LDL-induced monocyte chemotactic activity in the cocultures as was normal human HDL (FIGS. 2A and 2B in WO 02/15923). In addition, LDL taken from mice fed the atherogenic diet and injected daily with PBS was more readily oxidized and more readily induced monocyte chemotactic activity than LDL taken from mice fed the same diet but injected with 20 μg daily of peptide 5F. The D peptide did not appear to be immunogenic (FIG. 4 in WO 02/15923).

Figure 5:
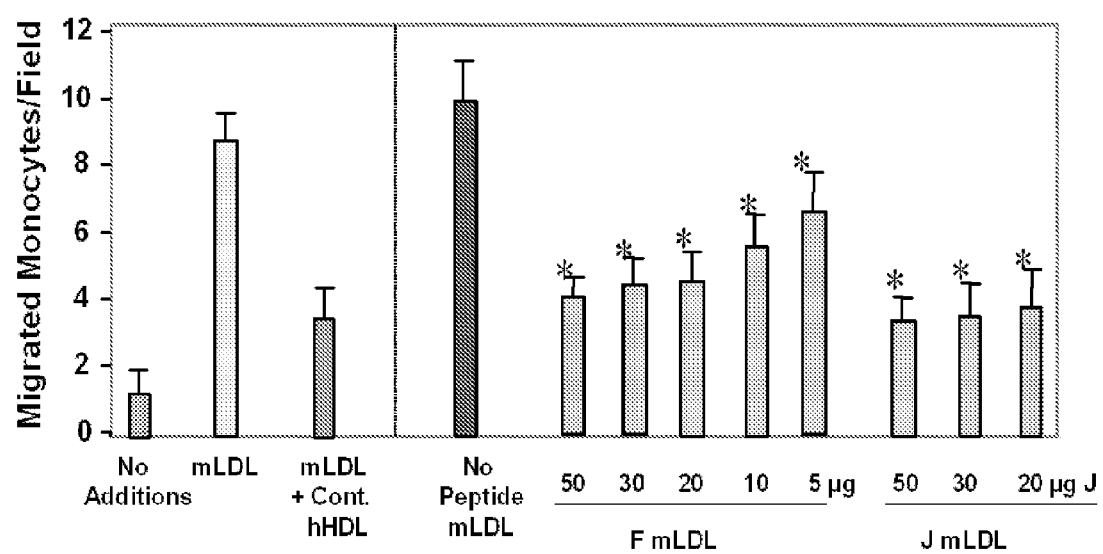
FIG. 5 illustrates the effect of oral apoA-1 peptide mimetic and apoJ peptide on LDL susceptibility to oxidation. The values are the mean ±SD of the number of migrated monocytes in 9 high power fields from each of quadruple assay wells. Asterisks indicate significant difference (p<0.05) as compared to No Peptide LDL.

The in vitro responses of human artery wall cells to HDL and LDL from mice fed the atherogenic diet and injected with a peptide according to this invention are consistent with the protective action shown by such peptides in vivo. Despite, similar levels of total cholesterol, LDL-cholesterol, IDL+VLDL-cholesterol, and lower HDL-cholesterol as a percent of total cholesterol, the animals fed the atherogenic diet and injected with the peptide had significantly lower lesion scores (FIG. 5 in WO 02/15923). The peptides of this invention thus prevented progression of atherosclerotic lesions in mice fed an atherogenic diet.

Thus, in one embodiment, this invention provides methods for ameliorating and/or preventing one or more symptoms of atherosclerosis by administering one or more of the active agents described herein.

It is also noted that c-reactive protein, a marker for inflammation, is elevated in congestive heart failure. Also, in congestive heart failure there is an accumulation of reactive oxygen species and vasomotion abnormalities. Because of their effects in preventing/reducing the formation of various oxidized species and/or because of their effect in improving vasoreactivity and/or arteriole function (see below) the active agents described herein will be effective in treating congestive heart failure.

B) Arteriole/Vascular Indications.

Vessels smaller than even the smallest arteries (i.e., arterioles) thicken, become dysfunctional and cause end organ damage to tissues as diverse as the brain and the kidney. It is believed the active agents described herein can function to improve areteriole structure and function and/or to slow the rate and/or severity of arteriole dysfunction. Without being bound to a particular theory, it is believed that arteriole dysfunction is a causal factor in various brain and kidney disorders. Use of the agents described herein thus provides a method to improve the structure and function of arterioles and preserve the function of end organs such as the brain and kidney.

Thus, for example, administration of one or more of the active agents described herein is expected to reduce one or more symptoms or to slow the onset or severity of arteriolar disease associated with aging, and/or Alzheimer's disease, and/or Parkinson's disease, and/or with multi-infarct dementia, and/or subarachnoid hemorrhage, and the like. Similarly, administration of one or more agents described herein is expected to mitigate one or more symptoms and/or to slow the onset and/or severity of chronic kidney disease, and/or hypertension.

Similarly, the agents described herein appear to improve vasoreactivity. Because of the improvement of vasoreactivity and/or arteriole function, the agents described herein are suitable for the treatment of peripheral vascular disease, erectile dysfunction, and the like.

C) Pulmonary Indications.

The agents described herein are also suitable for treatment of a variety of pulmonary indications. These include, but are not limited to chronic obstructive pulmonary disease (COPD), emphysema, pulmonary disease, asthma, idiopathic pulmonary fibrosis, and the like.

D) Mitigation of a Symptom or Condition Associated with Coronary Calcification and Osteoporosis.

Vascular calcification and osteoporosis often co-exist in the same subjects (Ouchi et al. (1993) *Ann NY Acad. Sci.*, 676: 297-307; Boukhris and Becker ('1972) *JAMA*, 219: 1307-1311; Banks et al. (1994) *Eur J Clin Invest.*, 24: 813-817; Laroche et al. (1994) *Clin Rheumatol.*, 13: 611-614; Broulik and Kapitola (1993) *Endocr Regul.*, 27: 57-60; Frye et al. (1992) *Bone Mine.*, 19: 185-194; Barengolts et al. (1998) *Calcif Tissue Int.*, 62: 209-213; Burnett and Vasikaran (2002) *Ann Clin Biochem.*, 39: 203-210. Parhami et al. (1997) *Arterioscl Thromb Vasc Biol.*, 17: 680-687, demonstrated that mildly oxidized LDL (MM-LDL) and the biologically active lipids in MM-LDL [i.e. oxidized 1-palmitoyl-2-arachidonoyl-sn-glycero-3-phosphorylcholine) (Ox-PAPC)], as well as the isoprostane, 8-iso prostaglandin $E_2$, but not the unoxidized phospholipid (PAPC) or isoprostane 8-iso progstaglandin $F_{2\alpha}$, induced alkaline phosphatase activity and osteoblastic differentiation of calcifying vascular cells (CVCs) in vitro, but inhibited the differentiation of MC3T3-E1 bone cells.

The osteon resembles the artery wall in that the osteon is centered on an endothelial cell-lined lumen surrounded by a subendothelial space containing matrix and fibroblast-like cells, which is in turn surrounded by preosteoblasts and osteoblasts occupying a position analogous to smooth muscle cells in the artery wall (Id.). Trabecular bone osteoblasts also interface with bone marrow subendothelial spaces (Id.). Parhami et al. postulated that lipoproteins could cross the endothelium of bone arteries and be deposited in the subendothelial space where they could undergo oxidation as in coronary arteries (Id.). Based on their in vitro data they predicted that LDL oxidation in the subendothelial space of bone arteries and in bone marrow would lead to reduced osteoblastic differentiation and mineralization which would contribute to osteoporosis (Id.). Their hypothesis further predicted that LDL levels would be positively correlated with osteoporosis as they are with coronary calcification (Pohle et al. (2001) *Circulation*, 104: 1927-1932), but HDL levels would be negatively correlated with osteoporosis (Parhami et al. (1997) *Arterioscl Thromb Vasc Biol.*, 17: 680-687).

In vitro, the osteoblastic differentiation of the marrow stromal cell line M2-10B4 was inhibited by MM-LDL but not native LDL (Parhami et al. (1999) *J Bone Miner Res.*, 14: 2067-2078). When marrow stromal cells from atherosclerosis susceptible C57BL/6 (BL6) mice fed a low fat chow diet were cultured there was robust osteogenic differentiation (Id.). In contrast, when the marrow stromal cells taken from the mice after a high fat, atherogenic diet were cultured they did not undergo osteogenic differentiation (Id.). This observation is particularly important since it provides a possible explanation for the decreased osteogenic potential of marrow stromal cells in the development of osteoporosis (Nuttall and Gimble (2000) *Bone*, 27:177-184). In vivo the decrease in osteogenic potential is accompanied by an increase in adipogenesis in osteoporotic bone (Id.).

It was found that adding D-4F to the drinking water of apoE null mice for 6 weeks dramatically increased trabecular bone mineral density and it is believed that the other active agents of this invention will act similarly.

Our data indicate that osteoporosis can be regarded as an "atherosclerosis of bone". It appears to be a result of the action of oxidized lipids. HDL destroys these oxidized lipids and promotes osteoblastic differentiation. Our data indicate that administering active agent (s) of this invention to a mammal (e.g., in the drinking water of apoE null mice) dramatically increases trabecular bone in just a matter of weeks.

This indicates that the active agents, described herein are useful for mitigation one or more symptoms of osteoporosis (e.g., for inhibiting decalcification) or for inducing recalcification of osteoporotic bone. The active agents are also useful as prophylactics to prevent the onset of symptom(s) of osteoporosis in a mammal (e.g., a patient at risk for osteoporosis).

We believe similar mechanisms are a cause of coronary calcification, e.g., calcific aortic stenosis. Thus, in certain embodiments, this invention contemplates the use of the active agents described herein to inhibit or prevent a symptom of a disease such as coronary calcification, calcific aortic stenosis, osteoporosis, and the like.

E) Inflammatory and Autoimmune Indications.

Chronic inflammatory and/or autoimmune conditions are also characterized by the formation of a number of reactive oxygen species and are amenable to treatment using one or more of the active agents described herein. Thus, without being bound to a particular theory, we also believe the active agents described herein are useful, prophylactically or therapeutically, to mitigate the onset and/or more or more symptoms of a variety of other conditions including, but not limited to rheumatoid arthritis, lupus erythematous, polyarteritis nodosa, polymyalgia rheumatica, scleroderma, multiple sclerosis, and the like.

In certain embodiments, the active agents are useful in mitigating one or more symptoms caused by, or associated with, an inflammatory response in these conditions.

Also, in certain embodiments, the active agents are useful in mitigating one or more symptoms caused by or associated with an inflammatory response associated with AIDS.

F) Infections/Trauma/Transplants.

We have observed that a consequence of influenza infection and other infections is the diminution in paraoxonase and platelet activating acetylhydrolase activity in the HDL. Without being bound by a particular theory, we believe that, as a result of the loss of these HDL enzymatic activities and also as a result of the association of pro-oxidant proteins with HDL during the acute phase response, HDL is no longer able to prevent LDL oxidation and is no longer able to prevent the LDL-induced production of monocyte chemotactic activity by endothelial cells.

We observed that in a subject injected with very low dosages of certain agents of this invention (e.g., 20 micrograms for mice) daily after infection with the influenza A virus paraoxonase levels did not fall and the biologically active oxidized phospholipids were not generated beyond background. This indicates that 4F, D4F (and/or other agents of this invention) can be administered (e.g. orally or by injection) to patients (including, for example with known coronary artery disease during influenza infection or other events that can generate an acute phase inflammatory response, e.g. due to viral infection, bacterial infection, trauma, transplant, various autoimmune conditions, etc.) and thus we can prevent by this short term treatment the increased incidence of heart attack and stroke associated with pathologies that generate such inflammatory states.

In addition, by restoring and/or maintaining paroxonase levels and/or monocyte activity, the agent(s) of this invention are useful in the treatment of infection (e.g., viral infection, bacterial infection, fungal infection) and/or the inflammatory pathologies associated with infection (e.g. meningitis) and/or trauma.

In certain embodiments, because of the combined anti-inflammatory activity and anti-infective activity, the agents described herein are also useful in the treatment of a wound or other trauma, mitigating adverse effects associated with organ or tissue transplant, and/or organ or tissue transplant rejection, and/or implanted prostheses, and/or transplant atherosclerosis, and/or biofilm formation. In addition, we believe that L-4F, D-4F, and/or other agents described herein are also useful in mitigating the effects of spinal cord injuries.

G) Diabetes and Associated Conditions.

Various active agents described herein have also been observed to show efficacy in reducing and/or preventing one or more symptoms associated with diabetes. Thus, in various embodiments, this invention provides methods of treating (therapeutically and/or prophylactically) diabetes and/or associated pathologies (e.g., Type I diabetes, Type II diabetes, juvenile onset diabetes, diabetic nephropathy, nephropathy, diabetic neuropathy, diabetic retinopathy, and the like.

H) Cancer.

NFκB is a transcription factor that is normally activated in response to proinflammatory cytokines and that regulates the expression of more than 200 genes. Many tumor cell lines show constitutive activation of NFκB signaling. Various studies of mouse models of intestinal, and mammary tumors conclude that activation of the NFκB pathway enhances tumor development and may act primarily in the late stages of tumorigenesis (see, e.g., (2004) Cell 118: 285; (2004) *J. Clin. Invest.*, 114: 569). Inhibition of NFκB signaling suppressed tumor development. Without being bound to a particular theory, mechanisms for this suppression are believed to include an increase in tumor cell apoptosis, reduced expression of tumor cell growth factors supplied by surrounding stromal cells, and/or abrogation of a tumor cell dedifferentiation program that is critical for tumor invasion/metastasis.

Without being bound by a particular theory, it is believed the administration of one or more active agents described herein will inhibit expression and/or secretion, and/or activity of NFκB. Thus, in certain embodiments, this invention provides methods of treating a pathology characterized by elevated NFκB by administering one or more active agents described herein. Thus, in various embodiments this invention contemplates inhibiting NFκB activation associated with cancer by administering one or more active agents described herein, optionally in combination with appropriate cancer therapeutics.

I) Biochemical Activity.

The active agent(s) described herein have been shown to exhibit a number of specific biological activities. Thus, for example, they increase heme oxygenase 1, they increase extracellular superoxide dismutase, they reduce or prevent the association of myeloperoxidase with apoA-I, they reduce or prevent the nitrosylation of tyrosine in apoA-I, they render HDL Anti-inflammatory or more anti-inflammatory, and they increase the formation cycling of pre-β HDL, they promote reverse cholesterol transport, in particular, reverse cholesterol transport from macrophages, and they synergize the activity of statins. The active agents described herein can thus be administered to a mammal to promote any of these activities, e.g. to treat a condition/pathology whose severity, and/or likelihood of onset is reduced by one or more of these activities.

J) Mitigation of a Symptom of Atherosclerosis Associated with an Acute Inflammatory Response.

The active agents, of this invention are also useful in a number of contexts. For example, we have observed that cardiovascular complications (e.g., atherosclerosis, stroke, etc.) frequently accompany or follow the onset of an acute phase inflammatory response, e.g., such as that associated with a recurrent inflammatory disease, a viral infection (e.g., influenza), a bacterial infection, a fungal infection, an organ transplant, a wound or other trauma, and so forth.

Thus, in certain embodiments, this invention contemplates administering one or more of the active agents described herein to a subject at risk for, or incurring, an acute inflammatory response and/or at risk for or incurring a symptom of atherosclerosis and/or an associated pathology (e.g., stroke).

Thus, for example, a person having or at risk for coronary disease may prophylactically be administered a one or more active agents of this invention during flu season. A person (or animal) subject to a recurrent inflammatory condition, e.g., rheumatoid arthritis, various autoimmune diseases, etc., can be treated with a one or more agents described herein to mitigate or prevent the development of atherosclerosis or stroke. A person (or animal) subject to trauma, e.g., acute injury, tissue transplant, etc. can be treated with a polypeptide of this invention to mitigate the development of atherosclerosis or stroke.

In certain instances such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase response, or risk therefore is evaluated by measuring one or more APPs. Measuring such markers is well known to those of skill in the art, and commercial companies exist that provide such measurement (e.g., AGP measured by Cardiotech Services, Louisville, Ky.).

K) Other Indications.

In various embodiments it is contemplated that the active agents described herein are useful in the treatment (e.g. mitigation and/or prevention) of corneal ulcers, endothelial sloughing, Crohn's disease, acute and chronic dermatitis (including, but not limited to eczema and/or psoriasis), macular degeneration, neuropathy, scleroderma, and ulcerative colitis.

A summary of indications/conditions for which the active agents have been shown to be effective and/or are believed to be effective is shown in Table 1.

TABLE 1

Summary of conditions in which the active agents (e.g., D-4F) have been shown to be or are believed to be effective.

atherosclerosis/symptoms/consequences thereof
    plaque formation
    lesion formation
    myocardial infarction
    stroke
congestive heart failure
vascular function:
    arteriole function
    arteriolar disease
        associated with aging
        associated with alzheimer's disease
        associated with chronic kidney disease
        associated with hypertension
        associated with multi-infarct dementia
        associated with subarachnoid hemorrhage
    peripheral vascular disease
pulmonary disease:
    chronic obstructive pulmonary disease (COPD),
    emphysema
    asthma
    idiopathic pulmonary fibrosis
    Pulmonary fibrosis
    adult respiratory distress syndrome
osteoporosis
Paget's disease
coronary calcification
autoimmune:
    rheumatoid arthritis
    polyarteritis nodosa
    polymyalgia rheumatica
    lupus erythematosus
    multiple sclerosis
    Wegener's granulomatosis
    central nervous system vasculitis (CNSV)
    Sjögren's syndrome
    Scleroderma
    polymyositis.
AIDS inflammatory response
infections:
    bacterial
    fungal
    viral
    parasitic
    influenza
        avian flu
    viral pneumonia
    endotoxic shock syndrome
    sepsis
    sepsis syndrome
    (clinical syndrome where it appears that the patient is septic but no organisms are recovered from the blood)
trauma/wound:
    organ transplant
    transplant atherosclerosis
    transplant rejection
    corneal ulcer
    chronic/non-healing wound
    ulcerative colitis TABLE 1-continued Summary of conditions in which the active agents (e.g., D-4F) have been shown to be or are believed to be effective.

reperfusion injury (prevent and/or treat)
    ischemic reperfusion injury (prevent and/or treat)
    spinal cord injuries (mitigating effects)
cancers
    myeloma/multiple myeloma
    ovarian cancer
    breast cancer
    colon cancer
    bone cancer
osteoarthritis
inflammatory bowel disease
allergic rhinitis
cachexia
diabetes
Alzheimer's disease
implanted prosthesis
biofilm formation
Crohns' disease
dermatitis, acute and chronic
    eczema
    psoriasis
    contact dermatitis
    scleroderma
diabetes and related conditions
    Type I Diabetes
    Type II Diabetes
    Juvenile Onset Diabetes
    Prevention of the onset of diabetes
    Diabetic Nephropathy
    Diabetic Neuropathy
    Diabetic Retinopathy
erectile dysfunction
macular degeneration
multiple sclerosis
nephropathy
neuropathy
Parkinson's Disease
peripheral Vascular Disease
meningitis
Specific biological activities:
    increase Heme Oxygenase 1
    increase extracellular superoxide dismutase
    prevent endothelial sloughing
    prevent the association of myeloperoxidase with ApoA-I
    prevent the nitrosylation of tyrosine in ApoA-I
    render HDL anti-inflammatory
    improve vasoreactivity
    increase the formation of pre-beta HDL
    promote reverse cholesterol transport
    promote reverse cholesterol transport from macrophages
    synergize the action of statins It is noted that the conditions listed in Table 1 are intended to be illustrative and not limiting.

L) Administration.

Typically the active agent(s) will be administered to a mammal (e.g., a human) in need thereof. Such a mammal will typically include a mammal (e.g., a human) having or at risk for one or more of the pathologies described herein.

The active agent(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g., as a syrup, capsule, or tablet).

The methods involve the administration of a single active agent of this invention or the administration of two or more different active agents. The active agents can be provided as monomers (e.g., in separate or combined formulations), or in dimeric, oligomeric or polymeric forms. In certain embodiments, the multimeric forms may comprise associated monomers (e.g., ionically or hydrophobically linked) while certain other multimeric forms comprise covalently linked monomers (directly linked or through a linker).

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

The methods of this invention are not limited to humans or non-human animals showing one or more symptom(s) of the pathologies described herein, but are also useful in a prophylactic context. Thus, the active agents of this invention can be administered to organisms to prevent the onset/development of one or more symptoms of the pathologies described herein (e.g., atherosclerosis, stroke, etc.). Particularly preferred subjects in this context are subjects showing one or more risk factors for the pathology. Thus, for example, in the case of atherosclerosis risk factors include family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.

II. Active Agents.

A wide variety of active agents are suitable for the treatment of one or more of the indications discussed above. These agents include, but are not limited to class A amphipathic helical peptides, class A amphipathic helical peptide mimetics of apoA-I having aromatic or aliphatic residues in the non-polar face, small peptides including penta-peptides, tetrapeptides, tripeptides, dipeptides and pairs of amino acids, Apo-J (G* peptides), and peptide mimetics, e.g., as described below.

A) Class A Amphipathic Helical Peptides.

In certain embodiments, the activate agents for use in the method of this invention include class A amphipathic helical peptides, e.g. as described in U.S. Pat. No. 6,664,230, and PCT Publications WO 02/15923 and WO 2004/034977. It was discovered that peptides comprising a class A amphipathic helix ("class A peptides"), in addition to being capable of mitigating one or more symptoms of atherosclerosis are also useful in the treatment of one or more of the other indications described herein.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) Meth. Enzymol, 128: 626-668). It is noted that the fourth exon of apo A-I, when folded into 3.667 residues/turn produces a class A amphipathic helical structure.

One class A peptide, designated 18A (see, e.g., Anantharamaiah (1986) Meth. Enzymol, 128: 626-668) was modified as described herein to produce peptides orally administrable and highly effective at inhibiting or preventing one or more symptoms of atherosclerosis and/or other indications described herein. Without being bound by a particular theory, it is believed that the peptides of this invention may act in vivo may by picking up seeding molecule(s) that mitigate oxidation of LDL.

We determined that increasing the number of Phe residues on the hydrophobic face of 18A would theoretically increase lipid affinity as determined by the computation described by Palgunachari et al. (1996) Arteriosclerosis, Thrombosis, & Vascular Biol. 16: 328-338. Theoretically, a systematic substitution of residues in the nonpolar face of 18A with Phe could yield six peptides. Peptides with an additional 2, 3 and 4 Phe would have theoretical lipid affinity (λ) values of 13, 14 and 15 units, respectively. However, the λ values jumped four units if the additional Phe were increased from 4 to 5 (to 19λunits). Increasing to 6 or 7 Phe would produce a less dramatic increase (to 20 and 21λunits, respectively).

A number of these class A peptides were made including, the peptide designated 4F, D4F, 5F, and D5F, and the like. Various class A peptides inhibited lesion development in atherosclerosis-susceptible mice. In addition, the peptides show varying, but significant degrees of efficacy in mitigating one or more symptoms of the various pathologies described herein. A number of such peptides are illustrated in Table 2.

TABLE 2

Illustrative class A amphipathic helical peptides for use in this invention.

| Peptide Name | Amino Acid Sequence | SEQ ID NO. |
| --- | --- | --- |
| 18A | D-W-L-K-A-F-Y-D-K-V-A-E-K-L-K-E-A-F | 1 |
| 2F | Ac-D-W-L-K-A-F-Y-D-K-V-A-E-K-L-K-E-A-F-NH$_2$ | 2 |
| 3F | Ac-D-W-F-K-A-F-Y-D-K-V-A-E-K-L-K-E-A-F-NH$_2$ | 3 |
| 3F14 | Ac-D-W-L-K-A-F-Y-D-K-V-A-E-K-F-K-E-A-F-NH$_2$ | 4 |
| 4F | Ac-D-W-F-K-A-F-Y-D-K-V-A-E-K-F-K-E-A-F-NH$_2$ | 5 |
| 5F | Ac-D-W-L-K-A-F-Y-D-K-V-F-E-K-F-K-E-F-F-NH$_2$ | 6 |
| 6F | Ac-D-W-L-K-A-F-Y-D-K-F-F-E-K-F-K-E-F-F-NH$_2$ | 7 |
| 7F | Ac-D-W-F-K-A-F-Y-D-K-F-F-E-K-F-K-E-F-F-NH$_2$ | 8 |
|  | Ac-D-W-L-K-A-F-Y-D-K-V-A-E-K-L-K-E-F-F-NH$_2$ | 9 |
|  | Ac-D-W-L-K-A-F-Y-D-K-V-F-E-K-F-K-E-A-F-NH$_2$ | 10 |
|  | Ac-D-W-L-K-A-F-Y-D-K-V-F-E-K-L-K-E-F-F-NH$_2$ | 11 |
|  | Ac-D-W-L-K-A-F-Y-D-K-V-A-E-K-F-K-E-F-F-NH$_2$ | 12 |

TABLE 2-continued

Illustrative class A amphipathic helical peptides for use in this invention.

| Peptide Name | Amino Acid Sequence | SEQ ID NO. |
|---|---|---|
| | Ac-D-W-L-K-A-F-Y-D-K-V-F-E-K-F-K-E-F-F-NH$_2$ | 13 |
| | Ac-E-W-L-K-L-F-Y-E-K-V-L-E-K-F-K-E-A-F-NH$_2$ | 14 |
| | Ac-E-W-L-K-A-F-Y-D-K-V-A-E-K-F-K-E-A-F-NH$_2$ | 15 |
| | Ac-E-W-L-K-A-F-Y-D-K-V-A-E-K-L-K-E-F-F-NH$_2$ | 16 |
| | Ac-E-W-L-K-A-F-Y-D-K-V-F-E-K-F-K-E-A-F-NH$_2$ | 17 |
| | Ac-E-W-L-K-A-F-Y-D-K-V-F-E-K-L-K-E-F-F-NH$_2$ | 18 |
| | Ac-E-W-L-K-A-F-Y-D-K-V-A-E-K-F-K-E-F-F-NH$_2$ | 19 |
| | Ac-E-W-L-K-A-F-Y-D-K-V-F-E-K-F-K-E-F-F-NH$_2$ | 20 |
| | AC-A-F-Y-D-K-V-A-E-K-L-K-E-A-F-NH$_2$ | 21 |
| | Ac-A-F-Y-D-K-V-A-E-K-F-K-E-A-F-NH$_2$ | 22 |
| | Ac-A-F-Y-D-K-V-A-E-K-F-K-E-A-F-NH$_2$ | 23 |
| | Ac-A-F-Y-D-K-F-F-E-K-F-K-E-F-F-NH$_2$ | 24 |
| | Ac-A-F-Y-D-K-F-F-E-K-F-K-E-F-F-NH$_2$ | 25 |
| | Ac-A-F-Y-D-K-V-A-E-K-F-K-E-A-F-NH$_2$ | 26 |
| | Ac-A-F-Y-D-K-V-A-E-K-L-K-E-F-F-NH$_2$ | 27 |
| | Ac-A-F-Y-D-K-V-F-E-K-F-K-E-A-F-NH$_2$ | 28 |
| | Ac-A-F-Y-D-K-V-F-E-K-L-K-E-F-F-NH$_2$ | 29 |
| | Ac-A-F-Y-D-K-V-A-E-K-F-K-E-F-F-NH$_2$ | 30 |
| | Ac-K-A-F-Y-D-K-V-F-E-K-F-E-F-NH$_2$ | 31 |
| | Ac-L-F-Y-E-K-V-L-E-K-F-K-E-A-F-NH$_2$ | 32 |
| | Ac-A-F-Y-D-K-V-A-E-K-F-K-E-A-F-NH$_2$ | 33 |
| | Ac-A-F-Y-D-K-V-A-E-K-L-K-E-F-F-NH$_2$ | 34 |
| | Ac-A-F-Y-D-K-V-F-E-K-F-K-E-A-F-NH$_2$ | 35 |
| | Ac-A-F-Y-D-K-V-F-E-K-L-K-E-F-F-NH$_2$ | 36 |
| | Ac-A-F-Y-D-K-V-A-E-K-F-K-E-F-F-NH$_2$ | 37 |
| | Ac-A-F-Y-D-K-V-F-E-K-F-K-E-F-F-NH$_2$ | 38 |
| Ac-D-W-L-K-A-L-Y-D-K-V-A-E-K-L-K-E-A-L-NH$_2$ | | 39 |
| Ac-D-W-F-K-A-F-Y-E-K-V-A-E-K-L-K-E-F-F-NH$_2$ | | 40 |
| Ac-D-W-F-K-A-F-Y-E-K-F-F-E-K-F-K-E-F-F-NH$_2$ | | 41 |
| Ac-E-W-L-K-A-L-Y-E-K-V-A-E-K-L-K-E-A-L-NH$_2$ | | 42 |
| Ac-E-W-L-K-A-F-Y-E-K-V-A-E-K-L-K-E-A-F-NH$_2$ | | 43 |
| Ac-E-W-F-K-A-F-Y-E-K-V-A-E-K-L-K-E-F-F-NH$_2$ | | 44 |
| Ac-E-W-L-K-A-F-Y-E-K-V-F-E-K-F-K-E-F-F-NH$_2$ | | 45 |
| Ac-E-W-L-K-A-F-Y-E-K-F-F-E-K-F-K-E-F-F-NH$_2$ | | 46 |
| Ac-E-W-F-K-A-F-Y-E-K-F-F-E-K-F-K-E-F-F-NH$_2$ | | 47 |
| Ac-D-F-L-K-A-W-Y-D-K-V-A-E-K-L-K-E-A-W-NH$_2$ | | 48 |

TABLE 2-continued

Illustrative class A amphipathic helical peptides for use in this invention.

| Peptide Name | Amino Acid Sequence | SEQ ID NO. |
|---|---|---|
| | Ac-E-F-L-K-A-W-Y-E-K-V-A-E-K-L-K-E-A-W-NH$_2$ | 49 |
| | Ac-D-F-W-K-A-W-Y-D-K-V-A-E-K-L-K-E-W-W-NH$_2$ | 50 |
| | Ac-E-F-W-K-A-W-Y-E-K-V-A-E-K-L-K-E-W-W-NH$_2$ | 51 |
| | Ac-D-K-L-K-A-F-Y-D-K-V-F-E-W-A-K-E-A-F-NH$_2$ | 52 |
| | Ac-D-K-W-K-A-V-Y-D-K-F-A-E-A-F-K-E-F-L-NH$_2$ | 53 |
| | Ac-E-K-L-K-A-F-Y-E-K-V-F-E-W-A-K-E-A-F-NH$_2$ | 54 |
| | Ac-E-K-W-K-A-V-Y-E-K-F-A-E-A-F-K-E-F-L-NH$_2$ | 55 |
| | Ac-D-W-L-K-A-F-V-D-K-F-A-E-K-F-K-E-A-Y-NH$_2$ | 56 |
| | Ac-E-K-W-K-A-V-Y-E-K-F-A-E-A-F-K-E-F-L-NH$_2$ | 57 |
| | Ac-D-W-L-K-A-F-V-Y-D-K-V-F-K-L-K-E-F-F-NH$_2$ | 58 |
| | Ac-E-W-L-K-A-F-V-Y-E-K-V-F-K-L-K-E-F-F-NH$_2$ | 59 |
| | Ac-D-W-L-R-A-F-Y-D-K-V-A-E-K-L-K-E-A-F-NH$_2$ | 60 |
| | Ac-E-W-L-R-A-F-Y-E-K-V-A-E-K-L-K-E-A-F-NH$_2$ | 61 |
| | Ac-D-W-L-K-A-F-Y-D-R-V-A-E-K-L-K-E-A-F-NH$_2$ | 62 |
| | Ac-E-W-L-K-A-F-Y-E-R-V-A-E-K-L-K-E-A-F-NH$_2$ | 63 |
| | Ac-D-W-L-K-A-F-Y-D-K-V-A-E-R-L-K-E-A-F-NH$_2$ | 64 |
| | Ac-E-W-L-K-A-F-Y-E-K-V-A-E-R-L-K-E-A-F-NH$_2$ | 65 |
| | Ac-D-W-L-K-A-F-Y-D-K-V-A-E-K-L-R-E-A-F-NH$_2$ | 66 |
| | Ac-E-W-L-K-A-F-Y-E-K-V-A-E-K-L-R-E-A-F-NH$_2$ | 67 |
| | Ac-D-W-L-K-A-F-Y-D-R-V-A-E-R-L-K-E-A-F-NH$_2$ | 68 |
| | Ac-E-W-L-K-A-F-Y-E-R-V-A-E-R-L-K-E-A-F-NH$_2$ | 69 |
| | Ac-D-W-L-R-A-F-Y-D-K-V-A-E-K-L-R-E-A-F-NH$_2$ | 70 |
| | Ac-E-W-L-R-A-F-Y-E-K-V-A-E-K-L-R-E-A-F-NH$_2$ | 71 |
| | Ac-D-W-L-R-A-F-Y-D-R-V-A-E-K-L-K-E-A-F-NH$_2$ | 72 |
| | Ac-E-W-L-R-A-F-Y-E-R-V-A-E-K-L-K-E-A-F-NH$_2$ | 73 |
| | Ac-D-W-L-K-A-F-Y-D-K-V-A-E-R-L-R-E-A-F-NH$_2$ | 74 |
| | Ac-E-W-L-K-A-F-Y-E-K-V-A-E-R-L-R-E-A-F-NH$_2$ | 75 |
| | Ac-D-W-L-R-A-F-Y-D-K-V-A-E-R-L-K-E-A-F-NH$_2$ | 76 |
| | Ac-E-W-L-R-A-F-Y-E-K-V-A-E-R-L-K-E-A-F-NH$_2$ | 77 |
| | D-W-L-K-A-F-Y-D-K-V-A-E-K-L-K-E-A-F-P-D-W-L-K-A-F-Y-D-K-V-A-E-K-L-K-E-A-F | 78 |
| | D-W-L-K-A-F-Y-D-K-V-A-E-K-L-K-E-F-P-D-W-L-K-A-F-Y-D-K-V-A-E-K-L-K-E-F-F | 79 |
| | D-W-F-K-A-F-Y-D-K-V-A-E-K-L-K-E-A-F-P-D-W-F-K-A-F-Y-D-K-V-A-E-K-L-K-E-A-F | 80 |
| | D-K-L-K-A-F-Y-D-K-V-F-E-W-A-K-E-A-F-P-D-K-L-K-A-F-Y-D-K-V-F-E-W-L-K-E-A-F | 81 |
| | D-K-W-K-A-V-Y-D-K-F-A-E-A-F-K-E-F-L-P-D-K-W-K-A-V-Y-D-K-F-A-E-A-F-K-E-F-L | 82 |

TABLE 2-continued

Illustrative class A amphipathic helical peptides for use in this invention.

| Peptide Name | Amino Acid Sequence | SEQ ID NO. |
|---|---|---|
| | D-W-F-K-A-F-Y-D-K-V-A-E-K-F-K-E-A-F-P-D-W-F-K-A-F-Y-D-K-V-A-E-K-F-K-E-A-F | 83 |
| | D-W-L-K-A-F-V-Y-D-K-V-F-K-L-K-E-F-F-P-D-W-L-K-A-F-V-Y-D-K-V-F-K-L-K-E-F-F | 84 |
| | D-W-L-K-A-F-Y-D-K-F-A-E-K-F-K-E-F-F-P-D-W-L-K-A-F-Y-D-K-F-A-E-K-F-K-E-F-F | 85 |
| | Ac-E-W-F-K-A-F-Y-E-K-V-A-E-K-F-K-E-A-F-NH$_2$ | 86 |
| | Ac-D-W-F-K-A-F-Y-D-K-V-A-E-K-F-NH$_2$ | 87 |
| | Ac-F-K-A-F-Y-D-K-V-A-E-K-F-K-E-NH$_2$ | 88 |
| | Ac-F-K-A-F-Y-E-K-V-A-E-K-F-K-E-NH$_2$ | 89 |
| | NMA-F-K-A-F-Y-D-K-V-A-E-K-F-K-E-NH$_2$ | 90 |
| | NMA-F-K-A-F-Y-E-K-V-A-E-K-F-K-E-NH$_2$ | 91 |
| | NMA-D-W-F-K-A-F-Y-D-K-V-A-E-K-F-K-E-A-F-NH$_2$ | 92 |
| | NMA-E-W-F-K-A-F-Y-E-K-V-A-E-K-F-K-E-A-F-NH$_2$ | 93 |
| | NMA-A-F-Y-D-K-V-A-E-K-F-K-E-A-F-NH$_2$ | 94 |
| | NMA-D-W-F-K-A-F-Y-D-K-V-A-E-K-F-NH$_2$ | 95 |
| | Ac-D-W-L-K-A-F-Y-D-K-V-F-E-K-F-K-E-F-F-NH$_2$ | 96 |
| | NMA-D-W-L-K-A-F-Y-D-K-V-F-E-K-F-K-E-F-F-NH$_2$ | 96 |
| | Ac-E-W-L-K-A-F-Y-E-K-V-F-E-K-F-K-E-F-F-NH$_2$ | 97 |
| | NMA-E-W-L-K-A-F-Y-E-K-V-F-E-K-F-K-E-F-F-NH$_2$ | 97 |
| | Ac-A-F-Y-D-K-V-F-E-K-F-K-E-F-F-NH$_2$ | 98 |
| | NMA-A-F-Y-D-K-V-F-E-K-F-K-E-F-F-NH$_2$ | 98 |
| | Ac-A-F-Y-E-K-V-F-E-K-F-K-E-F-F-NH$_2$ | 99 |
| | NMA-A-F-Y-E-K-V-F-E-K-F-K-E-F-F-NH$_2$ | 99 |
| | Ac-D-W-L-K-A-F-Y-D-K-V-F-E-K-F-NH$_2$ | 100 |
| | NMA-D-W-L-K-A-F-Y-D-K-V-F-E-K-F-NH$_2$ | 100 |
| | Ac-E-W-L-K-A-F-Y-E-K-V-F-E-K-F-NH$_2$ | 101 |
| | NMA-E-W-L-K-A-F-Y-E-K-V-F-E-K-F-NH$_2$ | 101 |
| | Ac-L-K-A-F-Y-D-K-V-F-E-K-F-K-E-NH$_2$ | 102 |
| | NMA-L-K-A-F-Y-D-K-V-F-E-K-F-K-E-NH$_2$ | 102 |
| | Ac-L-K-A-F-Y-E-K-V-F-E-K-F-K-E-NH$_2$ | 103 |
| | NMA-L-K-A-F-Y-E-K-V-F-E-K-F-K-E-NH$_2$ | 103 |

[1]Linkers are underlined.
NMA is N-Methyl Anthranilyl.

In certain preferred embodiments, the peptides include variations of 4F ((SEQ ID NO:5 in Table 2), also known as L-4F, where all residues are L form amino acids) or D-4F where one or more residues are D form amino acids). In any of the peptides described herein, the C-terminus, and/or N-terminus, and/or internal residues can be blocked with one or more blocking groups as described herein.

While various peptides of Table 2, are illustrated with an acetyl group or an N-methylanthranilyl group protecting the amino terminus and an amide group protecting the carboxyl terminus, any of these protecting groups may be eliminated and/or substituted with another protecting group as described herein. In particularly preferred embodiments, the peptides comprise one or more D-form amino acids as described herein. In certain embodiments, every amino acid (e.g., every enantiomeric amino acid) of the peptides of Table 2 is a D-form amino acid.

It is also noted that Table 2 is not fully inclusive. Using the teachings provided herein, other suitable class A amphipathic helical peptides can routinely be produced (e.g., by conservative or semi-conservative substitutions (e.g., D replaced by E), extensions, deletions, and the like). Thus, for example, one embodiment utilizes truncations of any one or more of peptides shown herein (e.g., peptides identified by SEQ ID Nos:2-20 and 39—in Table 2). Thus, for example, SEQ ID NO:21 illustrates a peptide comprising 14 amino acids from the C-terminus of 18A comprising one or more D amino acids, while SEQ ID NOS:22-38 illustrate other truncations.

Longer peptides are also suitable. Such longer peptides may entirely form a class A amphipathic helix, or the class A amphipathic helix (helices) can form one or more domains of the peptide. In addition, this invention contemplates multimeric versions of the peptides (e.g., concatamers). Thus, for example, the peptides illustrated herein can be coupled together (directly or through a linker (e.g., a carbon linker, or one or more amino acids) with one or more intervening amino acids). Illustrative polymeric peptides include 18A-Pro-18A and the peptides of SEQ ID NOs:78-85, in certain embodiments comprising one or more D amino acids, more preferably with every amino acid a D amino acid as described herein and/or having one or both termini protected.

It will also be appreciated in addition to the peptide sequences expressly illustrated herein, this invention also contemplates retro and retro-inverso forms of each of these peptides. In retro forms, the direction of the sequence is reversed. In inverse forms, the chirality of the constituent amino acids is reversed (i.e., L form amino acids become D form amino acids and D form amino acids become L form amino acids). In the retro-inverso form, both the order and the chirality of the amino acids is reversed. Thus, for example, a retro form of the 4F peptide (DWFKAFYDKVAEKFKEAF, SEQ ID NO:5), where the amino terminus is at the aspartate (D) and the carboxyl terminus is at the phenylalanine (F), has the same sequence, but the amino terminus is at the phenylalanine and the carboxy terminus is at the aspartate (i.e., FAEKFKEAVKDYFAKFWD, SEQ ID NO: 104). Where the 4F peptide comprises all L amino acids, the retro-inverso form will have the sequence shown above (SEQ ID NO:104) and comprise all D form amino acids. As illustrated in the helical wheel diagrams of FIG. 15, 4F and retroinverso (Rev-4F) are mirror images of each other with identical segregation of the polar and nonpolar faces with the positively charged residues residing at the polar-nonpolar interface and the negatively charged residues residing at the center of the polar face. These mirror images of the same polymer of amino acids are identical in terms of the segregation of the polar and nonpolar faces with the positively charged residues residing at the polar-nonpolar interface and the negatively charged residues residing at the center of the polar face. For a discussion of retro-and retro-inverso peptides see, e.g., Chorev and Goodman, (1995) *TibTech,* 13: 439-445.

Where reference is made to a sequence and orientation is not expressly indicated, the sequence can be viewed as representing the amino acid sequence in the amino to carboxyl orientation, the retro form (i.e., the amino acid sequence in the carboxyl to amino orientation), the inversoform where L amino acids are replaced with D amino acids or D amino acids are replaced with L amino acids, and the retro-inverso form where both the order is reversed and the amino acid chirality is reversed.

C) Class A Amphipathic Helical Peptide Mimetics of apoA-I Having Aromatic or Aliphatic Residues in the Nonpolar Face.

In certain embodiments, this invention also provides modified class A amphipathic helix peptides. Certain preferred peptides incorporate one or more aromatic residues at the center of the nonpolar face, e.g., $3F^{C\pi}$, (as present in 4F), or with one or more aliphatic residues at the center of the nonpolar face, e.g., $3F^{I\pi}$, see, e.g., Table 3. Without being bound to a particular theory, we believe the central aromatic residues on the nonpolar face of the peptide $3F^{C\pi}$, due to the presence of π electrons at the center of the nonpolar face, allow water molecules to penetrate near the hydrophobic lipid alkyl chains of the peptide-lipid complex, which in turn would enable the entry of reactive oxygen species (such as lipid hydroperoxides) shielding them from the cell surface. Similarly, we also believe the peptides with aliphatic residues at the center of the nonpolar face, e.g., $3F^{I\pi}$, will act similarly but not quite as effectively as $3F^{C\pi}$.

Preferred peptides will convert pro-inflammatory HDL to anti-inflammatory HDL or make anti-inflammatory HDL more anti-inflammatory, and/or decrease LDL-induced monocyte chemotactic activity generated by artery wall cells equal to or greater than D4F or other peptides shown in Table 2.

TABLE 3

Examples of certain preferred peptides.

| Name | Sequence | SEQ ID NO |
|---|---|---|
| ($3F^{C\pi}$) | Ac-DKWKAVYDKFAEAFKEFL-NH$_2$ | 105 |
| ($3F^{I\pi}$) | Ac-DKLKAFYDKVFEWAKEAF-NH$_2$ | 106 |

C) Other Class A and Some Class Y Amphipathic Helical Peptides.

In certain embodiments this invention also contemplates class a amphipathic helical peptides that have an amino acid composition identical to one or more of the class a amphipathic helical peptides described above. Thus, for example, in certain embodiments this invention contemplates peptides having an amino acid composition identical to 4F. Thus, in certain embodiments, this invention includes active agents that comprise a peptide that consists of 18 amino acids, where the 18 amino acids consist of 3 alanines (A), 2 aspartates (D), 2 glutamates (E), 4 phenylalanines (F), 4 lysines (K), 1 valine (V), 1 tryptophan (W), and 1 tyrosine (Y); and where the peptide forms a class A amphipathic helix; and protects a phospholipid against oxidation by an oxidizing agent. In various embodiments, the peptides comprise least one "D" amino acid residue; and in certain embodiments, the peptides comprise all "D: form amino acid residues. A variety of such peptides are illustrated in Table 4. Reverse (retro-), inverse, retro-inverso-, and circularly permuted forms of these peptides are also contemplated.

TABLE 4

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-4F analogs | | |
| [Switch D-E]-1-4F | Ac-EWFKAFYEKVADKFKDAF-NH2 | 107 |
| [Switch D-E]-2-4F | Ac-EWFKAFYDKVADKFKEAF-NH2 | 108 |
| [Switch D-E]-3-4F | Ac-DWFKAFYEKVADKFKEAF-NH2 | 109 |
| [Switch D-E]-4-4F | Ac-DWFKAFYEKVAEKFKDAF-NH2 | 110 |
| [W-2,F-3 positions reversed] | | |
| 4F-2 | Ac-DFWKAFYDKVAEKFKEAF-NH$_2$ | 111 |
| [Switch D-E]-1-4F-2 | Ac-EFWKAFYEKVADKFKDAF-NH2 | 112 |
| [Switch D-E]-2-4F-2 | Ac-EFWKAFYDKVADKFKEAF-NH2 | 113 |
| [Switch D-E]-3-4F-2 | Ac-DFWKAFYEKVADKFKEAF-NH2 | 114 |
| [Switch D-E]-4-4F-2 | Ac-DFWKAFYEKVAEKFKDAF-NH2 | 115 |
| [F-6 and Y-7 positions switched] | | |
| 4F-3 | Ac-DWFKAYFDKVAEKFKEAF-NH$_2$ | 116 |
| [Switch D-E]-1-4F-5 | Ac-EWFKAYFEKVADKFKDAF-NH2 | 117 |
| [Switch D-E]-2-4F-5 | Ac-EWFKAYFDKVADKFKEAF-NH2 | 118 |
| [Switch D-E]-3-4F-5 | Ac-DWFKAYFEKVADKFKEAF-NH2 | 119 |
| [Switch D-E]-4-4F-5 | Ac-DWFKAYFEKVAEKFKDAF-NH2 | 120 |
| [Y-7 and 10V positions switched] | | |
| 4F-4 | Ac-DWFKAFVDKYAEKFKEAF-NH$_2$ | 121 |
| [Switch D-E]-1-4F-4 | Ac-EWFKAFVEKYADKFKDAF-NH2 | 122 |
| [Switch D-E]-2-4F-4 | Ac-EWFKAFVDKYADKFKEAF-NH2 | 123 |
| [Switch D-E]-3-4F-4 | Ac-DWFKAFVEKYADKFKEAF-NH2 | 124 |
| [Switch D-E]-4-4F | Ac-DWFKAFVEKYAEKFKDAF-NH2 | 125 |
| [V-10 and A-11 switched] | | |
| 4-F-5 | Ac-DWFKAFYDKAVEKFKEAF-NH$_2$ | 126 |
| [Switch D-E]-1-4F-5 | Ac-EWFKAFYEKAVDKFKDAF-NH2 | 127 |
| [Switch D-E]-2-4F-5 | Ac-EWFKAFYDKAVDKFKEAF-NH2 | 128 |
| [Switch D-E]-3-4F-5 | Ac-DWFKAFYEKAVDKFKEAF-NH2 | 129 |
| [Switch D-E]-4-4F-5 | Ac-DWFKAFYEKAVEKFKDAF-NH2 | 130 |
| [A-11 and F-14 switched] | | |
| 4F-6 | Ac-DWFKAFYDKVFEKAKEAF-NH$_2$ | 131 |
| [Switch D-E]-1-4F-6 | Ac-EWFKAFYEKVFDKAKDAF-NH2 | 132 |
| [Switch D-E]-2-4F-6 | Ac-EWFKAFYDKVFDKAKEAF-NH2 | 133 |
| [Switch D-E]-3-4F-6 | Ac-DWFKAFYEKVFDKAKEAF-NH2 | 134 |
| [Switch D-E]-4-4F-6 | Ac-DWFKAFYEKVFEKAKDAF-NH2 | 135 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [F-14 and A-17 switched] | | |
| 4F-7 | Ac-DWFKAFYDKVAEKAKEFF-NH₂ | 136 |
| [Switch D-E]-1-4F-7 | Ac-EWFKAFYEKVADKAKDFF-NH2 | 137 |
| [Switch D-E]-2-4F-7 | Ac-EWFKAFYDKVADKAKEFF-NH2 | 138 |
| [Switch D-E]-3-4F-7 | Ac-DWFKAFYEKVADKAKEFF-NH2 | 139 |
| [Switch D-E]-4-4F-7 | Ac-DWFKAFYEKVAEKAKDFF-NH2 | 140 |
| [A-17 and F-18 switched] | | |
| 4F-8 | Ac-DWFKAFYDKVAEKFKEFA-NH₂ | 141 |
| [Switch D-E]-1-4F-8 | Ac-EWFKAFYEKVADKFKDFA-NH2 | 142 |
| [Switch D-E]-2-4F-8 | Ac-EWFKAFYDKVADKFKEFA-NH2 | 143 |
| [Switch D-E]-3-4F-8 | Ac-DWFKAFYEKVADKFKEFA-NH2 | 144 |
| [Switch D-E]-4-4F-8 | Ac-DWFKAFYEKVAEKFKDFA-NH2 | 145 |
| [W-2 and A-17 switched] | | |
| 4F-9 | Ac-DAFKAFYDKVAEKFKEWF-NH₂ | 146 |
| [Switch D-E]-1-4F-9 | Ac-EAFKAFYEKVADKFKDWF-NH2 | 147 |
| [Switch D-E]-2-4F-9 | Ac-EAFKAFYDKVADKFKEWF-NH2 | 148 |
| [Switch D-E]-3-4F-9 | Ac-DAFKAFYEKVADKFKEWF-NH2 | 149 |
| [Switch D-E]-4-4F-9 | Ac-DAFKAFYEKVAEKFKDWF-NH2 | 150 |
| [W-2 and A-11 switched] | | |
| 4F-10 | Ac-DAFKAFYDKVWEKFKEAF-NH₂ | 151 |
| [Switch D-E]-1-4F-10 | Ac-EAFKAFYEKVWDKFKDAF-NH2 | 152 |
| [Switch D-E]-2-4F-10 | Ac-EAFKAFYDKVWDKFKEAF-NH2 | 153 |
| [Switch D-E]-3-4F-10 | Ac-DAFKAFYEKVWDKFKEAF-NH2 | 154 |
| [Switch D-E]-4-4F-10 | Ac-DAFKAFYEKVWEKFKDAF-NH2 | 155 |
| [W-2 and Y-7 switched] | | |
| 4F-11 | Ac-DYFKAFWDKVAEKFKEAF-NH₂ | 156 |
| [Switch D-E]-1-4F-11 | Ac-EYFKAFWEKVADKFKDAF-NH2 | 157 |
| [Switch D-E]-2-4F-11 | Ac-EYFKAFWDKVADKFKEAF-NH2 | 158 |
| [Switch D-E]-3-4F-11 | Ac-DYFKAFWEKVADKFKEAF-NH2 | 159 |
| [Switch D-E]-4-4F-11 | Ac-DYFKAFWEKVAEKFKDAF-NH2 | 160 |
| [F-3 and A-17 switched] | | |
| 4F-12 | Ac-DWAKAFYDKVAEKFKEFF-NH₂ | 161 |
| [Switch D-E]-1-4F-12 | Ac-EWAKAFYEKVADKFKDFF-NH2 | 162 |
| [Switch D-E]-2-4F-12 | Ac-EWAKAFYDKVADKFKEFF-NH2 | 163 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
| --- | --- | --- |
| [Switch D-E]-3-4F-12 | Ac-DWAKAFYEKVADKFKEFF-NH2 | 164 |
| [Switch D-E]-4-4F-12 | Ac-DWAKAFYEKVAEKFKDFF-NH2 | 165 |
| [F-6 and A-17 switched] | | |
| 4F-13 | Ac-DWFKAAYDKVAEKFKEFF-NH₂ | 166 |
| [Switch D-E]-1-4F-13 | Ac-EWFKAAYEKVADKFKDFF-NH2 | 167 |
| [Switch D-E]-2-4F-13 | Ac-EWFKAAYDKVADKFKEFF-NH2 | 168 |
| [Switch D-E]-3-4F-13 | Ac-DWFKAAYEKVADKFKEFF-NH2 | 169 |
| [Switch D-E]-4-4F-13 | Ac-DWFKAAYEKVAEKFKDFF-NH2 | 170 |
| [Y-7 and A-17 switched | | |
| 4F-14 | Ac-DWFKAFADKVAEKFKEYF-NH₂ | 171 |
| [Switch D-E]-1-4F-14 | Ac-EWFKAFAEKVADKFKDYF-NH2 | 172 |
| [Switch D-E]-2-4F-14 | Ac-EWFKAFADKVADKFKEYF-NH2 | 173 |
| Switch D-E]-3-4F-14 | Ac-DWFKAFAEKVADKFKEYF-NH2 | 174 |
| [Switch D-E]-4-4F | Ac-DWFKAFAEKVAEKFKDYF-NH2 | 175 |
| [V-10 and A-17 switched] | | |
| 4F-15 | Ac-DWFKAFYDKAAEKFKEVF-NH₂ | 176 |
| [Switch D-E]-1-4F-15 | Ac-EWFKAFYEKAADKFKDVF-NH2 | 177 |
| [Switch D-E]-2-4F-15 | Ac-EWFKAFYDKAADKFKEVF-NH2 | 178 |
| [Switch D-E]-3-4F-15 | Ac-DWFKAFYEKAADKFKEVF-NH2 | 179 |
| [Switch D-E]-4-4F-15 | Ac-DWFKAFYEKAAEKFKDVF-NH2 | 180 |
| [F3 and Y-7 switched] | | |
| 4F-16 | Ac-DWYKAFFDKVAEKFKEAF-NH₂ | 181 |
| [Switch D-E]-1-4F-16 | Ac-EWYKAFFEKVADKFKDAF-NH2 | 182 |
| [Switch D-E]-2-4F-16 | Ac-EWYKAFFDKVADKFKEAF-NH2 | 183 |
| [Switch D-E]-3-4F-16 | Ac-DWYKAFFEKVADKFKEAF-NH2 | 184 |
| [Switch D-E]-4-4F-16 | Ac-DWYKAFFEKVAEKFKDAF-NH2 | 185 |
| [F-3 and V-10 switched] | | |
| 4F-17 | Ac-DWVKAFYDKFAEKFKEAF-NH₂ | 186 |
| [Switch D-E]-1-4F-17 | Ac-EWVKAFYEKFADKFKDAF-NH2 | 187 |
| [Switch D-E]-2-4F-17 | Ac-EWVKAFYDKFADKFKEAF-NH2 | 188 |
| [Switch D-E]-3-4F-17 | Ac-DWVKAFYEKFADKFKEAF-NH2 | 189 |
| [Switch D-E]-4-4F-17 | Ac-DWVKAFYEKFAEKFKDAF-NH2 | 190 |
| [Y-7 and F-14 switched] | | |
| 4F-18 | Ac-DWFKAFFDKVAEKYKEAF-NH₂ | 191 |
| [Switch D-E]-1-4F-18 | Ac-EWFKAFFEKVADKYKDAF-NH2 | 192 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-2-4F-18 | Ac-EWFKAFFDKVADKYKEAF-NH2 | 193 |
| [Switch D-E]-3-4F-18 | Ac-DWFKAFFEKVADKYKEAF-NH2 | 194 |
| [Switch D-E]-3-4F-18 | Ac-DWFKAFFEKVADKYKEAF-NH2 | 195 |
| [Y-7 and F-18 switched] | | |
| 4F-19 | Ac-DWFKAFFDKVAEKFKEAY-NH₂ | 196 |
| [Switch D-E]-1-4F-19 | Ac-EWFKAFFEKVADKFKDAY-NH2 | 197 |
| [Switch D-E]-2-4F-19 | Ac-EWFKAFFDKVADKFKEAY-NH2 | 198 |
| [Switch D-E]-3-4F-19 | Ac-DWFKAFFEKVADKFKEAY-NH2 | 199 |
| [Switch D-E]-4-4F-19 | Ac-DWFKAFFEKVAEKFKDAY-NH2 | 200 |
| [V-10 and F-18 switched | | |
| 4F-20 | Ac-DWFKAFYDKFAEKFKEAV-NH₂ | 201 |
| [Switch D-E]-1-4F-20 | Ac-EWFKAFYEKFADKFKDAV-NH2 | 202 |
| [Switch D-E]-2-4F-20 | Ac-EWFKAFYDKFADKFKEAV-NH2 | 203 |
| [Switch D-E]-3-4F-20 | Ac-DWFKAFYEKFADKFKEAV-NH2 | 204 |
| [Switch D-E]-4-4F-20 | Ac-DWFKAFYEKFAEKFKDAV-NH2 | 205 |
| [W-2 and K13 switched] | | |
| 4F-21 | Ac-DKFKAFYDKVAEKFWEAF-NH₂ | 206 |
| [Switch D-E]-1-4F-21 | Ac-EKFKAFYEKVADKFWDAF-NH2 | 207 |
| [Switch D-E]-2-4F-21 | Ac-EKFKAFYDKVADKFWEAF-NH2 | 208 |
| [Switch D-E]-3-4F-21 | Ac-DKFKAFYEKVADKFWEAF-NH2 | 209 |
| [Switch D-E]-4-4F-21 | Ac-DKFKAFYEKVAEKFWDAF-NH2 | 210 |
| [W-3, F-13 and K-2 4F] | | |
| 4F-22 | Ac-DKWKAFYDKVAEKFFEAF-NH₂ | 211 |
| [Switch D-E]-1-4F-22 | Ac-EKWKAFYEKVADKFFDAF-NH2 | 212 |
| [Switch D-E]-2-4F-22 | Ac-EKWKAFYDKVADKFFEAF-NH2 | 213 |
| [Switch D-E]-3-4F-22 | Ac-DKWKAFYEKVADKFFEAF-NH2 | 214 |
| [Switch D-E]-4-4F-22 | Ac-DKWKAFYEKVAEKFFDAF-NH2 | 215 |
| [K-2, W10, V-13] | | |
| 4F-23 | Ac-DKFKAFYDKWAEVFKEAF-NH₂ | 216 |
| [Switch D-E]-4F analogs | | |
| [Switch D-E]-1-4F-23 | Ac-EKFKAFYEKWADVFKDAF-NH2 | 217 |
| [Switch D-E]-2-4F-23 | Ac-EKFKAFYDKWADVFKEAF-NH2 | 218 |
| [Switch D-E]-3-4F-23 | Ac-DKFKAFYEKWADVFKEAF-NH2 | 219 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-4-4F-23 | Ac-DKFKAFYEKWAEVFKDAF-NH2 | 220 |
| [K-2, F-13, W-14 4F] | | |
| 4F-24 | Ac-DKFKAFYDKVAEFWKEAF-NH₂ | 221 |
| [Switch D-E]-4F analogs | | |
| [Switch D-E]-1-4F-24 | Ac-EKFKAFYEKVADFWKDAF-NH2 | 222 |
| [Switch D-E]-2-4F-24 | Ac-EKFKAFYDKVADFWKEAF-NH2 | 223 |
| [Switch D-E]-3-4F-24 | Ac-DKFKAFYEKVADFWKEAF-NH2 | 224 |
| [Switch D-E]-4-4F-24 | Ac-DKFKAFYEKVAEFWKDAF-NH2 | 225 |
| Reverse 4F analogs | | |
| Rev-4F | Ac-FAEKFKEAVKDYFAKFWD-NH2 | 226 |
| [Switch D-E]-1-Rev-4F | Ac-FADKFKDAVKEYFAKFWE-NH2 | 227 |
| [Switch D-E]-2-Rev-4F | Ac-FADKFKEAVKDYFAKFWE-NH2 | 228 |
| [Switch D-E]-3-Rev-4F | Ac-FAEKFKDAVKEYFAKFWD-NH2 | 229 |
| [Switch D-E]-4-Rev-4F | Ac-FAEKFKDAVKDYFAKFWE-NH2 | 230 |
| [A-2 and W-17 switched] | | |
| Rev-4F-1 | Ac-FWEKFKEAVKDYFAKFAD-NH2 | 231 |
| [Switch D-E]-1-Rev-4F-1 | Ac-FWDKFKDAVKEYFAKFAE-NH2 | 232 |
| [Switch D-E]-2-Rev-4F-1 | Ac-FADKFKEAVKDYFAKFWE-NH2 | 233 |
| [Switch D-E]-3-Rev-4F-1 | Ac-FAEKFKDAVKEYFAKFWD-NH2 | 234 |
| [Switch D-E]-4-Rev-4F-1 | Ac-FAEKFKDAVKDYFAKFWE-NH2 | 235 |
| [Switch A-2 and F-16] | | |
| Rev-4F-2 | Ac-FFEKFKEAVKDYFAKAWD-NH2 | 236 |
| [Switch D-E]-1-Rev-4F-2 | Ac-FFDKFKDAVKEYFAKAWE-NH2 | 237 |
| [Switch D-E]-2-Rev-4F-2 | Ac-FFDKFKEAVKDYFAKAWE-NH2 | 238 |
| [Switch D-E]-3-Rev-4F-2 | Ac-FFEKFKDAVKEYFAKAWD-NH2 | 239 |
| [Switch D-E]-4-Rev-4F-2 | Ac-FFEKFKDAVKDYFAKAWE-NH2 | 240 |
| [switch F-5 and A-8] | | |
| Rev-4F-3 | Ac-FAEKAKEFVKDYFAKFWD-NH2 | 241 |
| [Switch D-E]-1-Rev-4F-3 | Ac-FADKAKDFVKEYFAKFWE-NH2 | 242 |
| [Switch D-E]-2-Rev-4F-3 | Ac-FADKAKEFVKDYFAKFWE-NH2 | 243 |
| [Switch D-E]-3-Rev-4F-3 | Ac-FAEKAKDFVKEYFAKFWD-NH2 | 244 |
| [Switch D-E]-4-Rev-4F-3 | Ac-FAEKAKDFVKDYFAKFWE-NH2 | 245 |
| [Switch A-8 and V9] | | |
| Rev-4F-4 | Ac-FAEKFKEVAKDYFAKFWD-NH2 | 246 |
| [Switch D-E]-1-Rev-4F-4 | Ac-FADKFKDVAKEYFAKFWE-NH2 | 247 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
| --- | --- | --- |
| [Switch D-E]-2-Rev-4F-4 | Ac-FADKFKEVAKDYFAKFWE-NH2 | 248 |
| [Switch D-E]-3-Rev-4F-4 | Ac-FAEKFKDVAKEYFAKFWD-NH2 | 249 |
| [Switch D-E]-4-Rev-4F-4 | Ac-FAEKFKDVAKDYFAKFWE-NH2 | 250 |
| [Switch V-9 to Y-12] | | |
| Rev-4F-5 | Ac-FAEKFKEAYKDVFAKFWD-NH2 | 251 |
| [Switch D-E]-1-Rev-4F-5 | Ac-FADKFKDAYKEVFAKFWE-NH2 | 252 |
| [Switch D-E]-2-Rev-4F-5 | Ac-FADKFKEAYKDVFAKFWE-NH2 | 253 |
| [Switch D-E]-3-Rev-4F-5 | Ac-FAEKFKDAYKEVFAKFWD-NH2 | 254 |
| [Switch D-E]-4-Rev-4F-5 | Ac-FAEKFKDAYKDVFAKFWE-NH2 | 255 |
| [Switch Y-12 and F-13] | | |
| Rev-4F-6 | Ac-FAEKFKEAVKDFYAKFWD-NH2 | 256 |
| [Switch D-E]-1-Rev-4F-6 | Ac-FADKFKDAVKEFYAKFWE-NH2 | 257 |
| [Switch D-E]-2-Rev-4F-6 | Ac-FADKFKEAVKDFYAKFWE-NH2 | 258 |
| [Switch D-E]-3-Rev-4F-6 | Ac-FAEKFKDAVKEFYAKFWD-NH2 | 259 |
| [Switch D-E]-4-Rev-4F-6 | Ac-FAEKFKDAVKDFYAKFWE-NH2 | 260 |
| [Switch K-6 and W-17] | | |
| Rev-4F-7 | Ac-FAEKFWEAVKDYFAKFKD-NH2 | 261 |
| [Switch D-E]-1-Rev-4F-7 | Ac-FADKFWDAVKEYFAKFKE-NH2 | 262 |
| [Switch D-E]-2-Rev-4F-7 | Ac-FADKFWEAVKDYFAKFKE-NH2 | 263 |
| [Switch D-E]-3-Rev-4F-7 | Ac-FAEKFWDAVKEYFAKFKD-NH2 | 264 |
| [Switch D-E]-4-Rev-4F-7 | Ac-FAEKFWDAVKDYFAKFKE-NH2 | 265 |
| [Switch F-1 and A-2] | | |
| Rev-4F-8 | Ac-AFEKFKEAVKDYFAKFWD-NH2 | 266 |
| [Switch D-E]-1-Rev-4F-8 | Ac-AFDKFKDAVKEYFAKFWE-NH2 | 267 |
| [Switch D-E]-2-Rev-4F-8 | Ac-AFDKFKEAVKDYFAKFWE-NH2 | 268 |
| [Switch D-E]-3-Rev-4F-8 | Ac-AFEKFKDAVKEYFAKFWD-NH2 | 269 |
| [Switch D-E]-4-Rev-4F-8 | Ac-AFEKFKDAVKDYFAKFWE-NH2 | 270 |
| [F-1 and V-9 are switched] | | |
| Rev-F-9 | Ac-VAEKFKEAFKDYFAKFWD-NH2 | 271 |
| [Switch D-E]-1-Rev-4F-9 | Ac-VADKFKDAFKEYFAKFWE-NH2 | 272 |
| [Switch D-E]-2-Rev-4F-9 | Ac-VADKFKEAFKDYFAKFWE-NH2 | 273 |
| [Switch D-E]-3-Rev-4F-9 | Ac-VAEKFKDAFKEYFAKFWD-NH2 | 274 |
| [Switch D-E]-4-Rev-4F-9 | Ac-VAEKFKDAFKDYFAKFWE-NH2 | 275 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [F-1 and Y-12 are switched] | | |
| Rev-4F-10 | Ac-YAEKFKEAVKDFFAKFWD-NH2 | 276 |
| [Switch D-E]-1-Rev-4F-10 | Ac-YADKFKDAVKEFFAKFWE-NH2 | 277 |
| [Switch D-E]-2-Rev-4F-10 | Ac-YADKFKEAVKDFFAKFWE-NH2 | 278 |
| [Switch D-E]-3-Rev-4F-10 | Ac-YAEKFKDAVKEFFAKFWD-NH2 | 279 |
| [Switch D-E]-4-Rev-4F-10 | Ac-YAEKFKDAVKDFFAKFWE-NH2 | 280 |
| [F-1 and A-8 are switched] | | |
| Rev-4F-11 | Ac-AAEKFKEFVKDYFAKFWD-NH2 | 281 |
| [Switch D-E]-1-Rev-4F-11 | Ac-AADKFKDFVKEYFAKFWE-NH2 | 282 |
| [Switch D-E]-2-Rev-4F-11 | Ac-AADKFKEFVKDYFAKFWE-NH2 | 283 |
| [Switch D-E]-3-Rev-4F-11 | Ac-AAEKFKDFVKEYFAKFWD-NH2 | 284 |
| Switch D-E]-4-Rev-4F-11 | Ac-AAEKFKDFVKDYFAKFWE-NH2 | 285 |
| [A-2 and F-5 are switched] | | |
| Rev-4F-12 | Ac-FFEKAKEAVKDYFAKFWD-NH2 | 286 |
| [Switch D-E]-1-Rev-4F-12 | Ac-FFDKAKDAVKEYFAKFWE-NH2 | 287 |
| [Switch D-E]-2-Rev-4F-12 | Ac-FFDKAKEAVKDYFAKFWE-NH2 | 288 |
| [Switch D-E]-3-Rev-4F-12 | Ac-FFEKAKDAVKEYFAKFWD-NH2 | 289 |
| [Switch D-E]-4-Rev-4F-12 | Ac-FFEKAKDAVKDYFAKFWE-NH2 | 290 |
| [A-2 and Y12 are switched | | |
| Rev-4F-13 | Ac-FYEKFKEAVKDAFAKFWD-NH2 | 291 |
| [Switch D-E]-1-Rev-4F-13 | Ac-FYDKFKDAVKEAFAKFWE-NH2 | 292 |
| [Switch D-E]-2-Rev-4F-13 | Ac-FYDKFKEAVKDAFAKFWE-NH2 | 293 |
| [Switch D-E]-3-Rev-4F-13 | Ac-FYEKFKDAVKEAFAKFWD-NH2 | 294 |
| [Switch D-E]-4-Rev-4F-13 | Ac-FYEKFKDAVKDAFAKFWE-NH2 | 295 |
| [A-2 and V-9 are switched] | | |
| Rev-4F-14 | Ac-FVEKFKEAAKDYFAKFWD-NH2 | 296 |
| [Switch D-E]-1-Rev-4F-14 | Ac-FVDKFKDAAKEYFAKFWE-NH2 | 297 |
| [Switch D-E]-2-Rev-4F-14 | Ac-FVDKFKEAAKDYFAKFWE-NH2 | 298 |
| [Switch D-E]-3-Rev-4F-14 | Ac-FVEKFKDAAKEYFAKFWD-NH2 | 299 |
| [Switch D-E]-4-Rev-4F-14 | Ac-FVEKFKDAAKDYFAKFWE-NH2 | 300 |
| [F-5 and Y-12 are switched] | | |
| Rev-4F-15 | Ac-FAEKYKEAVKDFFAKFWD-NH2 | 301 |
| [Switch D-E]-1-Rev-4F-15 | Ac-FADKYKDAVKEFFAKFWE-NH2 | 302 |
| [Switch D-E]-2-Rev-4F-15 | Ac-FADKYKEAVKDFFAKFWE-NH2 | 303 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-3-Rev-4F-15 | Ac-FAEKYKDAVKEFFAKFWD-NH2 | 304 |
| [Switch D-E]-4-Rev-4F-15 | Ac-FAEKYKDAVKDFFAKFWE-NH2 | 305 |
| [F-5 and V-9 are switched] | | |
| Rev-4F-16 | Ac-FAEKVKEAFKDYFAKFWD-NH2 | 306 |
| [Switch D-E]-1-Rev-4F-16 | Ac-FADKVKDAFKEYFAKFWE-NH2 | 307 |
| [Switch D-E]-2-Rev-4F-16 | Ac-FADKVKEAFKDYFAKFWE-NH2 | 308 |
| [Switch D-E]-3-Rev-4F-16 | Ac-FAEKVKDAFKEYFAKFWD-NH2 | 309 |
| [Switch D-E]-4-Rev-4F-16 | Ac-FAEKVKDAFKDYFAKFWE-NH2 | 310 |
| [A-8 and Y-12 switched] | | |
| Rev-4F-17 | Ac-FAEKFKEYVKDAFAKFWD-NH2 | 311 |
| [Switch D-E]-1-Rev-4F-17 | Ac-FADKFKDYVKEAFAKFWE-NH2 | 312 |
| [Switch D-E]-2-Rev-4F-17 | Ac-FADKFKEYVKDAFAKFWE-NH2 | 313 |
| [Switch D-E]-3-Rev-4F-17 | Ac-FAEKFKDYVKEAFAKFWD-NH2 | 314 |
| [Switch D-E]-4-Rev-4F-17 | Ac-FAEKFKDYVKDAFAKFWE-NH2 | 315 |
| [V-9 and F-13 are switched] | | |
| Rev-4F-18 | Ac-FAEKFKEAFKDYVAKFWD-NH2 | 316 |
| [Switch D-E]-1-Rev-4F-18 | Ac-FADKFKDAFKEYVAKFWE-NH2 | 317 |
| [Switch D-E]-2-Rev-4F-18 | Ac-FADKFKEAFKDYVAKFWE-NH2 | 318 |
| [Switch D-E]-3-Rev-4F-18 | Ac-FAEKFKDAFKEYVAKFWD-NH2 | 319 |
| [Switch D-E]-4-Rev-4F-18 | Ac-FAEKFKDAFKDYVAKFWE-NH2 | 320 |
| [V-9 and F-16 switched] | | |
| Rev-4F-19 | Ac-FAEKFKEAFKDYFAKVWD-NH2 | 321 |
| [Switch D-E]-1-Rev-4F-19 | Ac-FADKFKDAFKEYFAKVWE-NH2 | 322 |
| [Switch D-E]-2-Rev-4F-19 | Ac-FADKFKEAFKDYFAKVWE-NH2 | 323 |
| [Switch D-E]-3-Rev-4F-19 | Ac-FAEKFKDAFKEYFAKVWD-NH2 | 324 |
| Switch D-E]-4-Rev-4F-19 | Ac-FAEKFKDAFKDYFAKVWE-NH2 | 325 |
| [Y-12 and F-16 are switched | | |
| Rev-4F-20 | Ac-FAEKFKEAVKDFFAKYWD-NH2 | 326 |
| [Switch D-E]-1-Rev-4F-20 | Ac-FADKFKDAVKEFFAKYWE-NH2 | 327 |
| [Switch D-E]-2-Rev-4F-20 | Ac-FADKFKEAVKDFFAKYWE-NH2 | 328 |
| [Switch D-E]-3-Rev-4F-20 | Ac-FAEKFKDAVKEFFAKYWD-NH2 | 329 |
| [Switch D-E]-4-Rev-4F-20 | Ac-FAEKFKDAVKDFFAKYWE-NH2 | 330 |
| [W-1, F-6 and K-17 Rev 4F] | | |
| Rev-4F-21 | Ac-WAEKFFEAVKDYFAKFKD-NH2 | 331 |
| [Switch D-E]-1-Rev-4F-7 | Ac-WADKFFDAVKEYFAKFKE-NH2 | 332 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-2-Rev-4F-7 | Ac-WA<u>D</u>KFFEAVKDYFAKFK<u>E</u>-NH2 | 333 |
| [Switch D-E]-3-Rev-4F-7 | Ac-WAEKFF<u>D</u>AVK<u>E</u>YFAKFKD-NH2 | 334 |
| Switch D-E]-4-Rev-4F-7 | Ac-WAEKFF<u>D</u>AVKDYFAKFK<u>E</u>-NH2 | 335 |
| [W-5, F-6 and K-17 Rev-4F] | | |
| Rev-4F-22 | Ac-FAEK<u>WF</u>EAVKDYFAKF<u>K</u>D-NH2 | 336 |
| [Switch D-E]-1-Rev-4F-22 | Ac-FA<u>D</u>KWF<u>D</u>AVK<u>E</u>YFAKFK<u>E</u>-NH2 | 337 |
| [Switch D-E]-2-Rev-4F-22 | Ac-FA<u>D</u>KWFEAVKDYFAKFK<u>E</u>-NH2 | 338 |
| [Switch D-E]-3-Rev-4F-22 | Ac-FAEKWF<u>D</u>AVK<u>E</u>YFAKFKD-NH2 | 339 |
| [Switch D-E]-4-Rev-4F-22 | Ac-FAEKWF<u>D</u>AVKDYFAKFK<u>E</u>-NH2 | 340 |
| [V-6, W-9, K-17 Rev-4F] | | |
| Rev-4F-23 | Ac-FAEKF<u>VEA</u>WKDYFAKF<u>K</u>D-NH2 | 341 |
| [Switch D-E]-1-Rev-4F-23 | Ac-FA<u>D</u>KFV<u>D</u>AWK<u>E</u>YFAKFK<u>E</u>-NH2 | 342 |
| [Switch D-E]-2-Rev-4F-23 | Ac-FA<u>D</u>KFVEAWKDYFAKFK<u>E</u>-NH2 | 343 |
| [Switch D-E]-3-Rev-4F-23 | Ac-FAEKFV<u>D</u>AWK<u>E</u>YFAKFKD-NH2 | 344 |
| [Switch D-E]-4-Rev-4F-23 | Ac-FAEKFV<u>D</u>AWKDYFAKFK<u>E</u>-NH2 | 345 |
| [Y-2, A-4, W-12, K-17 Rev-4F] | | |
| Rev-4F-24 | Ac-F<u>Y</u>EKF<u>A</u>EAVKD<u>W</u>FAKF<u>K</u>D-NH2 | 346 |
| [Switch D-E]-1-Rev-4F-24 | Ac-FY<u>D</u>KFA<u>D</u>AVK<u>E</u>WFAKFK<u>E</u>-NH2 | 347 |
| [Switch D-E]-2-Rev-4F-24 | Ac-FY<u>D</u>KFAEAVKDWFAKFK<u>E</u>-NH2 | 348 |
| [Switch D-E]-3-Rev-4F-24 | Ac-FYEKFA<u>D</u>AVK<u>E</u>WFAKFKD-NH2 | 349 |
| [Switch D-E]-4-Rev-4F-24 | Ac-FYEKFA<u>D</u>AVKDWFAKFK<u>E</u>-NH2 | 350 |

Figure 15:
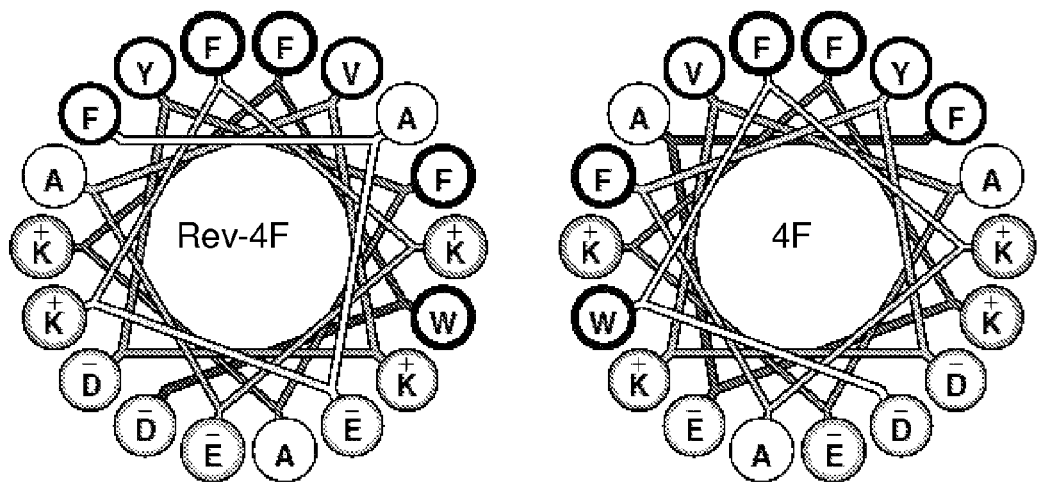
FIG. 15 illustrates a helical wheel representation of 4F (SEQ ID NO:5) and reverse (retro) 4F (SEQ ID NO:104). Reverse-4F is a mirror image of 4F with the relative positions of the amino acids to each other and to the hydrophilic and hydrophobic faces being identical.

Based on the helical wheel diagrams shown in FIG. 15 it is possible to readily identify biologically active and useful peptides. Thus, for example, the following peptides have been accurately identified as active: 3F1; 3F2; 4F the reverse (retro) forms thereof and the retro-inverso forms thereof. Thus, in certain embodiments, this invention contemplates active agents comprising a peptide that is 18 amino acids in length and forms a class A amphipathic helix where the peptide has the amino acid composition 2 aspartates, 2 glutamates, 4 lysines, 1 tryptophan, 1 tyrosine, no more than one leucine, no more than 1 valine, no less than 1 and no more than 3 alanines, and with 3 to 6 amino acids from the group: phenylalanine, alpha-naphthalanine, beta-naphthalanine, histidine, and contains either 9 or 10 amino acids on the polar face in a helical wheel representation of the class A amphipathic helix including 4 amino acids with positive charge at neutral pH with two of the positively charged residues residing at the interface between the polar and non-polar faces and with two of the four positively charged residues on the polar face that are contiguous and on the non-polar face two of the amino acid residues from the group: phenylalanine, alpha-naphthalanine, beta-naphthalanine, histidine are also contiguous and if there are 4 or more amino acids from this group on the non-polar face there are also at least 2 residues from this group that are not contiguous.

In certain embodiments, this invention also contemplates certain class Y as well as class A amphipathic helical peptides. Class Y amphipathic helical peptides are known to those of skill in the art (see, e.g., Segrest et al. (1992)*J. Lipid Res.* 33: 141-166; Oram and Heinecke (2005)*Physiol Rev.* 85: 1343-1372, and the like). In various embodiments these peptides include, but are not limited to an 18 amino acid peptide that forms a class A amphipathic helix or a class Y amphipathic helix described by formula III (SEQ ID NO:351):

D-X-X-K-Y-X-X-D-K-X-Y-D-KX-K-D-Y-X       III where the D's are independently Asp or Glu; the Ks are independently Lys or Arg; the Xs are independently Leu, norLeu, Val, Ile, Trp, Phe, Tyr, β-Nal, or α-Nal and all X residues are on the non-polar face (e.g., when viewed in a helical wheel diagram) except for one that can be on the polar face between two K residues; the Y's are independently Ala, His, Ser, Gln, Asn, or Thr non-polar face (e.g., when viewed in a helical wheel diagram) and the Y's are independently one Ala on the polar face, one His, one Ser, one Gln one Asn, or one Thr on the polar face (e.g., when viewed in a helical wheel diagram), where no more than two K are be contiguous (e.g., when viewed in a helical wheel diagram); and where no more than 3 D's are contiguous (e.g., when viewed in a helical wheel diagram) and the fourth D is be separated from the other D's by a Y. Illustrative peptides of this kind which include peptides with histidine, and/or alpha-and/or beta-napthalanine are shown in Table 5. Reverse (retro-), inverse, retro-inverso-, and circularly permuted forms of these peptides are also contemplated.

TABLE 5

Illustrates various class A and/or class Y peptide analogs with His incorporated into the sequence.

| Short name | Peptide sequence | SEQ ID NO |
|---|---|---|
| [A-5 > H]4F | Ac-DWFKHFYDKVAEKFKEAF-NH$_2$ | 352 |
| [A-5 > H, D-E switched]4F | Ac-EWFKHFYEKVADKFKDAF-NH$_2$ | 353 |
| [A-5 > H, D-1 > E]4F | Ac-EWFKHFYDKVAEKFKEAF-NH$_2$ | 354 |
| [A-5 > H, D-8 > E]4-F | Ac-DWFKHFYEKVAEKFKEAF-NH$_2$ | 355 |
| [A-5 > H, E-12 > D]4F | Ac-DWFKHFYDKVADKFKEAF-NH$_2$ | 356 |
| [A-5 > H, E-16 > D]4F | Ac-DWFKHFYDKVAEKFKDAF-NH$_2$ | 357 |
| [F-3 > H, A-5 > F]-4F | Ac-DWHKFFYDKVAEKFKEAF-NH$_2$ | 358 |
| [F-3 > H, A-5 > F, D-E switched]-4F | Ac-EWHKFFYEKVADKFKDAF-NH$_2$ | 359 |
| [F-3 > H, A-5 > F, D-1 > E]-4F | Ac-EWHKFFYDKVAEKFKEAF-NH$_2$ | 360 |
| [F-3 > H, A-5 > F, D-8 > E]-4F | Ac-DWHKFFYEKVAEKFKEAF-NH$_2$ | 361 |
| [F-3 > H, A-5 > F, E-12 > D]-4F | Ac-DWHKFFYDKVADKFKEAF-NH$_2$ | 362 |
| [F-3 > H, A-5 > F, E-16 > D]-4F | Ac-DWHKFFYDKVAEKFKDAF-NH$_2$ | 363 |
| [A-5 > F, F-6 > H]4F | Ac-DWFKF_H_YDKVAEKFKEAF-NH$_2$ | 364 |
| [A-5 > F, F-6 > H, D-E switched]4F | Ac-EWFKFHYEKVADKFKDAF-NH$_2$ | 365 |
| [[A-5 > F, F-6 > H, D-1 > E]4F | Ac-EWFKFHYDKVAEKFKEAF-NH$_2$ | 366 |
| [A-5 > F, F-6 > H, D-8 > E]4F | Ac-DWFKFHYEKVAEKFKEAF-NH$_2$ | 367 |
| [A-5 > F, F-6 > H, E-12 > D]4F | Ac-DWFKFHYDKVADKFKEAF-NH$_2$ | 368 |
| [A-5 > F, F-6 > H, E-16 > D]4F | Ac-DWFKFHYDKVAEKFKDAF-NH$_2$ | 369 |
| [A-5 > V, V-10 > H]4F | Ac-DWFKVFYDKHAEKFKEAF-NH$_2$ | 370 |
| [A-5 > V, V-10 > H, D-E switched]4F | Ac-EWFKVFYEKHADKFKDAF-NH$_2$ | 371 |
| [A-5 > V, V-10 > H, D-1 > E]4F | Ac-EWFKVFYDKHAEKFKEAF-NH$_2$ | 372 |
| [A-5 > V, V-10 > H, D-8 > E]4F | Ac-DWFKVFYEKHAEKFKEAF-NH$_2$ | 373 |
| [A-5 > V, V-10 > H, E-12 > D]4F | Ac-DWFKVFYDKHADKFKEAF-NH$_2$ | 374 |
| [A-5 > V, V-10 > H, E16 > D]4F | Ac-DWFKVFYDKHAEKFKDAF-NH$_2$ | 375 |
| [[A-17 > H]4F | Ac-DWFKAFYDKVAEKFKEHF-NH$_2$ | 376 |
| [A-17 > H, D-E switched]4F | Ac-EWFKAFYEKVADKFKDHF-NH$_2$ | 377 |
| [[A-17 > H, D-1 > E]4F | Ac-EWFKAFYDKVAEKFKEHF-NH$_2$ | 378 |
| [[A-17 > H, D-8 > E]4F | Ac-DWFKAFYEKVAEKFKEHF-NH$_2$ | 379 |
| [[A-17 > H, E-12 > D]4F | Ac-DWFKAFYDKVADKFKEHF-NH$_2$ | 380 |
| [[A-17 > H, E16 > D]4F | Ac-DWFKAFYDKVAEKFKDHF-NH$_2$ | 381 |
| [A-17 > F, F-18 > H]4F | Ac-DWFKAFYDKVAEKFKEFH-NH$_2$ | 382 |

TABLE 5-continued

Illustrates various class A and/or class Y peptide analogs with His incorporated into the sequence.

| Short name | Peptide sequence | SEQ ID NO |
|---|---|---|
| [A-17 > F, F-18 > H, D-E switched]4F | Ac-EWFKAFYEKVADKFKDFH-NH$_2$ | 383 |
| [A-17 > F, F-18 > H, D-1 > E]-4F | Ac-EWFKAFYDKVAEKFKEFH-NH$_2$ | 384 |
| [A-17 > F, F-18 > H]4F | Ac-DWFKAFYDKVAEKFKEFH-NH$_2$ | 385 |
| [A-17 > F, F-18 > H, D-8 > E]-4F | Ac-DWFKAFYEKVAEKFKEFH-NH$_2$ | 386 |
| [A-17 > F, F-18 > H, E-12 > D]4F | Ac-DWFKAFYDKVAEKFKEFH-NH$_2$ | 387 |
| [A-17 > F, F-18 > H], E-16 > D]-4F | Ac-DWFKAFYDKVAEKFKDFH-NH$_2$ | 388 |
| Rev-4F | Ac-FAEKFKEAVKDYFAKFWD-NH$_2$ | 389 |
| [A-2 > H]Rev4F | Ac-FHEKFKEAVKDYFAKFWD-NH$_2$ | 390 |
| Rev-[A-2 > H, D > E]-4F | Ac-FHEKFKEAVKEYFAKFWE-NH$_2$ | 391 |
| Rev-[A-2 > H, E > D]4F | Ac-FHDKFKDAVKEYFAKFWD-NH$_2$ | 392 |
| [A-2 > H, D-E switched]Rev-4F | Ac-FHDKFKDAVKEYFAKFWE-NH$_2$ | 393 |
| [A-2 > H, E-3 > D]Rev-4F | Ac-FHDKFKEAVKDYFAKFWD-NH$_2$ | 394 |
| [A-2 > H, E-7 > D]Rev-4F | Ac-FHEKFKDAVKDYFAKFWD-NH$_2$ | 395 |
| [A-2 > H, D-11 > E]Rev-4F | Ac-FHEKFKEAVKEYFAKFWD-NH$_2$ | 396 |
| [A-2 > H, D-18 > E]Rev-4F | Ac-FHEKFKEAVKDYFAKFWE-NH$_2$ | 397 |
| [F-1 > H, A-2 > F]Rev-4F | Ac-HFEKFKEAVKDYFAKFWD-NH$_2$ | 398 |
| [F-1 > H, A-2 > F, D-E switched]Rev-4F | Ac-HFDKFKDAVKEYFAKFWE-NH$_2$ | 399 |
| [F-1 > H, A-2 > F, D > E]Rev-4F | Ac-HFEKFKEAVKEYFAKFWE-NH$_2$ | 400 |
| [F-1 > H, A-2 > F, E-3 > D]Rev-4F | Ac-HFDKFKEAVKDYFAKFWD-NH$_2$ | 401 |
| [F-1 > H, A-2 > F, E-7 > D]Rev-4F | Ac-HFEKFKDAVKDYFAKFWD-NH$_2$ | 402 |
| [F-1 > H, A-2 > F, D-11 > E]Rev-4F | Ac-HFEKFKEAVKEYFAKFWD-NH$_2$ | 403 |
| [F-1 > H, A-2 > F, D-18 > E]Rev-4F | Ac-HFEKFKEAVKDYFAKFWE-NH$_2$ | 404 |
| [A-2 > F, F-5 > H]Rev D-4F | Ac-FFEKHKEAVKDYFAKFWD-NH$_2$ | 405 |
| [A-2 > F, F-5 > H, D-E switched]RevD-4F | Ac-FFDKHKDAVKEYFAKFWE-NH$_2$ | 406 |
| [A-2 > F, F-5 > H, D > E]Rev D-4F | Ac-FFEKHKEAVKEYFAKFWE-NH$_2$ | 407 |
| [A-2 > F, F-5 > H, E > D]Rev D-4F | Ac-FFDKHKDAVKDYFAKFWD-NH$_2$ | 408 |
| [A-2 > F, F-5 > H, E-3 > D]Rev D-4F | Ac-FFDKHKEAVKDYFAKFWD-NH$_2$ | 409 |
| [A-2 > F, F-5 > H, D-11 > E]Rev D-4F | Ac-FFEKHKEAVKEYFAKFWD-NH$_2$ | 410 |
| [A-2 > F, F-5 > H, D-18 > E]Rev D-4F | Ac-FFEKHKEAVKDYFAKFWE-NH$_2$ | 411 |
| [A-2 > V, V-9 > H]Rev D-4F | Ac-FVEKFKEAHKDYFAKFWD-NH$_2$ | 412 |
| [A-2 > V, V-9 > H, D-E switched]RevD-4F | Ac-FVDKFKDAHKEYFAKFWE-NH$_2$ | 413 |
| [A-2 > V, V-9 > H, D > E]Rev D-4F | Ac-FVEKFKEAHKEYFAKFWE-NH$_2$ | 414 |
| [A-2 > V, V-9 > H, E > D]Rev D-4F | Ac-FVDKFKDAHKDYFAKFWD-NH$_2$ | 415 |
| [A-2 > V, V-9 > H, E-3 > D]Rev D-4F | Ac-FVDKFKDAHKDYFAKFWD-NH$_2$ | 416 |
| [A-2 > V, V-9 > H, E-7 > D]Rev D-4F | Ac-FVEKFKDAHKDYFAKFWD-NH$_2$ | 417 |
| [A-2 > V, V-9 > H, D-11 > E]Rev D-4F | Ac-FVEKFKEAHKEYFAKFWD-NH$_2$ | 418 |
| [A-2 > V, V-9 > H, D-18 > E]Rev D-4F | Ac-FVEKFKEAHKDYFAKFWE-NH$_2$ | 419 |

TABLE 5-continued

Illustrates various class A and/or class Y peptide analogs with His incorporated into the sequence.

| Short name | Peptide sequence | SEQ ID NO |
|---|---|---|
| [A-8 > H]Rev-4F | Ac-FAEKFKEHVKDYFAKFWD-NH$_2$ | 420 |
| [A-8 > H, D-E switched]Rev-4F | Ac-FADKFKDHVKEYFAKFWE-NH$_2$ | 421 |
| [A-8 > H, D > E]Rev-4F | Ac-FAEKFKEHVKEYFAKFWE-NH$_2$ | 422 |
| [A-8 > H, E > D]Rev-4F | Ac-FADKFKDHVKDYFAKFWD-NH$_2$ | 423 |
| [A-8 > H, E-3 > D]Rev-4F | Ac-FADKFKEHVKDYFAKFWD-NH$_2$ | 424 |
| [A-8 > H, E-7 > D]Rev-4F | Ac-FAEKFKDHVKDYFAKFWD-NH$_2$ | 425 |
| [A-8 > H, D-11 > E]Rev-4F | Ac-FAEKFKEHVKEYFAKFWD-NH$_2$ | 426 |
| [A-8 > H, D-18 > E]Rev-4F | Ac-FAEKFKEHVKDYFAKFWE-NH$_2$ | 427 |
| [A-8 > F, F-1 3> H]Rev-4F | Ac-FAEKFKEFVKDYHAKFWD-NH$_2$ | 428 |
| [A-8 > F, F-13 > H, D-E switched]Rev-4F | Ac-FADKFKDFVKEYHAKFWE-NH$_2$ | 429 |
| [A-8 > F, F-13 > H, E-3 > D]Rev-4F | Ac-FADKFKEFVKDYHAKFWD-NH$_2$ | 430 |
| [A-8 > F, F-13 > H, E-7 > D]Rev-4F | Ac-FAEKFKDFVKDYHAKFWD-NH$_2$ | 431 |
| [A-8 > F, F-13 > H, E > D]Rev-4F | Ac-FADKFKDFVKDYHAKFWD-NH$_2$ | 432 |
| [A-8 > F, F-13 > H, D > E]Rev-4F | Ac-FAEKFKEFVKEYHAKFWE-NH$_2$ | 433 |
| [A-8 > F, F-13 > H, D-11 > E]Rev-4F | Ac-FAEKFKEFVKEYHAKFWD-NH$_2$ | 434 |
| [A-8 > F, F-13 > H, D-18 > E]Rev-4F | Ac-FAEKFKEFVKDYHAKFWE-NH$_2$ | 435 |
| [A-8 > F, F 16 > H]Rev.-4F | Ac-FAEKFKEFVKDYFAKHWD-NH$_2$ | 436 |
| [A-8 > F, F16 > H, D-E switched]Rev.-4F | Ac-FADKFKDFVKEYFAKHWE-NH$_2$ | 437 |
| [A-8 > F, F 16 > H, D > E]Rev.-4F | Ac-FAEKFKEFVKEYFAKHWE-NH$_2$ | 438 |
| [A-8 > F, F16 > H, E > D]Rev.-4F | Ac-FADKFKDFVKDYFAKHWD-NH$_2$ | 439 |
| [A-8 > F, F 16 > H, E-3 > D]Rev.-4F | Ac-FADKFKEFVKDYFAKHWD-NH$_2$ | 440 |
| [A-8 > F, F 16 > H, E-7 > D]Rev.-4F | Ac-FAEKFKDFVKDYFAKHWD-NH$_2$ | 441 |
| [A-8 > F, F 16 > H, D-11 > E]Rev.-4F | Ac-FAEKFKEFVKEYFAKHWD-NH$_2$ | 442 |
| [A-8 > F, F 16 > H, D-18 > E]Rev.-4F | Ac-FAEKFKEFVKDYFAKHWE-NH$_2$ | 443 |

Examples of class A 4F and Rev 4F analogs with beta-Nph. Similarly, alpha-Nph analogs can be designed. Similarly to the above analogs, His can be incorporated
to Nph analogs. D > E analogs, E > D analogs and D-E switch analogs are additional possibilities similarly to the above described analogs.

| 4Nph | Ac-DWNphKANphYDKVAEKNphKEANph-NH2 | 444 |
| [D-E switched]4Nph | Ac-EWNphKANphYEKVADKNphKDANph-NH2 | 445 |
| [D > E]4Nph | Ac-EWNphKANphYEKVAEKNphKEANph-NH2 | 446 |
| [E > D]4Nph | Ac-DWNphKANphYDKVADKNphKDANph-NH2 | 447 |
| [D-1 > E]4Nph | Ac-EWNphKANphYDKVAEKNphKEANph-NH2 | 448 |
| [D-8 > E]4Nph | Ac-DWNphKANphYEKVAEKNphKEANph-NH2 | 449 |
| [E-12 > D]4Nph | Ac-DWNphKANphYDKVADKNphKEANph-NH2 | 450 |
| [E-16 > D]4Nph | Ac-DWNphKANphYDKVAEKNphKDANph-NH2 | 451 |

TABLE 5-continued

Illustrates various class A and/or class Y peptide analogs with His incorporated into the sequence.

| Short name | Peptide sequence | SEQ ID NO |
|---|---|---|
| As described above for 4Nph, a minimum of 7 additional analogs for each of the analogs given below. | | |
| [F-3, 6, > Nph]4F | Ac-DWNphKANphYDKVAEKFKEAF-NH2 | 452 |
| [F-14, 18 > Nph]4F | Ac-DWFKAFYDKVAEKNphKEANph-NH2 | 453 |
| [[F-3 > Nph]4F | Ac-DWNphKAFYDKVAEKFKEAF-NH2 | 454 |
| [F-6 > Nph]4F | Ac-DWFKANphYDKVAEKFKEAF-NH2 | 455 |
| [F-14 > Nph]4F | Ac-DWFKAFYDKVAEKNphKEAF-NH2 | 456 |
| [F-18 > Nph]4F | Ac-DWFKAFYDKVAEKFKEANph-NH2 | 457 |
| For each of the analog described below, a minimum of 7 additional analogs are possible as described above by switching D-E, D > E and E > D and single D or E analogs. | | |
| Rev-4Nph | Ac-NphAEKNphKEAVKDYNphAKNphWD-NH2 | 458 |
| [F-3, 6 > Nph]Rev 4F | Ac-NphAEKNphKEAVKDYFAKFWD-NH2 | 459 |
| [F-13, 16]Rev-4F | Ac-FAEKFKEAVKDYNphAKNphWD-NH2 | 460 |
| [F-3 > Nph]Rev-4F | Ac-NphAEKFKEAVKDYFAKFWD-NH2 | 461 |
| [F-6 > Nph]Rev-4F | Ac-FAEKNphKEAVKDYFAKFWD-NH2 | 462 |
| [F-13 > Nph]Rev-4F | Ac-FAEKFKEAVKDYNphAKFWD-NH2 | 463 |
| [F-16 > Nph]Rev-4F | Ac-FAEKFKEAVKDYFAKNphWD-NH2 | 464 |
| For the analogs described below, additional analogs are possible by incorporating His or alpha-Nph and beta-Nph | | |
| Rev-[D > E]-4F | Ac-FAEKFKEAVKEYFAKFWE-NH2 | 465 |
| Rev-[E > D]4F | Ac-FADKFKDAVKDYFAKFWD-NH2 | 466 |
| Rev-R4-4F | Ac-FAERFREAVKDYFAKFWD-NH2 | 467 |
| Rev-R6-4F | Ac-FAEKFREAVKDYFAKFWD-NH2 | 468 |
| Rev-R10-4F | Ac-FAEKFKEAVRDYFAKFWD-NH2 | 469 |
| Rev-R14-4F | Ac-FAEKFKEAVKDYFARFWD-NH2 | 470 |
| Rev-[D > E]-4F | Ac-FAEKFKEAVKEYFAKFWE-NH2 | 471 |
| Rev-[E > D]4F | Ac-FADKFKDAVKDYFAKFWD-NH2 | 472 |
| Rev-R4-4F | Ac-FAERFREAVKDYFAKFWD-NH2 | 473 |
| Rev-R6-4F | Ac-FAEKFREAVKDYFAKFWD-NH2 | 474 |
| Rev-R10-4F | Ac-FAEKFKEAVRDYFAKFWD-NH2 | 475 |
| Rev-R14-4F | Ac-FAEKFKEAVKDYFARFWD-NH2 | 476 |
| Rev-[D > E]-4F | Ac-FAEKFKEAVKEYFAKFWE-NH2 | 477 |
| Rev-[E > D]4F | Ac-FADKFKDAVKDYFAKFWD-NH2 | 478 |
| Rev-R4-4F | Ac-FAERFREAVKDYFAKFWD-NH2 | 479 |
| Rev-R6-4F | Ac-FAEKFREAVKDYFAKFWD-NH2 | 480 |
| Rev-R10-4F | Ac-FAEKFKEAVRDYFAKFWD-NH2 | 481 |
| Rev-R14-4F | Ac-FAEKFKEAVKDYFARFWD-NH2 | 482 |

TABLE 5-continued

Illustrates various class A and/or class Y peptide analogs with His incorporated into the sequence.

| Short name | Peptide sequence | SEQ ID NO |
|---|---|---|
| Rev-R4-4F | Ac-FAERFREAVKDYFAKFWD-NH2 | 483 |
| Rev-R6-4F | Ac-FAEKFREAVKDYFAKFWD-NH2 | 484 |
| Rev-R10-4F | Ac-FAEKFKEAVRDYFAKFWD-NH2 | 485 |
| Rev-R14-4F | Ac-FAEKFKEAVKDYFARFWD-NH2 | 486 |
| Rev-[D > E]-4F | Ac-FAEKFKEAVKEYFAKFWE-NH2 | 487 |
| Rev-[E > D]4F | Ac-FADKFKDAVKDYFAKFWD-NH2 | 488 |
| Rev-R4-4F | Ac-FAERFREAVKDYFAKFWD-NH2 | 489 |
| Rev-R6-4F | Ac-FAEKFREAVKDYFAKFWD-NH2 | 490 |
| Rev-R10-4F | Ac-FAEKFKEAVRDYFAKFWD-NH2 | 491 |
| Rev-R14-4F | Ac-FAEKFKEAVKDYFARFWD-NH2 | 492 |

For each of the analogs below, additional H and Nph analogs are possible using the examples described above. Each analog can yield 7 analogs with the changes described in the examples given above.

| Short name | Peptide sequence | SEQ ID NO |
|---|---|---|
| Rev3F-2 | Ac-LFEKFAEAFKDYVAKWKD-NH2 | 493 |
| RevR4-3F-2 | Ac-LFERFAEAFKDYVAKWKD-NH2 | 494 |
| RevR10-3F2 | Ac-LFEKFAEAFRDYVAKWKD-NH2 | 495 |
| RevR15-3F-2 | Ac-LFEKFAEAFKDYVARWKD-NH2 | 496 |
| Rev R17-3F-2 | Ac-LFEKFAEAFKDYVAKWRD-NH2 | 497 |
| Rev[D > E]3F2 | Ac-LFEKFAEAFKEYVAKWKE-NH2 | 498 |
| Rev[E > D]3F-2 | Ac-LFDKFADAFKDYVAKWKD-NH2 | 499 |
| Rev-[E3 > D]-3F-2 | Ac-LFDKFAEAFKDYVAKWKD-NH2 | 500 |
| Rev-[E7 > D]-3F-2 | Ac-LFEKFADAFKDYVAKWKD-NH2 | 501 |
| Rev[D11 > E]3F-2 | Ac-LFEKFAEAFKEYVAKWKD-NH2 | 502 |
| Rev-[D18 > E]3F-2 | Ac-LFEKFAEAFKDYVAKWKE-NH2 | 503 |
| Rev3F-1 | Ac-FAEKAWEFVKDYFAKLKD-NH2 | 504 |
| RevR4-3F-1 | Ac-FAERAWEFVKDYFAKLKD-NH2 | 505 |
| RevR10-3F-1 | Ac-FAEKAWEFVKDYFAKLKD-NH2 | 506 |
| RevR15-3F-1 | Ac-FAEKAWEFVKDYFAKLKD-NH2 | 507 |
| RevR17-3F-1 | Ac-FAEKAWEFVKDYFAKLRD-NH2 | 508 |
| Rev[D > E]3F-1 | Ac-FAEKAWEFVKEYFAKLKE-NH2 | 509 |
| Rev[E > D ]3F-1 | Ac-FADKAWDFVKDYFAKLKD-NH2 | 510 |
| Rev[E3 > D]-3F-1 | Ac-FADKAWEFVKDYFAKLKD-NH2 | 511 |
| Rev[E7 > D]3F-1 | Ac-FAEKAWDFVKDYFAKLKD-NH2 | 512 |
| Rev-[D11 > E]3F-1 | Ac-FAEKAWEFVKEYFAKLKD-NH2 | 513 |
| Rev-[D18 > E]3F-1 | Ac-FAEKAWEFVKDYFAKLKE-NH2 | 514 |
| Rev-5F | Ac-FFEKFKEFVKDYFAKLWD-NH2 | 515 |
| Rev-[D > E]5F | Ac-FFEKFKEFVKEYFAKLWE-NH2 | 516 |

TABLE 5-continued

Illustrates various class A and/or class Y peptide analogs with His incorporated into the sequence.

| Short name | Peptide sequence | SEQ ID NO |
|---|---|---|
| Rev-[E > D]5F | Ac-FFDKFKDFVKDYFAKLWD-NH2 | 517 |
| Rev-R4-5F | Ac-FFERFKEFVKDYFAKLWD-NH2 | 518 |
| Rev-R6-5F | Ac-FFEKFREFVKDYFAKLWD-NH2 | 519 |
| Rev-R10-5F | Ac-FFEKFKEFVRDYFAKLWD-NH2 | 520 |
| Rev-R15-5F | Ac-FFEKFKEFVKDYFARLWD-NH2 | 521 |
| Rev-[E3 > D]-5F | Ac-FFDKFKEFVKDYFAKLWD-NH2 | 522 |
| Rev-[E7 > D]5F | Ac-FFEKFKDFVKDYFAKLWD-NH2 | 523 |
| Rev-[D11 > E]-5F | Ac-FFEKFKEFVKEYFAKLWD-NH2 | 524 |
| Rev-[D18 > E]-5F | Ac-FFEKFKEFVKDYFAKLWE-NH2 | 525 |
| Rev-5F-2 | Ac-FLEKFKEFVKDYFAKFWD-NH2 | 526 |
| Rev-[D > E]-5F-2 | Ac-FLEKFKEFVKEYFAKFWE-NH2 | 527 |
| Rev-[E > D]-5F-2 | Ac-FLDKFKEFVKDYFAKFWD-NH2 | 528 |
| Rev-[E3 > D]-5F-2 | Ac-FLDKFKEFVKDYFAKFWD-NH2 | 529 |
| Rev-[E7 > D]-5F-2 | Ac-FLEKFKDFVKDYFAKFWD-NH2 | 530 |
| Rev-[D11 > E]-5F-2 | Ac-FLEKFKEFVKEYFAKFWD-NH2 | 531 |
| Rev-[D18 > E]-5F-2 | Ac-FLEKFKEFVKDYFAKFWE-NH2 | 532 |
| Rev-R4-5F-2 | Ac-FLERFKEFVKDYFAKFWD-NH2 | 533 |
| Rev-R6-5F-2 | Ac-FLEKFREFVKDYFAKFWD-NH2 | 534 |
| RevR10-5F-2 | Ac-FLEKFKEFVRDYFAKFWD-NH2 | 535 |
| Rev-R16-5F-2 | Ac-FLEKFKEFVKDYFARFWD-NH2 | 536 |
| Rev-6F | Ac-FFEKFKEFFKDYFAKLWD-NH2 | 537 |
| Rev-[D > E]-6F | Ac-FFEKFKEFFKEYFAKLWE-NH2 | 538 |
| Rev-[E > D]-6F | Ac-FFDKFKDFFKDYFAKLWD-NH2 | 539 |
| Rev-R4-6F | Ac-FFERFKEFFKDYFAKLWD-NH2 | 540 |
| Rev-R6-6F | Ac-FFEKFREFFKDYFAKLWD-NH2 | 541 |
| Rev-R10-6F | Ac-FFEKFKEFFKRDYFAKLWD-NH2 | 542 |
| Rev-R14-6F | Ac-FFERFKEFFKDYFARLWD-NH2 | 543 |
| Rev-[E3 > D]-6F | Ac-FFDKFKEFFKDYFAKLWD-NH2 | 544 |
| Rev-[E7 > D]-6F | Ac-FFEKFKDFFKDYFAKLWD-NH2 | 545 |
| Rev-[D11 > E]-6F | Ac-FFEKFKEFFKEYFAKLWD-NH2 | 546 |
| Rev-[D18 > E]-6F | Ac-FFEKFKEFFKDYFAKLWE-NH2 | 547 |
| Rev-4F | Ac-FAEKFKEAVKDYFAKFWD-NH2 | 548 |
| Rev-[D > E]-4F | Ac-FAEKFKEAVKEYFAKFWE-NH2 | 549 |
| Rev-[E > D]4F | Ac-FADKFKDAVKDYFAKFWD-NH2 | 550 |
| Rev-R4-4F | Ac-FAERFKEAVKDYFAKFWD-NH2 | 551 |
| Rev-R6-4F | Ac-FAEKFREAVKDYFAKFWD-NH2 | 552 |

TABLE 5-continued

Illustrates various class A and/or class Y peptide analogs with His incorporated into the sequence.

| Short name | Peptide sequence | SEQ ID NO |
|---|---|---|
| Rev-R10-4F | Ac-FAEKFKEAVRDYFAKFWD-NH2 | 553 |
| Rev-R14-4F | Ac-FAEKFKEAVKDYFARFWD-NH2 | 554 |
| 4F-2 | Ac-DKWKAVYDKFAEAFKEFF-NH2 | 555 |
| [D > E]-4F-2 | Ac-EKWKAVYEKFAEAFKEFF-NH2 | 556 |
| [E > D]-4F-2 | Ac-DKWKAVYDKFADAFKDFF-NH2 | 557 |
| R2-4F-2 | Ac-DRWKAVYDKFAEAFKEFF-NH2 | 558 |
| R4-4F-2 | Ac-DKWRAVYDKFAEAFKEFF-NH2 | 559 |
| R9-4F-2 | Ac-DKWKAVYDRFAEAFKEFF-NH2 | 560 |
| R14-4F-2 | Ac-DKWKAVYDKFAEAFREFF-NH2 | 561 |
| Rev4F-2 | Ac-FFEKFAEAFKDYVAKWKD-NH2 | 562 |
| Rev-[D > E]-4F-2 | Ac-FFEKFAEAFKEYVAKWKE-NH2 | 563 |
| Rev-[E > D]-3F-2 | Ac-FFDKFADAFKDYVAKWKD-NH2 | 564 |
| Rev-R4-4F-2 | Ac-FFERFAEAFKDYVAKWKD-NH2 | 565 |
| Rev-R10-4F-2 | Ac-FFERFAEAFRDYVAKWKD-NH2 | 566 |
| Rev-R15-4F-2 | Ac-FFEKFAEAFKDYVARWKD-NH2 | 567 |
| Rev-R17-4F-2 | Ac-FFERFAEAFKDYVAKWRD-NH2 | 568 |
| Rev-[E3 > D]-4F-2 | Ac-FFDKFAEAFKDYVAKWKD-NH2 | 569 |
| Rev-[E7 > D]-4F-2 | Ac-FFEKFADAFKDYVAKWKD-NH2 | 570 |
| Rev-[D11 > E]-4F-2 | Ac-FFERFAEAFKEYVAKWKD-NH2 | 571 |
| Rev-[D18 > E]-4F-2 | Ac-FFERFAEAFKDYVAKWKE-NH2 | 572 |
| Rev-7F | Ac-FFEKFKEFFKDYFAKFWD-NH2 | 573 |
| Rev-[E > D]-7F | Ac-FFDKFKDFFKDYFAKFWD-NH2 | 574 |
| Rev-[D > E]-7F | Ac-FFEKFKEFFKEYFAKFWE-NH2 | 575 |
| Rev-R4-7F | Ac-FFERFKEFFKDYFAKFWD-NH2 | 576 |
| Rev-R6-7F | Ac-FFEKFREFFKDYFAKFWD-NH2 | 577 |
| Rev-R10-7F | Ac-FFEKFKEFFRDYFAKFWD-NH2 | 578 |
| Rev-R14-7F | Ac-FFEKFKEFFKDYFARFWD-NH2 | 579 |
| Rev-[E3 > D]-7F | Ac-FFDKFKEFFKDYFAKFWD-NH2 | 580 |
| Rev-[E7 > D]7F | Ac-FFEKFKDFFKDYFAKFWD-NH2 | 581 |
| Rev-[D11 > E]-7F | Ac-FFEKFKEFFKEYFAKFWD-NH2 | 582 |
| Rev-[D18 > E]-7F | Ac-FFEKFKEFFKDYFAKFWE-NH2 | 583 |

It is also noted that any of the peptides described herein can comprise non-natural amino acids in addition to or instead of the corresponding the natural amino acids identified herein. Such modifications include, but are not limited to acetylation, amidation, formylation, methylation, sulfation, and the like. Illustrative non-natural amino acids include, but are not limited to Ornithine, norleucine, norvaline, N-methylvaline, 6-N-methyllysine, N-methylisoleucine, N-methylglycine, sarcosine, inosine, allo-isoleucine, isodesmolysine, 4-hydroxyproline, 3-hydroxyproline, allo-hydroxylysine, hydroxylisine, N-ethylasparagine, N-ethylglycine, 2,3-diaminopropionic acid, 2,2'-diaminopropionic acid, desmosine, 2,4-diaminobutyric acid, 2-aminopimelic acid, 3-aminoisobutyric acid, 2-aminoisobutyric acid, 2-aminoheptanoic acid, 6-aminocaproic acid, 4-aminobutyric acid, 2-aminobutyric acid, beta-alanine, 3-aminoadipic acid, 2-aminoadipic acid, and the like. In certain embodiments andy one or more of the "natural" amino acids of the peptides described herein, can be substituted with the corresponding non-natural amino acid (e.g. as describe above).

In certain embodiments, this invention contemplates particularly the use of modified lysines. Such modifications include, but are not limited to, biotin modification of epsilon lysines and/or methylation of the epsilon lysines. Illustative peptide comprising epsilon methylated lysines include, but are not limited to: Ac-D-W-F-K(eCH$_3$)$_2$-A-F-Y-D-K(eCH$_3$)$_2$- VK(eCH$_3$)$_2$-F-K(eCH$_3$)$_2$-E-A-F—NH(CH$_3$)$_2$ (SEQ ID NO:584) and : Ac-DWFK(eCH$_3$)$_2$AFYDK(eCH$_3$)$_2$ VAEK(eCH$_3$)$_2$FK(eCH$_3$)$_2$EAF—NH(CH$_3$)(SEQ ID NO:585). Other modified amino acids include but are not limited to ornithine analogs and homoaminoalanine analogs (instead of (CH$_2$)$_4$—NH$_2$ for Lys it can be —(CH$_2$)$_2$—NH$_2$ for Haa and —(CH$_2$)$_3$—NH$_2$ for Orn] and the like. It is noted that these modifications are illustrative and not intended to be limiting. Illustrative 4F analogues that possess modified amino acids are shown in Table 6.

TABLE 6

Illustrative 4F analogs that comprise modified amino acids.

| | SEQ ID NO: |
|---|---|
| εN-Dimethyl-Lys derivative of 4F (εN-Dime) | |
| Ac-D-W-F-K(εN-Dime)-A-F-Y-D-K(εN-Dime)-V-A-E-K (εN-Dime)-F-K(εN-Dime)-E-A-F-NH$_2$ | 586 |
| Ac-D-W-F-K-(εN-Dime)-A-F-Y-D-K(εN-Dime)-V-A-E-K (εN-Dime)-F-K((εN-Dime)-E-A-F-NH-Me | 587 |
| Ac-D-W-F-K-(εN-Dime)-A-F-Y-D-K(εN-Dime)-V-A-E-K (εN-Dime)-F-K(εN-Dime)-E-A-F-N-(Me)$_2$ | 588 |
| εN-Diethyl-Lys derivatives of 4F (εN-Diet) | |
| Ac-D-W-F-K(εN-Diet)-A-F-Y-D-K(εN-Diet)-V-A-E-K (εN-Diet)-F-K(εN-Diet)-E-A-F-NH$_2$ | 589 |
| Ac-D-W-F-K(εN-Diet)-A-F-Y-D-K(εN-Diet)-V-A-E-K (εN-Diet)-F-K(εN-Diet)-E-A-F-NH-Et | 590 |
| Ac-D-W-F-K(εN-Diet)-A-F-Y-D-K(εN-Diet)-V-A-E-K (εN-Diet)-F-K(εN-Diet)-E-A-F-NH-(Et)$_2$ | 591 |
| εN-Monomethyl-Lys derivative of 4F (εN-Me) | |
| Ac-D-W-F-K(εN-Me)-A-F-Y-D-K(εN-Me)-V-A-E-K(εN-Me)-F-K(εN-Me)-E-A-F-NH$_2$ | 592 |
| Ac-D-W-F-K(εN-Me)-A-F-Y-D-K(εN-Me)-V-A-E-K(εN-Me)-F-K(εN-Me)-E-A-F-NH-Me | 593 |
| Ac-D-W-F-K(εN-Me)-A-F-Y-D-K(εN-Me)-V-A-E-K(εN-Me)-F-K(εN-Me)-E-A-F-N-(Me)$_2$ | 594 |
| εN-ethylLys derivative of 4F (εN-Et) | |
| Ac-D-W-F-K(εN-Et)-A-F-Y-D-K(εN-Et)-V-A-E-K(εN-Et)-F-K(εN-Et)-E-A-F-NH$_2$ | 595 |
| Ac-D-W-F-K(εN-Et)-A-F-Y-D-K(εN-Et)-V-A-E-K(εN-Et)-F-K(εN-Et)-E-A-F-NH-Et | 596 |

TABLE 6-continued

Illustrative 4F analogs that comprise modified amino acids.

| | SEQ ID NO: |
|---|---|
| Ac-D-W-F-K(εN-Et)-A-F-Y-D-K(εN-Et)-V-A-E-K(εN-Et)-F-K(εN-Et)-E-A-F-NH-(Et)$_2$ | 597 |
| HomoLys analogs of 4F (hK) (—CH$_2$)$_5$—NH$_2$ | |
| Ac-D-W-F-hK-A-F-Y-D-hK-V-A-E-hK-F-hK-E-A-F-NH$_2$ | 598 |
| Ac-D-W-F-hK(εN-Dime)-A-F-Y-D-hK(εN-Dime)-V-A-E-hK(εN-Dime)-F-hK(εN-Dime)-E-A-F-NH$_2$ | 599 |
| Ac-D-W-F-hK(εN-Dime)-A-F-Y-D-hK(εN-Dime)-V-A-E-hK(εN-Dime)-F-hK(εN-Dime)-E-A-F-N-(Me)$_2$ | 600 |
| Ac-D-W-F-hK(εN-Dime)-A-F-Y-D-hK(εN-Dime)-V-A-E-hK(εN-Dime)-F-hK(εN-Dime)-E-A-F-NH-Me | 601 |
| Ac-D-W-F-hK(εN-Diet)-A-F-Y-D-hK(εN-Diet)-V-A-E-hK(εN-Diet)-F-hK(εN-Diet)-E-A-F-NH-Et | 602 |
| Ac-D-W-F-hK(εN-Me)-A-F-Y-D-hK(εN-Me)-V-A-E-hK (εN-Me)-F-hK(εN-Me)-E-A-F-NH$_2$ | 603 |
| Ac-D-W-F-hK(εN-Me)-A-F-Y-D-hK(εN-Me)-V-A-E-hK (εN-Me)-F-hK(εN-Me)-E-A-F-NH-Me | 604 |
| Ac-D-W-F-hK(εN-Me)-A-F-Y-D-hK(εN-Me)-V-A-E-hK (εN-Me)-F-hK(εN-Me)-E-A-F-N-(Me)$_2$ | 605 |
| Ac-D-W-F-hK(εN-Et)-A-F-Y-D-hK(εN-Et)-V-A-E-hK (εN-Et)-F-hK(εN-Et)-E-A-F-NH$_2$ | 606 |
| Ac-D-W-F-hK(εN-Et)-A-F-Y-D-hK(εN-Et)-V-A-E-hK (εN-Et)-F-hK(εN-Et)-E-A-F-NH-Et | 607 |
| Ac-D-W-F-hK(εN-Et)-A-F-Y-D-hK(εN-Et)-V-A-E-hK (εN-Et)-F-hK(εN-Et)-E-A-F-NH-(Et)$_2$ | 608 |
| 4F analogs in which K is replaced O (O = Ornithine, —(CH$_2$)$_3$—NH$_2$) | |
| Ac-D-W-F-O-A-F-Y-D-O-V-A-E-O-F-O-E-A-F-NH$_2$ | 609 |
| Ac-D-W-F-O(δN-Dime)-A-F-Y-D-O(δN-Dime)-V-A-E-O (δN-Dime)-F-O(δN-Dime)-E-A-F-NH$_2$ | 610 |
| Ac-D-W-F-O(δN-Dime)-A-F-Y-D-)(δN-Dime)-V-A-E-O (δN-Dime)-F-O(δN-Dime)-E-A-F-N-(Me)$_2$ | 611 |
| Ac-D-W-F-O(δN-Dime)-A-F-Y-D-O(δN-Dime)-V-A-E-O (δN-Dime)-F-O(δN-Dime)-E-A-F-NH-Me | 612 |
| Ac-D-W-F-O(δN-Diet)-A-F-Y-D-O(δN-Diet)-V-A-E-O (δN-Diet)-F-O(δN-Diet)-E-A-F-NH-Et | 613 |
| Ac-D-W-F-O(δN-Me)-A-F-Y-D-O(δN-Me)-V-A-E-O(δN-Me)-F-O(δN-Me)-E-A-F-NH$_2$ | 614 |
| Ac-D-W-F-O(δN-Me)-A-F-Y-D-O(δN-Me)-V-A-E-O(δN-Me)-F-O(δN-Me)-E-A-F-NH-Me | 615 |
| Ac-D-W-F-O(δN-Me)-A-F-Y-D-O(δN-Me)-V-A-E-O(δN-Me)-F-O(δN-Me)-E-A-F-N-(Me)$_2$ | 616 |
| Ac-D-W-F-O(δN-Et)-A-F-Y-D-O(δN-Et)-V-A-E-O(δN-Et)-F-O(δN-Et)-E-A-F-NH$_2$ | 617 |
| Ac-D-W-F-O(δN-Et)-A-F-Y-D-O(δN-Et)-V-A-E-O(δN-Et)-F-O(δN-Et)-E-A-F-NH-Et | 618 |
| Ac-D-W-F-O(δN-Et)-A-F-Y-D-O(δN-Et)-V-A-E-OdεN-Et)-F-O(δN-Et)-E-A-F-NH-(Et)$_2$ | 619 |

The peptides and modifications shown above are intended to be illustrative and not limiting.

D) Smaller Peptides.

It was also a surprising discovery that certain small peptides consisting of a minimum of three amino acids preferentially (but not necessarily) with one or more of the amino acids being the D-stereoisomer of the amino acid, and possessing hydrophobic domains to permit lipid protein interactions, and hydrophilic domains to permit a degree of water solubility also possess significant anti-inflammatory properties and are useful in treating one or more of the pathologies described herein. The "small peptides" typically range in length from 2 amino acids to about 15 amino acids, more preferably from about 3 amino acids to about 10 or 11 amino acids, and most preferably from about 4 to about 8 or 10 amino acids. In various embodiments the peptides are typically characterized by having hydrophobic terminal amino acids or terminal amino acids rendered hydrophobic by the attachment of one or more hydrophobic "protecting" groups. Various "small peptides" are described in copending applications U.S. Ser. No. 10/649,378, filed Aug. 26, 2003, and in U.S. Ser. No. 10/913,800, filed on Aug. 6, 2004, and in PCT Application PCT/US2004/026288.

In certain embodiments, the peptides can be characterized by Formula I (SEQ ID NO:620), below:

$$X^1\text{—}X^2\text{—}X^3{}_n\text{—}X^4 \qquad \text{I}$$

where, n is 0 or 1, $X^1$ is a hydrophobic amino acid and/or bears a hydrophobic protecting group, $X^4$ is a hydrophobic amino acid and/or bears a hydrophobic protecting group; and when n is 0 $X^2$ is an acidic or a basic amino acid; when n is 1: $X^2$ and $X^3$ are independently an acidic amino acid, a basic amino acid, an aliphatic amino acid, or an aromatic amino acid such that when $X^2$ is an acidic amino acid; $X^3$ is a basic amino acid, an aliphatic amino acid, or an aromatic amino acid; when $X^2$ is a basic amino acid; $X^3$ is an acidic amino acid, an aliphatic amino acid, or an aromatic amino acid; and when $X^2$ is an aliphatic or aromatic amino acid, $X^3$ is an acidic amino acid, or a basic amino acid.

Longer peptides (e.g., up to 10, 11, or 15 amino acids) are also contemplated within the scope of this invention. Typically where the shorter peptides (e.g., peptides according to formula I) are characterized by an acidic, basic, aliphatic, or aromatic amino acid, the longer peptides are characterized by acidic, basic, aliphatic, or aromatic domains comprising two or more amino acids of that type.

1) Functional Properties of Active Small Peptides.

It was a surprising finding of this invention that a number of physical properties predict the ability of small peptides (e.g., less than 10 amino acids, preferably less than 8 amino acids, more preferably from about 3 to about 5 or 6 amino acids) of this invention to render HDL more anti-inflammatory and to mitigate atherosclerosis and/or other pathologies characterized by an inflammatory response in a mammal. The physical properties include high solubility in ethyl acetate (e.g., greater than about 4 mg/mL), and solubility in aqueous buffer at pH 7.0. Upon contacting phospholipids such as 1,2-Dimyristoyl-sn-glycero-3-phosphocholine (DMPC), in an aqueous environment, the particularly effective small peptides induce or participate in the formation of particles with a diameter of approximately 7.5 nm (±0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm). In certain preferred embodiments, the small peptides have a molecular weight of less than about 900 Da.

Thus, in certain embodiments, this invention contemplates small peptides that ameliorate one or more symptoms of an indication/pathology described herein, e.g., an inflammatory condition, where the peptide(s): ranges in length from about 3 to about 8 amino acids, preferably from about 3 to about 6, or 7 amino acids, and more preferably from about 3 to about 5 amino acids; are soluble in ethyl acetate at a concentration greater than about 4mg/mL; are soluble in aqueous buffer at pH 7.0; when contacted with a phospholipid in an aqueous environment, form particles with a diameter of approximately 7.5 nm and/or form stacked bilayers with a bilayer dimension on the order of 3.4 to 4.1 nm with spacing between the bilayers in the stack of approximately 2 nm; have a molecular weight less than about 900 daltons; convert pro-inflammatory HDL to anti-inflammatory HDL or make anti-inflammatory HDL more anti-inflammatory; and do not have the amino acid sequence Lys-Arg-Asp-Ser (SEQ ID NO:751), especially in which Lys-Arg-Asp and Ser are all L amino acids. In certain embodiments, these small peptides protect a phospholipid against oxidation by an oxidizing agent.

While these small peptides need not be so limited, in certain embodiments, these small peptides can include the small peptides described below.

2) Tripeptides.

It was discovered that certain tripeptides (3 amino acid peptides) can be synthesized that show desirable properties as described herein (e.g., the ability to convert pro-inflammatory HDL to anti-inflammatory HDL, the ability to decrease LDL-induced monocyte chemotactic activity generated by artery wall cells, the ability to increase pre-beta HDL, etc.). In certain embodiments, the peptides are characterized by formula I, wherein N is zero, shown below as Formula II (SEQ ID NO:622):

$$X^1\text{—}X^2\text{—}X^4 \qquad \text{II}$$

where the end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, nicotinyl-, etc., and the C-terminus blocked with (tBu)-OtBu, etc.). In certain embodiments, the $X^2$ amino acid is either acidic (e.g., aspartic acid, glutamic acid, etc.) or basic (e.g., histidine, arginine, lysine, etc.). The peptide can be all L-amino acids or include one or more or all D-amino acids.

Certain preferred tripeptides of this invention include, but are not limited to the peptides shown in Table 7.

TABLE 7

Examples of certain preferred tripeptides bearing hydrophobic blocking groups and acidic, basic, or histidine central amino acids.

| $X^1$ | $X^2$ | $X^3$ | $X^4$ | SEQ ID NO |
|---|---|---|---|---|
| Boc-Lys(εBoc) | Arg | | Ser(tBu)-OtBu | 622 |
| Boc-Lys(εBoc) | Arg | | Thr(tBu)-OtBu | 623 |
| Boc-Trp | Arg | | Ile-OtBu | 624 |
| Boc-Trp | Arg | | Leu-OtBu | 625 |

TABLE 7-continued

Examples of certain preferred tripeptides bearing hydrophobic blocking groups and acidic, basic, or histidine central amino acids.

| X¹ | X² | X³ X⁴ | SEQ ID NO |
|---|---|---|---|
| Boc-Phe | Arg | Ile-OtBu | 626 |
| Boc-Phe | Arg | Leu-OtBu | 627 |
| Boc-Lys(εBoc) | Glu | Ser(tBu)-OtBu | 628 |
| Boc-Lys(εBoc) | Glu | Thr(tBu)-OtBu | 629 |
| Boc-Lys(εBoc) | Asp | Ser(tBu)-OtBu | 630 |
| Boc-Lys(εBoc) | Asp | Thr(tBu)-OtBu | 631 |
| Boc-Lys(εBoc) | Arg | Ser(tBu)-OtBu | 632 |
| Boc-Lys(εBoc) | Arg | Thr(tBu)-OtBu | 633 |
| Boc-Leu | Glu | Ser(tBu)-OtBu | 634 |
| Boc-Leu | Glu | Thr(tBu)-OtBu | 635 |
| Fmoc-Trp | Arg | Ser(tBu)-OtBu | 636 |
| Fmoc-Trp | Asp | Ser(tBu)-OtBu | 637 |
| Fmoc-Trp | Glu | Ser(tBu)-OtBu | 638 |
| Fmoc-Trp | Arg | Ser(tBu)-OtBu | 639 |
| Boc-Lys(εBoc) | Glu | Leu-OtBu | 640 |
| Fmoc-Leu | Arg | Ser(tBu)-OtBu | 641 |
| Fmoc-Leu | Asp | Ser(tBu)-OtBu | 642 |
| Fmoc-Leu | Glu | Ser(tBu)-OtBu | 643 |
| Fmoc-Leu | Arg | Ser(tBu)-OtBu | 644 |
| Fmoc-Leu | Arg | Thr(tBu)-OtBu | 645 |
| Boc-Glu | Asp | Tyr(tBu)-OtBu | 646 |
| Fmoc-Lys(εFmoc) | Arg | Ser(tBu)-OtBu | 647 |
| Fmoc-Trp | Arg | Ile-OtBu | 648 |
| Fmoc-Trp | Arg | Leu-OtBu | 649 |
| Fmoc-Phe | Arg | Ile-OtBu | 650 |
| Fmoc-Phe | Arg | Leu-OtBu | 651 |
| Boc-Trp | Arg | Phe-OtBu | 652 |
| Boc-Trp | Arg | Tyr-OtBu | 653 |
| Fmoc-Trp | Arg | Phe-OtBu | 654 |
| Fmoc-Trp | Arg | Tyr-OtBu | 655 |
| Boc-Orn(δBoc) | Arg | Ser(tBu)-OtBu | 656 |
| Nicotinyl Lys(εBoc) | Arg | Ser(tBu)-OtBu | 657 |
| Nicotinyl Lys(εBoc) | Arg | Thr(tBu)-OtBu | 658 |
| Fmoc-Leu | Asp | Thr(tBu)-OtBu | 659 |
| Fmoc-Leu | Glu | Thr(tBu)-OtBu | 660 |
| Fmoc-Leu | Arg | Thr(tBu)-OtBu | 661 |
| Fmoc-norLeu | Arg | Ser(tBu)-OtBu | 662 |
| Fmoc-norLeu | Asp | Ser(tBu)-OtBu | 663 |
| Fmoc-norLeu | Glu | Ser(tBu)-OtBu | 664 |
| Fmoc-Lys(εBoc) | Arg | Ser(tBu)-OtBu | 665 |
| Fmoc-Lys(εBoc) | Arg | Thr(tBu)-OtBu | 666 |
| Fmoc-Lys(εBoc) | Glu | Ser(tBu)-OtBu | 667 |
| Fmoc-Lys(εBoc) | Glu | Thr(tBu)-OtBu | 668 |
| Fmoc-Lys(εBoc) | Asp | Ser(tBu)-OtBu | 669 |
| Fmoc-Lys(εBoc) | Asp | Thr(tBu)-OtBu | 670 |
| Fmoc-Lys(εBoc) | Glu | Leu-OtBu | 671 |
| Fmoc-Lys(εBoc) | Arg | Leu-OtBu | 672 |
| Fmoc-Lys(εFmoc) | Arg | Thr(tBu)-OtBu | 673 |
| Fmoc-Lys(εFmoc) | Glu | Ser(tBu)-OtBu | 674 |
| Fmoc-Lys(εFmoc) | Glu | Thr(tBu)-OtBu | 675 |
| Fmoc-Lys(εFmoc) | Asp | Ser(tBu)-OtBu | 676 |
| Fmoc-Lys(εFmoc) | Asp | Thr(tBu)-OtBu | 677 |
| Fmoc-Lys(εFmoc) | Arg | Ser(tBu)-OtBu | 678 |
| Fmoc-Lys(εFmoc)) | Glu | Leu-OtBu | 679 |
| Boc-Lys(εFmoc) | Asp | Ser(tBu)-OtBu | 680 |
| Boc-Lys(εFmoc) | Asp | Thr(tBu)-OtBu | 681 |
| Boc-Lys(εFmoc) | Arg | Thr(tBu)-OtBu | 682 |
| Boc-Lys(εFmoc) | Glu | Leu-OtBu | 683 |
| Boc-Orn(δFmoc) | Glu | Ser(tBu)-OtBu | 684 |
| Boc-Orn(δFmoc) | Asp | Ser(tBu)-OtBu | 685 |
| Boc-Orn(δFmoc) | Asp | Thr(tBu)-OtBu | 686 |
| Boc-Orn(δFmoc) | Arg | Thr(tBu)-OtBu | 687 |
| Boc-Orn(δFmoc) | Glu | Thr(tBu)-OtBu | 688 |
| Fmoc-Trp | Asp | Ile-OtBu | 689 |
| Fmoc-Trp | Arg | Ile-OtBu | 690 |
| Fmoc-Trp | Glu | Ile-OtBu | 691 |
| Fmoc-Trp | Asp | Leu-OtBu | 692 |
| Fmoc-Trp | Glu | Leu-OtBu | 693 |
| Fmoc-Phe | Asp | Ile-OtBu | 694 |
| Fmoc-Phe | Asp | Leu-OtBu | 695 |
| Fmoc-Phe | Glu | Leu-OtBu | 696 |
| Fmoc-Trp | Arg | Phe-OtBu | 697 |

TABLE 7-continued

Examples of certain preferred tripeptides bearing hydrophobic blocking groups and acidic, basic, or histidine central amino acids.

| X¹ | X² | X³ | X⁴ | SEQ ID NO |
|---|---|---|---|---|
| Fmoc-Trp | Glu | | Phe-OtBu | 698 |
| Fmoc-Trp | Asp | | Phe-OtBu | 699 |
| Fmoc-Trp | Asp | | Tyr-OtBu | 700 |
| Fmoc-Trp | Arg | | Tyr-OtBu | 701 |
| Fmoc-Trp | Glu | | Tyr-OtBu | 702 |
| Fmoc-Trp | Arg | | Thr(tBu)-OtBu | 703 |
| Fmoc-Trp | Asp | | Thr(tBu)-OtBu | 704 |
| Fmoc-Trp | Glu | | Thr(tBu)-OtBu | 705 |
| Boc-Phe | Arg | | norLeu-OtBu | 706 |
| Boc-Phe | Glu | | norLeu-OtBu | 707 |
| Fmoc-Phe | Asp | | norLeu-OtBu | 708 |
| Boc-Glu | His | | Tyr(tBu)-OtBu | 709 |
| Boc-Leu | His | | Ser(tBu)-OtBu | 710 |
| Boc-Leu | His | | Thr(tBu)-OtBu | 711 |
| Boc-Lys(εBoc) | His | | Ser(tBu)-OtBu | 712 |
| Boc-Lys(εBoc) | His | | Thr(tBu)-OtBu | 713 |
| Boc-Lys(εBoc) | His | | Leu-OtBu | 714 |
| Boc-Lys(εFmoc) | His | | Ser(tBu)-OtBu | 715 |
| Boc-Lys(εFmoc) | His | | Thr(tBu)-OtBu | 716 |
| Boc-Lys(εFmoc) | His | | Leu-OtBu | 717 |
| Boc-Orn(δBoc) | His | | Ser(tBu)-OtBu | 718 |
| Boc-Orn(δFmoc) | His | | Thr(tBu)-OtBu | 719 |
| Boc-Phe | His | | Ile-OtBu | 720 |
| Boc-Phe | His | | Leu-OtBu | 721 |
| Boc-Phe | His | | norLeu-OtBu | 722 |
| Boc-Phe | Lys | | Leu-OtBu | 723 |
| Boc-Trp | His | | Ile-OtBu | 724 |
| Boc-Trp | His | | Leu-OtBu | 725 |
| Boc-Trp | His | | Phe-OtBu | 726 |
| Boc-Trp | His | | Tyr-OtBu | 727 |
| Boc-Phe | Lys | | Leu-OtBu | 728 |
| Fmoc-Lys(εFmoc) | His | | Ser(tBu)-OtBu | 729 |
| Fmoc-Lys(εFmoc) | His | | Thr(tBu)-OtBu | 730 |
| Fmoc-Lys(εFmoc) | His | | Leu-OtBu | 731 |
| Fmoc-Leu | His | | Ser(tBu)-OtBu | 732 |
| Fmoc-Leu | His | | Thr(tBu)-OtBu | 733 |
| Fmoc-Lys(εBoc) | His | | Ser(tBu)-OtBu | 734 |
| Fmoc-Lys(εBoc) | His | | Thr(tBu)-OtBu | 735 |
| Fmoc-Lys(εBoc) | His | | Leu-OtBu | 736 |
| Fmoc-Lys(εFmoc) | His | | Ser(tBu)-OtBu | 737 |
| Fmoc-Lys(εFmoc) | His | | Thr(tBu)-OtBu | 738 |
| Fmoc-norLeu | His | | Ser(tBu)-OtBu | 739 |
| Fmoc-Phe | His | | Ile-OtBu | 740 |
| Fmoc-Phe | His | | Leu-OtBu | 741 |
| Fmoc-Phe | His | | norLeu-OtBu | 742 |
| Fmoc-Trp | His | | Ser(tBu)-OtBu | 743 |
| Fmoc-Trp | His | | Ile-OtBu | 744 |
| Fmoc-Trp | His | | Leu-OtBu | 745 |
| Fmoc-Trp | His | | Phe-OtBu | 746 |
| Fmoc-Trp | His | | Tyr-OtBu | 747 |
| Fmoc-Trp | His | | Thr(tBu)-OtBu | 748 |
| Nicotinyl Lys(εBoc) | His | | Ser(tBu)-OtBu | 749 |
| Nicotinyl Lys(εBoc) | His | | Thr(tBu)-OtBu | 750 |

While the peptides of Table 7 are illustrated with particular protecting groups, it is noted that these groups may be substituted with other protecting groups as described herein and/or one or more of the shown protecting group can be eliminated.

3) Small Peptides with Central Acidic and Basic Amino Acids.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic amino acid and an acidic amino acid (e.g., in a 4 mer) or a basic domain and/or an acidic domain in a longer molecule.

These four-mers can be represented by Formula I in which $X^1$ and $X^4$ are hydrophobic and/or bear hydrophobic protecting group(s) as described herein and $X^2$ is acidic while $X^3$ is basic or $X^2$ is basic while $X^3$ is acidic. The peptide can be all L-amino acids or include one or more or all D-amino acids.

Certain preferred of this invention include, but are not limited to the peptides shown in Table 8.

TABLE 8

Illustrative examples of small peptides with central acidic and basic amino acids.

| X¹ | X² | X³ | X⁴ | SEQ ID NO |
|---|---|---|---|---|
| Boc-Lys(εBoc) | Arg | Asp | Ser(tBu)-OtBu | 751 |
| Boc-Lys(εBoc) | Arg | Asp | Thr(tBu)-OtBu | 752 |
| Boc-Trp | Arg | Asp | Ile-OtBu | 753 |
| Boc-Trp | Arg | Asp | Leu-OtBu | 754 |
| Boc-Phe | Arg | Asp | Leu-OtBu | 755 |
| Boc-Phe | Arg | Asp | Ile-OtBu | 756 |
| Boc-Phe | Arg | Asp | norLeu-OtBu | 757 |
| Boc-Phe | Arg | Glu | norLeu-OtBu | 758 |
| Boc-Phe | Arg | Glu | Ile-OtBu | 759 |
| Boc-Phe | Asp | Arg | Ile-OtBu | 760 |
| Boc-Phe | Glu | Arg | Ile-OtBu | 761 |
| Boc-Phe | Asp | Arg | Leu-OtBu | 762 |
| Boc-Phe | Arg | Glu | Leu-OtBu | 763 |
| Boc-Phe | Glu | Arg | Leu-OtBu | 764 |
| Boc-Phe | Asp | Arg | norLeu-OtBu | 765 |
| Boc-Phe | Glu | Arg | norLeu-OtBu | 766 |
| Boc-Lys(εBoc) | Glu | Arg | Ser(tBu)-OtBu | 767 |
| Boc-Lys(εBoc) | Glu | Arg | Thr(tBu)-OtBu | 768 |
| Boc-Lys(εBoc) | Asp | Arg | Ser(tBu)-OtBu | 769 |
| Boc-Lys(εBoc) | Asp | Arg | Thr(tBu)-OtBu | 770 |
| Boc-Lys(εBoc) | Arg | Glu | Ser(tBu)-OtBu | 771 |
| Boc-Lys(εBoc) | Arg | Glu | Thr(tBu)-OtBu | 772 |
| Boc-Leu | Glu | Arg | Ser(tBu)-OtBu | 773 |
| Boc-Leu | Glu | Arg | Thr(tBu)-OtBu | 774 |
| Fmoc-Trp | Arg | Asp | Ser(tBu)-OtBu | 775 |
| Fmoc-Trp | Asp | Arg | Ser(tBu)-OtBu | 776 |
| Fmoc-Trp | Glu | Arg | Ser(tBu)-OtBu | 777 |
| Fmoc-Trp | Arg | Glu | Ser(tBu)-OtBu | 778 |
| Boc-Lys(εBoc) | Glu | Arg | Leu-OtBu | 779 |
| Fmoc-Leu | Arg | Asp | Ser(tBu)-OtBu | 780 |
| Fmoc-Leu | Asp | Arg | Ser(tBu)-OtBu | 781 |
| Fmoc-Leu | Glu | Arg | Ser(tBu)-OtBu | 782 |
| Fmoc-Leu | Arg | Glu | Ser(tBu)-OtBu | 783 |
| Fmoc-Leu | Arg | Asp | Thr(tBu)-OtBu | 784 |
| Boc-Glu | Asp | Arg | Tyr(tBu)-OtBu | 785 |
| Fmoc-Lys(εFmoc) | Arg | Asp | Ser(tBu)-OtBu | 786 |
| Fmoc-Trp | Arg | Asp | Ile-OtBu | 787 |
| Fmoc-Trp | Arg | Asp | Leu-OtBu | 788 |
| Fmoc-Phe | Arg | Asp | Ile-OtBu | 789 |
| Fmoc-Phe | Arg | Asp | Leu-OtBu | 790 |
| Boc-Trp | Arg | Asp | Phe-OtBu | 791 |
| Boc-Trp | Arg | Asp | Tyr-OtBu | 792 |
| Fmoc-Trp | Arg | Asp | Phe-OtBu | 793 |
| Fmoc-Trp | Arg | Asp | Tyr-OtBu | 794 |
| Boc-Orn(δBoc) | Arg | Glu | Ser(tBu)-OtBu | 795 |
| Nicotinyl Lys(εBoc) | Arg | Asp | Ser(tBu)-OtBu | 796 |
| Nicotinyl Lys(εBoc) | Arg | Asp | Thr(tBu)-OtBu | 797 |
| Fmoc-Leu | Asp | Arg | Thr(tBu)-OtBu | 798 |
| Fmoc-Leu | Glu | Arg | Thr(tBu)-OtBu | 799 |
| Fmoc-Leu | Arg | Glu | Thr(tBu)-OtBu | 800 |
| Fmoc-norLeu | Arg | Asp | Ser(tBu)-OtBu | 801 |
| Fmoc-norLeu | Asp | Arg | Ser(tBu)-OtBu | 802 |
| Fmoc-norLeu | Glu | Arg | Ser(tBu)-OtBu | 803 |
| Fmoc-norLeu | Arg | Glu | Ser(tBu)-OtBu | 804 |
| Fmoc-Lys(εBoc) | Arg | Asp | Ser(tBu)-OtBu | 805 |
| Fmoc-Lys(εBoc) | Arg | Asp | Thr(tBu)-OtBu | 806 |
| Fmoc-Lys(εBoc) | Glu | Arg | Ser(tBu)-OtBu | 807 |
| Fmoc-Lys(εBoc) | Glu | Arg | Thr(tBu)-OtBu | 808 |
| Fmoc-Lys(εBoc) | Asp | Arg | Ser(tBu)-OtBu | 809 |
| Fmoc-Lys(εBoc) | Asp | Arg | Thr(tBu)-OtBu | 810 |
| Fmoc-Lys(εBoc) | Arg | Glu | Ser(tBu)-OtBu | 811 |
| Fmoc-Lys(εBoc) | Arg | Glu | Thr(tBu)-OtBu | 812 |
| Fmoc-Lys(εBoc) | Glu | Arg | Leu-OtBu | 813 |
| Fmoc-Lys(εBoc) | Arg | Glu | Leu-OtBu | 814 |
| Fmoc-Lys(εFmoc) | Arg | Asp | Thr(tBu)-OtBu | 815 |
| Fmoc-Lys(εFmoc) | Glu | Arg | Ser(tBu)-OtBu | 816 |
| Fmoc-Lys(εFmoc) | Glu | Arg | Thr(tBu)-OtBu | 817 |
| Fmoc-Lys(εFmoc) | Asp | Arg | Ser(tBu)-OtBu | 818 |
| Fmoc-Lys(εFmoc) | Asp | Arg | Thr(tBu)-OtBu | 819 |
| Fmoc-Lys(εFmoc) | Arg | Glu | Ser(tBu)-OtBu | 820 |
| Fmoc-Lys(εFmoc) | Arg | Glu | Thr(tBu)-OtBu | 821 |
| Fmoc-Lys(εFmoc)) | Glu | Arg | Leu-OtBu | 822 |
| Boc-Lys(εFmoc) | Arg | Asp | Ser(tBu)-OtBu | 823 |

TABLE 8-continued

Illustrative examples of small peptides with central acidic and basic amino acids.

| $X^1$ | $X^2$ | $X^3$ | $X^4$ | SEQ ID NO |
|---|---|---|---|---|
| Boc-Lys(εFmoc) | Arg | Asp | Thr(tBu)-OtBu | 824 |
| Boc-Lys(εFmoc) | Glu | Arg | Ser(tBu)-OtBu | 825 |
| Boc-Lys(εFmoc) | Glu | Arg | Thr(tBu)-OtBu | 826 |
| Boc-Lys(εFmoc) | Asp | Arg | Ser(tBu)-OtBu | 827 |
| Boc-Lys(εFmoc) | Asp | Arg | Thr(tBu)-OtBu | 828 |
| Boc-Lys(εFmoc) | Arg | Glu | Ser(tBu)-OtBu | 829 |
| Boc-Lys(εFmoc) | Arg | Glu | Thr(tBu)-OtBu | 830 |
| Boc-Lys(εFmoc) | Glu | Arg | Leu-*OtBu* | 831 |
| Boc-Orn(δFmoc) | Arg | Glu | Ser(tBu)-OtBu | 832 |
| Boc-Orn(δFmoc) | Glu | Arg | Ser(tBu)-OtBu | 833 |
| Boc-Orn(δFmoc) | Arg | Asp | Ser(tBu)-OtBu | 834 |
| Boc-Orn(δFmoc) | Asp | Arg | Ser(tBu)-OtBu | 835 |
| Boc-Orn(δFmoc) | Asp | Arg | Thr(tBu)-OtBu | 836 |
| Boc-Orn(δFmoc) | Arg | Asp | Thr(tBu)-OtBu | 837 |
| Boc-Orn(δFmoc) | Glu | Arg | Thr(tBu)-OtBu | 838 |
| Boc-Orn(δFmoc) | Arg | Glu | Thr(tBu)-OtBu | 839 |
| Fmoc-Trp | Asp | Arg | Ile-OtBu | 840 |
| Fmoc-Trp | Arg | Glu | Ile-OtBu | 841 |
| Fmoc-Trp | Glu | Arg | Ile-OtBu | 842 |
| Fmoc-Trp | Asp | Arg | Leu-OtBu | 843 |
| Fmoc-Trp | Arg | Glu | Leu-OtBu | 844 |
| Fmoc-Trp | Glu | Arg | Leu-OtBu | 845 |
| Fmoc-Phe | Asp | Arg | Ile-OtBu | 846 |
| Fmoc-Phe | Arg | Glu | Ile-OtBu | 847 |
| Fmoc-Phe | Glu | Arg | Ile-OtBu | 848 |
| Fmoc-Phe | Asp | Arg | Leu-OtBu | 849 |
| Fmoc-Phe | Arg | Glu | Leu-OtBu | 850 |
| Fmoc-Phe | Glu | Arg | Leu-OtBu | 851 |
| Fmoc-Trp | Arg | Asp | Phe-OtBu | 852 |
| Fmoc-Trp | Arg | Glu | Phe-OtBu | 853 |
| Fmoc-Trp | Glu | Arg | Phe-OtBu | 854 |
| Fmoc-Trp | Asp | Arg | Tyr-OtBu | 855 |
| Fmoc-Trp | Arg | Glu | Tyr-OtBu | 856 |
| Fmoc-Trp | Glu | Arg | Tyr-OtBu | 857 |
| Fmoc-Trp | Arg | Asp | Thr(tBu)-OtBu | 858 |
| Fmoc-Trp | Asp | Arg | Thr(tBu)-OtBu | 859 |
| Fmoc-Trp | Arg | Glu | Thr(tBu)-OtBu | 860 |
| Fmoc-Trp | Glu | Arg | Thr(tBu)-OtBu | 861 |
| Fmoc-Phe | Arg | Asp | norLeu-OtBu | 862 |
| Fmoc-Phe | Arg | Glu | norLeu-OtBu | 863 |
| Boc-Phe | Lys | Asp | Leu-OtBu | 864 |
| Boc-Phe | Asp | Lys | Leu-OtBu | 865 |
| Boc-Phe | Lys | Glu | Leu-OtBu | 866 |
| Boc-Phe | Glu | Lys | Leu-OtBu | 867 |
| Boc-Phe | Lys | Asp | Ile-OtBu | 868 |
| Boc-Phe | Asp | Lys | Ile-OtBu | 869 |
| Boc-Phe | Lys | Glu | Ile-OtBu | 870 |
| Boc-Phe | Glu | Lys | Ile-OtBu | 871 |
| Boc-Phe | Lys | Asp | norLeu-OtBu | 872 |
| Boc-Phe | Asp | Lys | norLeu-OtBu | 873 |
| Boc-Phe | Lys | Glu | norLeu-OtBu | 874 |
| Boc-Phe | Glu | Lys | norLeu-OtBu | 875 |
| Boc-Phe | His | Asp | Leu-OtBu | 876 |
| Boc-Phe | Asp | His | Leu-OtBu | 877 |
| Boc-Phe | His | Glu | Leu-OtBu | 878 |
| Boc-Phe | Glu | His | Leu-OtBu | 879 |
| Boc-Phe | His | Asp | Ile-OtBu | 880 |
| Boc-Phe | Asp | His | Ile-OtBu | 881 |
| Boc-Phe | His | Glu | Ile-OtBu | 882 |
| Boc-Phe | Glu | His | Ile-OtBu | 883 |
| Boc-Phe | His | Asp | norLeu-OtBu | 884 |
| Boc-Phe | Asp | His | norLeu-OtBu | 885 |
| Boc-Phe | His | Glu | norLeu-OtBu | 886 |
| Boc-Phe | Glu | His | norLeu-OtBu | 887 |
| Boc-Lys(εBoc) | Lys | Asp | Ser(tBu)-OtBu | 888 |
| Boc-Lys(εBoc) | Asp | Lys | Ser(tBu)-OtBu | 889 |
| Boc-Lys(εBoc) | Lys | Glu | Ser(tBu)-OtBu | 890 |
| Boc-Lys(εBoc) | Glu | Lys | Ser(tBu)-OtBu | 891 |
| Boc-Lys(εBoc) | His | Asp | Ser(tBu)-OtBu | 892 |
| Boc-Lys(εBoc) | Asp | His | Ser(tBu)-OtBu | 893 |
| Boc-Lys(εBoc) | His | Glu | Ser(tBu)-OtBu | 894 |
| Boc-Lys(εBoc) | Glu | His | Ser(tBu)-OtBu | 895 |

While the peptides of Table 8 are illustrated with particular protecting groups, it is noted that these groups may be substituted with other protecting groups as described herein and/or one or more of the shown protecting group can be eliminated.

4) Small Peptides Having Either an Acidic or Basic Amino Acid in the Center Together with a Central Aliphatic Amino Acid.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups. End amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aliphatic amino acid (e.g., in a 4 mer) or a basic domain or an acidic domain and an aliphatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aliphatic or $X^2$ is aliphatic while $X^3$ is acidic or basic. The peptide can be all L-amino acids or include one, or more, or all D-amino acids.

Certain preferred peptides of this invention include, but are not limited to the peptides shown in Table 9.

TABLE 9

Examples of certain preferred peptides having either an acidic or basic amino acid in the center together with a central aliphatic amino acid.

| $X^1$ | $X^2$ | $X^3$ | $X^4$ | SEQ ID NO |
|---|---|---|---|---|
| Fmoc-Lys(εBoc) | Leu | Arg | Ser(tBu)-OtBu | 896 |
| Fmoc-Lys(εBoc) | Arg | Leu | Ser(tBu)-OtBu | 897 |
| Fmoc-Lys(εBoc) | Leu | Arg | Thr(tBu)-OtBu | 898 |
| Fmoc-Lys(εBoc) | Arg | Leu | Thr(tBu)-OtBu | 899 |
| Fmoc-Lys(εBoc) | Glu | Leu | Ser(tBu)-OtBu | 900 |
| Fmoc-Lys(εBoc) | Leu | Glu | Ser(tBu)-OtBu | 901 |
| Fmoc-Lys(εBoc) | Glu | Leu | Thr(tBu)-OtBu | 902 |
| Fmoc-Lys( Boc) | Leu | Glu | Thr(tBu)-OtBu | 903 |
| Fmoc-Lys(εFmoc) | Leu | Arg | Ser(tBu)-OtBu | 904 |
| Fmoc-Lys(εFmoc) | Leu | Arg | Thr(tBu)-OtBu | 905 |
| Fmoc-Lys(εFmoc) | Glu | Leu | Ser(tBu)-OtBu | 906 |
| Fmoc-Lys(εFmoc) | Glu | Leu | Thr(tBu)-OtBu | 907 |
| Boc-Lys(Fmoc) | Glu | Ile | Thr(tBu)-OtBu | 908 |
| Boc-Lys(εFmoc) | Leu | Arg | Ser(tBu)-OtBu | 909 |
| Boc-Lys(εFmoc) | Leu | Arg | Thr(tBu)-OtBu | 910 |
| Boc-Lys(εFmoc) | Glu | Leu | Ser(tBu)-OtBu | 911 |
| Boc-Lys(εFmoc) | Glu | Leu | Thr(tBu)-OtBu | 912 |
| Boc-Lys(εBoc) | Leu | Arg | Ser(tBu)-OtBu | 913 |
| Boc-Lys(εBoc) | Arg | Phe | Thr(tBu)-OtBu | 914 |
| Boc-Lys(εBoc) | Leu | Arg | Thr(tBu)-OtBu | 915 |
| Boc-Lys(εBoc) | Glu | Ile | Thr(tBu) | 916 |
| Boc-Lys(εBoc) | Glu | Val | Thr(tBu) | 917 |
| Boc-Lys(εBoc) | Glu | Ala | Thr(tBu) | 918 |
| Boc-Lys(εBoc) | Glu | Gly | Thr(tBu) | 919 |
| Boc-Lys(εBoc) | Glu | Leu | Ser(tBu)-OtBu | 920 |
| Boc-Lys(εBoc) | Glu | Leu | Thr(tBu)-OtBu | 921 |

While the peptides of Table 9 are illustrated with particular protecting groups, it is noted that these groups may be substituted with other protecting groups as described herein and/or one or more of the shown protecting group can be eliminated.

5) Small Peptides Having Either an Acidic or Basic Amino Acid in the Center Together with a Central Aromatic Amino Acid.

In certain embodiments, the "small" peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aromatic amino acid (e.g., in a 4 mer) or a basic domain or an acidic domain and an aromatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aromatic or $X^2$ is aromatic while $X^3$ is acidic or basic. The peptide can be all L-amino acids or include one, or more, or all D-amino acids. Five-mers can be represented by a minor modification of Formula I in which $X^5$ is inserted as shown in Table 10 and in which $X^5$ is typically an aromatic amino acid.

Certain preferred peptides of this invention include, but are not limited to the peptides shown in Table 10.

TABLE 10

Examples of certain preferred peptides having either an acidic or basic amino acid in the center together with a central aromatic amino acid.

| X¹ | X² | X³ | X⁵ | X⁴ | SEQ ID NO |
|---|---|---|---|---|---|
| Fmoc-Lys(εBoc) | Arg | Trp | | Tyr(tBu)-OtBu | 922 |
| Fmoc-Lys(εBoc) | Trp | Arg | | Tyr(tBu)-OtBu | 923 |
| Fmoc-Lys(εBoc) | Arg | Tyr | | Trp-OtBu | 924 |
| Fmoc-Lys(εBoc) | Tyr | Arg | | Trp-OtBu | 925 |
| Fmoc-Lys(εBoc) | Arg | Tyr | Trp | Thr(tBu)-OtBu | 926 |
| Fmoc-Lys(εBoc) | Arg | Tyr | | Thr(tBu)-OtBu | 927 |
| Fmoc-Lys(εBoc) | Arg | Trp | | Thr(tBu)-OtBu | 928 |
| Fmoc-Lys(εFmoc) | Arg | Trp | | Tyr(tBu)-OtBu | 929 |
| Fmoc-Lys(εFmoc) | Arg | Tyr | | Trp-OtBu | 930 |
| Fmoc-Lys(εFmoc) | Arg | Tyr | Trp | Thr(tBu)-OtBu | 931 |
| Fmoc-Lys(εFmoc) | Arg | Tyr | | Thr(tBu)-OtBu | 932 |
| Fmoc-Lys(εFmoc) | Arg | Trp | | Thr(tBu)-OtBu | 933 |
| Boc-Lys(εFmoc) | Arg | Trp | | Tyr(tBu)-OtBu | 934 |
| Boc-Lys(εFmoc) | Arg | Tyr | | Trp-OtBu | 935 |
| Boc-Lys(εFmoc) | Arg | Tyr | Trp | Thr(tBu)-OtBu | 936 |
| Boc-Lys(εFmoc) | Arg | Tyr | | Thr(tBu)-OtBu | 937 |
| Boc-Lys(εFmoc) | Arg | Trp | | Thr(tBu)-OtBu | 938 |
| Boc-Glu | Lys(εFmoc) | Arg | | Tyr(tBu)-OtBu | 939 |
| Boc-Lys(εBoc) | Arg | Trp | | Tyr(tBu)-OtBu | 940 |
| Boc-Lys(εBoc) | Arg | Tyr | | Trp-OtBu | 941 |
| Boc-Lys(εBoc) | Arg | Tyr | Trp | Thr(tBu)-OtBu | 942 |
| Boc-Lys(εBoc) | Arg | Tyr | | Thr(tBu)-OtBu | 943 |
| Boc-Lys(εBoc) | Arg | Phe | | Thr(tBu)-OtBu | 944 |
| Boc-Lys(εBoc) | Arg | Trp | | Thr(tBu)-OtBu | 945 |

While the peptides of Table 10 are illustrated with particular protecting groups, it is noted that these groups may be substituted with other protecting groups as described herein and/or one or more of the shown protecting group can be eliminated.

6) Small Peptides Having Aromatic Amino Acids or Aromatic Amino Acids Separated by Histidine(s) at the Center.

In certain embodiments, the peptides of this invention are characterized by π electrons that are exposed in the center of the molecule which allow hydration of the particle and that allow the peptide particles to trap pro-inflammatory oxidized lipids such as fatty acid hydroperoxides and phospholipids that contain an oxidation product of arachidonic acid at the sn-2 position.

In certain embodiments, these peptides consist of a minimum of 4 amino acids and a maximum of about 10 amino acids, preferentially (but not necessarily) with one or more of the amino acids being the D-sterioisomer of the amino acid, with the end amino acids being hydrophobic either because of a hydrophobic side chain or because the terminal amino acid(s) bear one or more hydrophobic blocking group(s), (e.g., an N-terminus blocked with Boc-, Fmoc-, Nicotinyl-, and the like, and a C-terminus blocked with (tBu)-OtBu groups and the like). Instead of having an acidic or basic amino acid in the center, these peptides generally have an aromatic amino acid at the center or have aromatic amino acids separated by histidine in the center of the peptide.

Certain preferred peptides of this invention include, but are not limited to the peptides shown in Table 11.

TABLE 11

Examples of peptides having aromatic amino acids in the center or aromatic amino acids or aromatic domains separated by one or more histidines.

| X¹ | X² | X³ | X⁴ | X⁵ | SEQ ID NO |
|---|---|---|---|---|---|
| Boc-Lys(εBoc) | Phe | Trp | Phe | Ser(tBu)-OtBu | 946 |
| Boc-Lys(εBoc) | Phe | Trp | Phe | Thr(tBu)-OtBu | 947 |
| Boc-Lys(εBoc) | Phe | Tyr | Phe | Ser(tBu)-OtBu | 948 |
| Boc-Lys(εBoc) | Phe | Tyr | Phe | Thr(tBu)-OtBu | 949 |
| Boc-Lys(εBoc) | Phe | His | Phe | Ser(tBu)-OtBu | 950 |
| Boc-Lys(εBoc) | Phe | His | Phe | Thr(tBu)-OtBu | 951 |
| Boc-Lys(εBoc) | Val | Phe | Phe-Tyr | Ser(tBu)-OtBu | 952 |
| Nicotinyl-Lys(εBoc) | Phe | Trp | Phe | Ser(tBu)-OtBu | 953 |
| Nicotinyl-Lys(εBoc) | Phe | Trp | Phe | Thr(tBu)-OtBu | 954 |
| Nicotinyl-Lys(εBoc) | Phe | Tyr | Phe | Ser(tBu)-OtBu | 955 |

TABLE 11-continued

Examples of peptides having aromatic amino acids in the center or aromatic amino acids or aromatic domains separated by one or more histidines.

| X¹ | X² | X³ | X⁴ | X⁵ | SEQ ID NO |
|---|---|---|---|---|---|
| Nicotinyl-Lys(εBoc) | Phe | Tyr | Phe | Thr(tBu)-OtBu | 956 |
| Nicotinyl-Lys(εBoc) | Phe | His | Phe | Ser(tBu)-OtBu | 957 |
| Nicotinyl-Lys(εBoc) | Phe | His | Phe | Thr(tBu)-OtBu | 958 |
| Boc-Leu | Phe | Trp | Phe | Thr(tBu)-OtBu | 959 |
| Boc-Leu | Phe | Trp | Phe | Ser(tBu)-OtBu | 960 |

While the peptides of Table 11 are illustrated with particular protecting groups, it is noted that these groups may be substituted with other protecting groups as described herein and/or one or more of the shown protecting group can be eliminated.

7) Summary of Tripeptides and Tetrapeptides.

For the sake of clarity, a number of tripeptides and tetrapeptides of this invention are generally summarized below in Table 12.

TABLE 12

General structure of certain peptides of this invention.

| X¹ | X² | X³ | X⁴ |
|---|---|---|---|
| hydrophobic side chain or hydrophobic protecting group(s) | Acidic or Basic | — | hydrophobic side chain or hydrophobic protecting group(s) |
| hydrophobic side chain or hydrophobic protecting group(s) | Basic | Acidic | hydrophobic side chain or hydrophobic protecting group(s) |
| hydrophobic side chain or hydrophobic protecting group(s) | Acidic | Basic | hydrophobic side chain or hydrophobic protecting group(s) |
| hydrophobic side chain or hydrophobic protecting group(s) | Acidic or Basic | Aliphatic | hydrophobic side chain or hydrophobic protecting group(s) |
| hydrophobic side chain or hydrophobic protecting group(s) | Aliphatic | Acidic or Basic | hydrophobic side chain or hydrophobic protecting group(s) |
| hydrophobic side chain or hydrophobic protecting group(s) | Acidic or Basic | Aromatic | hydrophobic side chain or hydrophobic protecting group(s) |
| hydrophobic side chain or hydrophobic protecting group(s) | Aromatic | Acidic or Basic | hydrophobic side chain or hydrophobic protecting group(s) |
| hydrophobic side chain or hydrophobic protecting group(s) | Aromatic | His Aromatic | hydrophobic side chain or hydrophobic protecting group(s) |

Where longer peptides are desired, X² and X³ can represent domains (e.g., regions of two or more amino acids of the specified type) rather than individual amino acids. Table 12 is intended to be illustrative and not limiting. Using the teaching provided herein, other suitable peptides can readily be identified.

8) Paired Amino Acids and Dipeptides.

In certain embodiments, this invention pertains to the discovery that certain pairs of amino acids, administered in conjunction with each other or linked to form a dipeptide have one or more of the properties described herein. Thus, without being bound to a particular theory, it is believed that when the pairs of amino acids are administered in conjunction with each other, as described herein, they are capable participating in or inducing the formation of micelles in vivo.

Similar to the other small peptides described herein, it is believed that the pairs of peptides will associate in vivo, and demonstrate physical properties including high solubility in ethyl acetate (e.g., greater than about 4 mg/mL), solubility in aqueous buffer at pH 7.0. Upon contacting phospholipids such as 1,2-Dimyristoyl-sn-glycero-3-phosphocholine (DMPC), in an aqueous environment, it is believed the pairs of amino acids induce or participate in the formation of particles with a diameter of approximately 7.5 nm (±0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm).

Moreover, it is further believed that the pairs of amino acids can display one or more of the following physiologically relevant properties:

1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-βHDL;
4. They raise HDL cholesterol; and/or
5. They increase HDL paraoxonase activity.

The pairs of amino acids can be administered as separate amino acids (administered sequentially or simultaneously, e.g. in a combined formulation) or they can be covalently coupled directly or through a linker (e.g. a PEG linker, a carbon linker, a branched linker, a straight chain linker, a heterocyclic linker, a linker formed of derivatized lipid, etc.). In certain embodiments, the pairs of amino acids are covalently linked through a peptide bond to form a dipeptide. In various embodiments while the dipeptides will typically comprise two amino acids each bearing an attached protecting group, this invention also contemplates dipeptides wherein only one of the amino acids bears one or more protecting groups.

The pairs of amino acids typically comprise amino acids where each amino acid is attached to at least one protecting group (e.g., a hydrophobic protecting group as described herein). The amino acids can be in the D or the L form. In certain embodiments, where the amino acids comprising the pairs are not attached to each other, each amino acid bears two protecting groups (e.g., such as molecules 1 and 2 in Table 13).

TABLE 13

Illustrative amino acid pairs of this invention.

| | Amino Acid Pair/dipeptide |
|---|---|
| 1. | Boc-Arg-OtBu* |
| 2. | Boc-Glu-OtBu* |
| 3. | Boc-Phe-Arg-OtBu** |
| 4. | Boc-Glu-Leu-OtBu** |
| 5. | Boc-Arg-Glu-OtBu*** |

*This would typically be administered in conjunction with a second amino acid.
**In certain embodiments, these dipeptides would be administered in conjunction with each other.
***In certain embodiments, this peptide would be administered either alone or in combination with one of the other peptides described herein..

Suitable pairs of amino acids can readily be identified by providing the pair of protected amino acids and/or a dipeptide and then screening the pair of amino acids/dipeptide for one or more of the physical and/or physiological properties described above. In certain embodiments, this invention excludes pairs of amino acids and/or dipeptides comprising aspartic acid and phenylalanine. In certain embodiments, this invention excludes pairs of amino acids and/or dipeptides in which one amino acid is (−)-N-[(trans-4-isopropylcyclohexane)carbonyl]-D-phenylalanine (nateglinide).

In certain embodiments, the amino acids comprising the pair are independently selected from the group consisting of an acidic amino acid (e.g., aspartic acid, glutamic acid, etc.), a basic amino acid (e.g., lysine, arginine, histidine, etc.), and a non-polar amino acid (e.g., alanine, valine, leucine, isoleucine, proline, phenylalanine, tryptophan, methionine, etc.). In certain embodiments, where the first amino acid is acidic or basic, the second amino acid is non-polar and where the second amino acid is acidic or basic, the first amino acid is non-polar. In certain embodiments, where the first amino acid is acidic, the second amino acid is basic, and vice versa. (see, e.g., Table 14).

Similar combinations can be obtained by administering pairs of dipeptides. Thus, for example in certain embodiments, molecules 3 and 4 in Table 13 would be administered in conjunction with each other.

TABLE 14

Certain generalized amino acid pairs/dipeptides.

| | First Amino acid | Second Amino acid |
|---|---|---|
| 1. | Acidic | Basic |
| 2. | Basic | Acidic |
| 3. | Acidic | Non-polar |
| 4. | Non-polar | Acidic |
| 5. | Basic | Non-polar |
| 6. | Non-polar | Basic |

It is noted that these amino acid pairs/dipeptides are intended to be illustrative and not limiting. Using the teaching provided herein other suitable amino acid pairs/dipeptides can readily be determined.

E) Apo-J (G* Peptides).

In certain It was a discovery of this invention that peptides that mimicking the amphipathic helical domains of apo J are capable of mitigating one or more symptoms of atherosclerosis and/or other pathologies described herein. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A number of suitable G* amphipathic peptides are described in copending applications U.S. Ser. No. 10/120, 508, filed Apr. 5, 2002, U.S. Ser. No. 10/520,207, filed Apr. 1, 2003, and PCT Application PCT/US03/09988, filed Apr. 1, 2003. In addition, a variety of suitable peptides of this invention that are related to G* amphipathic helical domains of apo J are illustrated in Table 15.

TABLE 15

Certain illustrative peptides for use in this invention related to G* amphipathic helical domains of apo J.

| Amino Acid Sequence | SEQ ID NO |
|---|---|
| LLEQLNEQFNWVSRLANLTQGE | 961 |
| LLEQLNEQFNWVSRLANL | 962 |
| NELQEMSNQGSKYVNKEIQNAVNGV | 963 |
| IQNAVNGVKQIKTLIEKTNEE | 964 |
| RKTLLSNLEEAKKKKEDALNETRESETKLKEL | 965 |
| PGVCNETMMALWEECK | 966 |
| PCLKQTCMKFYARVCR | 967 |
| ECKPCLKQTCMKFYARVCR | 968 |
| LVGRQLEEFL | 969 |
| MNGDRIDSLLEN | 970 |
| QQTHMLDVMQD | 971 |
| FSRASSIIDELFQD | 972 |
| PFLEMIHEAQQAMDI | 973 |
| PTEFIREGDDD | 974 |
| RMKDQCDKCREILSV | 975 |
| PSQAKLRRELDESLQVAERLTRKYNELLKSYQ | 976 |
| LLEQLNEQFNWVSRLANLTEGE | 977 |
| DQYYLRVTTVA | 978 |
| PSGVTEVVVKLFDS | 979 |
| PKFMETVAEKALQEYRKKHRE | 980 |

The peptides of this invention, however, are not limited to G* variants of apo J. Generally speaking G* domains from essentially any other protein preferably apo proteins are also suitable. The particular suitability of such proteins can readily be determined using assays for protective activity (e.g., protecting LDL from oxidation, and the like), e.g. as illustrated herein in the Examples. Some particularly preferred proteins include G* amphipathic helical domains or variants thereof (e.g., conservative substitutions, and the like) of proteins including, but not limited to apo AI, apo AIV, apo E, apo CII, apo CIII, and the like.

Certain preferred peptides for related to G* amphipathic helical domains related to apoproteins other than apo J are illustrated in Table 16.

TABLE 16

Peptides for use in this invention related to G* amphipathic helical domains related to apoproteins other than apo J.

| Amino Acid Sequence | SEQ ID NO |
|---|---|
| WDRVKDLATVYVDVLKDSGRDYVSQF (Related to the 8 to 33 region of apo AI) | 981 |
| VATVMWDYFSQLSNNAKEAVEHLQK (Related to the 7 to 31 region of apo AIV) | 982 |
| RWELALGRFWDYLRWVQTLSEQVQEEL (Related to the 25 to 51 region of apo E) | 983 |
| LSSQVTQELRALMDETMKELKELKAYKSELEEQLT (Related to the 52 to 83 region of apo E) | 984 |
| ARLSKELQAAQARLGADMEDVCGRLV (Related to the 91 to 116 region of apo E) | 985 |
| VRLASHLRKLRKRLLRDADDLQKRLA (Related to the 135 to 160 region of apo E) | 986 |
| PLVEDMQRQWAGLVEKVQA (267 to 285 of apo E.27) | 987 |
| MSTYTGIFTDQVLSVLK (Related to the 60 to 76 region of apo CII) | 988 |
| LLSFMQGYMKHATKTAKDALSS (Related to the 8 to 29 region of apo CIII) | 989 |

Additional illustrative G* peptides are shown in Table 17.

TABLE 17

Additional illustrative G* peptides.

| Peptide | SEQ ID NO |
|---|---|
| Ac-Lys-Trp-Ile-Tyr-His-Leu-Thr-Glu-Gly-Ser-Thr-Asp-Leu-Arg-Thr-Glu-Gly-NH$_2$ | 990 |
| Ac-Lys-Trp-Phe-Tyr-His-Leu-Thr-Glu-Gly-Ser-Thr-Asp-Leu-Arg-Thr-Glu-Gly-NH$_2$ | 991 |
| Ac-Lys-Trp-Leu-Tyr-His-Leu-Thr-Glu-Gly-Ser-Thr-Asp-Leu-Arg-Thr-Glu-Gly-NH$_2$ | 992 |
| Ac-Lys-Trp-Val-Tyr-His-Leu-Thr-Glu-Gly-Ser-Thr-Asp-Leu-Arg-Thr-Glu-Gly-NH$_2$ | 993 |
| Ac-Lys-Tyr-Ile-Trp-His-Leu-Thr-Glu-Gly-Ser-Thr-Asp-Leu-Arg-Thr-Glu-Gly-NH$_2$ | 994 |
| Ac-Lys-Trp-Ile-Tyr-His-Phe-Thr-Glu-Gly-Ser-Thr-Asp-Leu-Arg-Thr-Glu-Gly-NH$_2$ | 995 |
| Ac-Lys-Trp-Phe-Tyr-His-Ile-Thr-Glu-Gly-Ser-Thr-Asp-Leu-Arg-Thr-Glu-Gly-NH$_2$ | 996 |
| Ac-Lys-Trp-Leu-Tyr-His-Val-Thr-Glu-Gly-Ser-Thr-Asp-Leu-Arg-Thr-Glu-Gly-NH$_2$ | 997 |
| Ac-Lys-Trp-Val-Tyr-His-Tyr-Thr-Glu-Gly-Ser-Thr-Asp-Leu-Arg-Thr-Glu-Gly-NH$_2$ | 998 |
| Ac-Lys-Tyr-Ile-Trp-His-Phe-Thr-Glu-Gly-Ser-Thr-Asp-Leu-Arg-Thr-Glu-Gly-NH$_2$ | 999 |
| Ac-Lys-Tyr-Ile-Trp-His-Ile-Thr-Glu-Gly-Ser-Thr-Asp-Leu-Arg-Thr-Glu-Gly-NH$_2$ | 1000 |
| Ac-Lys-Tyr-Ile-Trp-His-Val-Thr-Glu-Gly-Ser-Thr-Asp-Leu-Arg-Thr-Glu-Gly-NH$_2$ | 1001 |
| Ac-Lys-Tyr-Ile-Trp-His-Tyr-Thr-Glu-Gly-Ser-Thr-Asp-Leu-Arg-Thr-Glu-Gly-NH$_2$ | 1002 |
| Ac-Lys-Phe-Ile-Trp-His-Leu-Thr-Glu-Gly-Ser-Thr-Asp-Leu-Arg-Thr-Glu-Gly-NH$_2$ | 1003 |
| Ac-Lys-Leu-Ile-Trp-His-Leu-Thr-Glu-Gly-Ser-Thr-Asp-Leu-Arg-Thr-Glu-Gly-NH$_2$ | 1004 |
| Ac-Lys-Ile-Ile-Trp-His-Leu-Thr-Glu-Gly-Ser-Thr-Asp-Leu-Arg-Thr-Glu-Gly-NH$_2$ | 1005 |
| Ac-Lys-Tyr-Ile-Trp-Phe-Leu-Thr-Glu-Gly-Ser-Thr-Asp-Leu-Arg-Thr-Glu-Gly-NH$_2$ | 1006 |
| Ac-Lys-Trp-Ile-Tyr-Phe-Leu-Thr-Glu-Gly-Ser-Thr-Asp-Leu-Arg-Thr-Glu-Gly-NH$_2$ | 1007 |
| Ac-Lys-Trp-Ile-Tyr-Leu-Leu-Thr-Glu-Gly-Ser-Thr-Asp-Leu-Arg-Thr-Glu-Gly-NH$_2$ | 1008 |
| Ac-Lys-Trp-Ile-Tyr-His-Phe-Thr-Glu-Gly-Ser-Thr-Asp-Leu-Arg-Thr-Glu-Gly-NH$_2$ | 1009 |
| Ac-Lys-Trp-Ile-Tyr-His-Tyr-Thr-Glu-Gly-Ser-Thr-Asp-Leu-Arg-Thr-Glu-Gly-NH$_2$ | 1010 |
| Ac-Lys-Trp-Ile-Tyr-His-Ile-Thr-Glu-Gly-Ser-Thr-Asp-Leu-Arg-Thr-Glu-Gly-NH$_2$ | 1011 |
| Ac-Lys-Trp-Ile-Tyr-His-Leu-Ser-Glu-Gly-Ser-Thr-Asp-Leu-Arg-Thr-Glu-Gly-NH$_2$ | 1012 |
| Ac-Lys-Trp-Ile-Tyr-His-Leu-Thr-Asp-Gly-Ser-Thr-Asp-Leu-Arg-Thr-Glu-Gly-NH$_2$ | 1013 |
| Ac-Lys-Trp-Ile-Tyr-His-Leu-Thr-Glu-Gly-Thr-Ser-Asp-Leu-Arg-Thr-Glu-Gly-NH$_2$ | 1014 |
| Ac-Lys-Trp-Ile-Tyr-His-Leu-Thr-Glu-Gly-Ser-Thr-Glu-Leu-Arg-Thr-Glu-Gly-NH$_2$ | 1015 |
| Ac-Lys-Trp-Ile-Tyr-His-Leu-Thr-Glu-Gly-Ser-Thr-Asp-Phe-Arg-Thr-Glu-Gly-NH$_2$ | 1016 |
| Ac-Lys-Trp-Ile-Tyr-His-Leu-Thr-Glu-Gly-Ser-Thr-Asp-Tyr-Arg-Thr-Glu-Gly-NH$_2$ | 1017 |
| Ac-Lys-Trp-Ile-Tyr-His-Leu-Thr-Glu-Gly-Ser-Thr-Asp-Ile-Arg-Thr-Glu-Gly-NH$_2$ | 1018 |
| Ac-Lys-Trp-Ile-Tyr-His-Leu-Thr-Glu-Gly-Ser-Thr-Asp-Val-Arg-Thr-Glu-Gly-NH$_2$ | 1019 |
| Ac-Lys-Trp-Ile-Tyr-His-Leu-Thr-Glu-Gly-Ser-Thr-Asp-Leu-Lys-Thr-Glu-Gly-NH$_2$ | 1020 |
| Ac-Lys-Trp-Ile-Tyr-His-Leu-Thr-Glu-Gly-Ser-Thr-Asp-Leu-Arg-Ser-Glu-Gly-NH$_2$ | 1021 |

TABLE 17-continued

Additional illustrative G* peptides.

| Peptide | SEQ ID NO |
|---|---|
| Ac-Lys-Trp-Ile-Tyr-His-Leu-Thr-Glu-Gly-Ser-Thr-Asp-Leu-Arg-Thr-Asp-Gly-NH$_2$ | 1022 |
| Ac-Lys-Trp-Ile-Tyr-His-Leu-Thr-Glu-Gly-Ser-Thr-Asp-Ile-Lys-Thr-Glu-Gly-NH$_2$ | 1023 |
| Ac-Lys-Trp-Ile-Tyr-His-Leu-Thr-Glu-Gly-Ser-Thr-Asp-Ile-Arg-Ser-Glu-Gly-NH$_2$ | 1024 |
| Ac-Lys-Trp-Ile-Tyr-His-Leu-Thr-Glu-Gly-Ser-Thr-Asp-Ile-Lys-Ser-Glu-Gly-NH$_2$ | 1025 |
| Ac-Lys-Trp-Ile-Tyr-His-Leu-Thr-Glu-Gly-Ser-Thr-Asp-Ile-Lys-Ser-Asp-Gly-NH$_2$ | 1026 |
| Ac-Arg-Trp-Ile-Tyr-His-Leu-Thr-Glu-Gly-Ser-Thr-Asp-Leu-Arg-Thr-Glu-Gly-NH$_2$ | 1027 |
| Ac-Arg-Tyr-Ile-Trp-His-Leu-Thr-Glu-Gly-Ser-Thr-Asp-Ile-Arg-Thr-Glu-Gly-NH$_2$ | 1028 |
| Ac-Arg-Trp-Ile-Tyr-His-Leu-Thr-Glu-Gly-Ser-Thr-Asp-Ile-Arg-Thr-Asp-Gly-NH$_2$ | 1029 |
| Ac-Arg-Trp-Ile-Phe-His-Leu-Thr-Glu-Gly-Ser-Thr-Asp-Ile-Arg-Thr-Glu-Gly-NH$_2$ | 1030 |
| Ac-Arg-Trp-Ile-Tyr-His-Leu-Thr-Glu-Gly-Ser-Thr-Asp-Leu-Lys-Thr-Glu-Gly-NH$_2$ | 1031 |
| Ac-Arg-Trp-Ile-Tyr-His-Leu-Thr-Asp-Gly-Ser-Thr-Asp-Ile-Arg-Thr-Glu-Gly-NH$_2$ | 1032 |
| Ac-Arg-Trp-Ile-Tyr-His-Leu-Thr-Asp-Gly-Ser-Thr-Asp-Leu-Arg-Thr-Glu-Gly-NH$_2$ | 1033 |
| Ac-Arg-Trp-Ile-Tyr-Phe-Leu-Thr-Glu-Gly-Ser-Thr-Asp-Ile-Arg-Thr-Glu-Gly-NH$_2$ | 1034 |
| Ac-Arg-Trp-Ile-Tyr-Phe-Leu-Thr-Glu-Gly-Ser-Thr-Asp-Leu-Arg-Thr-Glu-Gly-NH$_2$ | 1035 |
| Ac-Lys-Trp-Phe-Tyr-His-Leu-Thr-Glu-Gly-Ser-Thr-Asp-Phe-Arg-Thr-Glu-Gly-NH$_2$ | 1036 |
| Ac-Arg-Trp-Phe-Tyr-His-Leu-Thr-Glu-Gly-Ser-Thr-Asp-Leu-Arg-Thr-Glu-Gly-NH$_2$ | 1037 |
| Ac-Lys-Trp-Ile-Phe-His-Leu-Thr-Glu-Gly-Ser-Thr-Asp-Ile-Arg-Thr-Asp-Gly-NH$_2$ | 1038 |
| Ac-Arg-Trp-Ile-Tyr-His-Leu-Thr-Glu-Gly-Ser-Thr-Asp-Ile-Arg-Thr-Asp-Gly-NH$_2$ | 1039 |
| Ac-Arg-Trp-Ile-Tyr-His-Leu-Thr-Glu-Gly-Ser-Thr-Asp-Leu-Arg-Thr-Asp-Gly-NH$_2$ | 1040 |
| Ac-Lys-Trp-Ile-Tyr-His-Leu-Thr-Glu-Gly-Ser-Thr-Asp-Ile-Lys-Thr-Glu-Gly-NH$_2$ | 1041 |
| Ac-Lys-Trp-Ile-Tyr-His-Leu-Thr-Glu-Gly-Ser-Thr-Asp-Ile-Lys-Thr-Asp-Gly-NH$_2$ | 1042 |
| Ac-Lys-Trp-Ile-Tyr-His-Leu-Thr-Glu-Gly-Ser-Thr-Asp-Phe-Lys-Thr-Glu-Gly-NH$_2$ | 1043 |
| Ac-Lys-Trp-Ile-Tyr-His-Leu-Thr-Glu-Gly-Ser-Thr-Asp-Tyr-Lys-Thr-Glu-Gly-NH$_2$ | 1044 |
| Ac-Lys-Trp-Ile-Tyr-His-Leu-Thr-Glu-Gly-Ser-Thr-Asp-Ile-Arg-Thr-Glu-Gly-NH$_2$ | 1045 |
| Ac-Lys-Trp-Phe-Tyr-His-Phe-Thr-Glu-Gly-Ser-Thr-Asp-Leu-Arg-Thr-Glu-Gly-NH$_2$ | 1046 |
| Ac-Arg-Trp-Phe-Tyr-His-Phe-Thr-Glu-Gly-Ser-Thr-Asp-Leu-Arg-Thr-Glu-Gly-NH$_2$ | 1047 |
| Ac-Lys-Trp-Phe-Tyr-His-Phe-Thr-Glu-Gly-Ser-Thr-Asp-Phe-Arg-Thr-Glu-Gly-NH$_2$ | 1048 |
| Ac-Lys-Trp-Phe-Tyr-His-Phe-Thr-Asp-Gly-Ser-Thr-Asp-Ile-Arg-Thr-Glu-Gly-NH$_2$ | 1049 |
| Ac-Arg-Trp-Phe-Tyr-His-Phe-Thr-Glu-Gly-Ser-Thr-Asp-Leu-Arg-Thr-Glu-Gly-NH$_2$ | 1050 |
| Ac-Arg-Trp-Phe-Tyr-His-Phe-Thr-Glu-Gly-Ser-Thr-Asp-Phe-Arg-Thr-Glu-Gly-NH$_2$ | 1051 |
| Ac-Arg-Trp-Phe-Tyr-His-Phe-Thr-Glu-Gly-Ser-Thr-Asp-Phe-Arg-Thr-Asp-Gly-NH$_2$ | 1052 |
| Ac-Glu-Lys-Cys-Val-Glu-Glu-Phe-Lys-Ser-Leu-Thr-Ser-Cys-Leu-Asp-Ser-Lys-Ala-Phe-NH$_2$ | 1053 |
| Ac-Asp-Lys-Cys-Val-Glu-Glu-Phe-Lys-Ser-Leu-Thr-Ser-Cys-Leu-Asp-Ser-Lys-Ala-Phe-NH$_2$ | 1054 |
| Ac-Glu-Lys-Cys-Val-Asp-Glu-Phe-Lys-Ser-Leu-Thr-Ser-Cys-Leu-Asp-Ser-Lys-Ala-Phe-NH$_2$ | 1055 |
| Ac-Glu-Lys-Cys-Val-Glu-Asp-Phe-Lys-Ser-Leu-Thr-Ser-Cys-Leu-Asp-Ser-Lys-Ala-Phe-NH$_2$ | 1056 |
| Ac-Glu-Arg-Cys-Val-Glu-Glu-Phe-Lys-Ser-Leu-Thr-Ser-Cys-Leu-Asp-Ser-Lys-Ala-Phe-NH$_2$ | 1057 |
| Ac-Asp-Lys-Cys-Val-Asp-Asp-Phe-Lys-Ser-Leu-Thr-Ser-Cys-Leu-Asp-Ser-Lys-Ala-Phe-NH$_2$ | 1058 |
| Ac-Asp-Arg-Cys-Val-Glu-Glu-Phe-Lys-Ser-Leu-Thr-Ser-Cys-Leu-Asp-Ser-Lys-Ala-Phe-NH$_2$ | 1059 |
| Ac-Glu-Arg-Cys-Val-Asp-Asp-Phe-Lys-Ser-Leu-Thr-Ser-Cys-Leu-Asp-Ser-Lys-Ala-Phe-NH$_2$ | 1060 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1061 |
| Ac-Glu-Lys-Cys-Val-Glu-Glu-Phe-Lys-Ser-Ile-Thr-Ser-Cys-Leu-Asp-Ser-Lys-Ala-Phe-NH$_2$ | 1062 |
| Ac-Glu-Lys-Cys-Val-Glu-Glu-Phe-Lys-Ser-Val-Thr-Ser-Cys-Leu-Asp-Ser-Lys-Ala-Phe-NH$_2$ | 1063 |
| Ac-Glu-Arg-Cys-Val-Glu-Glu-Phe-Lys-Ser-Tyr-Thr-Ser-Cys-Leu-Asp-Ser-Lys-Ala-Phe-NH$_2$ | 1064 |
| Ac-Glu-Arg-Cys-Val-Glu-Glu-Phe-Lys-Ser-Phe-Thr-Ser-Cys-Leu-Asp-Ser-Lys-Ala-Phe-NH$_2$ | 1065 |
| Ac-Glu-Arg-Cys-Val-Glu-Glu-Phe-Lys-Ser-Ile-Thr-Ser-Cys-Leu-Asp-Ser-Lys-Ala-Phe-NH$_2$ | 1066 |
| Ac-Glu-Arg-Cys-Val-Glu-Glu-Phe-Lys-Ser-Val-Thr-Ser-Cys-Leu-Asp-Ser-Lys-Ala-Phe-NH$_2$ | 1067 |
| Ac-Glu-Arg-Cys-Val-Glu-Glu-Phe-Lys-Ser-Tyr-Thr-Ser-Cys-Leu-Asp-Ser-Lys-Ala-Phe-NH$_2$ | 1068 |
| Ac-Glu-Lys-Cys-Val-Glu-Glu-Phe-Lys-Ser-Phe-Thr-Thr-Cys-Leu-Asp-Ser-Lys-Ala-Phe-NH$_2$ | 1069 |
| Ac-Glu-Lys-Cys-Val-Glu-Glu-Phe-Lys-Ser-Ile-Ser-Ser-Cys-Leu-Asp-Ser-Lys-Ala-Phe-NH$_2$ | 1070 |
| Ac-Glu-Lys-Cys-Val-Glu-Glu-Phe-Lys-Ser-Val-Ser-Thr-Cys-Leu-Asp-Ser-Lys-Ala-Phe-NH$_2$ | 1071 |

TABLE 17-continued

Additional illustrative G* peptides.

| Peptide | SEQ ID NO |
|---|---|
| Ac-Glu-Lys-Cys-Val-Glu-Glu-Phe-Lys-Ser-Tyr-Thr-Ser-Cys-Leu-Asp-Ser-Lys-Ala-Phe-NH$_2$ | 1072 |
| Ac-Glu-Lys-Cys-Val-Glu-Glu-Phe-Lys-Ser-Phe-Thr-Thr-Cys-Leu-Asp-Ser-Lys-Ala-Phe-NH$_2$ | 1073 |
| Ac-Glu-Lys-Cys-Val-Glu-Glu-Phe-Lys-Ser-Phe-Ser-Ser-Cys-Leu-Asp-Ser-Lys-Ala-Phe-NH$_2$ | 1074 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1075 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1076 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1077 |
| Ac-Glu-Lys-Cys-Val-Glu-Glu-Phe-Lys-Ser-Phe-Thr-Ser-Cys-Phe-Asp-Ser-Lys-Ala-Phe-NH$_2$ | 1078 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 1079 |
| Ac-Glu-Lys-Cys-Val-Glu-Glu-Phe-Lys-Ser-Phe-Thr-Ser-Cys-Leu-Glu-Ser-Lys-Ala-Phe-NH$_2$ | 1080 |
| Ac-Glu-Lys-Cys-Val-Glu-Glu-Phe-Lys-Ser-Phe-Thr-Ser-Cys-Ile-Asp-Ser-Lys-Ala-Phe-NH$_2$ | 1081 |
| Ac-Glu-Lys-Cys-Val-Glu-Glu-Leu-Lys-Ser-Phe-Thr-Ser-Cys-Phe-Asp-Ser-Lys-Ala-Phe-NH$_2$ | 1082 |
| Ac-Asp-Lys-Cys-Val-Glu-Glu-Phe-Lys-Ser-Phe-Thr-Ser-Cys-Phe-Asp-Ser-Lys-Ala-Phe-NH$_2$ | 1083 |
| Ac-Asp-Lys-Cys-Val-Glu-Glu-Phe-Lys-Ser-Phe-Thr-Ser-Cys-Phe-Glu-Ser-Lys-Ala-Phe-NH$_2$ | 1084 |
| Ac-Glu-Arg-Cys-Val-Glu-Glu-Phe-Lys-Ser-Phe-Thr-Ser-Cys-Phe-Asp-Ser-Lys-Ala-Phe-NH$_2$ | 1085 |
| Ac-Glu-Lys-Cys-Phe-Glu-Glu-Phe-Lys-Ser-Phe-Thr-Ser-Cys-Phe-Asp-Ser-Lys-Ala-Phe-NH$_2$ | 1086 |
| Ac-Glu-Lys-Cys-Phe-Glu-Glu-Phe-Lys-Ser-Phe-Thr-Ser-Cys-Phe-Glu-Ser-Lys-Ala-Phe-NH$_2$ | 1087 |
| Ac-Glu-Lys-Cys-Val-Glu-Glu-Phe-Lys-Ser-Phe-Ser-Ser-Cys-Phe-Glu-Ser-Lys-Ala-Phe-NH$_2$ | 1088 |
| Ac-Glu-Lys-Cys-Val-Glu-Glu-Phe-Lys-Ser-Phe-Gln-Ser-Cys-Phe-Asp-Ser-Lys-Ala-Phe-NH$_2$ | 1089 |
| Ac-Glu-Lys-Cys-Phe-Glu-Glu-Phe-Lys-Ser-Phe-Gln-Ser-Cys-Phe-Asp-Ser-Lys-Ala-Phe-NH$_2$ | 1090 |
| Ac-Glu-Lys-Cys-Val-Glu-Glu-Phe-Lys-Gln-Phe-Thr-Ser-Cys-Phe-Asp-Ser-Lys-Ala-Phe-NH$_2$ | 1091 |
| Ac-Glu-Lys-Cys-Val-Glu-Glu-Phe-Lys-Gln-Leu-Thr-Ser-Cys-Leu-Asp-Ser-Lys-Ala-Phe-NH$_2$ | 1092 |
| Ac-Glu-Lys-Cys-Phe-Glu-Glu-Phe-Lys-Ser-Phe-Gln-Ser-Cys-Leu-Asp-Ser-Lys-Ala-Phe-NH$_2$ | 1093 |
| Ac-Glu-Lys-Cys-Val-Glu-Glu-Phe-Lys-Gln-Phe-Thr-Ser-Cys-Phe-Asp-Ser-Lys-Ala-Phe-NH$_2$ | 1094 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 1095 |
| Ac-Glu-Arg-Cys-Phe-Glu-Glu-Phe-Lys-Ser-Phe-Thr-Ser-Cys-Phe-Asp-Ser-Lys-Ala-Phe-NH$_2$ | 1096 |
| Ac-Asp-Lys-Cys-Phe-Glu-Glu-Phe-Lys-Ser-Phe-Thr-Ser-Cys-Phe-Asp-Ser-Lys-Ala-Phe-NH$_2$ | 1097 |
| Ac-Glu-Arg-Cys-Val-Glu-Glu-Phe-Lys-Ser-Leu-Thr-Ser-Cys-Leu-Glu-Ser-Lys-Ala-Phe-NH$_2$ | 1098 |
| Ac-Glu-Lys-Cys-Val-Glu-Glu-Phe-Lys-Ser-Leu-Thr-Ser-Cys-Leu-Asp-Ser-Lys-Phe-Phe-NH$_2$ | 1099 |
| Ac-Glu-Lys-Cys-Phe-Glu-Glu-Phe-Lys-Ser-Phe-Thr-Ser-Cys-Phe-Asp-Ser-Lys-Phe-Phe-NH$_2$ | 1100 |
| Ac-Asp-Lys-Cys-Phe-Glu-Glu-Phe-Lys-Ser-Phe-Thr-Ser-Cys-Leu-Asp-Ser-Lys-Phe-Phe-NH$_2$ | 1101 |
| Ac-Asp-Lys-Cys-Phe-Glu-Glu-Phe-Lys-Ser-Phe-Thr-Ser-Cys-Leu-Glu-Ser-Lys-Phe-Phe-NH$_2$ | 1102 |
| Ac-Asp-Lys-Cys-Phe-Glu-Glu-Leu-Lys-Ser-Phe-Thr-Ser-Cys-Leu-Asp-Ser-Lys-Phe-Phe-NH$_2$ | 1103 |
| Ac-Glu-Arg-Cys-Phe-Glu-Glu-Phe-Lys-Ser-Phe-Thr-Ser-Cys-Leu-Asp-Ser-Lys-Phe-Phe-NH$_2$ | 1104 |
| Ac-Glu-Lys-Ala-Val-Glu-Glu-Phe-Lys-Ser-Phe-Thr-Ser-Cys-Leu-Asp-Ser-Lys-Ala-Phe-NH$_2$ | 1105 |
| Ac-Asp-Lys-Ala-Val-Glu-Glu-Phe-Lys-Ser-Phe-Thr-Ser-Cys-Leu-Asp-Ser-Lys-Phe-Phe-NH$_2$ | 1106 |
| Ac-Glu-Lys-Ala-Val-Glu-Glu-Phe-Lys-Ser-Phe-Thr-Ser-Ala-Leu-Asp-Ser-Lys-Ala-Phe-NH$_2$ | 1107 |
| Ac-Asp-Lys-Ala-Val-Glu-Glu-Phe-Lys-Ser-Phe-Thr-Ser-Ala-Leu-Asp-Ser-Lys-Ala-Phe-NH$_2$ | 1108 |
| Ac-Asp-Arg-Ala-Phe-Glu-Glu-Phe-Lys-Ser-Phe-Thr-Ser-Cys-Leu-Asp-Ser-Lys-Phe-Phe-NH$_2$ | 1109 |
| Ac-Asp-Arg-Ala-Phe-Glu-Glu-Phe-Lys-Ser-Phe-Thr-Ser-Ala-Leu-Asp-Ser-Lys-Phe-Phe-NH$_2$ | 1110 |
| Ac-Asp-Lys-Cys-Phe-Glu-Glu-Phe-Lys-Ser-Phe-Thr-Ser-Cys-Phe-Glu-Ser-Lys-Phe-Phe-NH$_2$ | 1111 |
| Ac-Glu-Lys-Cys-Tyr-Glu-Glu-Phe-Lys-Ser-Phe-Thr-Ser-Cys-Leu-Asp-Ser-Lys-Phe-Phe-NH$_2$ | 1112 |
| Ac-Asp-Lys-Cys-Trp-Glu-Glu-Phe-Lys-Ser-Phe-Thr-Ser-Cys-Leu-Asp-Ser-Lys-Phe-Phe-NH$_2$ | 1113 |
| Ac-Glu-Lys-Cys-Phe-Glu-Glu-Phe-Lys-Ser-Tyr-Thr-Ser-Cys-Leu-Asp-Ser-Lys-Phe-Phe-NH$_2$ | 1114 |
| Ac-Glu-Lys-Cys-Phe-Glu-Glu-Phe-Lys-Ser-Trp-Thr-Ser-Cys-Leu-Asp-Ser-Lys-Phe-Phe-NH$_2$ | 1115 |
| Ac-Glu-Lys-Cys-Val-Glu-Glu-Phe-Lys-Ser-Trp-Thr-Ser-Cys-Leu-Asp-Ser-Lys-Ala-Phe-NH$_2$ | 1116 |
| Ac-Asp-Lys-Cys-Phe-Glu-Glu-Phe-Lys-Ser-Trp-Thr-Ser-Cys-Leu-Asp-Ser-Lys-Ala-Phe-NH$_2$ | 1117 |

Other suitable peptides include, but are not limited to the peptides of Table 18.

TABLE 18

Illustrative peptides having an improved hydrophobic phase.

| Name | Sequence | SEQ ID NO |
|---|---|---|
| V2W3A5F10,17-D-4F | Ac-Asp-Val-Trp-Lys-Ala-Ala-Tyr-Asp-Lys-Phe-Ala-Glu-Lys-Phe-Lys-Glu-Phe-Phe-NH2 | 1118 |
| V2W3F10-D-4F | Ac-Asp-Val-Trp-Lys-Ala-Phe-Tyr-Asp-Lys-Phe-Ala-Glu-Lys-Phe-Lys-Glu-Ala-Phe-NH2 | 1119 |
| W3-D-4F | Ac-Asp-Phe-Trp-Lys-Ala-Phe-Tyr-Asp-Lys-Val-Ala-Glu-Lys-Phe-Lys-Glu-Ala-Phe-NH2 | 1120 |

The peptides described here (V2W3A5F10,17-D-4F; V2W3F10-D-4F; W3-D-4F) may be more potent than the original D-4F.

Still other suitable peptides include, but are not limited to: $P^1$-Dimethyltyrosine-D-Arg-Phe-Lys-$P^2$ (SEQ ID NO:1121) and $P^1$-Dimethyltyrosine-Arg-Glu-Leu-$P^2$ where P1 and P2 are protecting groups as described herein. In certain embodiments, these peptides include, but are not limited to BocDimethyltyrosine-D-Arg-Phe-Lys(OtBu) and BocDimethyltyrosine-Arg-Glu-Leu(OtBu).

In certain embodiments, the peptides of this invention include peptides comprising or consisting of the amino acid sequence LAEYHAK (SEQ ID NO:1122) comprising at least one D amino acid and/or at least one or two terminal protecting groups. In certain embodiments, this invention includes a peptide that ameliorates one or more symptoms of an inflammatory condition, wherein the peptide: ranges in length from about 3 to about 10 amino acids; comprises an amino acid sequence where the sequence comprises acidic or basic amino acids alternating with aromatic or hydrophobic amino acids; comprises hydrophobic terminal amino acids or terminal amino acids bearing a hydrophobic protecting group; is not the sequence LAEYHAK (SEQ ID NO:1122) comprising all L amino acids; where the peptide converts pro-inflammatory HDL to anti-inflammatory HDL and/or makes anti-inflammatory HDL more anti-inflammatory.

It is also noted that the peptides listed in the Tables herein are not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos:961-989.

Longer peptides are also suitable. Such longer peptides may entirely form a class G or G* amphipathic helix, or the G amphipathic helix (helices) can form one or more domains of the peptide. In addition, this invention contemplates multimeric versions of the peptides. Thus, for example, the peptides illustrated in the tables herein can be coupled together (directly or through a linker (e.g. a carbon linker, or one or more amino acids) with one or more intervening amino acids). Suitable linkers include, but are not limited to Proline (-Pro-), Gly$_4$Ser$_3$ (SEQ ID NO:1123), and the like. Thus, one illustrative multimeric peptide according to this invention is (D-J336)-P-(D-J336) (i.e. Ac-L-L-E-Q-L-N-E-Q-F-N-W-V-S-R-L-A-N-L-T-Q-G-E-P-L-L-E-Q-L-N-E-Q-F-N-W-V-S-R-L-A-N-L-T-Q-G-E-NH$_2$, SEQ ID NO:1124.

This invention also contemplates the use of "hybrid" peptides comprising a one or more G or G* amphipathic helical domains and one or more class A amphipathic helices. Suitable class A amphipathic helical peptides are described in PCT publication WO 02/15923. Thus, by way of illustration, one such "hybrid" peptide is (D-J336)-Pro-(4F)(i.e. Ac-L-L-E-Q-L-N-E-Q-F-N-W-V-S-R-L-A-N-L-T-Q-G-E-P-D-W-F-K-A-F-Y-D-K-V-A-E-K-F-K-E-A-F-NH$_2$, SEQ ID NO:1125), and the like.

Using the teaching provided herein, one of skill can routinely modify the illustrated amphipathic helical peptides to produce other suitable apo J variants and/or amphipathic G and/or A helical peptides of this invention. For example, routine conservative or semi-conservative substitutions (e.g., E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328-338. The peptides can be lengthened or shortened as long as the class helix structure(s) are preserved. In addition, substitutions can be made to render the resulting peptide more similar to peptide(s) endogenously produced by the subject species.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, epsilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

New peptides can be designed and/or evaluated using computational methods. Computer programs to identify and classify amphipathic helical domains are well known to those of skill in the art and many have been described by Jones et al. (1992) *J. Lipid Res.* 33: 287-296). Such programs include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

F) Blocking Groups and D Residues.

While the various peptides and/or amino acid pairs described herein may be shown with no protecting groups, in certain embodiments (e.g. particularly for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g. an acetyl group protecting the amino terminus and/or an amide group protecting the carboxyl terminus. One example of such a "dual protected peptide is Ac-L-L-E-Q-L-N-E-Q-F-N-W-V-S-R-L-A-N-L-T-Q-G-E-NH$_2$ (SEQ ID NO:961 with blocking groups), either or both of these protecting groups can be eliminated and/or substituted with another protecting group as described herein.

Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis*, 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

In certain particularly preferred embodiments, the peptides comprise one or more D-form (dextro rather than levo) amino acids as described herein. In certain embodiments at least two enantiomeric amino acids, more preferably at least 4 enantiomeric amino acids and most preferably at least 8 or 10 enantiomeric amino acids are "D" form amino acids. In certain embodiments every other, ore even every amino acid (e.g. every enantiomeric amino acid) of the peptides described herein is a D-form amino acid.

In certain embodiments at least 50% of the enantiomeric amino acids are "D" form, more preferably at least 80% of the enantiomeric amino acids are "D" form, and most preferably at least 90% or even all of the enantiomeric amino acids are "D" form amino acids.

G) Peptide Mimetics.

In addition to the peptides described herein, peptidomimetics are also contemplated. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res*. 15: 29; Veber and Freidinger (1985) *TINS* p. 392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (e.g. SEQ ID NO:5 shown in Table 1), but have one or more peptide linkages optionally replaced by a linkage selected from the group consisting of: $—CH_2NH—$, $—CH_2S—$, $—CH_2—CH_2—$, $—CH=CH—$ (cis and trans), $—COCH_2—$, $—CH(OH)CH_2—$, $—CH_2SO—$, etc. by methods known in the art and further described in the following references: Spatola (1983) p. 267 in *Chemistry and Biochemistry of Amino Acids, Peptides, and Proteins*, B. Weinstein, eds., Marcel Dekker, New York,; Spatola (1983) *Vega Data* 1(3) *Peptide Backbone Modifications*. (general review); Morley (1980) *Trends Pharm Sci* pp. 463-468 (general review); Hudson et al. (1979) *Int J Pept Prot Res* 14:177-185 ($—CH_2NH—$, $CH_2CH_2—$); Spatola et al. (1986) *Life Sci* 38:1243-1249 ($—CH_2—S$); Hann, (1982) *J Chem Soc Perkin Trans* 1307-314 ($—CH—CH—$, cis and trans); Almquist et al. (1980) *J Med. Chem*. 23:1392-1398 ($—COCH_2—$); Jennings-White et al. (1982) *Tetrahedron Lett.* 23:2533 ($—COCH_2—$); Szelke et al., European Appln. EP 45665 (1982) CA: 97:39405 (1982) ($—CH(OH)CH2-$); Holladay et al. (1983) *Tetrahedron Lett* 24:4401-4404 ($—C(OH)CH_2—$); and Hruby (1982) *Life Sci.*, 31:189-199 ($—CH_2—S—$)).

One particularly preferred non-peptide linkage is $—CH_2NH—$. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

H) Small Organic Molecules.

In certain embodiments, the active agents of this invention include small organic molecules, e.g. as described in copending application U.S. Ser. No. 60/600,925, filed Aug. 11, 2004. In various embodiments the small organic molecules are similar to, and in certain cases, mimetics of the tetra-and penta-peptides described in copending application U.S. Ser. No. 10/649,378, filed on Aug. 26, 2003 and U.S. Ser. No. 60/494,449, filed on August 11.

The small organic molecules of this invention typically have molecular weights less than about 900 Daltons. Typically the molecules are highly soluble in ethyl acetate (e.g., at concentrations equal to or greater than 4 mg/mL), and also are soluble in aqueous buffer at pH 7.0.

Contacting phospholipids such as 1,2-dimyristoyl-sn-glycero-3-phosphocholine (DMPC), with the small organic molecules of this invention in an aqueous environment typically results in the formation of particles with a diameter of approximately 7.5 nm (±0.1 nm). In addition, stacked bilayers are often formed with a bilayer dimension on the order of 3.4 to 4.1 nm with spacing between the bilayers in the stack of approximately 2 nm. Vesicular structures of approximately 38 nm are also often formed. Moreover, when the molecules of this invention are administered to a mammal they render HDL more anti-inflammatory and mitigate one or more symptoms of atherosclerosis and/or other conditions characterized by an inflammatory response.

Thus, in certain embodiments, the small organic molecule is one that ameliorates one or more symptoms of a pathology characterized by an inflammatory response in a mammal (e.g. atherosclerosis), where the small molecule is soluble in ethyl acetate at a concentration greater than 4 mg/mL, is soluble in aqueous buffer at pH 7.0, and, when contacted with a phospholipid in an aqueous environment, forms particles with a diameter of approximately 7.5 nm and forms stacked bilayers with a bilayer dimension on the order of 3.4 to 4.1 nm with spacing between the bilayers in the stack of approximately 2 nm, and has a molecular weight less than 900 daltons.

In certain embodiment, the molecule has the formula:

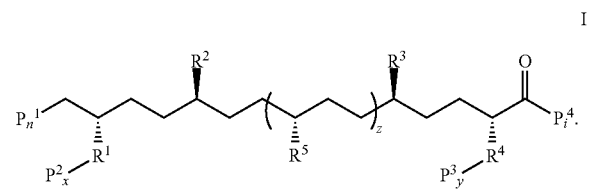

I where $P^1$, $P^2$, $P^3$, and $P^4$ are independently selected hydrophobic protecting groups; $R^1$ and $R^4$ are independently selected amino acid R groups; n, i, x, y, and z are independently zero or 1 such that when n and x are both zero, $R^1$ is a hydrophobic group and when y and i are both zero, $R^4$ is a hydrophobic group; $R^2$ and $R^3$ are acidic or basic groups at pH 7.0 such that when $R^2$ is acidic, $R^3$ is basic and when $R^2$ is basic, $R^3$ is acidic; and $R^5$, when present is selected from the group consisting of an aromatic group, an aliphatic group, a positively charged group, or a negatively charged group. In certain embodiments, $R^2$ or $R^3$ is —$(CH_2)$j-COOH where j=1, 2, 3, or 4 and/or —$(CH_2)$j-$NH_2$ where j=1, 2, 3, 4, or 5, or —$(CH_2)$j-NH—C(=NH)—$NH_2$ where n=1, 2, 3 or 4. In certain embodiments, $R^2$, $R^3$, and $R^5$, when present, are amino acid R groups. Thus, for example, In various embodiments $R^2$ and $R^3$ are independently an aspartic acid R group, a glutamic acid R group, a lysine R group, a histidine R group, or an arginine R group (e.g., as illustrated in Table 1).

In certain embodiments, $R^1$ is selected from the group consisting of a Lys R group, a Trp R group, a Phe R group, a Leu R group, an Orn R group, pr a norLeu R group. In certain embodiments, $R^4$ is selected from the group consisting of a Ser R group, a Thr R group, an Ile R group, a Leu R group, a norLeu R group, a Phe R group, or a Tyr R group.

In various embodiments x is 1, and $R^5$ is an aromatic group (e.g., a Trp R group).

In various embodiments at least one of n, x, y, and i is 1 and $P^1$, $P^2$, $P^3$, and $P^4$ when present, are independently selected from the group consisting of polyethylene glycol (PEG), an acetyl, amide, a 3 to 20 carbon alkyl group, fmoc, 9-fluoreneacetyl group, 1-fluorenecarboxylic group, 9-fluorenecarboxylic, 9-fluorenone-1-carboxylic group, benzyloxycarbonyl, xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), -4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and trifluoroacetyl (TFA). In certain embodiments, $P^1$ when present and/or $P^2$ when present are independently selected from the group consisting of Boc-, Fmoc-, and Nicotinyl-and/or $P^3$ when present and/or $P^4$ when present are independently selected from the group consisting of tBu, and OtBu.

While a number of protecting groups ($P^1$, $P^2$, $P^3$, $P^4$) are illustrated above, this list is intended to be illustrative and not limiting. In view of the teachings provided herein, a number of other protecting/blocking groups will also be known to one of skill in the art. Such blocking groups can be selected to minimize digestion (e.g., for oral pharmaceutical delivery), and/or to increase uptake/bioavailability (e.g., through mucosal surfaces in nasal delivery, inhalation therapy, rectal administration), and/or to increase serum/plasma half-life. In certain embodiments, the protecting groups can be provided as an excipient or as a component of an excipient.

In certain embodiments, z is zero and the molecule has the formula:

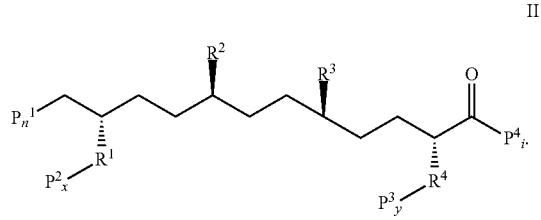

II where $P^1$, $P^2$, $P^3$, $P^4$, $R^1$, $R^2$, $R^3$, $R^4$, n, x, y, and i are as described above.

In certain embodiments, z is zero and the molecule has the formula:

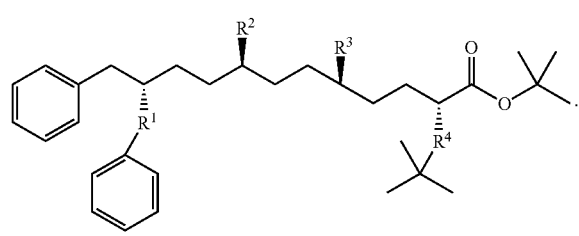

where $R^1$, $R^2$, $R^3$, and $R^4$ are as described above.

In one embodiment, the molecule has the formula:

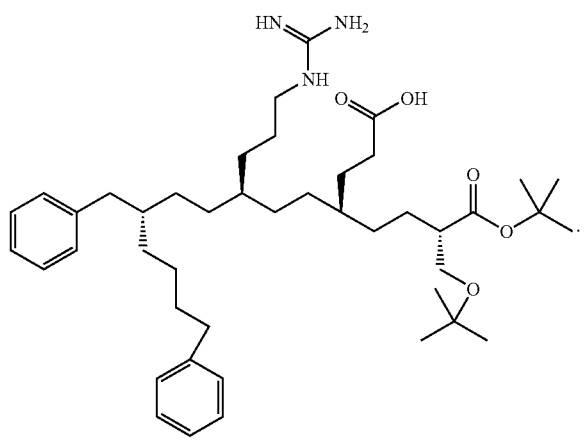

In certain embodiments, this invention contemplates small molecules having one or more of the physical and/or functional properties described herein and having the formula:

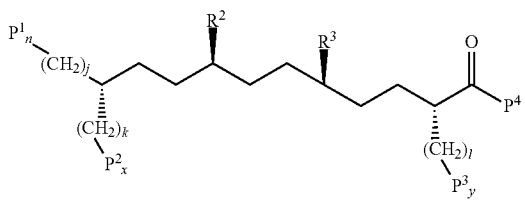

where $P^1$, $P^2$, $P^3$, and $P^4$ are independently selected hydrophobic protecting groups as described above, n, x, and y are independently zero or 1; j, k, and 1 are independently zero, 1, 2, 3, 4, or 5; and $R^2$ and $R^3$ are acidic or basic groups at pH 7.0 such that when $R^2$ is acidic, $R^3$ is basic and when $R^2$ is basic, $R^3$ is acidic. In certain preferred embodiments, the small molecule is soluble in water; and the small molecule has a molecular weight less than about 900 Daltons. In certain embodiments, n, x, y, j, and 1 are 1; and k is 4.

In certain embodiments, $P^1$ and/or $P^2$ are aromatic protecting groups. In certain embodiments, $R^2$ and $R^3$ are amino acid R groups, e.g., as described above. In various embodiments least one of n, x, and y, is 1 and $P^1$, $P^2$, $P^3$ and $P^4$ when present, are independently protecting groups, e.g. as described above. In certain embodiments the protecting groups, when present, are independently selected from the group consisting of poly-ethylene glycol (PEG), an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), -4,4-dimethoxybenzhydryl (Mbh), Tosyl (Tos), 2,2,5, 7,8-penta III. Functional Assays of Active Agents.

Certain active agents for use in the methods of this invention are described herein by various formulas (e.g., Formula I, above) and/or by particular sequences. In certain embodiments, preferred active agents of this invention are characterized by one or more of the following functional properties:

1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-βHDL;
4. They raise HDL cholesterol; and/or
5. They increase HDL paraoxonase activity.

The specific agents disclosed herein, and/or agents corresponding to the various formulas described herein can readily be tested for one or more of these activities as desired.

Methods of screening for each of these functional properties are well known to those of skill in the art. In particular, it is noted that assays for monocyte chemotactic activity, HDL cholesterol, and HDL HDL paraoxonase activity are illustrated in PCT/US01/26497 (WO 2002/15923).

IV. Peptide Preparation.

The peptides used in this invention can be chemically synthesized using standard chemical peptide synthesis techniques or, particularly where the peptide does not comprise "D" amino acid residues, can be recombinantly expressed. In certain embodiments, even peptides comprising "D" amino acid residues are recombinantly expressed. Where the polypeptides are recombinantly expressed, a host organism (e.g. bacteria, plant, fungal cells, etc.) in cultured in an environment where one or more of the amino acids is provided to the organism exclusively in a D form. Recombinantly expressed peptides in such a system then incorporate those D amino acids.

In preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis, Biology. Vol. 2: Special Methods in Peptide Synthesis, Part A*; Merrifield et al. (1963) *J. Am. Chem. Soc.*, 85: 2149-2156, and Stewart et al. (1984) *Solid Phase Peptide Synthesis,* 2nd ed. Pierce Chem. Co., Rockford, Ill.

In certain embodiments, the peptides are synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are described in a miniprint supplement accompanying Anantharamaiah et al. (1985) *J. Biol. Chem.*, 260(16): 10248-10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

V. Pharmaceutical Formulations and Devices.

A) Pharmaceutical Formulations.

In order to carry out the methods of the invention, one or more active agents of this invention are administered, e.g. to an individual diagnosed as having one or more symptoms of atherosclerosis, or as being at risk for atherosclerosis and/or the various other pathologies described herein. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The active agents of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of the one or more pathologies described herein, or at risk for one or more of the pathologies described herein in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain preferred embodiments, the active agents of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) *Biotechnol. Prog.*, 14: 108; Johnson et al. (1996) *Nature Med.* 2: 795; Herbert et al. (1998), *Pharmaceut. Res.* 15, 357) a dry powder composed of biodegradable polymeric microspheres containing the active agent in a polymer matrix that can be compounded as a dry formulation with or without other agents.

The ProLease microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., $-40°$ C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

B) Lipid-based Formulations.

In certain embodiments, the active agents of this invention are administered in conjunction with one or more lipids. The lipids can be formulated as an excipient to protect and/or enhance transport/uptake of the active agents or they can be administered separately.

Without being bound by a particular theory, it was discovered of this invention that administration (e.g. oral administration) of certain phospholipids can significantly increase HDL/LDL ratios. In addition, it is believed that certain medium-length phospholipids are transported by a process different than that involved in general lipid transport. Thus, co-administration of certain medium-length phospholipids with the active agents of this invention confer a number of advantages: They protect the active agents from digestion or hydrolysis, they improve uptake, and they improve HDL/LDL ratios.

The lipids can be formed into liposomes that encapsulate the active agents of this invention and/or they can be complexed/admixed with the active agents and/or they can be covalently coupled to the active agents. Methods of making liposomes and encapsulating reagents are well known to those of skill in the art (see, e.g., Martin and Papahadjopoulos (1982) *J. Biol. Chem.*, 257: 286-288; Papahadjopoulos et al. (1991) *Proc. Natl. Acad. Sci. USA*, 88: 11460-11464; Huang et al. (1992) *Cancer Res.*, 52:6774-6781; Lasic et al. (1992) *FEBS Lett.*, 312: 255-258, and the like).

Preferred phospholipids for use in these methods have fatty acids ranging from about 4 carbons to about 24 carbons in the sn-1 and sn-2 positions. In certain preferred embodiments, the fatty acids are saturated. In other preferred embodiments, the fatty acids can be unsaturated. Various preferred fatty acids are illustrated in Table 19.

TABLE 19

Suitable fatty acids in the sn-1 and/or sn-2 position of the preferred phospholipids for administration of active agents described herein.

| Carbon No. | Common Name | IUPAC Name |
|---|---|---|
| 3:0 | Propionoyl | Trianoic |
| 4:0 | Butanoyl | Tetranoic |
| 5:0 | Pentanoyl | Pentanoic |
| 6:0 | Caproyl | Hexanoic |
| 7:0 | Heptanoyl | Heptanoic |
| 8:0 | Capryloyl | Octanoic |
| 9:0 | Nonanoyl | Nonanoic |
| 10:0 | Capryl | Decanoic |
| 11:0 | Undcanoyl | Undecanoic |
| 12:0 | Lauroyl | Dodecanoic |
| 13:0 | Tridecanoyl | Tridecanoic |
| 14:0 | Myristoyl | Tetradecanoic |
| 15:0 | Pentadecanoyl | Pentadecanoic |
| 16:0 | Palmitoyl | Hexadecanoic |
| 17:0 | Heptadecanoyl | Heptadecanoic |
| 18:0 | Stearoyl | Octadecanoic |
| 19:0 | Nonadecanoyl | Nonadecanoic |
| 20:0 | Arachidoyl | Eicosanoic |
| 21:0 | Heniecosanoyl | Heniecosanoic |
| 22:0 | Behenoyl | Docosanoic |
| 23:0 | Trucisanoyl | Trocosanoic |
| 24:0 | Lignoceroyl | Tetracosanoic |
| 14:1 | Myristoleoyl (9-cis) | |
| 14:1 | Myristelaidoyl (9-trans) | |
| 16:1 | Palmitoleoyl (9-cis) | |
| 16:1 | Palmitelaidoyl (9-trans) | |

The fatty acids in these positions can be the same or different. Particularly preferred phospholipids have phosphorylcholine at the sn-3 position.

C) Specialized Delivery/Devices.

1. Drug-eluting Stents.

Restenosis, the reclosure of a previously stenosed and subsequently dilated peripheral or coronary vessel occurs at a significant rate (e.g., 20-50% for these procedures) and is dependent on a number of clinical and morphological variables. Restenosis may begin shortly following an angioplasty procedure, but usually ceases at the end of approximately six (6) months.

A recent technology that has been developed to address the problem of restenosis in intravascular stents. Stents are typically devices that are permanently implanted (expanded) in coronary and peripheral vessels. The goal of these stents is to provide a long-term "scaffolding" or support for the diseased (stenosed) vessels. The theory being, if the vessel is supported from the inside, it will not close down or restenose.

Known stent designs include, but are not limited to monofilament wire coil stents (see, e.g., U.S. Pat. No. 4,969,458 which is incorporated herein by reference); welded metal cages (see, e.g., U.S. Pat. Nos. 4,733,665 and 4,776,337 which are incorporated herein by reference), thin-walled metal cylinders with axial slots formed around the circumference (see, e.g., U.S. Pat. Nos. 4,733,665, 4,739,762, 4,776, 337 which are incorporated herein by reference). Known construction materials for use in stents include, but are not limited to polymers, organic fabrics and biocompatible metals, such as, stainless steel, gold, silver, tantalum, titanium, and shape memory alloys such as Nitinol.

To further prevent restenosis, stents can be covered and/or impregnated with one or more pharmaceutical, e.g., in controlled release formulations to inhibit cell proliferation associated with rest enosis. Most commonly such "drug-eluting" stents are designed to deliver various cancer drugs (cytotoxins).

However, because of their activity in mitigating inflammatory responses, reducing and/or eliminated oxidized lipids and/or other oxidized species, inhibiting macrophage chemotactic activity and the like, the active agents described herein are well suited to prevent restenosis. Thus, in certain embodiments, this invention contemplates stents having one or more of the active agents described herein coated on the surface and/or retained within cavities or microcavities in the surface of the stent.

In certain embodiments the active agents are contained within biocompatible matrices (e.g. biocompatible polymers such as urethane, silicone, and the like). Suitable biocompatible materials are described, for example, in U.S. Patent Publications 2005/0084515, 2005/00791991, 2005/0070996, and the like which are incorporated herein by reference. In various embodiments the polymers include, but are not limited to silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer Thus, in certain embodiments this invention provides a stent for delivering drugs to a vessel in a body. The stent typically comprises stent framework including a plurality of reservoirs formed therein. The reservoirs typically include an active agent and/or active agent-containing polymer positioned in the reservoir and/or coated on the surface of the stent. In various embodiments the stent is a metallic base or a polymeric base. Certain preferred stent materials include, but are not limited to stainless steel, nitinol, tantalum, MP35N alloy, platinum, titanium, a suitable biocompatible alloy, a suitable biocompatible polymer, and/or a combination thereof.

In various embodiments where the stent comprises pores (e.g. reservoirs), the pores can include micropores (e.g., having a diameter that ranges from about 10 to about 50 µm, preferably about 20 µm or less). In various embodiments the micropores have a depth in the range of about 10 µm to about 50 µm. In various embodiments the micropores extend through the stent framework having an opening on an interior surface of the stent and an opening on an exterior surface of the stent. In certain embodiments the stent can, optionally comprise a cap layer disposed on the interior surface of the stent framework, the cap layer covering at least a portion of the through-holes and providing a barrier characteristic to control an elution rate of the active agent(s) in the polymer from the interior surface of the stent framework. In various embodiments the reservoirs comprise channels along an exterior surface of the stent framework. The stent can optionally have multiple layers of polymer where different layers of polymer carry different active agent(s) and/or other drugs.

In certain embodiments the stent comprises: an adhesion layer positioned between the stent framework and the polymer. Suitable adhesion layers include, but are not limited to a polyurethane, a phenoxy, poly(lactide-co-glycolide)-, polylactide, polysulfone, polycaprolactone, an adhesion promoter, and/or a combination thereof.

In addition to stents, the active agents can be coated on or contained within essentially any implantable medical device configured for implantation in a extravascular and/or intravascular location.

Also provided are methods of manufacturing a drug-polymer stent, comprising. The methods involve providing a stent framework; cutting a plurality of reservoirs in the stent framework, e.g., using a high power laser; applying one or more of the active agents and/or a drug polymer to at least one reservoir; drying the drug polymer; applying a polymer layer to the dried drug polymer; and drying the polymer layer. The active agent(s) and/or polymer(s) can be applied by any convenient method including but not limited to spraying, dipping, painting, brushing and dispensing.

Also provided are methods of treating a vascular condition and/or a condition characterized by an inflammatory response and/or a condition characterized by the formation of oxidized reactive species. The methods typically involve positioning a stent or other implantable device as described above within the body (e.g. within a vessel of a body) and eluting at least active agent from at least one surface of the implant.

2. Impregnated Grafts and Transplants.

Vascular grafts can be classified as either biological or synthetic. There are two commonly used types of biological grafts. An autograft is one taken from another site in the patient. In peripheral vascular surgery by far the most commonly used such graft is the long saphenous vein. This can be used in situ with the valves surgically destroyed with an intraluminal cutting valvutome.

Alternatively, the vein can be removed and reversed but this typically produces a discrepancy between the anastomotic size of the artery and vein. In thoracic surgery the use of internal mammary artery for coronary artery bypass surgery is another example of an autograft. An allograft is one taken from another animal of the same species. Externally supported umbilical vein is rarely used but is an example of such a graft.

Synthetic grafts are most commonly made from Dacron or polytetrafluoroethylene (PTFE). Dacron grafts are frequently used in aortic and aorto-iliac surgery. Below the inguinal ligament the results of all synthetic grafts are inferior to those obtained with the use of vein grafts. Suitable vein is not always available and in this situation PTFE is typically used. It can be used in conjunction with vein as a composite graft. Neointimal hyperplasia at the distal anastomosis can be reduced by the incorporation of a segment of vein as either a Millar Cuff or Taylor Patch to improve the long-term patency of the grafts.

The commonest complications associated with the use of vascular grafts include Graft occlusion, Graft infection, true and false aneurysms at the site of anastomosis, distal embolization, and erosion in to adjacent structures—e.g. Aorto-enteric fistulae. Many of these conditions are associated with an inflammatory response, macrophage migration into the site, and/or the formation of reactive oxygen species (e.g., oxidized lipids). To reduce such complications, the graft (synthetic or biological can be soaked, or otherwise coated, with one or more of the active agents described herein.

In addition, it is contemplated that other implantable tissues or materials can similarly be impregnated or coated with one or more active agents of this invention. Thus, for example, in certain embodiments this invention contemplates the use of impregnated sutures to minimize inflammation and/or infection and/or tissue rejection.

3. Subcutaneous Matrices.

In certain embodiments, one or more active agents described herein are administered alone or in combination with other therapeutics as described herein in implantable (e.g., subcutaneous) matrices.

A major problem with standard drug dosing is that typical delivery of drugs results in a quick burst of medication at the time of dosing, followed by a rapid loss of the drug from the body. Most of the side effects of a drug occur during the burst phase of its release into the bloodstream. Secondly, the time the drug is in the bloodstream at therapeutic levels is very short, most is used and cleared during the short burst.

Drugs (e.g., the active agents described herein) imbedded in various matrix materials for sustained release provides some solution to these problems. Drugs embedded, for example, in polymer beads or in polymer wafers have several advantages. First, most systems allow slow release of the drug, thus creating a continuous dosing of the body with small levels of drug. This typically prevents side effects associated with high burst levels of normal injected or pill based drugs. Secondly, since these polymers can be made to release over hours to months, the therapeutic span of the drug is markedly increased. Often, by mixing different ratios of the same polymer components, polymers of different degradation rates can be made, allowing remarkable flexibility depending on the agent being used. A long rate of drug release is beneficial for people who might have trouble staying on regular dosage, such as the elderly, but is also an ease of use improvement that everyone can appreciate. Most polymers can be made to degrade and be cleared by the body over time, so they will not remain in the body after the therapeutic interval.

Another advantage of polymer based drug delivery is that the polymers often can stabilize or solubilize proteins, peptides, and other large molecules that would otherwise be unusable as medications. Finally, many drug/polymer mixes can be placed directly in the disease area, allowing specific targeting of the medication where it is needed without losing drug to the "first pass" effect. This is certainly effective for treating the brain, which is often deprived of medicines that can't penetrate the blood/brain barrier.

A number of implantable matrix (sustained release) systems are know to those of skill and can readily be adapted for use with one or more of the active agents described herein. Suitable sustained release systems include, but are not limited to Re-Gel®, SQ2Gel®, and Oligosphere® by MacroMed, ProLease® and Medisorb® by Alkermes, Paclimer® and Gliadel® Wafer by Guilford pharmaceuticals, the Duros implant by Alza, acoustic bioSpheres by Point Biomedical, the Intelsite capsule by Scintipharma, Inc., and the like.

4. Other "Specialty Delivery Systems".

Other "specialty" delivery systems include, but are not limited to lipid based oral mist that allows absorption of drugs across the oral mucosa, developed by Generex Biotechnology, the oral transmucosal system (OTS™) by Anesta Corp., the inhalable dry powder and PulmoSpheres technology by Inhale Therapeutics, the AERx® Pulmonary Drug Delivery System by Aradigm, the AIR mechanism by Alkermes, and the like.

Another approach to delivery developed by Alkermes is a system targeted for elderly and pediatric use, two populations for which taking pills is often difficult is known as Drug Sipping Technology (DST). The medication is placed in a drinking straw device, prevented from falling out by filters on either end of it. The patient merely has to drink clear liquid (water, juice, soda) through the straw. The drug dissolves in the liquid as it is pulled through and is ingested by the patient. The filter rises to the top of the straw when all of the medication is taken. This method has the advantage in that it is easy to use, the liquid often masks the medication's taste, and the drug is pre-dissolved for more efficient absorption.

It is noted that these uses and delivery systems are intended to be illustrative and not limiting. Using the teachings provided herein, other uses and delivery systems will be known to those of skill in the art.

VI. Additional Pharmacologically Active Agents.

Combined Active Agents

In various embodiments, the use of combinations of two or more active agents described is contemplated in the treatment of the various pathologies/indications described herein. The use of combinations of active agents can alter pharmacological activity, bioavailability, and the like.

By way of illustration, it is noted that D-4F rapidly associates with pre-beta HDL and HDL and then is rapidly cleared from the circulation (it is essentially non-detectable 6 hours after an oral dose), while D-[113-122]apoJ slowly associates with pre-beta HDL and to a lesser extent with HDL but remains associated with these HDL fractions for at least 36 hours. FREL associates with HDL and only HDL but remains detectable in HDL for much longer than D-4F (i.e., it is detectable in HDL 48 hours after a single oral dose in mice). In certain embodiments this invention thus contemplates combinations of, for example, these three peptides to reduce the amount to reduce production expense, and/or to optimize dosage regimen, therapeutic profile, and the like. In certain embodiments combinations of the active agents described herein can be simply coadministered and/or added together to form a single pharmaceutical formulation. In certain embodiments the various active agent(s) can be complexed together (e.g. via hydrogen bonding) to form active agent complexes that are more effective than the parent agents.

Use with Additional Pharmacologically Active Materials.

Additional pharmacologically active materials (i.e., drugs) can be delivered in conjunction with one or more of the active agents described herein. In certain embodiments, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

It was discovered that, adding a low dosage active agent (e.g., of D-4F) (1 µg/ml) to the drinking water of apoE null mice for 24 hours did not significantly improve HDL function (see, e.g., related application U.S. Ser. No. 10/423,830, filed on Apr. 25, 2003, which is incorporated herein by reference). In addition, adding 0.05 mg/ml of atorvastatin or pravastatin alone to the drinking water of the apoE null mice for 24 hours did not improve HDL function. However, when D-4F 1 µg/ml was added to the drinking water together with 0.05 mg/ml of atorvastatin or pravastatin there was a significant improvement in HDL function). Indeed the pro-inflammatory apoE null HDL became as anti-inflammatory as 350 µg/ml of normal human HDL (h, HDL see, e.g., related application U.S. Ser. No. 10/423,830).

Thus, doses of D-4F alone, or statins alone, which by themselves had no effect on HDL function when given together acted synergistically. When D-4F and a statin were given together to apo E null mice, their pro-inflammatory HDL at 50 µg/ml of HDL-cholesterol became as effective as normal human HDL at 350 µg/ml of HDL-cholesterol in preventing the inflammatory response induced by the action of HPODE oxidizing PAPC in cocultures of human artery wall cells.

Thus, in certain embodiments this invention provides methods for enhancing the activity of statins. The methods generally involve administering one or more of the active agents described herein, as described herein in conjunction with one or more statins. The active agents achieve synergistic action between the statin and the agent(s) to ameliorate one or more symptoms of atherosclerosis. In this context statins can be administered at significantly lower dosages thereby avoiding various harmful side effects (e.g., muscle wasting) associated with high dosage statin use and/or the anti-inflammatory properties of statins at any given dose are significantly enhanced.

Suitable statins include, but are not limited to pravastatin (Pravachol/Bristol-Myers Squibb), simvastatin (Zocor/Merck), lovastatin (Mevacor/Merck), and the like.

In various embodiments the active agent(s) described herein are administered in conjunction with one or more beta blockers. Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable ace inhibitors include, but are not limited to captopril (e.g. Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g. Prinivil™ by Merck or Zestril™ by Astra-Zeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

In various embodiments, one or more agents described herein are administered with one or more of the drugs identified below.

Thus, in certain embodiments one or more active agents are administered in conjunction with cholesteryl ester transfer protein (CETP) inhibitors (e.g., torcetrapib, JTT-705.

CP-529414) and/or acyl-CoA:cholesterol O-acyltransferase (ACAT) inhibitors (e.g., Avasimibe (CI-1011), CP 113818, F-1394, and the like), and/or immunomodulators (e.g., FTY720 (sphingosine-1-phosphate receptor agonist), Thalomid (thalidomide), Imuran (azathioprine), Copaxone (glatiramer acetate), Certican® (everolimus), Neoral® (cyclosporine), and the like), and/or dipeptidyl-peptidase-4 (DPP4) inhibitors (e.g., 2-Pyrrolidinecarbonitrile, 1-[[[2-[(5-cyano-2-pyridinyl)amino]ethyl]amino]acetyl], see also U.S. Patent Publication 2005-0070530), and/or calcium channel blockers (e.g., Adalat, Adalat CC, Calan, Calan SR, Cardene, Cardizem, Cardizem CD, Cardizem SR, Dilacor-XR, DynaCirc, Isoptin, Isoptin SR, Nimotop, Norvasc, Plendil, Procardia, Procardia XL, Vascor, Verelan), and/or peroxisome proliferator-activated receptor (PPAR) agonists for, e.g., $\alpha$, $\gamma$; $\delta$ receptors (e.g., Azelaoyl PAF, 2-Bromohexadecanoic acid, Ciglitizone, Clofibrate, 15-Deoxy-$\delta^{12,14}$-prostaglandin $J_2$, Fenofibrate, Fmoc-Leu-OH, GW1929, GW7647, 8(S)-Hydroxy-(5Z,9E,11Z,14Z)-eicosatetraenoic acid (8(S)-HETE), Leukotriene $B_4$, LY-171,883 (Tomelukast), Prostaglandin $A_2$, Prostaglandin $J_2$, Tetradecylthioacetic acid (TTA), Troglitazone (CS-045), WY-14643 (Pirinixic acid)), and the like.

In certain embodiments one or more of the active agents are administered in conjunction with fibrates (e.g., clofibrate (atromid), gemfibrozil (lopid), fenofibrate (tricor), etc.), bile acid sequestrants (e.g., cholestyramine, colestipol, etc.), cholesterol absorption blockers (e.g., ezetimibe (Zetia), etc.), Vytorin ((ezetimibe/simvastatin combination), and/or steroids, warfarin, and/or aspirin, and/or Bcr-Abl inhibitors/antagonists (e.g., Gleevec (Imatinib Mesylate), AMN107, STI571 (CGP57148B), ON 012380, PLX225, and the like), and/or renin angiotensin pathway blockers (e.g., Losartan (Cozaar®), Valsartan (Diovan®), Irbesartan (Avapro®), Candesartan (Atacand®), and the like), and/or angiotensin II receptor antagonists (e.g., losartan (Cozaar), valsartan (Diovan), irbesartan (Avapro), candesartan (Atacand) and telmisartan (Micardis), etc.), and/or PKC inhibitors (e.g., Calphostin C, Chelerythrine chloride, Chelerythrine.chloride, Copper bis-3,5-diisopropylsalicylate, Ebselen, EGF Receptor (human) (651-658) (N-Myristoylated), Gö 6976, H-7. dihydrochloride, 1-O-Hexadecyl-2-O-methyl-rac-glycerol, Hexadecyl-phosphocholine ($C_{16:0}$); Miltefosine, Hypericin, Melittin (natural), Melittin (synthetic), ML-7. hydrochloride, ML-9. hydrochloride, Palmitoyl-DL-camitine. hydrochloride, Protein Kinase C (19-31), Protein Kinase C (19-36), Quercetin.dihydrate, Quercetin.dihydrate, D-erythro-Sphingosine (isolated), D-erythro-Sphingosine (synthetic), Sphingosine, N,N-dimethyl, D-erythro-Sphingosine, Dihydro-, D-erythro-Sphingosine, N,N-Dimethyl-, D-erythro-Sphingosine chloride, N,N,N-Trimethyl-, Staurosporine, Bisindolylmaleimide I, G-6203, and the like).

In certain embodiments, one or more of the active agents are administered in conjunction with ApoAI, Apo A-I derivatives and/or agonists (e.g., ApoAI milano, see, e.g., U.S. Patent Publications 20050004082, 20040224011, 20040198662, 20040181034, 20040122091, 20040082548, 20040029807, 20030149094, 20030125559, 20030109442, 20030065195, 20030008827, and 20020071862, and U.S. Pat. Nos. 6,831,105, 6,790,953, 6,773,719, 6,713,507, 6,703,422, 6,699,910, 6,680,203, 6,673,780, 6,646,170, 6,617,134, 6,559,284, 6,506,879, 6,506,799, 6,459,003, 6,423,830, 6,410,802, 6,376,464, 6,367,479, 6,329,341, 6,287,590, 6,090,921, 5,990,081, and the like), renin inhibitors (e.g., SPP630 and SPP635, SPP100, Aliskiren, and the like), and/or MR antagonist (e.g., spironolactone, aldosterone glucuronide, and the like), and/or aldosterone synthase inhibitors, and/or alpha-adrenergic antagonists (e.g., Aldomet® (Methyldopa), Cardura® (Doxazosin), Catapres®; Catapres-TTS®; Duraclon™ (Clonidine), Dibenzyline® (Phenoxybenzamine), Hylorel® (Guanadrel), Hytrin® (Terazosin), Minipress® (Prazosin), Tenex® (Guanfacine), Guanabenz, Phentolamine, Reserpine, and the like), and/or liver X receptor (LXR) agonists (e.g., T0901317, GW3965, ATI-829, acetyl-podocarpic dimer (APD), and the like), and/or framesoid X receptor (FXR) agonists (e.g., GW4064, 6alpha-ethyl-chenodeoxycholic acid (6-ECDCA), T0901317, and the like), and/or plasminogen activator-1 (PAI-1) inhibitors (see, e.g., oxime-based PAI-1 inhibitors, see also U.S. Pat. No. 5,639,726, and the like), and/or low molecular weight heparin, and/or AGE inhibitors/breakers (e.g., Benfotiamine, aminoguanidine, pyridoxamine, Tenilsetam, Pimagedine, and the like) and/or ADP receptor blockers (e.g., Clopidigrel, AZD6140, and the like), and/or ABCA1 agonists, and/or scavenger receptor B1 agonists, and/or Adiponectic receptor agonist or adiponectin inducers, and/or stearoyl-CoA Desaturase I (SCD1) inhibitors, and/or Cholesterol synthesis inhibitors (non-statins), and/or Diacylglycerol Acyltransferase I (DGAT1) inhibitors, and/or Acetyl CoA Carboxylase 2 inhibitors, and/or LP-PLA2 inhibitors, and/or GLP-1, and/or glucokinase activator, and/or CB-1 agonists, and/or anti-thrombotic/coagulants, and/or Factor Xa inhibitors, and/or GPIIb/IIIa inhibitors, and/or Factor VIIa inhibitors, and/or Tissue factor inhibitors, and/or anti-inflammatory drugs, and/or Probucol and derivatives (e.g. AGI-1067, etc.), and/or CCR2 antagonists, and/or CX3CR1 antagonists, and/or IL-1 antagonists, and/or nitrates and NO donors, and/or phosphodiesterase inhibitors, and the like.

IX. Kits for the Treatment of One or More Indications.

In another embodiment this invention provides kits for amelioration of one or more symptoms of atherosclerosis or for the prophylactic treatment of a subject (human or animal) at risk for atherosclerosis and/or the treatment or prophylaxis of one or more of the conditions described herein. The kits preferably comprise a container containing one or more of the active agents described herein. The active agent(s) can be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of the condition/pathology of interest. Such agents include, but are not limited to, beta blockers, vasodilators, aspirin, statins, ace inhibitors or ace receptor inhibitors (ARBs) and the like, e.g. as described above.

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to mitigate one or more symptoms of atherosclerosis (or other pathologies described herein) and/or to prevent the onset or increase of one or more of such symptoms in an individual at risk for atherosclerosis (or other pathologies described herein). The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical

EXAMPLES

The following examples are offered to illustrate, but not to limit the claimed invention.

Example 1

Use of ApoJ-Related Peptides to Mediate Symptoms of Atherosclerosis

Prevention of LDL-induced Monocyte Chemotactic Activity

FIG. 1 illustrates a comparison of the effect of D-4F (Anantharamaiah et al. (2002) *Circulation*, 105: 290-292) with the effect of an apoJ peptide made from D amino acids (D-J336, Ac-L-L-E-Q-L-N-E-Q-F-N-W-V-S-R-L-A-N-L-T-Q-G-E-NH$_2$, SEQ ID NO:1126) on the prevention of LDL-induced monocyte chemotactic activity in vitro in a co-incubation. Human aortic endothelial cells were incubated with medium alone (no addition), with control human LDL (200 μg protein/ml) or control human LDL+control human HDL (350 μg HDL protein/ml). D-J336 or D-4F was added to other wells in a concentration range as indicated plus control human LDL (200 μg protein/ml). Following overnight incubation, the supernatants were assayed for monocyte chemotactic activity. As shown in FIG. 1, the in vitro concentration of the apoJ variant peptide that prevents LDL-induced monocyte chemotactic activity by human artery wall cells is 10 to 25 times less than the concentration required for the D-4F peptide.

Prevention of LDL-induced Monocyte Chemotactic Activity by Pre-Treatment of Artery Wall Cells with D-J336

FIG. 2 illustrates a comparison of the effect of D-4F with the effect of D-J336 on the prevention of LDL induced monocyte chemotactic activity in a pre-incubation. Human aortic endothelial cells were pre-incubated with D-J336 or D-4F at 4, 2, and 1 μg/ml for DJ336 or 100, 50, 25, and 12.5 μg/ml for D-4F for 6 hrs. The cultures were then washed and were incubated with medium alone (no addition), or with control human LDL (200 μg protein/ml), or with control human LDL+control human HDL (350 μg HDL protein/ml) as assay controls. The wells that were pre-treated with peptides received the control human LDL at 200 μg protein/ml. Following overnight incubation, the supernatants were assayed for monocyte chemotactic activity.

As illustrated in FIG. 2, the ApoJ variant peptide was 10-25 times more potent in preventing LDL oxidation by artery wall cells in vitro.

The Effect of apo J Peptide Mimetics on HDL Protective Capacity in LDL Receptor Null Mice.

D-4F designated as F, or the apoJ peptide made from D amino acids (D-J336, designated as J) was added to the drinking water of LDL receptor null mice (4 per group) at 0.25 or 0.5 mg per ml of drinking water. After 24- or 48-hrs blood was collected from the mice and their HDL was isolated and tested for its ability to protect against LDL-induced monocyte chemotactic activity. Assay controls included culture wells that received no lipoproteins (no addition), or control human LDL alone (designated as LDL, 200 μg cholesterol/ml), or control LDL+control human HDL (designated as +HDL, 350 μg HDL cholesterol). For testing the mouse HDL, the control LDL was added together with mouse HDL (+F HDL or +J HDL) to artery wall cell cultures. The mouse HDL was added at 100 μg cholesterol/ml respectively. After treatment with either D-4F or D-J336 the mouse HDL at 100 μg/ml was as active as 350 μg/ml of control human HDL in preventing the control LDL from inducing the artery wall cells to produce monocyte chemotactic activity. The reason for the discrepancy between the relative doses required for the D-J336 peptide relative to D-4F in vitro and in vivo may be related to the solubility of the peptides in water and we believe that when measures are taken to achieve equal solubility the D-J peptides will be much more active in vivo as they are in vitro.

Protection Against LDL-induced Monocyte Chemotactic Activity by HDL from apo E Null Mice Given Oral Peptides.

FIG. 4 illustrates the effect of oral apoA-1 peptide mimetic and apoJ peptide on HDL protective capacity. ApoE null mice (4 per group) were provided with D-4F (designated as F) at 50, 30, 20, 10, 5 μg per ml of drinking water or apoJ peptide (designated as J) at 50, 30 or 20 μg per ml of drinking water. After 24 hrs blood was collected, plasma fractionated by FPLC and fractions containing LDL (designated as mLDL for murine LDL) and fractions containing HDL (designated as mHDL) were separately pooled and HDL protective capacity against LDL oxidation as determined by LDL-induced monocyte chemotactic activity was determined. For the assay controls the culture wells received no lipoproteins (no additions), mLDL alone (at 200 μg cholesterol/ml), or mLDL+standard normal human HDL (designated as Cont. h HDL, at 350 μg HDL cholesterol/ml).

For testing the murine HDL, mLDL together with murine HDL (+F mHDL or +J mHDL) were added to artery wall cell cultures. The HDL from the mice that did not receive any peptide in their drinking water is designated as no peptide mHDL. The murine HDL was used at 100 μg cholesterol/ml. After receiving D-4F or D-J336 the murine HDL at 100 μg/ml was as active as 350 μg/ml of normal human HDL. As shown in FIG. 4, when added to the drinking water the D-J peptide was as potent as D-4F in enhancing HDL protective capacity in apo E null mice.

Ability of LDL Obtained from apoE Null Mice Given Oral Peptides to Induce Monocyte Chemotactic Activity.

FIG. 5 illustrates the effect of oral apo A-I peptide mimetic and apoJ peptide on LDL susceptibility to oxidation. ApoE null mice (4 per group) were provided, in their drinking water, with D-4F (designated as F) at 50, 30, 20, 10, 5 μg per ml of drinking water or the apoJ peptide (D-J336 made from D amino acids and designated as J) at 50, 30 or 20 μg per ml of drinking water. After 24 hrs blood was collected from the mice shown in FIG. 4, plasma fractionated by FPLC and fractions containing LDL (designated as mLDL for murine LDL) were pooled and LDL susceptibility to oxidation as determined by induction of monocyte chemotactic activity was determined. For the assay controls the culture wells received no lipoproteins (no additions), mLDL alone (at 200 μg cholesterol/ml), or mLDL+standard normal human HDL (designated as Cont. h HDL, 350 μg HDL cholesterol).

Murine LDL, mLDL, from mice that received the D-4F (F mLDL) or those that received the apoJ peptide (J mLDL) were added to artery wall cell cultures. LDL from mice that did not receive any peptide in their drinking water is designated as No peptide LDL.

As shown in FIG. 5, when added to the drinking water, D-J336 was slightly more potent than D-4F in rendering the LDL from apo E null mice resistant to oxidation by human artery wall cells as determined by the induction of monocyte chemotactic activity.

Protection Against Phospholipid Oxidation and Induction of Monocyte Chemotactic Activity by HDL obtained from apo E Null Mice Given Oral Peptides.

Figure 6:
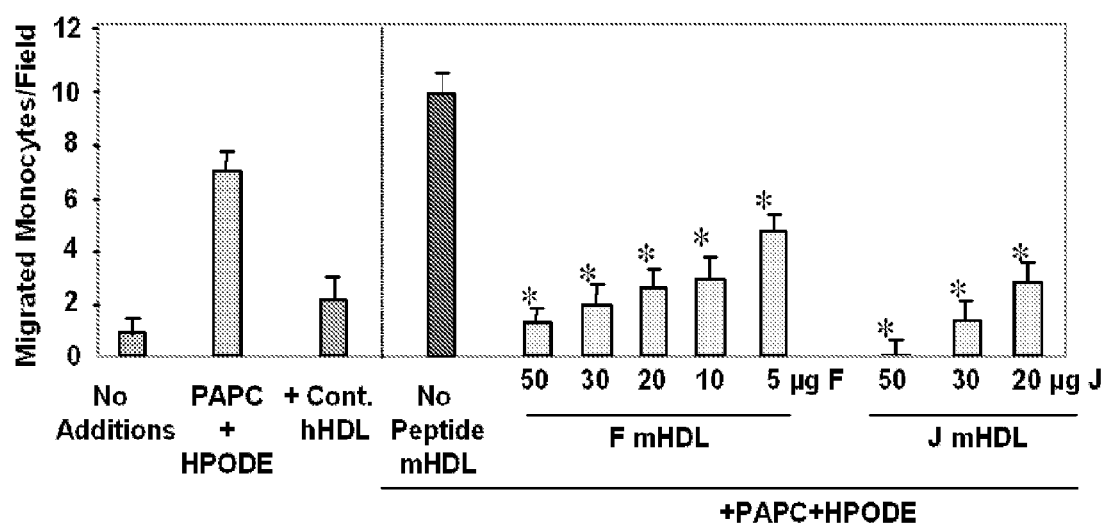
FIG. 6 illustrates the effect of oral apoA-1 peptide mimetic and apoJ peptide on HDL protective capacity. The values are the mean ±SD of the number of migrated monocytes in 9 high power fields from each of quadruple assay wells. Asterisks indicate significant difference (p<0.05) as compared to No Peptide mHDL.

FIG. 6 illustrates the effect of oral apoA-1 peptide mimetic and apoJ peptide on HDL protective capacity. ApoE null mice (4 per group) were provided with D-4F (designated as F) at 50, 30, 20, 10, 5 μg per ml of drinking water or apoJ peptide (D-J336 made from D amino acids and designated as J) at 50, 30 or 20 μg per ml of drinking water. After 24 hrs blood was collected, plasma fractionated by FPLC and fractions containing HDL (designated as mHDL) were pooled and HDL protective capacity against PAPC oxidation as determined by the induction of monocyte chemotactic activity was determined. For the assay controls the culture wells received no lipoproteins (no additions), the phospholipid PAPC at 20 μg/ml+HPODE, at 1.0 μg/ml, or PAPC+HPODE plus standard normal human HDL (at 350 μg HDL cholesterol/ml and designated as +Cont. h HDL).

For testing the murine HDL, PAPC+HPODE together with murine HDL (+F mHDL or +J mHDL) were added to artery wall cell cultures. The HDL from mice that did not receive any peptide in their drinking water is designated as "no peptide mHDL". The murine HDL was used at 100 μg cholesterol/ml.

The data show in FIG. 6 indicate that, when added to the drinking water, D-J336 was as potent as D-4F in causing HDL to inhibit the oxidation of a phospholipid PAPC by the oxidant HPODE in a human artery wall co-culture as measured by the generation of monocyte chemotactic activity
Effect of Oral apoA-1 Peptide Mimetic and apoJ Peptide on Plasma Paraoxonase Activity in Mice.

Figure 7:
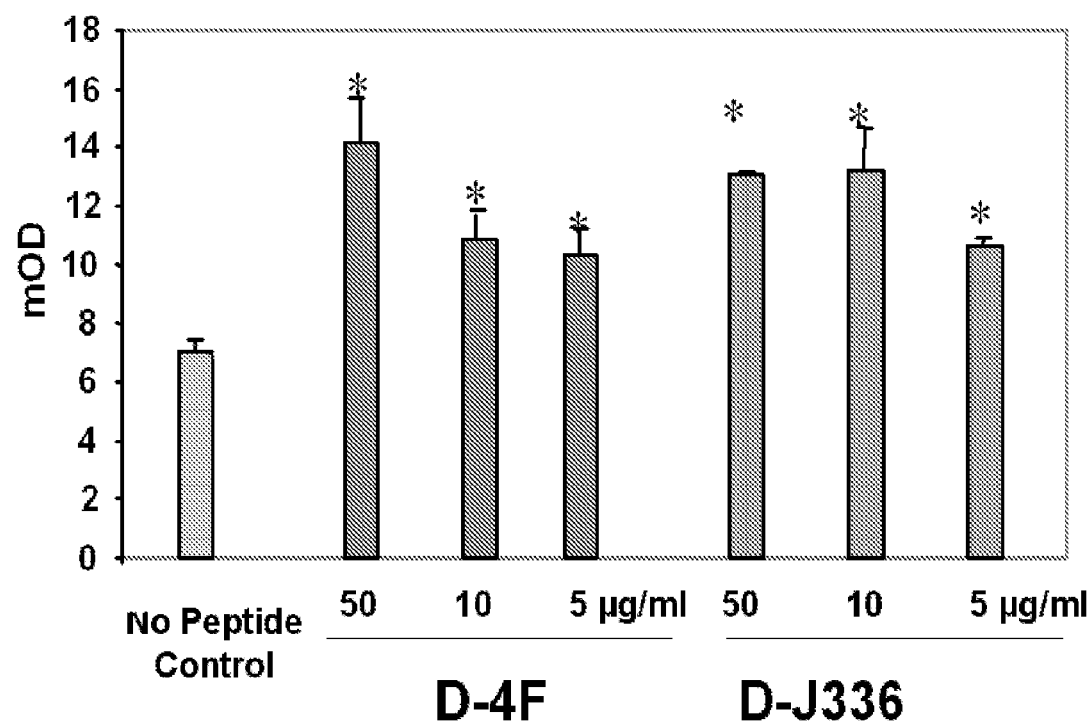
FIG. 7 illustrates the effect of oral apoA-1 peptide mimetic and apoJ peptide on plasma paraoxonase activity. The values are the mean ±SD of readings from quadruple plasma aliquots. Asterisks indicate significant differences (p<0.05) as compared to No Peptide control plasma.

FIG. 7 shows the effect of oral apoA-1 peptide mimetic and apoJ peptide on plasma paraoxonase activity in mice. ApoE null mice (4 per group) were provided with D-4F designated as F at 50, 10, 5 or 0 μg per ml of drinking water or apoJ peptide (D-J336 made from D amino acids and designated as J) at 50, 10 or 5 μg per ml of drinking water. After 24 hrs blood was collected and plasma was assayed for PON1 activity. These data demonstrate that, when added to the drinking water, D-J336 was at least as potent as D-4F in increasing the paraoxonase activity of apo E null mice.

Example 2

Oral G* Peptides Increase HDL Protective Capacity in Apo E Deficient Mice

Female, 4 month old apoE deficient mice (n=4 per group) were treated with G* peptides having the following amino acid sequences. Peptide 113-122=Ac-L-V-G-R-Q-L-E-E-F-L-NH$_2$(SEQ ID NO:969), Peptide 336-357=Ac-L-L-E-Q-L-N-E-Q-F-N-W-V-S-R-L-A-N-L-T-Q-G-E-NH$_2$(SEQ ID NO:961), and Peptide 377-390=Ac-P-S-G-V-T-E-V-V-V-K-L-F-D-S-NH$_2$ (SEQ ID NO:979).

Figure 8:
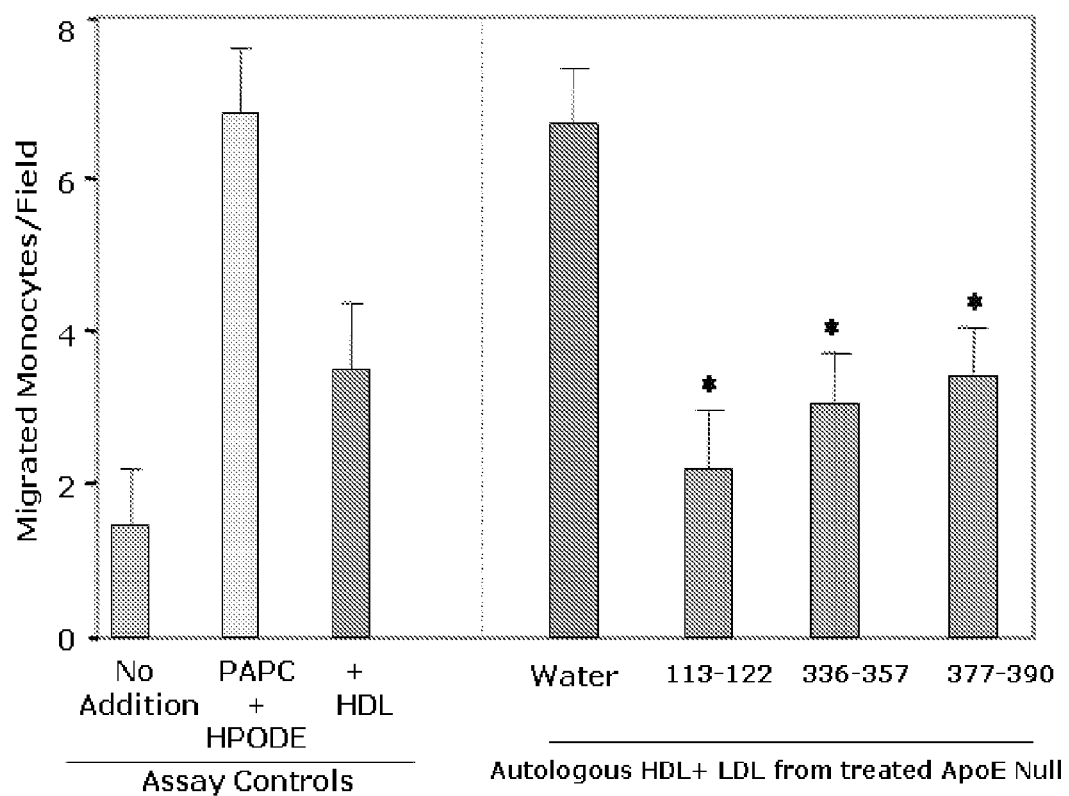
FIG. 8 shows the effect of oral G* peptides on HDL protective capacity in apoE−/− mice. The values are the mean ±SD of readings from quadruple plasma aliquots. Asterisks indicate significant differences (p<0.05) as compared to no peptide control plasma.

Each mouse received 200 μg of the peptide by stomach tube. Four hours later blood was obtained, plasma separated, lipoproteins fractionated and HDL (at 25 μg per ml) was assayed for protective capacity against the oxidation of LDL (at 100 μg per ml) in cultures of human artery wall cells. The data are shown in FIG. 8. The peptide afforded significant HDL-protective capacity in the mice.

Figure 9:
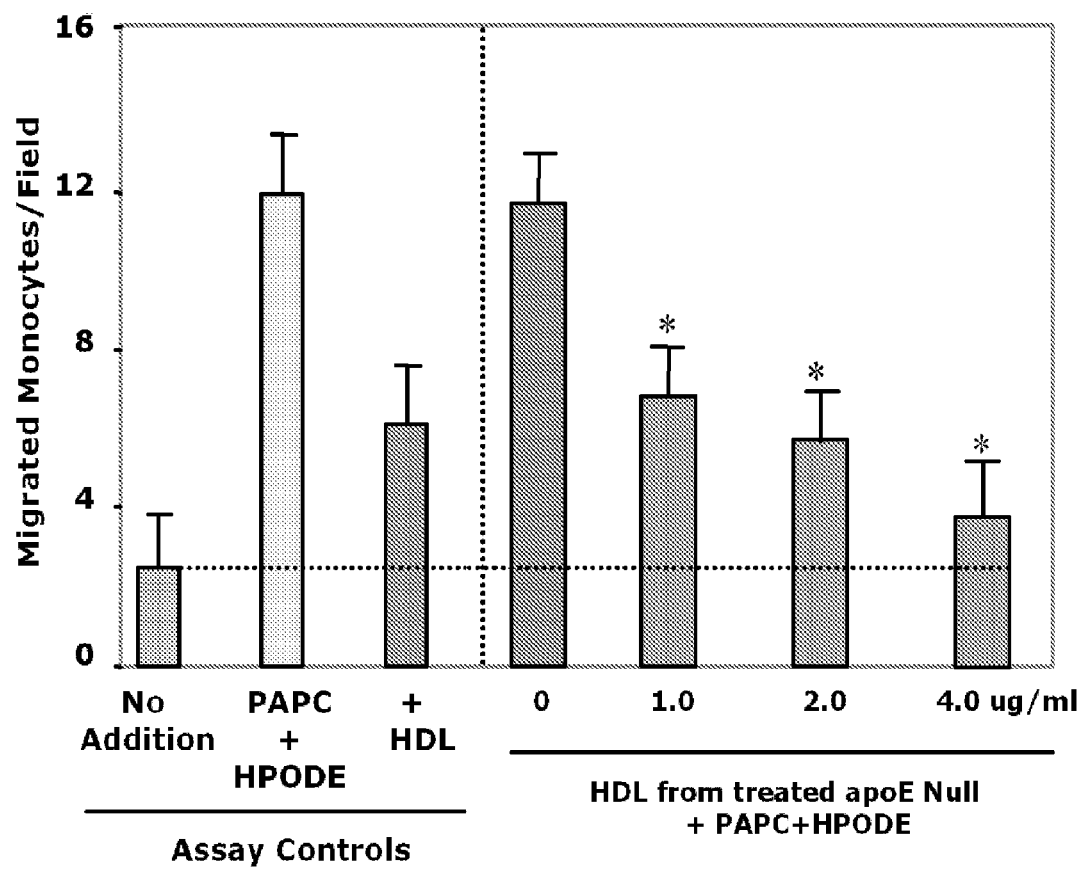
FIG. 9 shows the effect of Oral G* peptide, 146-156, on HDL protective capacity in ApoE−/− mice.
Figure 10A:
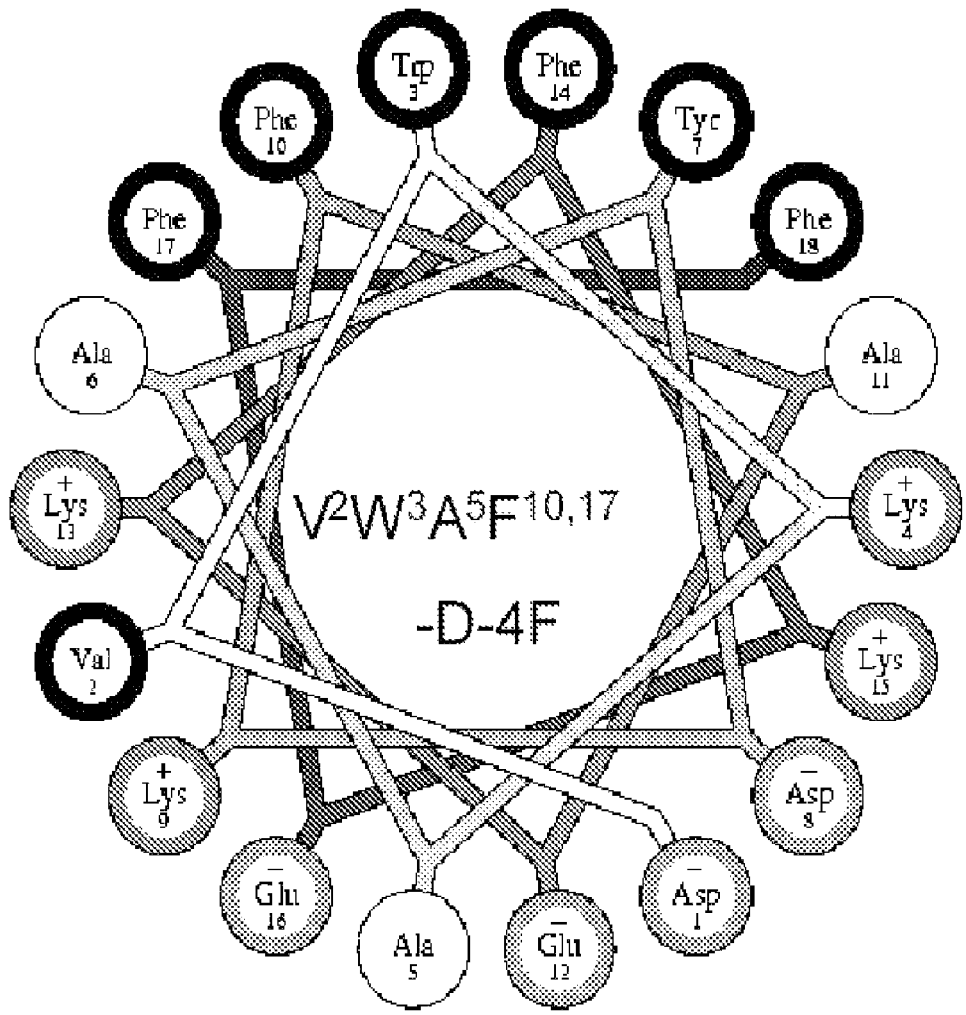
FIGS. 10A through 10C illustrate helical wheel diagrams of certain peptides of this invention.
Figure 10B:
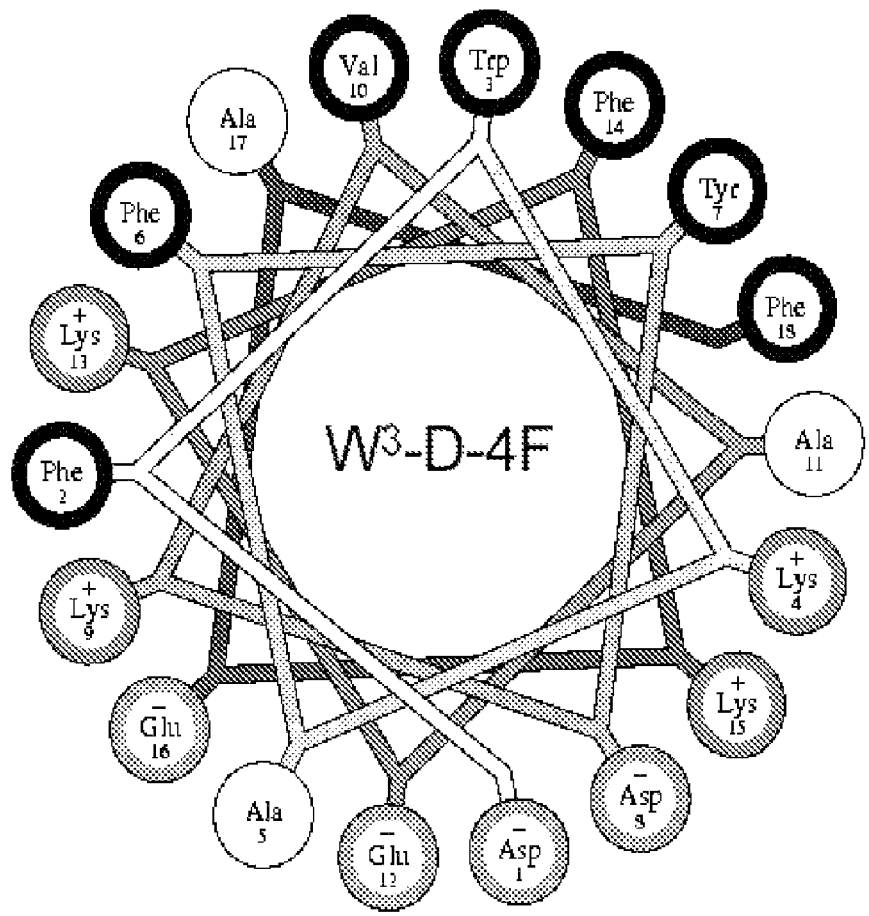
Figure 10C:
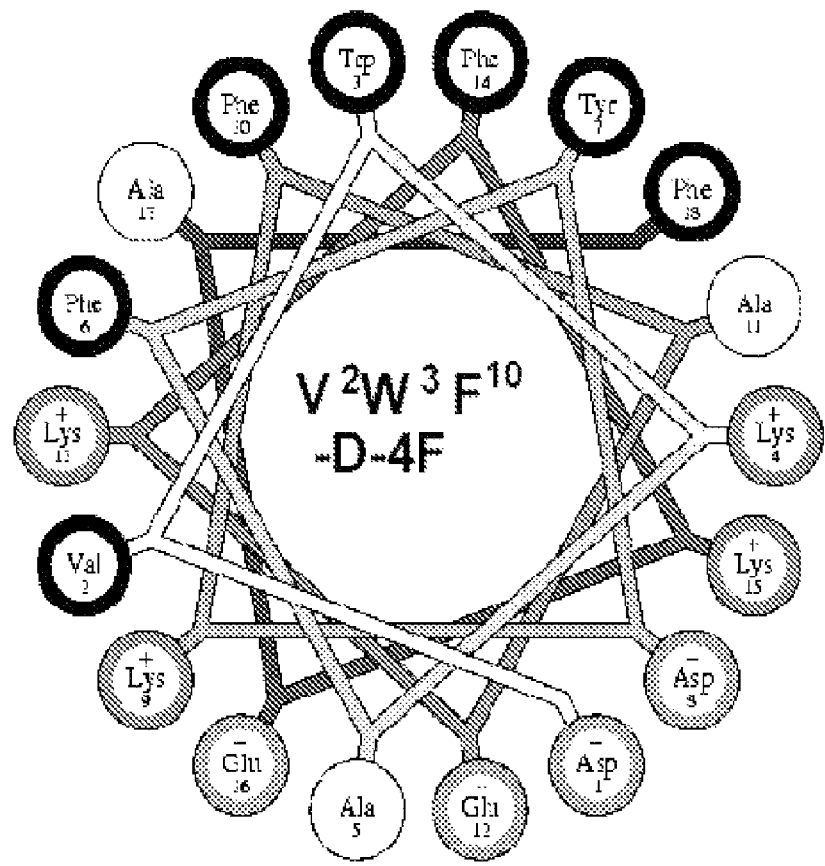
Figure 11:
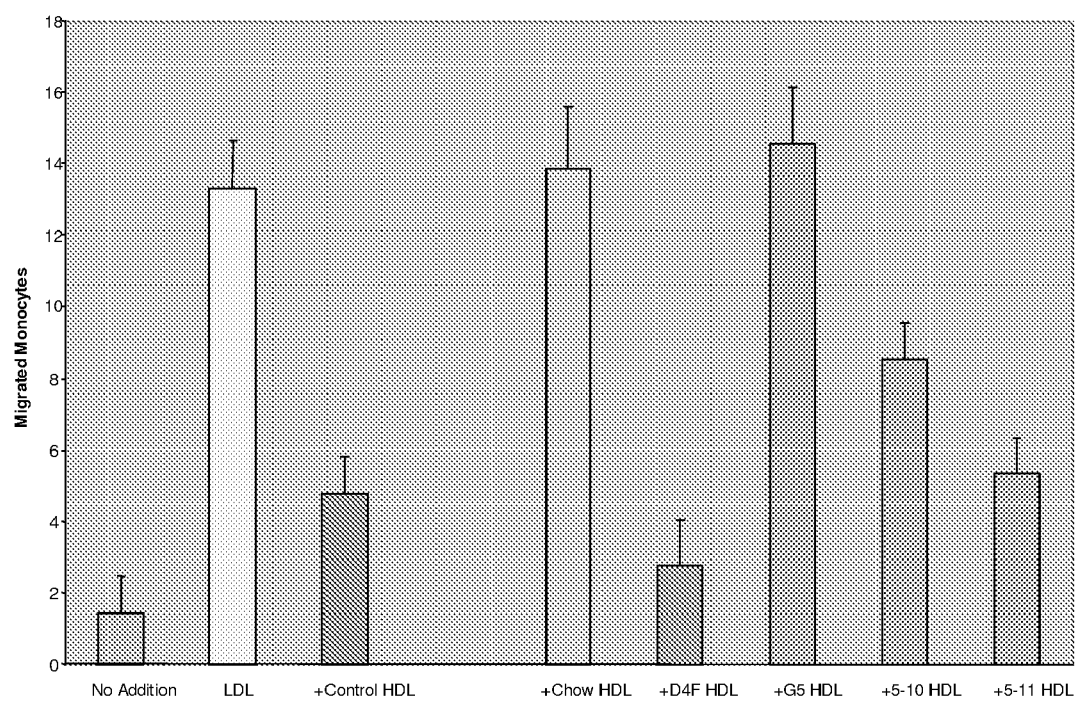
FIG. 11 A standard human LDL (LDL) was added to human artery wall cocultures without (No Addition) or with human HDL (+Control HDL) or with mouse HDL from apoE null mice given Chow overnight (+Chow HDL), or given D-4F in the chow overnight (+D4F HDL) or given G5-D-4F in the chow overnight (+G5 HDL), or given G5,10-D-4F in the chow overnight (+5-10 HDL), or given G5,11-D-4F in the chow overnight (+5-11 HDL) and the resulting monocyte chemotactic activity determined as previously described (Navab et al. (2002) *Circulation*, 105: 290-292).
Figure 12:
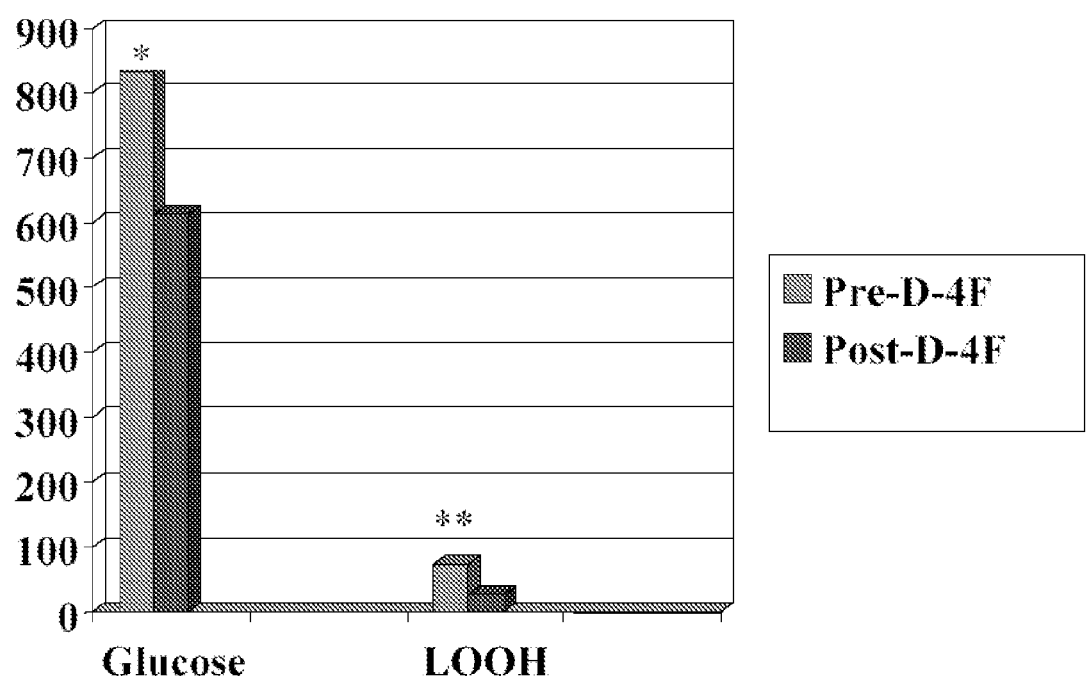
FIG. 12 shows that peptides of this invention are effective in mitigating symptoms of diabetes (e.g., blood glucose). Obese Zucker rats 26 weeks of age were bled and then treated with daily intraperitoneal injections of D-4F (5.0 mg/kg/day). After 10 days the rats were bled again plasma glucose and lipid hydroperoxides (LOOH) were determined. *p=0.027; **p=0.0017.
Figure 13:
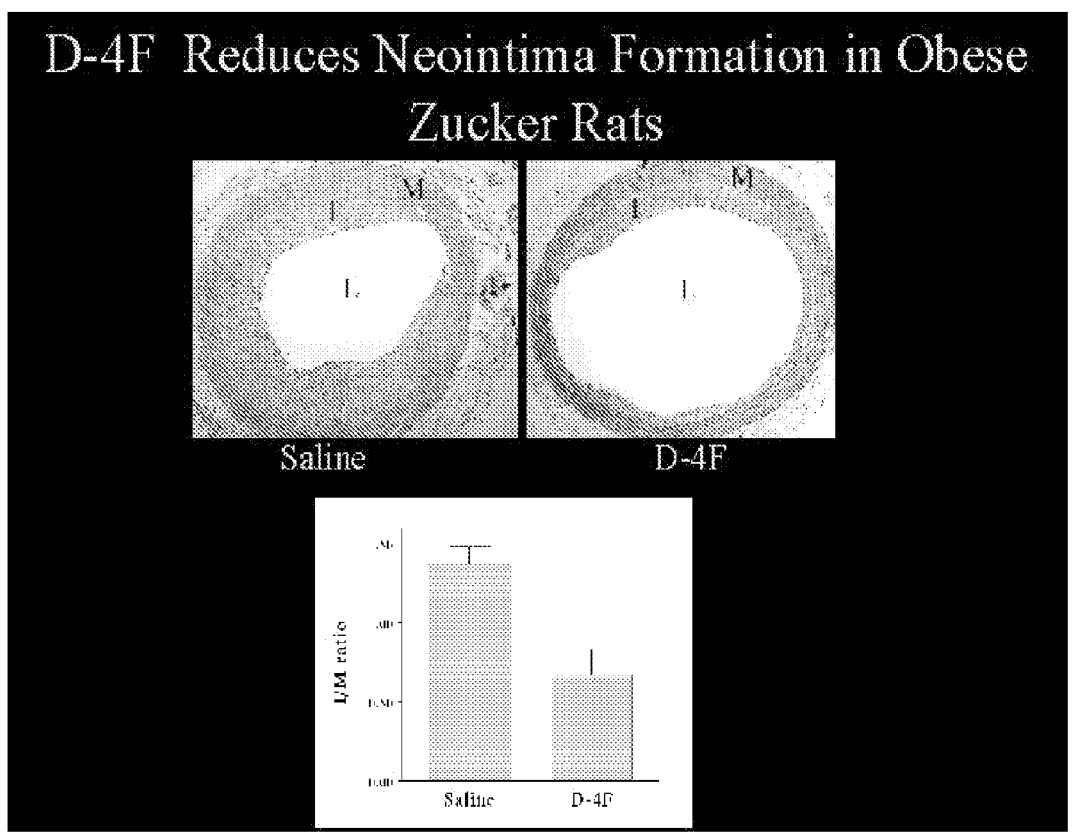
FIG. 13. Sixteen week old Obese Zucker Rats were injected with D-4F (5 mg/kg/daily) for 1 week at which time they underwent balloon injury of the common carotid artery. Two weeks later the rats were sacrificed and the intimal media ratio determined.

In another experiment, female, 4 month old apoE deficient mice (n=4 per group) were treated with the 11 amino acid G* peptide 146-156 with the sequence: Ac-Q-Q-T-H-M-L-D-V-M-Q-D-NH$_2$ (SEQ ID NO:971). The mice received the peptide in their drinking water at the indicated concentrations (see FIG. 9). Following eighteen hrs, blood was obtained, plasma separated, lipoproteins fractionated and HDL (at 50 μg cholesterol per ml) was assayed for protective capacity against the oxidation of PAPC (at 25 μg per ml)+HPODE (at 1.0 μg per ml) in cultures of human artery wall cells. Assay controls included No additions, PAPC+HPODE and PAPC+HPODE plus Control HDL (designated as +HDL). The data are mean+/−SD of the number of migrated monocytes in nine high power fields in triplicate cultures. Asterisks indicate significance at the level of $p<0.05$ vs. the water control (0 μg/ml).

Example 3

Solution Phase Chemistry for Peptide Synthesis

In certain embodiments, a solution-phase synthesis chemistry provides a more economical means of synthesizing peptides of this invention.

Prior to this invention synthesis was typically performed using an all-solid phase synthesis chemistry. The solid phase synthesis of peptides of less than 9 amino acids is much more economical than the solid phase synthesis of peptides of more than 9 amino acids. Synthesis of peptides of more than 9 amino acids results in a significant loss of material due to the physical dissociation of the elongating amino acid chain from the resin. The solid phase synthesis of peptides containing less than 9 amino acids is much more economical because the there is relatively little loss of the elongating chain from the resin.

In certain embodiments, the solution phase synthesis functions by converting the synthesis of the 18 amino acid apoA-I mimetic peptide, 4F (and other related peptides) from an all solid phase synthesis to either an all solution phase synthesis or to a combination of solid phase synthesis of three chains each containing, e.g., 6 amino acids followed by the assembly of the three chains in solution. This provides a much more economical overall synthesis. This procedure is readily modified where the peptides are not 18 amino acids in length. Thus, for example, a 15 mer can be synthesized by solid phase synthesis of three 5 mers followed by assembly of the three chains in solution. A 14 mer can be synthesized by the solid phase synthesis of two 5 mers and one 4 mer followed by assembly of these chains in solution, and so forth.

A) Summary of Synthesis Protocol.

An scheme for the synthesis of the peptide D4F (Ac-D-W-F-K-A-F-Y-D-K-V-A-E-K-F-K-E-A-F-NH$_2$, (SEQ ID NO:5) is illustrated in Table 20. (The scheme and yields for the synthesis are shown in Table 20.

TABLE 20

Illustrative solution phase synthesis scheme.

| Synthesis | Resin | Fmoc Amino Acid | Coupling Reagent | Final Wt. of Resin (gms) | Wt. of Crude Peptide (gms) Yield (%) | Wt. of Pure Peptide (mg) Yield ((%) |
|---|---|---|---|---|---|---|
| Methods Used for D4F Synthesis | | | | | | |
| Stepwise Solid Phase | Rink Amide (1 mmole) 1.8 gms | 6 Equiv | HBTU/ HOBT | 4 | 2.0 86 | 500 25 |

TABLE 20-continued

Illustrative solution phase synthesis scheme.

| Synthesis | Resin | Fmoc Amino Acid | Coupling Reagent | Final Wt. of Resin (gms) | Wt. of Crude Peptide (gms) Yield (%) | Wt. of Pure Peptide (mg) Yield ((%) |
|---|---|---|---|---|---|---|
| Stepwise Solid Phase | Rink Amide (1 mmole) 1.8 gms | 2 Equiv | DIC/HOBT | 3.9 | 2.0 86 | 450 22.5 |
| Fragment coupling (6 + 6 + 6) | Rink Amide (1 mmole) 1.8 gms* | | HBTU/ HOBT | 3.3 | 1.0 43 | 100 10 |

Synthesis of D4F Fragments
Fragment 1 (2HN-KFKEAF (SEQ ID NO: 1127) on
rink amide resin (K and E are properly protected)

| Fragment 2 6 residues stepwise Solid Phase | Cl-TrT-Resin (5 mmol) 6.5 gms | 6 Equiv | HBTU/ HOBT | 11 | 2.2 crude protected 36 | |

Fmoc-Y(But)-D(But)-K(Boc)-V-A-E(But)-COOH
(SEQ ID NO: 1128)

| Fragment 2 6 residues stepwise Solid Phase | Cl-TrT-Resin (5 mmol) 6.5 gms | 6 Equiv | HBTU/ HOBT | 10 | 1.8 crude protected 32 | |

Ac-D(But)-W-F-K(Boc)-A-F-COOH (SEQ ID NO: 1129)

Synthesis by solution phase using fragments produced by the solid phase method.
Fragment 1. Wang resin. C-terminal hexapeptide (subjected to ammonolysis). Yield quantitative.
NH2-K(Boc)-F-K(Boc)-E(But)-A-F-Wang resin (SEQ ID NO: 1130)
NH2-K(Boc)-F-K(Boc)-E(But)-A-F-CO-NH2 (SEQ ID NO: 1131)
Fragment 2 from above was coupled to fragment 1 in DMF using DIC/HOBT.
Fmoc-Y(But)-D(But)-K(Bpc)-V-A-E(But)-K(Boc)-F-K(Boc)-E(But)-F-Co-NH2 (SEQ ID NO: 1132) 12 residue peptide was characterized as free peptide after removing protecting groups. Yield was 50%
Fmoc from the above-12 residue was removed by piperidine in DMF (20%). After drying the peptide was coupled to Fragment 3 using DCI/HOBT in DMF.
Ac-D(But)-W-F-K(Boc)-A-F-Y(But)-D(but)-K(Boc)-V-A-E(But)-K(Boc)-F-K(Boc)-E(But)-A-FCO-NH2 (SEQ ID NO: 1133)
Protected peptide yield was quantitative.
Protecting groups removed using mixture of TFA (80%), phenol (5%), thioanisole (5%). water) 5%), triisopropylsilane (TIS, 5%), stirred for 90 min.
Precipitated by ether and purified by C-4 HPLC column. Yield 25%

Fragments synthesized for fragment condensation on solid phase are:
Fragment 1: Ac-D(OBut)-W-F-K(εBoc)-A-F-COOH (SEQ ID NO:1134);
Fragment 2: Fmoc-Y(OBut)-D(OBut)-K(εBoc)-V-A-E(OBut)-COOH (SEQ ID NO:1135); and
Fragment 3 Fmoc-K(εBoc)F-K(εBoc)-E(OBut)-A-F-Rink amide resin (SEQ ID NO:1136).

Fragment 1 was left on the resin to obtain final peptide amide after TFA treatment.

To synthesize fragment 1: Fmoc-Phe (1.2 equivalents) was added to chlorotrityl resin (Nova Biochem, 1.3 mMol/g substitution, 5 mMol or 6.5 g was used) in presence of six equivalents of DIEA in DMF:dichloromethane (1:1)) and stirred for 4h. Excess of functionality on the resin was capped with methanol in presence of dichloromethane and DIEA. After the removal of Fmoc-Fmoc amino acid derivatives (2 equivalents) were added using HOBt/HBTU reagents as described above. Final Fmoc-D(OBut)-W-F-K(εBoc)-A-F Chlorotrityl resin was treated with Fmoc deblocking agent and acetylated with 6 equivalents of acetic anhydride in presence of diisoprolylethyl amine. The resulting Ac-D(OBut)-W-F-K(εBoc)-A-F-resin was treated with a mixture of triflouroethanol-acetic acid-dichloromethane (2:2:6, 10 ml/g of resin) for 4h at room temperature. After removal of the resin by filtration, the solvent was removed by aziotropic distillation with n-hexane under vacuum. The residue (1.8 g) was determined by mass spectral analysis to be Ac-D(OBut)-W-F-K(εBoc)-A-F-COOH (SEQ ID NO:1137).

Fragment 2, Fmoc-Y(OBut)-D(OBut)-K(εBoc)-V-A-E(OBut)-COOH (SEQ ID NO:1138), was obtained using the procedure described for Fragment 1. Final yield was 2.2 g.

Fragment 3. 0.9 g (0.5 mmol) of Rink amide resin (Nova Biochem) was used to obtain fragment Rink amide resin was treated with 20% pipetidine in dichloromethane for 5 min once and 15 min the second time (Fmoc deblocking reagents). 1. 2 equivalents of Fmoc-Phe was condensed using condensing agents HOBt/HBTU (2 equivalents in presence of few drops of diisopropylethyl amine) (amino acid condensation). Deblocking and condensation of the rest of the amino acids were continued to obtain the of Fmoc-K(εBoc)F-K(εBoc)-E(OBut)-A-F-rink amide resin (SEQ ID NO:1139). Fmoc was cleaved and the peptide resin K(εBoc)F-K(εBoc)-E(OBut)-A-F-rink amide resin (SEQ ID NO:1139) was used for fragment condensation as described below.

Fragment 2 in DMF was added to Fragment 3 (1.2 equivalents) using HOBt-HBTU procedure in presence of DIEA overnight. After washing the resin with DMF and deblocking Fmoc-Fragment 1 (1.2 equivalents) was added to the dodecapeptide resin using HOBt-HBTU procedure overnight.

The final peptide resin (3.3 g) was treated with a mixture of TFA-Phenol-triisopropylsilane-thioanisole-water (80:5:5:5) for 1.5 h (10 ml of the reagent/g of the resin). The resin was filtered off and the solution was diluted with 10 volumes of ether. Precipitated peptide was isolated by centrifugation and washed twice with ether. 1 g of the crude peptide was subjected to HPLC purification to obtain 100 mg of the peptide.

2. Characterization of Peptide.

The peptide was identified by mass spectral and analytical HPLC methods.

Figure 14:
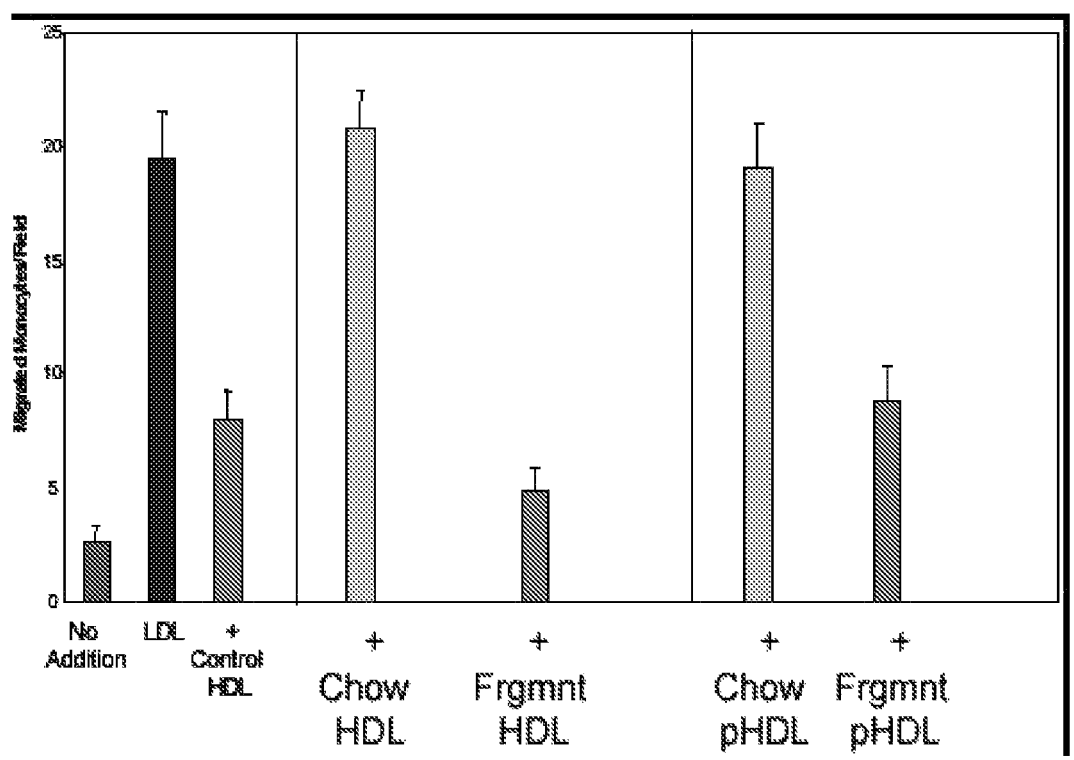
FIG. 14 demonstrates that the product of the solution phase synthesis scheme is very biologically active in producing HDL and pre-beta HDL that inhibit LDL-induced monocyte chemotaxis in apo E null mice. ApoE null mice were fed 5 micrograms of the D-4F synthesized as described above (Frgmnt) or the mice were given the same amount of mouse chow without D-4F (Chow). Twelve hours after the feeding was started, the mice were bled and their plasma was fractionated on FPLC. LDL (100 micrograms LDL-cholesterol) was added to cocultures of human artery wall cells alone (LDL) or with a control human HDL (Control HDL) or with HDL (50 micrograms HDL-cholesterol) or post-HDL (pHDL; prebeta HDL) from mice that did (Frgmnt) or did not (Chow) receive the D-4F and the monocyte chemotactic activity produced was determined

As shown in FIG. 14 the product of the solution phase synthesis scheme is very biologically active in producing HDL and pre-beta HDL that inhibit LDL-induced monocyte chemotaxis in apo E null mice. ApoE null mice were fed 5 micrograms of the D-4F synthesized as described above (Frgmnt) or the mice were given the same amount of mouse chow without D-4F (Chow). Twelve hours after the feeding was started, the mice were bled and their plasma was fractionated on FPLC. LDL (100 micrograms LDL-cholesterol) was added to cocultures of human artery wall cells alone (LDL) or with a control human HDL (Control HDL) or with HDL (50 micrograms HDL-cholesterol) or post-HDL (pHDL; prebeta HDL) from mice that did (Frgmnt) or did not (Chow) receive the D-4F and the monocyte chemotactic activity produced was determined

Example 4

Comparison of D-4F and Reverse (Retro-) D-4F Activity

Figure 16:
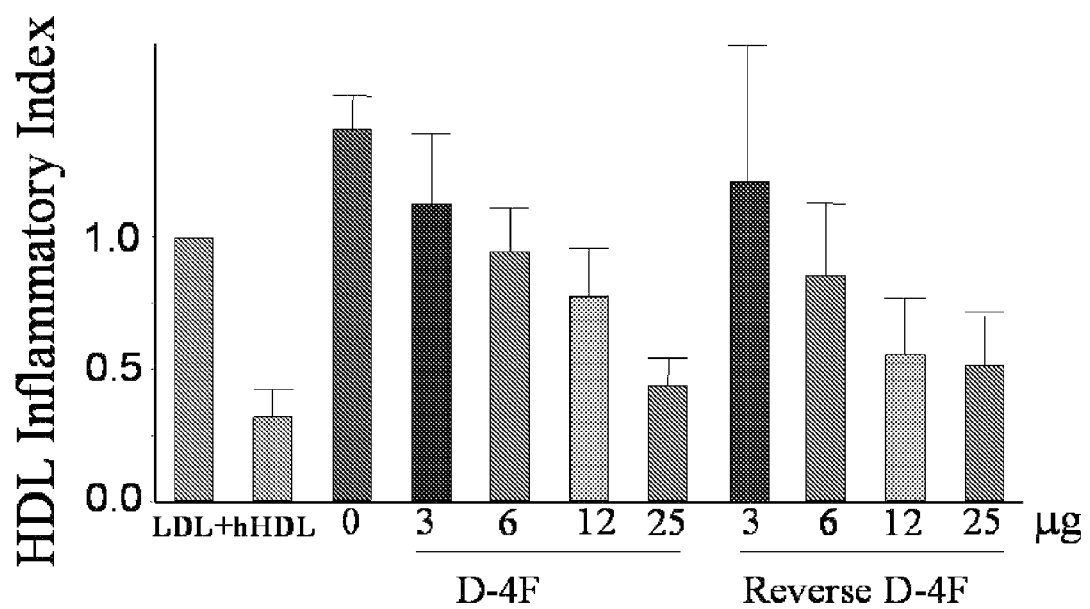
FIG. 16 shows a comparison of the HDL inflammatory index of D-4F versus reverse D-4F.

As shown in FIG. 16, the biological activities of D-4F and reverse RD-4F are not significantly different. Female apoE null mice were administered by stomach tube 0, 3, 6, 12, or 25 micrograms of D-4F or Reverse D-4F in 100 microliters of water. Blood was obtained 7 hours later and the plasma was fractionated by FPLC. A standard control human LDL was added to human artery wall cells at a concentration of 100 micrograms of LDL-cholesterol/mL (LDL). The resulting monocyte chemotactic activity was normalized to 1.0. The same LDL at the same concentration was added to the human artery wall cells together with HDL at 50 micrograms HDL-cholesterol/mL from a normal human (hHDL) or from the apoE null mice that received the dose of D-4F or Reverse D-4F shown on the X-axis. The resulting monocyte chemotactic activity was normalized to that of the LDL added without HDL. The resulting value is the HDL Inflammatory Index. The results shown are the Mean ±S.D. for the data from three separate experiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A peptide that ameliorates a symptom of atherosclerosis, wherein said peptide comprises a retro form of the amino acid sequence D-W-F-K-A-F-Y-D-K-V-A-E-K-F-K-E-A-F-P-D-W-F-K-A-F-Y-D-K-V-A-E-K-F-K-E-A-F (SEQ ID NO:83), wherein said peptide comprises all "L" amino acids.

2. The peptide of claim 1, wherein said peptide further comprises a protecting group coupled to the amino or carboxyl terminus.

3. The peptide of claim 1, wherein said peptide further comprises a first protecting group coupled to the amino terminus and a second protecting group coupled to the carboxyl terminus.

4. The peptide of claim 3, wherein said first protecting group and said second protecting group are independently selected from the group consisting of acetyl (Ac), amide, a 3 to 20 carbon alkyl group, Fmoc, 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts),4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (tBoc), cyclohexyloxy (cHxO),t-butoxymethyl (Bum), t-butoxy (tBuO), t-Butyl (tBu), and Trifluoroacetyl (TFA).

5. The peptide of claim 1, wherein said peptide is mixed with a pharmacologically acceptable excipient.

6. The peptide of claim 1, wherein said peptide is mixed with a pharmacologically acceptable excipient suitable for oral administration to a mammal.

7. The peptide of claim 3, wherein said first protecting group is a protecting group selected from the group consisting of acetyl, propionyl, and a 3 to 20 carbon alkyl.

8. The peptide of claim 3, wherein said second protecting group is an amide.

9. The peptide of claim 7, wherein said first protecting group is an acetyl and said second protecting group is an amide.

10. A method of treating a vascular condition and/or a condition characterized by an inflammatory response and/or a condition characterized by the formation of oxidized reactive species in a mammal, said method comprising:
    administering to a mammal in need thereof one or more of the peptides according to any one of claims 1-4, and 5-9.

11. A method of ameliorating one or more symptoms of a condition selected from the group consisting of atherosclerosis, said method comprising administering to a mammal in need thereof a peptide according to any one of claims 1-4, and 5-9.

12. A stent for delivering drugs to a vessel in a body, said stent comprising:
    a stent framework including a plurality of reservoirs formed therein; and
    a peptide according to any one of claims 1-4, and 5-9.

13. A method of manufacturing a drug-polymer stent, said method comprising:
    providing a stent framework;
    cutting a plurality of reservoirs in the stent framework; and
    applying to said reservoirs a composition comprising a peptide according to any one of claims 1-4, and 5-9.

14. A method of treating a vascular condition, said method comprising:
    positioning a stent according to claim 12 within a vessel of a body;
    expanding the stent; and
    eluting said peptide from at least a surface of the stent.

* * * * *